United States Patent
Rossi et al.

(10) Patent No.: US 10,080,354 B2
(45) Date of Patent: Sep. 25, 2018

(54) HEMATOPOIETIC STEM CELL SPECIFIC REPORTER MOUSE AND USES THEREOF

(71) Applicant: Children's Medical Center Corporation, Boston, MA (US)

(72) Inventors: Derrick J. Rossi, Roslindale, MA (US); Roi Gazit, Brookline, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 14/426,482

(22) PCT Filed: Sep. 6, 2013

(86) PCT No.: PCT/US2013/058380
§ 371 (c)(1),
(2) Date: Mar. 6, 2015

(87) PCT Pub. No.: WO2014/039745
PCT Pub. Date: Mar. 13, 2014

(65) Prior Publication Data
US 2015/0223436 A1    Aug. 13, 2015

Related U.S. Application Data

(60) Provisional application No. 61/697,843, filed on Sep. 7, 2012.

(51) Int. Cl.
| | | |
|---|---|---|
| *A01K 67/027* | (2006.01) | |
| *A61K 48/00* | (2006.01) | |
| *C07H 21/04* | (2006.01) | |
| *C12Q 1/6897* | (2018.01) | |
| *G01N 33/50* | (2006.01) | |

(52) U.S. Cl.
CPC ........ *A01K 67/0278* (2013.01); *C12Q 1/6897* (2013.01); *G01N 33/5073* (2013.01); *A01K 67/0275* (2013.01); *A01K 2217/072* (2013.01); *A01K 2227/105* (2013.01); *A01K 2267/02* (2013.01); *C07H 21/04* (2013.01); *C12N 2517/02* (2013.01)

(58) Field of Classification Search
CPC ............ A01K 67/0275; A01K 67/0278; A01K 2217/072; A01K 2227/105; C12N 2517/02; C07H 21/04
USPC ................ 800/18; 424/93.21; 536/23.5, 24.1
See application file for complete search history.

(56) References Cited

U.S. PATENT DOCUMENTS

2011/0123534 A1    5/2011    Duckers

FOREIGN PATENT DOCUMENTS

| JP | 2008102012 A | 5/2008 |
|---|---|---|
| WO | 2005/030240 A2 | 4/2005 |
| WO | 2005/056778 A1 | 6/2005 |
| WO | 2005/121320 A1 | 12/2005 |
| WO | 2007/046398 A1 | 4/2007 |
| WO | 2011/056073 A2 | 5/2011 |
| WO | 2011/102444 A1 | 8/2011 |
| WO | 2012/111772 A1 | 7/2012 |

OTHER PUBLICATIONS

Duckers, HJ, 2011, N_Geneseq Accession No. AZH88790, computer printout pp. 3-7.*
Duckers, HJ, 2011, N_Geneseq Accession No. AZH88790, computer printout pp. 6-9.*
Brustle et al., 2005, US 20050272149 A1.*
Goldman et al., 2004, Med Sci Monit, vol. 10, No. 11, RA274-285.*
Shinohara et al., 2007, Transgenic research, vol. 16, p. 333-339.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Maksimenko et al., 2013, Acta Naturae, vol. 5, No. 1, p. 33-46.*
Chen et al., "Identification of endoglin as a functional marker that defines long term repopulating hematopoietic stem cells", PNAS, 99(24):15468-15473 (2002).
Cheng et al., "Endothelial cell-specific FGD5 Involvement in Vascular prunning defines neovessel fate in mice", Circulation, 2012(125):3142-3158 (2012).
Christensen et al., "Flk 2 is a marker in hematopoietic stem cell differentiation: A simple method to isolate long term stem cells", PNAS 98(25):14541-14546 (2001).
Colonna et al. "Molecular characterization of two C-type lectin-like receptors, one of which is selectively expressed in human dendritic cells", Eur. J. Immunol., 30:697-704 (2000).
Hildebrandt et al., "Very important pharmacogene summary: sulfotransferase A", Pharmacogenet Genomics 19, 404-406 (2009).
Kataoka et al., "Evi1 i essential for hematopoietic stem cell self-renewal and its expression marks hematopoeitic cells with long-term multilineage repopulating activity", J. Exp. Med. 208(12):2403-2416 (2011).
Kristov et al., "Transformation from committed progenitor to leukaemia stem cell initiated by MLL-F", Nature 442: 818-822 (2006).
Kurogane et al., "FGD5 mediates proangiogenic action of vascular endothelial growth factor in human vascular endothelial cells", Arterioscler Thromb Vasc Biol. 32:988-966 (2012).
Morita et al., "Non-side-population hematopoietic stem cells in mouse bone marrow", Blood. 108:2850-2856 (2006).

(Continued)

*Primary Examiner* — Shin Lin Chen
(74) *Attorney, Agent, or Firm* — Nixon Peabody LLP; Mark J. FitzGerald; Srividya Subramanian

(57) ABSTRACT

Described herein are nucleic acid constructs, hematopoietic stem cell identifier animals, and methods of using thereof for isolating hematopoietic stem cell populations. Also provided are methods of using the identifier animals and cells isolated from them to screen for agents that affect the growth, proliferation, potency, expansion, or maintenance of the stem cells. Such agents can be used for promoting growth of stem cells in vitro or in vivo, and also for inhibiting cancer cells that have been determined to resemble a stem cell.

2 Claims, 40 Drawing Sheets

Specification includes a Sequence Listing.

(56) References Cited

OTHER PUBLICATIONS

Ooi et al., "The adhesion molecule ESAM1 is a novel hematopoietic stem cell marker", Stem Cells. 27(3):653-661 (2009).
Raftogianis et al., "Phenol sulfotransferase pharmacogenetics in humans: Association of common SULT1A1 alleles with TS PST phenotype", Biochemical and biophysical research communications 239:2398-304 (1997).
Sobanov et al., "A Novel cluster of lectin-like receptor genes expressed in monocytic, dendritic and endothelial cells maps close to the NK receptor genes in the human NK gene complex", Eur. J. Immunol. 31:3493-3503 (2001).
Thebault et al., "The C-type lectin-like receptor CLEC-1 expressed by myeloid cells and endothelial cells, is up-regulated by immunoregularoty mediators and moderates T cell activation", J. Immunol. 183:3099-3108 (2009).
Wilborn et al., "Sequence analysis and expression of the cDNA for the phenol-sulfating form of human liver phenol sulfotransferase", Molecular Pharmacoloy 43:70-77 (1992).
Davis et al., Blood 111(4):1876-1884 (2007). "Targeting a GFP reporter gene to the MIXL1 locus of human embroyic stem cells identifies human primitive streak-like cells and enables isolation of primitive hematopoietic precursors.".
GENBANK accession No. NC_000072. Feb. 23, 2012.
Gomez et al., PLoS One. 4(3):e4994 (2009). "Discovery and characterization of novel vascular and hematopoietic genes downstream of etsrp in zebrafish.".
Narumiya et al., Biochem Biophys Res Commun. 357(4):896-902 (2007). "Endocardiogenesis in embryoid bodies: novel markers identified by gene expression profiling.".

\* cited by examiner

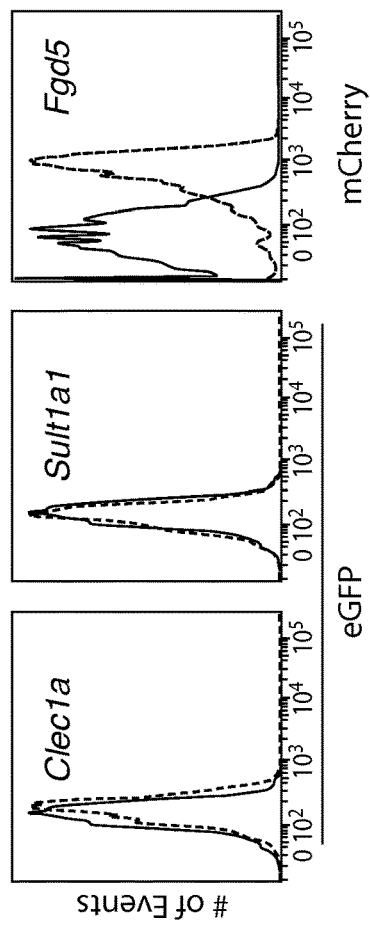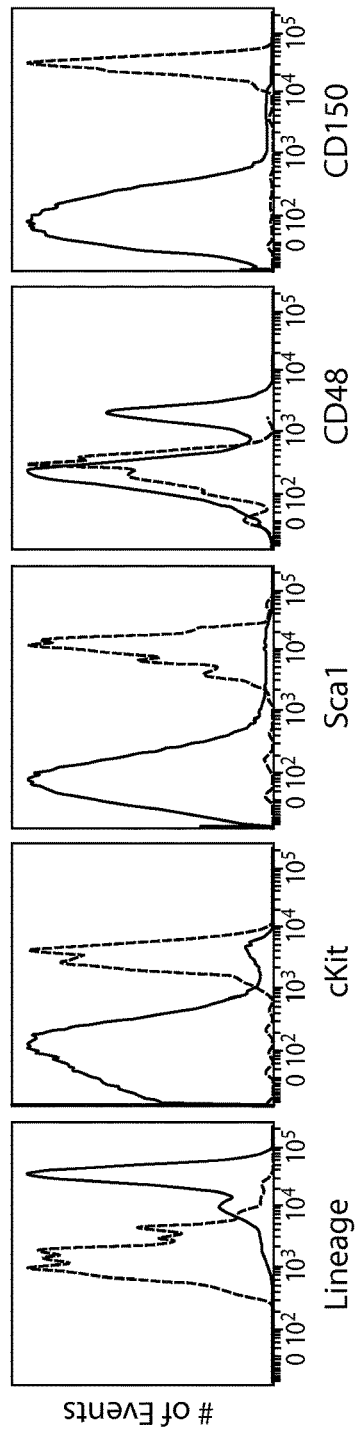
Fig. 2A
Fig. 2B

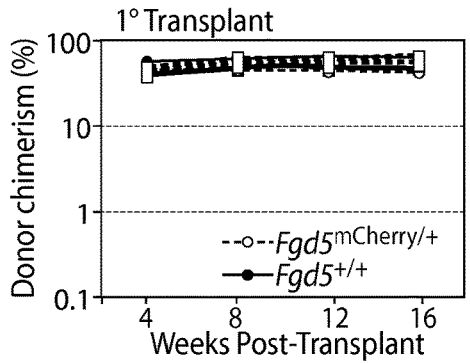
Fig. 3A
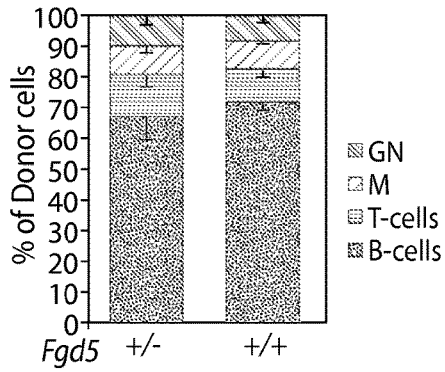
Fig. 3B
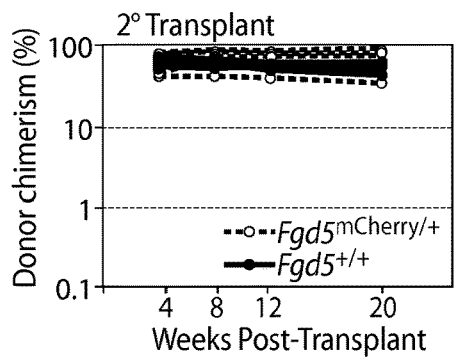
Fig. 3C
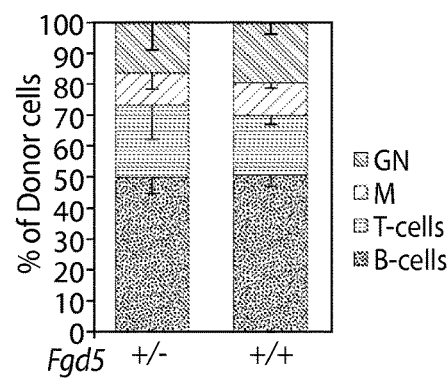
Fig. 3D
| Genotype<br>Day | WT | Het | Null |
|---|---|---|---|
| E9.5 | 0 | 5 | 3 |
| E11.5 | 10 | 29 | 13* |
| E12.0 | 5 | 17 | 3* |
| E12.5 | 9 | 22 | 1* |
| E13.5 | 2 | 5 | 0 |
| E15.5 | 4 | 10 | 0 |
| E16.5 | 8 | 6 | 0 |
| E17.5 | 8 | 7 | 0 |
Fig. 3E

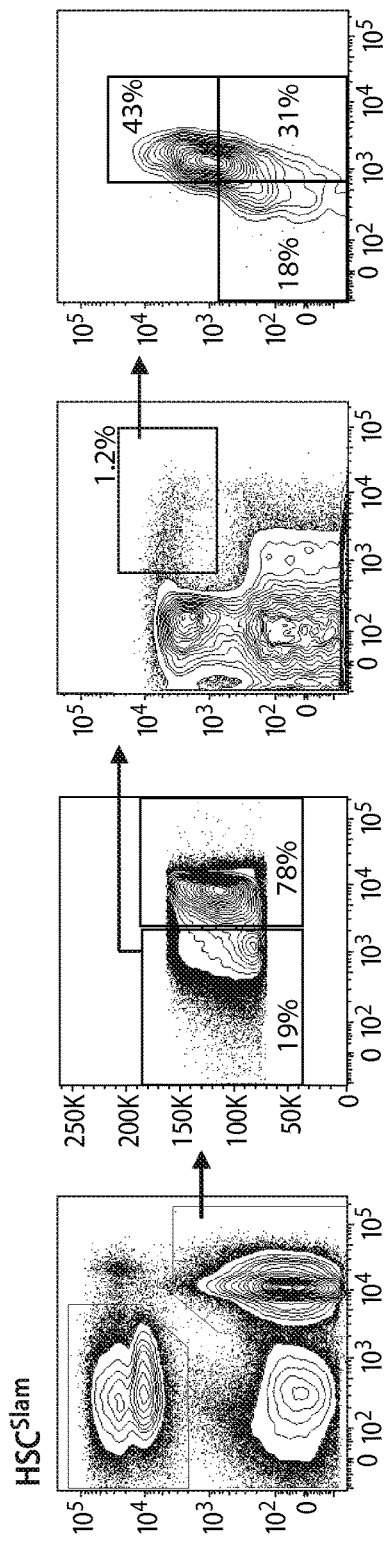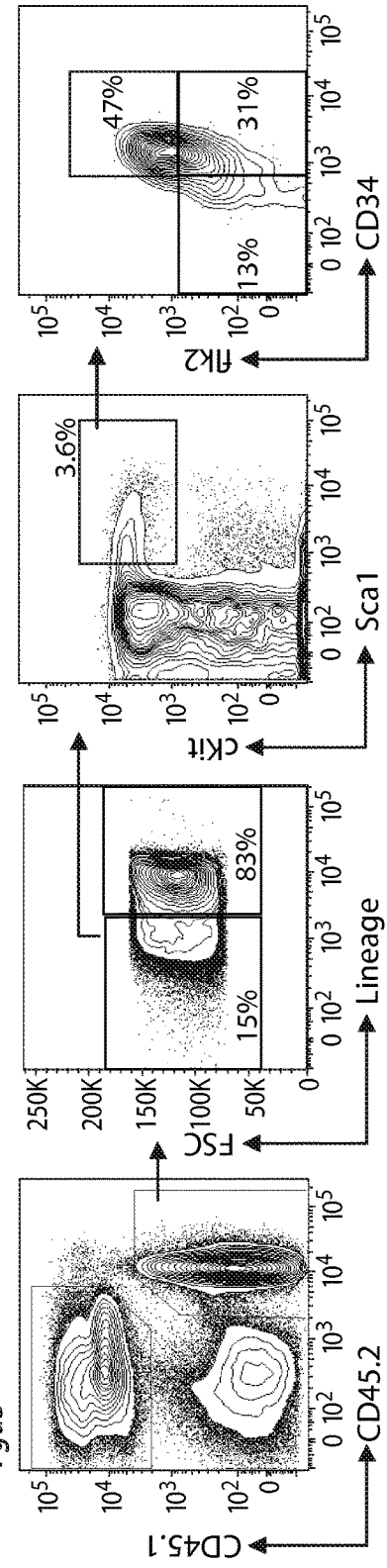
Fig. 6A
Fig. 6B

HEMATOPOIETIC STEM CELL SPECIFIC REPORTER MOUSE AND USES THEREOF

CROSS-REFERENCE TO RELATED APPLICATIONS

This application is a 35 U.S.C. § 371 National Phase Entry Application of International Application No. PCT/US13/58380 filed Sep. 6, 2013, and which claims benefit under 35 U.S.C. § 119(e) of U.S. Provisional Application No. 61/697,843 filed Sep. 7, 2012, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Sep. 6, 2013, is named 033393-074991-PCT_SL.txt and is 142,773 bytes in size.

FIELD OF THE INVENTION

The present invention relates to a mouse hematopoietic stem cell specific reporter and uses thereof.

BACKGROUND

Hematopoietic stem cells (HSCs) are a subset of multipotent stem cells that are responsible for the ability to sustain lifelong hematopoiesis, and continuously generate myriad and various blood cell types, while maintaining adequate number of stem cells in the bone marrow. Hematopoietic stem cells give rise to all the blood or immune cell types, including monocytes and macrophages, neutrophils, basophils, eosinophils, erythrocytes, megakaryocytes/platelets, dendritic cells, T-cells, B-cells, NKT-cells, and NK-cells. Hematopoietic tissues contain cells with long-term and short-term regeneration capacities, and committed multipotent, oligopotent, and unipotent progenitors.

SUMMARY

Hematopoietic stem cells (HSCs) are the best-characterized tissue-specific stem cells, yet the experimental study of HSCs remains challenging, due to the fact that they are exceedingly rare and methods to purify them are cumbersome, and vary between different laboratories. Moreover, genetic tools for specifically addressing issues related to HSC biology are lacking. As described herein, the inventors have identified genes uniquely expressed in HSCs within the hematopoietic system, and used such information to develop a unique reporter mouse strain that specifically labels HSCs. As described herein, the inventors have performed a microarray expression screen of the murine hematopoietic system, and identified a number of genes with HSC-restricted expression. Generation of mice with targeted reporter knock-in/knock-out alleles of three of the identified genes, Clec1a, Fgd5, and, Sult1a1 revealed that HSCs isolated from these mice functioned normally, and though Fgd5 was required for embryonic development, it was not required for definitive hematopoiesis or sustained HSC function. Further, and importantly, as demonstrated herein, Fgd5-reporter expression almost exclusively labeled cells that expressed a panel of markers consistent with HSCs. Bone marrow cells isolated based solely on reporter signal showed potent HSC activity that was comparable and equivalent to HSCs purified by immunophenotypic means. Reporter labeled HSCs also retained HSC-specific labeling after transplantation. As demonstrated herein, it was determined that all HSC activity resides within the labeled fraction of the Fgd5-reporter mice, and that reporter molecule expression from the Fgd5 locus permits identification and purification of HSCs based on single color fluorescence. Further, the inventors have demonstrated, using whole transcriptome microarray data of human hematopoietic cell types, that human FGD5 expression is largely restricted to cord blood (CB) HSCs, and adult bone marrow hematopoietic stem cells that are lineage-CD90+CD38-CD34+, proving that FDG5 expression is an HSC-specific marker in human cells as well. Also demonstrated herein are screening methods and assays for identifying small molecules that can maintain or expand HSCs using bone marrow cells derived from Fgd5-reporter mice.

Accordingly, provided herein, in some aspects are nucleic acid constructs comprising, in a 5' to 3' direction, a 5' sequence of an Fgd5 gene of SEQ ID NO: 1, a hematopoietic stem cell identifier sequence, and a 3' sequence of an Fgd5 gene of SEQ ID NO: 1.

In some embodiments of these aspects and all such aspects described herein, the hematopoietic stem cell identifier is a fluorescent reporter sequence. In some embodiments of these aspects and all such aspects described herein, the fluorescent reporter sequence is an mCherry fluorescent reporter sequence of SEQ ID NO: 5

In some embodiments of these aspects and all such aspects described herein, the 5' sequence of the Fgd5 gene of SEQ ID NO: 1 comprises SEQ ID NO: 3.

In some embodiments of these aspects and all such aspects described herein, the 3' sequence of the Fgd5 gene of SEQ ID NO: 1 comprises SEQ ID NO: 4.

In some embodiments of these aspects and all such aspects described herein, the nucleic acid construct further comprises a sequence encoding a positive selection marker, or a sequence encoding a negative selection marker or both.

Also provided herein, in some aspects, are vectors comprising a nucleic acid construct comprising, in a 5' to 3' direction, a 5' sequence of an Fgd5 gene of SEQ ID NO: 1, a hematopoietic stem cell identifier sequence, and a 3' sequence of an Fgd5 gene of SEQ ID NO: 1.

In some embodiments of these aspects and all such aspects described herein, the hematopoietic stem cell identifier is a fluorescent reporter sequence. In some embodiments of these aspects and all such aspects described herein, the fluorescent reporter sequence is an mCherry fluorescent reporter sequence of SEQ ID NO: 5

In some embodiments of these aspects and all such aspects described herein, the 5' sequence of the Fgd5 gene of SEQ ID NO: 1 comprises SEQ ID NO: 3.

In some embodiments of these aspects and all such aspects described herein, the 3' sequence of the Fgd5 gene of SEQ ID NO: 1 comprises SEQ ID NO: 4.

In some embodiments of these aspects and all such aspects described herein, the nucleic acid construct further comprises a sequence encoding a positive selection marker, or a sequence encoding a negative selection marker or both.

Provided herein, in some aspects, are heterozygous hematopoietic stem cell identifier knock-in mice comprising a nucleic acid construct comprising, in a 5' to 3' direction, a 5' sequence of an Fgd5 gene of SEQ ID NO: 1, a hematopoietic stem cell identifier sequence, and a 3' sequence of an Fgd5 gene of SEQ ID NO: 1 at an endogenous Fgd5 gene locus, wherein the nucleic acid construct is/has been introduced into the endogenous Fgd5 gene locus by homologous recombination, wherein the expression of the hematopoietic stem cell identifier sequence is operably linked to the endogenous Fgd5 gene locus, and wherein said hematopoietic stem cell identifier sequence replaces a portion of a sequence of the endogenous Fgd5 gene locus.

In some embodiments of these aspects and all such aspects described herein, the hematopoietic stem cell identifier is a fluorescent reporter sequence. In some embodiments of these aspects and all such aspects described herein, the fluorescent reporter sequence is an mCherry fluorescent reporter sequence of SEQ ID NO: 5

In some embodiments of these aspects and all such aspects described herein, the 5' sequence of the Fgd5 gene of SEQ ID NO: 1 comprises SEQ ID NO: 3.

In some embodiments of these aspects and all such aspects described herein, the 3' sequence of the Fgd5 gene of SEQ ID NO: 1 comprises SEQ ID NO: 4.

In some embodiments of these aspects and all such aspects described herein, the nucleic acid construct further comprises a sequence encoding a positive selection marker, or a sequence encoding a negative selection marker or both.

Also provided herein, in some aspects, are isolated hematopoietic stem cell comprising a hematopoietic stem cell identifier sequence operably linked to the endogenous Fgd5 gene locus obtained from a heterozygous hematopoietic stem cell identifier knock-in mouse comprising a nucleic acid construct comprising, in a 5' to 3' direction, a 5' sequence of an Fgd5 gene of SEQ ID NO: 1, a hematopoietic stem cell identifier sequence, and a 3' sequence of an Fgd5 gene of SEQ ID NO: 1 at an endogenous Fgd5 gene locus, wherein the nucleic acid construct is/has been introduced into the endogenous Fgd5 gene locus by homologous recombination, wherein the expression of the hematopoietic stem cell identifier sequence is operably linked to the endogenous Fgd5 gene locus, and wherein said hematopoietic stem cell identifier sequence replaces a portion of a sequence of the endogenous Fgd5 gene locus.

In other aspects, provided herein are methods of isolating hematopoietic stem cells comprising selecting or removing cells from a heterozygous hematopoietic stem cell identifier knock-in mouse of any of the aspects and embodiments described herein expressing the hematopoietic stem cell identifier sequence.

In some embodiments of these aspects and all such aspects described herein, the selecting or removing comprises physical sorting of cells from a heterozygous hematopoietic stem cell identifier knock-in mouse of any of the aspects and embodiments described herein. In some embodiments of these aspects and all such aspects described herein, the physical sorting comprises flow cytometric based sorting. In some embodiments of these aspects and all such aspects described herein, the physical sorting comprises magnetic-bead based sorting.

In some aspects, provided herein are ex vivo methods for screening agents to expand hematopoietic stem cells comprising the steps of: exposing a population of cells isolated or selected from a heterozygous hematopoietic stem cell identifier knock-in mouse of any of the aspects and embodiments described herein expressing the hematopoietic stem cell identifier to a candidate agent ex vivo; and comparing cell growth rate of the population of cells expressing the hematopoietic stem cell identifier exposed to the candidate agent to a population of cells expressing the hematopoietic stem cell identifier that has not been exposed to the candidate agent, wherein if the cell growth rate is increased in the population of cells expressing the hematopoietic stem cell identifier exposed to the candidate agent compared to the population of cells expressing the hematopoietic stem cell identifier that has not been exposed to the candidate agent, the agent is indicated as an agent that expands hematopoietic stem cells.

In other aspects, provided herein are methods of screening agents to modulate hematopoietic stem cell activity comprising the steps of: exposing a population of cells isolated from a heterozygous hematopoietic stem cell identifier knock-in mouse of any of the aspects and embodiments described herein expressing the hematopoietic stem cell identifier to a candidate agent ex vivo; and comparing hematopoietic stem cell activity of the population of cells expressing the hematopoietic stem cell identifier exposed to the candidate agent to a population of cells expressing the hematopoietic stem cell identifier that has not been exposed to the candidate agent, wherein if the hematopoietic stem cell activity is increased or decreased in the population of cells expressing the hematopoietic stem cell identifier exposed to the candidate agent compared to the population of cells expressing the hematopoietic stem cell identifier that has not been exposed to the candidate agent, the agent is indicated as an agent that modulates hematopoietic stem cell activity.

In other aspects, provided herein are methods of screening for agents that maintain hematopoietic stem cell activity comprising the steps of: exposing a population of cells isolated from a heterozygous hematopoietic stem cell identifier knock-in mouse of any of the aspects and embodiments described herein expressing the hematopoietic stem cell identifier to a candidate agent ex vivo; and comparing hematopoietic stem cell activity of the population of cells expressing the hematopoietic stem cell identifier exposed to the candidate agent to a population of cells expressing the hematopoietic stem cell identifier that has not been exposed to the candidate agent, wherein if the hematopoietic stem cell activity is increased or maintained in the population of cells expressing the hematopoietic stem cell identifier exposed to the candidate agent compared to the population of cells expressing the hematopoietic stem cell identifier that has not been exposed to the candidate agent, the agent is indicated as an agent that maintains hematopoietic stem cell activity.

In some embodiments of these methods and all such methods described herein, the number of the population of cells expressing the hematopoietic stem cell identifier is increased.

In some embodiments of these methods and all such methods described herein, number of the population of cells expressing the hematopoietic stem cell identifier and the function of the population of cells expressing the hematopoietic stem cell identifier is maintained.

Also provided herein, in some aspects are methods and assays for large-scale screening of small molecule compounds that can modulate hematopoietic stem cell activity comprising the steps of: exposing one or more populations of cells isolated from a heterozygous hematopoietic stem cell identifier knock-in mouse of any of the aspects and embodiments described herein expressing the hematopoietic stem cell identifier to a plurality or library of small molecule candidate agents ex vivo or in vitro; and comparing hematopoietic stem cell activity of the population of cells expressing the hematopoietic stem cell identifier exposed to the library of small molecule candidate agents to the population of cells expressing the hematopoietic stem cell identifier that have not been exposed to the library of small molecule candidate agents, wherein when the hematopoietic stem cell activity is increased or decreased in the populations of cells expressing the hematopoietic stem cell identifier exposed to the library of small molecule candidate agents compared to the populations of cells expressing the hematopoietic stem cell identifier that have not been exposed to the library of small molecule candidate agents, the small molecule agent is indicated as an agent that modulates, i.e., increases or decreases hematopoietic stem cell activity.

In some embodiments of these aspects and all such aspects described herein, the hematopoietic stem cell activity is self-renewal.

In some embodiments of these aspects and all such aspects described herein, the hematopoietic stem cell activity is hematopoietic multipotency.

In some embodiments of these aspects and all such aspects described herein, the hematopoietic stem cell activity is hematopoietic stem cell expansion.

In some embodiments of these aspects and all such aspects described herein, the cells isolated from a heterozygous hematopoietic stem cell identifier knock-in mouse are bone marrow cells.

In some embodiments of these aspects and all such aspects described herein, the cells isolated from a heterozygous hematopoietic stem cell identifier knock-in mouse are pre-sorted prior to the exposing step to identify cells expressing the hematopoietic stem cell identifier.

In some embodiments of these aspects and all such aspects described herein, the cells or populations of cells exposed to the candidate agent or library of small molecule candidate agents are cultured. For example, in some embodiments, the cells or populations of cells are cultured prior to, during, and/or after exposure to the candidate agent or library of small molecule candidate agents.

In some embodiments of these aspects and all such aspects described herein, the candidate agent(s) or small molecule candidate agent(s) identified using the screening methods and assays described herein are further subjected to an in vivo or in vitro validation step. In some embodiments of these aspects and all such aspects described herein, the in vivo validation step evaluates functional potential of cells exposed to the candidate agent(s) or small molecule candidate agent(s) in a transplantation model, such as animal model.

Provided herein in some aspects are methods of high-throughput screening of small molecule libraries for identifying small molecules that modulate HSC activity or function comprising: (i) Exposing or contacting in vitro, ex vivo, or in vivo a plurality of HSC cells or cell populations isolated from a heterozygous Fdg5 knock-in animal expressing an HSC identifier to a small molecule compound, or a combination of small molecule compounds, wherein the cells or cell populations are plated or cultured in parallel, for example, on one or more multiwall cell culture plates; and (ii) Measuring an HSC activity or function of each of the exposed or contacted plurality of HSC cells or cell populations, and measuring the HSC activity of HSC cells or cell populations isolated from a heterozygous Fdg5 knock-in animal expressing a HSC identifier that have not been exposed to a small molecule compound, wherein when the HSC activity or function is increased or decreased in any of the exposed or contacted plurality of HSC cells or cell populations compared to the HSC cells or cell populations that have not been exposed to a small molecule compound, the small molecule compound is identified as small molecule that modulates HSC activity or function.

In some embodiments of these methods and all such methods described herein, the plurality of HSC cells or cell populations isolated from a heterozygous Fdg5 knock-in animal are bone marrow cells.

In some embodiments of these methods and all such methods described herein, the plurality of HSC cells or cell populations isolated from a heterozygous Fdg5 knock-in animal are sorted prior to the exposing or contacting step. In some embodiments, the plurality of HSC cells or cell populations isolated from a heterozygous Fdg5 knock-in animal are sorted on the basis of being Lineage$^-$Sca1$^+$CD48$^-$CD150$^+$HSC identifier$^+$.

In some embodiments of these methods and all such methods described herein, the HSC activity or function is selected from HSC proliferation, HSC differentiation, HSC migration, HSC survival, and HSC self-renewal activities.

In some embodiments of these methods and all such methods described herein, the plurality of HSC cells or cell populations isolated from a heterozygous Fdg5 knock-in animal expressing an HSC identifier are exposed or contacted with the different small molecule compounds for at least 30 minutes.

In some embodiments of these methods and all such methods described herein, the plurality of HSC cells or cell populations isolated from a heterozygous Fdg5 knock-in animal expressing an HSC identifier are exposed or contacted in a media solution.

In some embodiments of these methods and all such methods described herein, the method further comprises a step of in vitro validation, in vivo validation, or both, of each of small molecules that modulates HSC activity or function identified in step (ii). In some embodiments of these aspects and all such aspects described herein, the in vivo validation step evaluates functional potential of HSCs exposed to the small molecule(s) in a transplantation model, such as an animal model.

BRIEF DESCRIPTION OF THE DRAWINGS

FIG. 1A depicts a schematic representation of hematopoietic hierarchy with cell-types present in the database used herein marked. FIG. 1B depicts a heatmap showing representative cell-type specific genes, asterisks mark known genes. FIG. 1C depicts a Heatmap showing relative expression of representatives HSC-specific genes. FIG. 1D shows expression of Clec1a, Sult1a1, and Fgd5 in young (4 month), mid-age (12 month), and old (24 month) HSCs or MPPs. Histogram shows individual arrays replica at linear-scale.

FIGS. 2A-2F demonstrate that labeled cells in bone marrow of Fgd5$^{mCherry}$ mice are synonymous with immunophenotypic HSCs. FIG. 2A shows reporter gene expression within immunophenotypic HSCs (LIN$^-$Sca1$^+$cKit$^+$CD48$^-$CD150$^+$) of mice targeted at Clec1a$^{eGFP}$, Sult1a1$^{eGFP}$, and Fgd5$^{mCherry}$ as depicted in histograms overlaying the wildtype background (Gray). FIG. 2B shows bone marrow mCherry-positive and mCherry-negative cells of Fgd5$^{mCherry/+}$ mice co-stained and gated individually (top panel) or sequentially (lower panel) through lineage (Ter119, Mac-1, Gr-1, B220, CD3, CD4, CD8), c-Kit, Sca1, CD48, and CD150. FIGS. 2C-2F show sub-fractionation of primitive lineage$^-$Sca1$^-$c-Kit$^+$ (LSK) cells from Fgd5$^{mCherry/+}$ or Fgd5$^{+/+}$ mice into immunophenotypic HSCs (green gates on the left panels), and multi-potent progenitors (blue and black gates) by (FIG. 2C) CD150 and CD48, (FIG. 2D) CD34 and flk2, (FIG. 2E) PROCR and CD34, and (FIG. 2F) ESAM and CD34.

FIGS. 3A-3J demonstrate that Fgd5 is required for embryonic development but is dispensable for definitive HSC formation and function. FIG. 3A Transplants of heterozygous and wildtype littermates whole-bone marrows are shown for primary recipients, and their lineages composition at 16 weeks post-transplant (FIG. 3B). Secondary transplants of Fgd5$^{mCherry}$ heterozygous whole-bone marrows, and their lineages shown as above (FIGS. 3C-3D). FIGS. 3A-3D show total donor reconstitution (left panels) over the time course of transplantation, and lineage breakdown of donor cells at 16 (1°) and 20 (2°) weeks post-transplant. FIG. 3E shows genotypes of several litters from heterozygous crosses (Fgd5$^{+/mCherry}$×Fgd5$^{+/mCherry}$ crosses) that are summarized in the table for the indicated timepoints of embryonic development (E9.5 through E17.5) and Fgd5$^{+/+}$ (WT), Fgd5$^{+/mCherry}$ (Het) and Fgd5$^{mCherry/mCherry}$ (null). * Indicates the presence of one or more morphologically abnormal embryos. FIG. 3F depicts a schematic of an experimental strategy for AGM-transplant indicating AGM explant at E11.5, culturing for 4 days and transplantation into lethally irradiated adult congenic recipients. FIGS. 3G-3J show Primary (1°) and, secondary (2°) transplantation of AGM explants from Fgd5$^{+/+}$, Fgd5$^{mCherry/+}$, and Fgd5$^{mCherry/mCherry}$ mice showing total donor reconstitution over the time course of transplantation, and lineage breakdown of donor cells in individual recipient at 16 weeks post-transplant. Peripheral blood chimerism of Fgd5$^{++}$ (WT), Fgd5$^{+/mCherry}$ (Het), and Fgd5$^{mCherry/mCherry}$ (Null) are shown of AGM-transplants along 16 weeks (FIG. 3G). Lineages composition of the primary transplants (FIG. 3H) shows B cells, T cells, Mac1$^+$Gr1$^-$, and Mac1$^+$Gr1$^+$ granulocytes. Secondary transplant total peripheral blood chimerism (FIG. 3I) and lineages composition at 16 weeks (FIG. 3J) is shown as above. Granulocytes (GN), macrophage/monocytes (M), B-cells and T-cells are indicated by color. Error bars indicate standard deviation.

FIGS. 4A-4K demonstrate total peripheral blood chimerism of control HSCs (LSKCD48$^-$CD150$^+$ as Slam-code) or Fgd5$^{mCherry}$ positive cells over 16 weeks of primary transplant experiments using 200 (FIG. 4A), 120 (FIG. 4B) 40 (FIG. 4C), 20 (FIG. 4D) or 5 cells (FIG. 4E). Total donor reconstitution and lineage compositions of each are shown for individual recipient mice in the right histograms for B cells, T cells Mac1$^-$Gr1$^-$, and Mac1$^+$Gr1$^+$ at 16 weeks post-transplant (FIGS. 4G-4K). Granulocytes (GN), macrophage/monocytes (M), B-cells and T-cells are indicated. FIG. 4F is a histogram showing average total-chimerism of each cell-dose of the experiments above, error bars indicating S.D. and lack of statistical-difference (non-significant, n.s.) indicated according to Student's t-test.

FIGS. 5A-5D show primary (1°) transplantation of 250 mCherry-positive cells from Fgd5$^{mCherry/+}$ mice, or 250 control LIN$^-$Sca1$^+$cKit$^+$CD48$^-$CD150$^+$-sorted HSCs (HSC$^{Slam}$) from wild-type mice (b showing total donor reconstitution over the time course of transplantation. Secondary (2°), and tertiary (3°) transplantation of whole bone marrow cells from the 1 recipients described in (FIG. 5A) mice showing total donor reconstitution over the time course of transplantation, and lineage breakdown of donor cells at individual recipients at 20 weeks post-transplant from the 3° transplants are also shown. Serial transplants are shown with primary (250 cells transplanted, FIG. 5A), secondary (2×10$^6$ WBM serially-transplanted, FIG. 5B) and tertiary (5×10$^6$ WBM cells serially transplanted, FIG. 5C) having control Slam-HSCs and Fgd5$^{mCherry}$ at the indicated time points post transplants. Total donor reconstitution and lineage composition of donor cells at the 20 weeks timepoint of tertiary transplant is shown on the histograms of (FIG. 5D) for B cells, T cells, Mac1$^+$Gr1$^-$, and Mac1$^+$Gr1$^+$.

FIGS. 6A-6C demonstrate that exclusive labeling of HSCs by Fgd5$^{mCherry/+}$ is retained after transplantation. Bone-marrow analysis after transplant of 120 wildtype LSKCD48$^-$CD150$^+$HSCs (HSC$^{Slam}$) (FIG. 6A) or 120 mCherry+ cells from Fgd5$^{mCherry}$-HSCs (FIG. 6B) analyzed 8-months post-transplant showing donor-derived (CD45.2) chimerism (left panel) and contribution to bone marrow compartments revealed by co-staining with antibodies against lineage, c-Kit, Sca1, flk2 and CD34, and FACS plots showing the Lineage$^{neg/low}$, cKit$^+$Sca1$^+$ and CD34/flk2 dissection. FIG. 6C histograms show expression of mCherry for each indicated subpopulation from the bone marrow of recipient mice transplanted with 120 HSC$^{Slam}$ cells from wild-type mice (left panel) or 120 mCherry+ cells from Fgd5$^{mCherry}$ mice 8-months post-transplant is shown in the histograms from WT (left) or Fgd5$^{mCherry}$ (right).

FIG. 7A shows a gating strategy used for sorting reporter-positive and -negative fractions set using Fgd5$^{+/+}$ (top panel) and Fgd5$^{mCherry/+}$ (lower panel) mice and depicts reporter positive- and negative-cells that were sorted from the bone marrow of Fgd5$^{mCherry}$ (bottom dot-plot), showing wildtype as control of gating (top dot-plot). FIGS. 7B-7C show transplantation of 100 mCherry-positive or 100,000 cells mCherry-negative cells from Fgd5$^{mCherry/+}$ mice showing total donor reconstitution over the time course of transplantation in experiment 1 and experiment 2. FIGS. 7B-7C demonstrate total peripheral blood chimerism from 100 Fgd5$^{mCherry}$ positive cells or 100,000 Fgd5$^{mCherry}$-negative cells is shown at the 4, 8, 12 and 24 weeks post-transplant time points. FIG. 7D shows peripheral blood analysis of representative recipients from experiment 2 showing donor reconstitution (CD45.2), and contribution to granulocytes (Mac1$^+$Gr1$^+$), macrophages/monocytes (Mac1$^+$Gr1$^-$), B-cells (Mac1$^-$, B220$^+$CD3$^-$) and T-cells (Mac1$^+$, B220-CD3$^+$) analyzed 24-weeks post-transplant. FIG. 7D depicts a representative FACS plots of late time point bleed data from the 100 mCherry+ (top) or 100,000 mCherry− (bottom), where donor cells are CD45.2 and lineage composition analyzed for Granulocytes (Mac1+Gr1$^+$), Myeloids (Mac1$^+$Gr1$^-$), B cells (Mac1$^-$, B220$^+$ CD3$^-$) and T cells (Mac1$^+$, B220-CD3$^+$). FIGS. 7E-7F demonstrate peripheral blood analysis showing granulocyte chimerism plotted against the time-course of transplantation in experiments 1 and 2 Granulocyte chimerism (% donor cells of all peripheral blood Mac1$^+$Gr1$^+$ cells) is plotted for mCherry+ cells and mCherry− cells at indicated time points of Experiment#1 (FIG. 7E) and Experiment#2 (FIG. 7F).

FIG. 8A depicts a heatmap showing relative expression of all 323 probe sets identified as significantly HSC-specific in our dataset. FIG. 8B depicts a heatmap of the indicated-genes targeted for HSC-reporter mice generation from the dataset.

FIGS. 9D-9F show Southern blots identifying correct targeting are shown at right for each gene, with an upstream (5') and a downstream (3') probes.

FIGS. 10A-10B depict total peripheral blood chimerism of Sult1A1-deficient or Clec1a deficient donors over 16 weeks, and lineage-distribution of donors cells at the 16 weeks timepoint (FIG. 10C).

FIG. 13 shows dissecting microscope images of E12.0 embryos derived from Fgd5$^{mCherry/+}$× Fgd5$^{mCherry/+}$ timed matings showing genotype and gross morphology of the embryos.

FIG. 17A shows a schematic of a knock-in strategy at the murine Fgd5 locus. Respective constructs were knocked-in to Exon2 of Fgd5 gene together with positive selection marker Neomycin cassette. mCherry cassette was replaced with tandem array of gene encoding ZsGreen together with ZsGreen, CerERT2 or HbEGF (also called Diephtheria toxin receptor) separated by self-cleavage 2A peptide sequence (T2A, gray box) that allows expression of two different proteins from same poly-cis-tronic mRNA transcript. FIG. 17B shows a Southern blot result showing two correctly knocked-in ES cell clones (lane 3 & 7) probed with 5' Fgd5 Probe on BamHI-digested genomic DNA.

FIG. 18A shows a panel of histograms showing the expression of Lineage, cKit, Sca1, CD48 and CD150 antigens on ZsGreen+ cell population in the bone marrow of Fgd5 ZsGreen knock-in reporter mouse. ZsGreen− cells (gray filled histogram) are shown for comparison. FIG. 18B shows a FACS plot demonstrating that ZsGreen expression is largely restricted to Lineage$^-$, cKit$^+$ Sca1$^+$, CD48$^-$ and CD150$^+$ hematopoietic stem and progenitor cells in bone marrow of ZsGreen knock-in reporter mice.

DETAILED DESCRIPTION

Figure 1A:
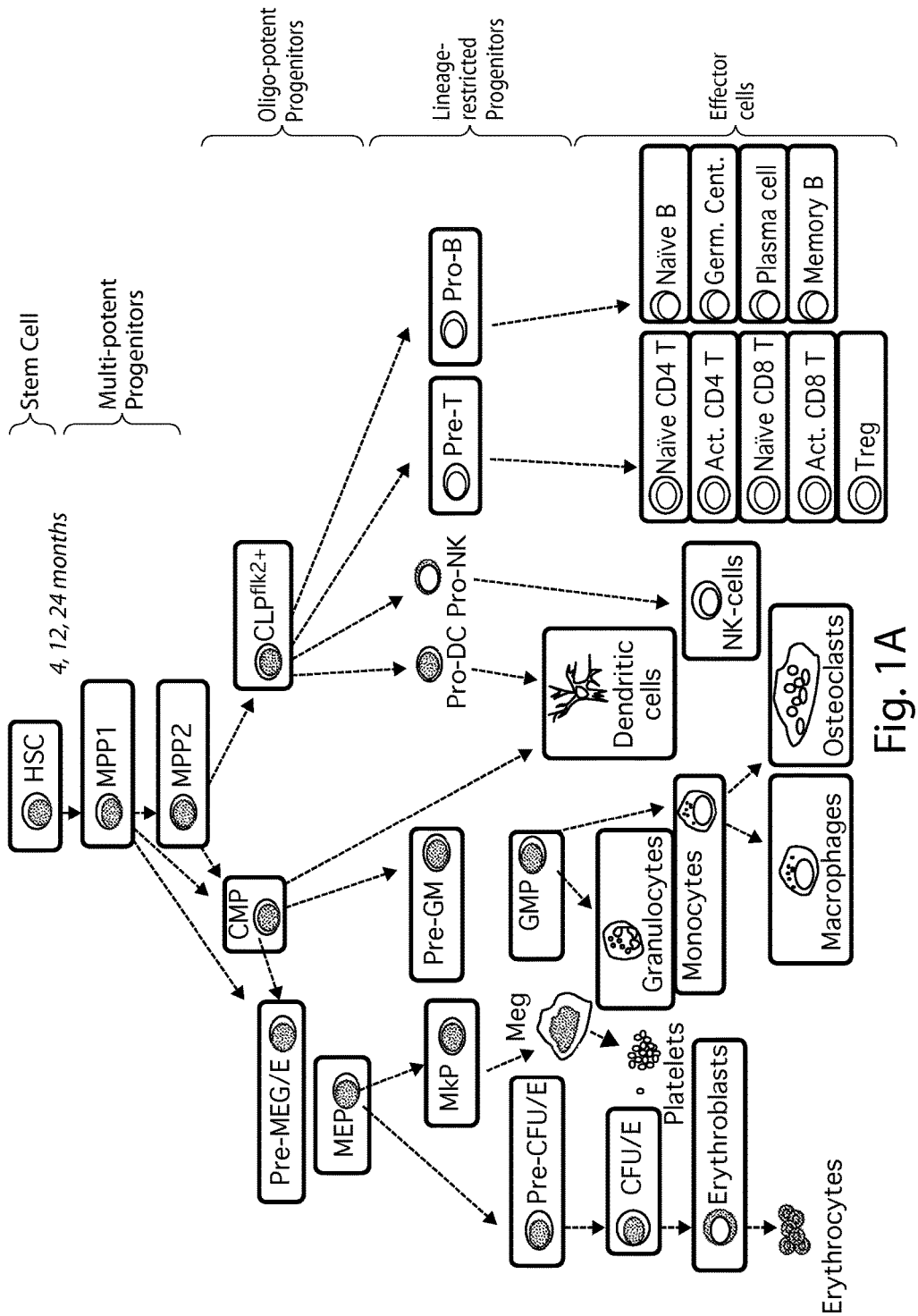
FIGS. 1A-1D demonstrate identification of HSC-specific genes.

Provided herein are nucleic acid constructs, hematopoietic stem cell identifier animals, and methods of using thereof for isolating hematopoietic stem cell populations based, in part, on the inventors' discovery that Fgd5 expression is specific to hematopoietic stem cells (HSCs) and is not expressed in cells differentiated or derived from HSCs, and labels all hematopoietic stem cells. Also provided are methods of using the identifier animals and cells isolated from them to screen for agents that affect the growth and proliferation of the stem cells. Such agents can be used for promoting growth of stem cells in vitro or in vivo, and also for inhibiting cancer cells that have been determined to resemble a stem cell.

As described herein, the inventors have determined that Fgd5 expression can be used as a sole marker for identification and isolation of highly pure and functionally competent HSCs, and that FGD5 expression is also specific to human hematopoietic stem cells. The hematopoietic stem cell identifier animals or Fdg5 knock-in animal models and methods thereof described herein permit enrichment or isolation of a purified or substantially pure population of hematopoietic stem cells, as well as permit methods to screen for agents that modulate HSC function and activity, such as self-renewing proliferation by simply following expression of the single marker, which can be, e.g., fluorescently labeled.

While many schemes exist for identifying true HSCs from more differentiated precursor populations, these methods relay on various combinations of multiple positive and negative cell-surface marker. In contrast, as demonstrated herein, the inventors have determined that expression of a single molecule, Fdg5, can be used to distinguish between hematopoietic stem cells and the most closely related population of multipotent progenitor cells, which are committed to the hematopoietic cell lineage but generally do not self-renew, in both humans and in mice.

Hematopoietic stem cells refer to a subset of multipotent stem cells that give rise to all the blood or immune cell types, including myeloid (monocytes and macrophages, neutrophils, basophils, eosinophils, erythrocytes, megakaryocytes/platelets, dendritic cells), and lymphoid lineages (T-cells, B-cells, NKT-cells, NK-cells). "Stem cells," as used herein, refer to cells that retain the ability to renew themselves through mitotic cell division and can differentiate into a diverse range of specialized cell types. The two broad types of mammalian stem cells are: embryonic stem (ES) cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Hematopoietic tissues contain cells with long-term and short-term regeneration capacities, and committed multipotent, oligopotent, and unipotent progenitors. HSCs can be can be found in a variety of tissue sources, such as the bone marrow of adults, which includes femurs, hip, ribs, sternum, and other bones, as well as umbilical cord blood and placenta, and mobilized peripheral blood. HSCs can be obtained directly by removal from, for example, the hip using a needle and syringe, or from the blood following pre-treatment with cytokines, such as G-CSF (granulocyte colony-stimulating factors), that induce cells to be released from the bone marrow compartment.

Accordingly, "hematopoietic stem cells," or "HSCs," as the terms are used herein, encompass all multipotent cells capable of differentiating into all the cell types of the hematopoietic system, including, but not limited to, granulocytes, monocytes, erythrocytes, megakaryocytes, B-cells and T-cells, and having multi-lineage hematopoietic differentiation potential and sustained self-renewal activity. "Self-renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. In contrast, a committed progenitor cell has typically lost the self-renewal capacity, and upon cell division produces two daughter cells that display a more differentiated (i.e., restricted) phenotype. True hematopoietic stem cells have the ability to regenerate long term multi-lineage hematopoiesis (e.g., "long-term engraftment" or "hematopoietic multipotency") in individuals receiving a bone marrow or umbilical cord blood transplant, as described herein.

Hematopoietic stem cells are traditionally identified as being lineage marker negative, Sca1-positive, cKit-positive (or "LSK cells"), CD34-negative, Flk2-negative, CD48-negative, and CD150 positive. HSCs give rise to "multipotent progenitor cells" or "hematopoietic progenitor cells," which, as the terms are used herein, refer to a more differentiated subset of multipotent stem cells that are committed to the hematopoietic cell lineage but generally do not self-renew. The terms "hematopoietic progenitor cells" or "multi-potent progenitor cells" (MPPs) encompass short term hematopoietic stem cells (also known as ST-HSCs, which are lineage marker negative, Sca1-positive, cKit-positive, CD34-positive, and Flk2-negative); common myeloid progenitor cells (CMPs); lymphoid-primed progenitor cells (LMPPs), granulocyte-monocyte progenitor cells (GMPs), and megakaryocyte-erythrocyte progenitor cells (MEPs). Hematopoietic stem cells subsets are sometimes also identified and discriminated on the basis of additional cell-surface marker phenotypes, such as by using combinations of members of the SLAM family, or the "SLAM phenotype," such as, long-term multi-lineage repopulating and self-renewing hematopoietic stem cells (HSCs): $CD150^+CD48^-CD244^-$; MPPs: $CD150^-CD48^-CD244^+$; lineage-restricted progenitor cells (LRPs): $CD150^-CD48^+CD244^+$; common myeloid progenitor cells (CMP): $lin^-SCA-1^-c-kit^+CD34^+CD16/32^{hi}$; granulocyte-macrophage progenitor (GMP): $lin^-SCA-1^-c-kit^+CD34^+CD16/32^{hi}$; and megakaryocyte-erythroid progenitor (MEP): $lin^-SCA-1^-c-kit^+CD34^+CD16/32^{low}$.

Accordingly, identification of true hematopoietic stem cells typically requires multiple different cell-surface molecules and combinations thereof for any isolation or characterization. In contrast, as demonstrated herein, the inventors have determined that expression of a single molecule, Fdg5, can be used to distinguish between self-renewing and multipotent hematopoietic stem cells and the most closely related population of multipotent progenitor cells, which are committed to the hematopoietic cell lineage but generally do not self-renew, in both mice and human. Accordingly, the nucleic acid constructs, HSC identifier animals, and HSCs derived therefrom described herein provide novel methods of characterizing, identifying, and modulating HSCs in vivo and for screening agents that modulate HSC activity, as described herein in more detail below.

Nucleic Acid Constructs

Provided herein, in various aspects, are nucleic acid constructs and replacement cassettes for use in generating clonal cell lines and animal models thereof in which a portion of the sequence of one allele of an endogenous Fgd5 gene is replaced, in part, by a sequence encoding a hematopoietic stem cell identifier molecule, such that hematopoietic stem cell identifier molecule is operably linked to the endogenous Fgd5 gene locus. By incorporating a hematopoietic stem cell identifier molecule into the endogenous Fgd5 gene locus by homologous recombination, progeny cells expressing Fgd5, which the inventors have shown is a marker specific to hematopoietic stem cells, will express the hematopoietic stem cell identifier molecule and be easy to identify and/or purify and/or track and/or delete, as described herein.

Accordingly, in some aspects, provided herein are nucleic acid construct or replacement cassette comprising, in part, a 5' sequence of an Fgd5 gene of SEQ ID NO: 1 (or a 5' Fgd5 homologous arm), a sequence encoding a hematopoietic stem cell identifier molecule, and a 3' sequence of an Fgd5 gene of SEQ ID NO: 1 (or a 3' Fgd5 homologous arm). The 5' and 3' sequences of the Fgd5 gene of SEQ ID NO: 1 serve as arms of homology for homologous recombination into the endogenous Fgd5 gene locus. Each of the homologous arms include a length of genomic DNA homologous to a region of the Fgd5 gene adjacent to a targeted region of the Fgd5 gene locus, such that one arm is homologous to genomic sequence on one side of the targeted region of the Fgd5 gene locus, and the other arm is homologous to genomic sequence on the other side of the targeted region of the Fgd5 gene locus. In this manner, the regions of homology to the targeted Fgd5 gene locus in the respective targeting arms flank the targeted region of the Fgd5 gene locus. The lengths of each of the homologous arms can vary as discussed herein.

When introduced into embryonic stem (ES) cells, the 5' and 3' homologous arms will undergo recombination with their matching or homologous sequences at the Fgd5 locus on one chromosome, and the sequence of the replacement cassette will be introduced into the ES cell genome along with them. The genomic DNA at the Fgd5 locus between the regions of homology on the chromosome is thereby replaced by the replacement cassette and any other intervening sequences flanked by the homology arms of the targeting genetic construct or insert.

The degree to which the homologous arms match the same sequences in the endogenous Fgd5 genomic locus in the cell being targeted helps determine the frequency and precision of homologous recombination. Three important characteristics of homology arms for successful homologous recombination include: (i) length, (ii) sequence homology, and (iii) limited repetitive sequences. Typically, a longer homologous arm has a higher degree of success in homologous recombination, but one may be limited by the capacity of the cloning vector and the need to maintain a unique restriction enzyme site that can be used to linearize the construct prior to transfection into ES cells. With regard to sequence homology, the homologous arms can be cloned from the genome of the ES cells that will be targeted, or from the subject they were derived from. Long-range PCR with a high-fidelity polymerase is an effective method for sub-cloning the homologous arms. Preferably, the homologous arms lack substantial repetitive sequences. One of skill in the art can use, e.g., on-line programs such as Repeat-Masker, to search for repetitive sequences in the homology arms. Large regions of repetitive DNA should be avoided, as these will result in a lower frequency of homologous recombination. In some embodiments of the aspects described herein, the sequences for use in the homologous arms can be cloned from a library of sequences from the same species as the cell being targeted. For example, libraries of bacterial artificial chromosomes (BACs) can be used as a source of the sequences for use in the homology arms of the targeting genetic constructs used in the methods and compositions provided herein.

"Homologous recombination" (HR) (which can also be referred to in the art as "legitimate recombination") as the term is used herein, refers to the exchange of DNA sequences between two DNA molecules, mainly two homologous sequences, such as chromosomes, that involves sequences or genomic loci with complete or far-reaching base sequence identity. Homologous recombination can also occur between a chromosome or other cellular DNA and an extra-chromosomal element introduced into the cell, provided that the extracellular element carries a region with complete or nearly complete sequence complementarity.

As used herein, the term "Fgd5" refers to the nucleic acid sequence encoding FYVE, RhoGEF and PH domain containing 5gene. In some embodiments of all aspects of the invention, one can use Fgd5 isoforms and homologs thereof, including conservative substitutions, additions, and/or deletions therein not adversely affecting the structure or function. The genomic sequence of mouse Fgd5 is encoded by nucleic acid sequence corresponding to base pairs 91987110-92076005 of NC_000072.6 (SEQ ID NO: 1) and the mRNA sequence of NM_172731.2 (SEQ ID NO: 2), and encodes the Fgd5 protein of NP_766319.2 (SEQ ID NO: 6).

In some embodiments of the nucleic acid constructs described herein, the 5' sequence of an Fgd5 gene of SEQ ID NO: 1 comprises SEQ ID NO: 3. In some embodiments of these nucleic acid constructs, the 5' sequence of an Fgd5 gene of SEQ ID NO: 1 consists essentially of SEQ ID NO: 3. In some embodiments of these nucleic acid constructs, the 3' sequence of an Fgd5 gene of SEQ ID NO: 1 comprises SEQ ID NO: 4. In some embodiments of these nucleic acid constructs, the 3' sequence of an Fgd5 gene of SEQ ID NO: 1 consists essentially of SEQ ID NO: 4.

```
An exemplary 5' homologous arm sequence or SEQ ID NO: 3 :
TACCAGTGGGCTCAAATGCTTGATGTGTTAGAGCACCCAGTCCTCTGTTACATCTTCTCCTGGGTCAGGACCAGGCTGGCATC TGGAGCTGCTATCACACTCAGACCTCAGCAAAGATAGACAGAAGATGAGGCCTGTCTGAAGGTGTCAGCTTAGAGTTACATGT CTGAGAAGTTCACTTTGCTGGAGTATGGATAGAGATGTGACCAGGCCCTGCTGGCTGCTCAGGAGAGACATGGGACTTGGACC TTGGAGACTGTGCCACTGGTCTGCTTCTTGTCTTAACATGTCCTACGCTATTCTTCTCAGGGGTTCACCTTCTCCCAGAGGCC TCTCAGTCACGGCAGTACTTCCTGGCTAACTCCTGACGCGTGTGCTCACTGCACATCCCCTTACCTTCCAGTCTGCGTGCCTC TGCATCCCTGAGGGTCACAGTCTTTTGTAGCTACCCATATTAATATATGCCATTTCCTTTCTTCCATGACATTTGGGGGTGCT GGCTGGATACTCCAGAAATACGCAGACTTCCTCAGTCAAAGGACATACAGCATTGTGTGTCCTTGTTGTGTCAGTTGTGAACA GATGAAGTGATGGCTATTCAACCATAGCATCCCATAGCTGCAGCTTGCTTTCTCTCTCTCCCCCCGCACCCCCCCCTGATG TTCTAACTTCACAACGGATTTTCCTCTGGGCCCAATGAAAGCGTCTCGTCTGTAGTGTTGGTCTGGCTGGCTTGGTTAGGGTG CTCATGAACACCAGCTCTGTGAGGACCCTGGGAGCCTGACCGTCAAGTTCATCTTTTTCTCATGGTGGCAGGACACACAGAGA TCATTCAATCAGTAGTTTCTGGTGAATGAATGAAAAGATCTTGGCACATTGTTCAAGGTACACAGGATTTTGTTGAGTTGATC GCTGTTAGCTGGACTGGAGGAAGCTCTGTTCCCCCATTCACAGAATGAACTGTTACTATTAGGTCAGAGACTTTCTGTGTTTC AGATAGGATTTCATGTGGGCCAGGCTGGCCTTGAACTCACTATGTTGCTGAGGATGACCTTGACCTTGAATTTTTGAACCCCT AGCTTCTACTCTCCAGACCTGGGGTACTAGGTTTATGGGGGCTGGGGATCAAATTTAGGGTTGCCTGCGTGGGAGGCAAATAT TCTAGCAATGAGGCTATATCCACATCTCTGCTAAAGGATTTCAAGGATGTGGGATGAAGGAAGGGGATGAAGGTCCGAAACAA GTCACAGAGTGGGAACTCTCCTCCATCTTTCCTTCACCAGGCTGTTTGAACAATTTTGAGCATAAGTTAATTGTGTTTCTTCT CCTTGTCTCTGTTTTTGCGCTGCAGATTCACCAAAGCCACCACTTGCTCCCAAGCCAAAGGTTGCTACCAACCCTTATGCACC GGCAGCCAAGTTTCCCCCTTCACAGAGGCCTGACAGCTTCCCCAGTCCCAACTCCATGTCCAGGGGCCCCAAGCCCCCTATCG CTCCTAAGCCCAGACTGACTGGCCCCAGTGAGTACCTGAACAACAGCCTCGGCAAATGCAGCAATGGGAGGCTGCTCTGTGAG
```

-continued

GACCGGGGCCTGTACGACGGACACCACTCCACCCTGAATTGCTTGGAGTTGGAGCCTGATGAGCAGTATATCATGGTTCCCAG

GGCTCCACAGAAAGAAGATACTCCCGTGGATGGGGCTACCGAGGAGCCGGGGTTTGAGGGGGAAGTCCAGGAGCATGGTACAG

AGCAGACAGGAACTGAGGGGGACCTGGAAGCTCCAGATGAAGAGGCACCAAGTAGAGACAGTGAGGAAGC

An exemplary 3' homologous arm sequence or SEQ ID NO: 4:
GAAGAAACGGGACCAGAAACCTGTTCATCAGGCATGGGCATCAGAGATACCAGTGATGAAGTGAGGAAGATAGGTATATTGCC AGAGGGAAAGCCTCCCGAGTGTGTTCGGGCCTTGCCGGCCAAGCCCAGAGCATTTACTCTCTACCCAAGGTCCTTCTCTGTAG AAGGCCGGGAGAGTCCCCTGTCCATGTTCCGGGAGCCAGAGGGAGCCGGGCTGGACAGCCACCGTGTAAGGAGGAAAGAGGAC AACCTCTCTCTGCCGGGCGCCATCGGCTCCTCCGGTAGCTTCTCACAGCGCAGCCACCTGCCTTCCAGTGGCACCTCCACACC ATCCTCTGTGGTTGACATCCCACCCCCTTTTGACTTGGCCTGCATCACGAAGAAACCCATCACTAAAAGCTCACCCTCACTCC TGATAGACGGAGACACCCTGGAAAAAGCCTCTAAGAAGAAGAAGTCCTCCTTCAAACGCTTCCTGGAGCTGACGTTCAGGAAG AAGACAGAGAGCAAGGTGCACGTGGACATGAACCTGTCGTCTTCCAGGTCTTCCTCTGAGTCCAGCTACCATGGTCCAGCCAG GGTACTGGAACTTGACCGCAGAAGCCTCAGCAACTCGCCCCAGCTCAAGTGTCGCACTGGAAAGCTCCGGGCCTCTGACTCCC CGGCCGCCCTCATCTTCTACAGGGACAGCAAGAGGAAAGGCGTCCCCTTCAGCAGGACGGTGTCCAGAGTGGAGTCCTTCGAA GACCGCTCCCGGCCGCCCTTTCTGCCTCTGCCCCTCACCAAGCCACGGTCCATCTCATTCCCCAATGCCGACACTTCGGACTA TGAGAACATTCCAGCCATGAACTCAGACTATGAGAATATCCAGATCCCCCCTCGCAGGCCGGTGAGGACTGGCACTTTCACAA AGCTGTTCGAAGAACAGAGCCGAGCCCTGTCCACCGCAAATGAAAATGACGGCTACGTGGACATGAGCAGCTTCAATGCCTTC GAGAGCAAGCAGCAGAGTTCAGAGCAGGAAGCTGAGAGGTACGTGAGTGGCGGGTCCTTTCTCACAGTGTGGGCCTTTGTGAG GCATAGGGGGTGGAATGGATGTGCggctctgtttctttctagctgtgtgatttggggtgagtggctctatctccccgaaccac tgtcacttcacctgggaagtggggctcatGTTTAGGAAGACTGGAGTAGCTTGTCTGTGTGAGACTACAGTATAAATGGGACA GTTCTCATGCATGTCTAAAGGAGATTGCTGTcatacacacacacacacacacacacacacacacacacaAAGCAACTAA GCAAGAACGTTCTGGAATCTGGCCAAACGAAATATCTTTCATCATCAGAAAAATACCCTAATTGATTGATGCCTTCTTATTGT GTACACGAAGAACTAGAAAAGACAATTTATTTAAACTGTCCAAAGAGCTCACGATGCCTCGAGCTGAATTTCTGAATAGAAGT CTTGAGGAGGTGTATTTAAGTTGATTTTTAAAAACTGGATCACTCTGAAGGTGGGAGCAGAAACACTGTGGATATTGAACAATA GTGGGTTTTTCTGCTTCCCTTCCCTCTGGCTGAAAGCCCCTCGCTTACTTTACCTGGATTGGCTGTTCCCTATGTACTGTAGA TGCAACCTAGATAGGACACAACAGCCTGTCTGCTTGCACCTCGATGGGGCTCTCATCGGAGTCACAGATAATTCCCCAAGGTT GCAGTTTAATGGAGGAGCCCCAGAGTTCCTTCTTGTGTGGGGGACTAAACCGCCTTGTCTGCTGCCTGGTGACACCGCCAGGC GTGTCCGGTGAGCTGCAAGGGAGCTAGAAAGATACCATGTCTGCCCGTGGCCTGGAGAAGACTGGTAAGGTGTGCCAGCTTCA TTTCCTGGAGTATGCCATGTGGTTCCCACCTGGGTTCCATCTTCTCCCTACACCCTGGCCAAGGTTGGACTACATCCTATTTT GGTTTGTTTACCAGCGTCAAAGTAGACACCAGCCTTGGAGAGGGGCTGAATTTAACTTGGAGAGTGAGAAGGCTAGAGACTGG AGCTGACTGGTTTATTTCATTAATAATTATCACATGGTCCCAATTAGATCCTGCATTGTTTCAACCTCATAGCACTGGTGAAA ACAAGACCACGTTTGAAACACAGCATCTTCAGGTGTAACGTGTGGTCGCCCAGCTTGCTAGTTTTTCCCTTGCGGCTGGTTAC TCATCACTTCCCAAAATTCCCTCCCCAGGTTCTTGGACTGCAGAATAATAGGAAGTGTTGGTTTGCtttgtttccccaagtca tggtttctctgtgaaaccctggctgacttggaactactcagtaggctgatcagctaggctttgagctcagagatctgtctgcc tctgtctcctaagatcaaaggtgtttgccctcacctcccgCTCCAAAGATTTTCTGTGTAACCGAGGCTAAATCCCTCATTTC TCCTTTCTGCCTACCCAGTTCACACCACCTTATCACTCAAGGCAGATAAGTTTGCTGCTTTCATCTTTGGAGTGACAGCCTTT TGAAGATTAAAACACACTTCTGCGGAACCACAGTTTATTGTTgaagggacatttcagatgtcattgtgtcccgcagtggaagg gaaaactgaggggcagagaggaaaagtgagttgcccagggtctcacaggtttaggagaaacccattctgcgactcagacttcc taactcctaACATAAGAATTTGCAGTGGGTCGTGCTAAGGGGCGCCAGGGTGAGTTGTACAGGCTGTACACTACAACCCCACA

GGTAGGGCCTTCCCCTCTCAGTGTGTATACTGTGCCCAATGGGATTGTGCTGTACACAGGCGCTTGGCTATATATGC

The terms "hematopoietic stem cell identifier molecule" or "HSC identifier molecule" as used herein, refer to any molecule that can be used to identify an HSC for any purpose desired by one of ordinary skill in the art. Accordingly, sequences encoding such molecules are inserted into the endogenous Fdg5 locus using the replacement cassettes described herein, to be driven under endogenous Fdg5 regulation. Such HSC identifier molecules include, for example, reporter molecules, which adds a detectable phenotype to HSCs, as well as molecules that are toxic to a cell that can be used to, for example, identify and specifically delete HSCs, for asking questions about HSC biology, and therapeutic molecules, that can be used to specifically express a therapeutic product in HSCs for example.

In some embodiments of the nucleic acid constructs described herein, the hematopoietic stem cell identifier molecule is a reporter molecule or reporter sequence. The terms "reporter molecule," "reporter sequence" or "reporter" or "reporter gene," as used herein, encompass any gene that is genetically introduced into a cell that adds a detectable tion of luciferin to a luciferase reporter molecule, or by detecting binding of nickel ion to a polypeptide containing a polyhistidine tag.

In some embodiments of the nucleic acid constructs described herein, a reporter is an optically detectable molecule, such as a fluorescent reporter or fluorescent reporter sequence. In some embodiments of the aspects described herein, the fluorescent reporter molecule is selected from: Cherry fluorescent reporter; green fluorescent protein (GFP); green fluorescent-like protein (GFP-like); yellow fluorescent protein (YFP); blue fluorescent protein (BFP); enhanced green fluorescent protein (EGFP); enhanced blue fluorescent protein (EBFP); cyan fluorescent protein (CFP); enhanced cyan fluorescent protein (ECFP); red fluorescent protein (dsRED); and modifications and fluorescent fragments thereof. In some embodiments of these and all such aspects described herein, the Cherry fluorescent reporter comprises SEQ ID NO: 5. In some embodiments of these and all such aspects described herein, the Cherry fluorescent reporter sequence consists essentially of SEQ ID NO: 5.

```
Cherry fluorescent reporter sequence of SEQ ID NO: 5:
ATGGTGAGCAAGGGCGAGGAGGATAACATGGCCATCATCAAGGAGTTCATGCGCTTCAAGGTGCACAT

GGAGGGCTCCGTGAACGGCCACGAGTTCGAGATCGAGGGCGAGGGCGAGGGCCGCCCCTACGAGGGCA

CCCAGACCGCCAAGCTGAAGGTGACCAAGGGTGGCCCCCTGCCCTTCGCCTGGGACATCCTGTCCCCT

CAGTTCATGTACGGCTCCAAGGCCTACGTGAAGCACCCCGCCGACATCCCCGACTACTTGAAGCTGTC

CTTCCCCGAGGGCTTCAAGTGGGAGCGCGTGATGAACTTCGAGGACGGCGGCGTGGTGACCGTGACCC

AGGACTCCTCCCTGCAGGACGGCGAGTTCATCTACAAGGTGAAGCTGCGCGGCACCAACTTCCCCTCC

GACGGCCCCGTAATGCAGAAGAAGACCATGGGCTGGGAGGCCTCCTCCGAGCGGATGTACCCCGAGGA

CGGCGCCCTGAAGGGCGAGATCAAGCAGAGGCTGAAGCTGAAGGACGGCGGCCACTACGACGCTGAGG

TCAAGACCACCTACAAGGCCAAGAAGCCCGTGCAGCTGCCCGGCGCCTACAACGTCAACATCAAGTTG

GACATCACCTCCCACAACGAGGACTACACCATCGTGGAACAGTACGAACGCGCCGAGGGCCGCCACTC

CACCGGCGGCATGGACGAGCTGTACAAGTAA
``` phenotype to the cell. Reporter genes as disclosed herein are intended to encompass, for example, fluorescent and enzymatic genes, but also other sequences encoding molecules that can easily be detected by persons of ordinary skill in the art, such as unique cell surface molecules. Reporter molecules, which confer a detectable phenotype on a cell, are well known in the art and include, in different embodiments, for example, fluorescent polypeptides such as cherry protein, green fluorescent protein, cyan fluorescent protein, red fluorescent protein, or enhanced forms thereof; any cell surface protein marker or ligand that is not normally not expressed by any cell in an animal, for example, a cell surface molecule found in a different species, such as, for example, truncated forms of human CD2 or human CD25 which are commonly used as ectopic-markers that are expressed in cells of interest, enabling their detection with mAbs and having no profound side-effects; enzymes, such as beta-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or small peptide tags such as a c-myc peptide, a polyhistidine, a FLAG epitope, etc. Expression of a reporter molecule can be detected using the appropriate instrumentation or reagent, for example, by detecting fluorescence of a fluorescent reporter protein or, for example, light emission upon addi- In some embodiments of the nucleic acid constructs described herein, an HSC identifier is a toxic molecule, a suicide molecule, or a molecule that causes the cell in which it is expressed to die, causing specific and/or temporal control of ablation of HSCs, for example. Exemplary toxic molecules include botulinum neurotoxin, anthrax toxin, diphtheria toxin, shiga toxin, shiga like toxin, exotoxin A, cholera toxin, ricin, abrins, caspase or the genes encoding any of these molecules. Alternatively, in some embodiments, the toxic molecule can be a suicide gene, such as the gene encoding thymidine kinas or the diphtheria toxin receptor. Suicide molecules (or genes encoding such molecules) can make targeted cells expressing these molecules susceptible to specific drugs or agents, such that administering or exposing the drug or agent to cells carrying such suicide genes results in cell death only of those cells. For example, expression of the diphtheria toxin receptor (DTR) permits specific ablation of cells expressing it due to the absence of this receptor in the mouse, and the efficient killing of cells that express it once diphtheria toxin is provided. Similarly, cells expressing the thymidine gene are killed following treatment with ganglocyclovir or a similar drug, whereas cells not expressing the thymidine kinase gene are unharmed by ganglocyclovir treatment. In some embodiments, for example, a molecule that can be expressed under the control of the Fdg5 locus can be used to induce apoptosis in a cell (e.g., a cancer stem cell) by increasing the expression of a death receptor, a death receptor ligand or a combination thereof. Some non-limiting examples of death receptors include FAS (CD95, Apo1), TNFR1 (p55, CD120a), DR3 (Apo3, WSL-1, TRAMP, LARD), DR4, DR5 (Apo2, TRAIL-R2, TRICK2, KILLER), CAR1, and the adaptor molecules FADD, TRADD, and DAXX. Some non-limiting examples of death receptor ligands include FASL (CD95L), TNF, lymphotoxin alpha, Apo3L (TWEAK), and TRAIL (Apo2L).

In some embodiments of the nucleic acid constructs described herein, an HSC identifier molecule is a ligand or cell-surface receptor. For example, by expressing a ligand or ligand receptor on the surface of an HSC, under the control of the Fdg5 locus (e.g., a homing moiety). A ligand or ligand receptor moiety attached to the cell surface permits the HSC to have a desired biological interaction with a tissue or an agent in vivo. Such a ligand can be, in some embodiments, an antibody, an antibody fragment, an aptamer, a peptide, a vitamin, a carbohydrate, a protein or polypeptide, a receptor, e.g., cell-surface receptor, an adhesion molecule, a glycoprotein, a sugar residue, a therapeutic agent, a drug, a glycosaminoglycan, or any combination thereof. Such a ligand can confer the ability of an HSC cell expressing the ligand to accumulate in a particular desired tissue, for example, or to be reactive to a particular agent or drug, as desired.

The phrases "operably linked," "operatively positioned," "operatively linked," "under control," and "under transcriptional control" indicate that a nucleic acid sequence, such as a sequence encoding an HSC identifier molecule, is in a correct functional location and/or orientation in relation to a promoter and/or endogenous regulatory sequences, such that the promoter and/or endogenous regulatory sequences controls transcriptional initiation and/or expression of that sequence. Accordingly, upon homologous recombination into the Fgd5 locus, a hematopoietic stem cell identifier molecule, such as a reporter molecule sequence, becomes operably linked to the promoter and endogenous regulatory sequences of the Fgd5 locus.

The terms "promoter" or "promoter sequence," as used herein, refer to a nucleic acid sequence that regulates the expression of another nucleic acid sequence by driving RNA polymerase-mediated transcription of the nucleic acid sequence, which can be a heterologous target gene, such as a reporter molecule sequence. A promoter is a control region of a nucleic acid sequence at which initiation and rate of transcription of the remainder of a nucleic acid sequence are controlled. A promoter can also contain one or more genetic elements at which regulatory proteins and molecules can bind. Such regulatory proteins include RNA polymerase and other transcription factors. Accordingly, a promoter can be said to "drive expression" or "drive transcription" of the nucleic acid sequence that it regulates, such as a sequence encoding an HSC identifier molecule.

Nucleic acid constructs or replacement constructs for use in generating the clonal cell lines and animal models described herein can further comprise, in some embodiments, one or more sequences encoding selection markers for positive and negative selection of cells having undergone appropriate homologous recombination. Such selection marker sequences typically provide properties of resistance or sensitivity to antibiotics that are not normally found in the cells in the absence of introduction of the nucleic acid construct. A selectable marker can be used in conjunction with a selection agent, such as an antibiotic, to select in culture for embryonic stem cells expressing the inserted nucleic acid construct. Introduction of a vector comprising a nucleic acid construct as described herein into cells, followed by simultaneous or stepwise positive and negative selection results in the isolation of cells that have a roughly eight to twelve-fold enriched probability of undergoing site-specific homologous recombination due to application of the negative selectable marker.

Sequences encoding positive selection markers typically provide antibiotic resistance, i.e., when the positive selection marker sequence is present in the genome of a cell, the cell is sensitive to the antibiotic or agent. Sequences encoding positive selection markers are designed to be located between the 5' and 3' homologous arms, for example, 5' or 3' of the HSC identified sequence, such that any cell that has undergone recombination (whether homologous or non-homologous) will survive in the presence of the antibiotic to which the selection marker provides resistance. Accordingly, in some embodiments, positive selection markers used in the nucleic acid constructs described herein include, but are not limited to, the neo gene (neomycin phosphotransferase G418) or its mutants; the puromycin resistance gene (puro); the hygromycin resistance gene (hygro); and the hypoxanthine phosphoribosyl transferase (hprt) gene (which can be used also as a negative selectable marker if the starting cell is hprt deficient).

Sequences encoding negative selection markers typically provide sensitivity to an antibiotic or agent, i.e., when the negative selection marker is present in the genome of a cell, the cell is sensitive to the antibiotic or agent. Sequences encoding negative selection markers are designed to be located outside of the homologous arms (i.e., 5 of the 5' homologous arm, or 3' of the 3' homologous arm), such that any cell in which the nucleic acid construct has undergone homologous recombination or targeted insertion at the Fdg5 locus will not comprise the negative selection marker, while those cells in which the nucleic acid construct has been inserted in its entirety will be sensitive to the presence of the antibiotic or agent which the negative selection marker provides sensitivity. Accordingly, in some embodiments, exemplary negative selection markers used in the nucleic acid constructs described herein include, but are not limited to, the thymidine kinase gene from the herpes simplex virus (thHSV) and mutants thereof that confers sensitivity to gancylovir, and diphtheria toxin A component (DTA), as used herein in the cassette for negative selection.

Nucleic acid constructs or replacement constructs for use in generating the clonal cell lines and animal models described herein can further comprise, in some embodiments, recombinase recognition sequences or recombinase sites flanking the 5' and 3' Fgd5 homologous arms, which allows removal of the nucleic acid construct or replacement cassette in the presence of or following expression of the corresponding recombinase enzyme. For example, in some embodiments of the aspects described herein, any Lox site or its operational mutants can be used with Cre recombinase, or, in some embodiments, FRT recombinase recognition sites or operational mutants thereof can be used with Flp recombinase.

Nucleic acid constructs for use in generating the clonal cell lines and animal models thereof described herein can further comprise, in some embodiments, other genomic elements for the regulation, expression, stabilization of the replacement cassette or of other vector genetic elements, for example, promoters, enhancers, TATA-box, ribosome binding sites, IRES, as known to one of ordinary skill in the art.

Nucleic acid constructs or replacement cassettes are inserted or incorporated into a suitable vector for transfection of stem cells using standard molecular biology techniques. As used herein, a "vector" refers to a nucleic acid molecule, such as a dsDNA molecule that provides a useful biological or biochemical property to an inserted nucleotide sequence, such as the nucleic acid constructs or replacement cassettes described herein. Examples include plasmids, phages, autonomously replicating sequences (ARS), centromeres, and other sequences that are able to replicate or be replicated in vitro or in a host cell, or to convey a desired nucleic acid segment to a desired location within a host cell. A vector can have one or more restriction endonuclease recognition sites (whether type I, II or IIs) at which the sequences can be cut in a determinable fashion without loss of an essential biological function of the vector, and into which a nucleic acid fragment can be spliced or inserted in order to bring about its replication and cloning. Vectors can also comprise one or more recombination sites that permit exchange of nucleic acid sequences between two nucleic acid molecules. Vectors can further provide primer sites, e.g., for PCR, transcriptional and/or translational initiation and/or regulation sites, recombination signals, replicons, additional selectable markers, etc. A vector can further comprise one or more selectable markers suitable for use in the identification of cells transformed with the vector. For example, in some embodiments, a vector already comprising one or more negative selection marker sequences is used with the nucleic acid constructs or replacement cassettes described herein.

Vectors known in the art and those commercially available (and variants or derivatives thereof) can be used with the nucleic acid constructs described herein. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. General classes of vectors include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest for use with the various aspects and embodiments described herein include, but are not limited to, the W vector used herein the Examples, and eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.), pTrxFus, pThioHis, pLEX, pTrcHis, pTrcHis2, pRSET, pBlueBacHis2, pcDNA3.1/His, pcDNA3.1 (−)/Myc-His, pSecTag, pEBVHis, pPIC9K, pPIC3.5K, pAO815, pPICZ, pPICZ.alpha., pGAPZ, pGAPZ.alpha., pBlueBac4.5, pBlueBacHis2, pMelBac, pSinRep5, pSinHis, pIND, pIND(SP1), pVgRXR, pcDNA2.1, pYES2, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; .lamda. ExCell, .lamda. gt11, pTrc99A, pKK223-3, pGEX-1.lamda.T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32LIC, pET-30LIC, pBAC-2 cp LIC, pBACgus-2cp LIC, pT7Blue-2 LIC, pT7Blue-2, .lamda. SCREEN-1, .lamda.BlueSTAR, pET-3abcd, pET-7abc, pET9abcd, pET11 abcd, pET12abc, pET-14b, pET-15b, pET-16b, pET-17b-pET-17xb, pET-19b, pET-20b(+), pET-21 abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6×His-GFP ("6×His" disclosed as SEQ ID NO: 7), pSEAP2-Basic, pSEAP2-Contral, pSEAP2-Promoter, pSEAP2-Enhancer, pβgal-Basic, pβgal-Control, pβgal-Promoter, pβgal-Enhancer, pCMVP, pTet-Off, pTet-On, pTK-Hyg, pRetro-Off, pRetro-On, pIRESlneo, pIRESlhyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and XTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRT3GAL, pNEOPGAL, pRS403, pRS404, pRS405, pRS406, pRS413, pRS414, pRS415, and pRS416 from Stratagene, and variants or derivatives thereof.

Heterozygous Reporter Fgd5 Knock-in Mouse

The expression of the nucleic acid constructs described herein in a non-human animal or non-human mammal creates a "knock-in" animal in which a hematopoietic stem cell identifier molecule, e.g., a reporter molecule, such as Cherry, is expressed under the regulation of the endogenous Fdg5 locus. Such animals are termed herein as "hematopoietic stem cell identifier mammals," or "Fdg5 knock-in hematopoietic stem cell identifier animals," or "Fdg5 knock-in animals." Various methods to make knock-in animals as described herein can be employed. Generally speaking, vectors comprising the nucleic acid constructs described herein are incorporated into isolated embryonic stem cells by electroporation, plasmid transfection or microinjection, lipofection, followed by reintroduction of the stem cells into an embryo where they colonize and contribute to the germ line (Methods for microinjection of mammalian species is described in U.S. Pat. No. 4,873,191). As used herein, "nonhuman mammal" means any mammal other than a human, e.g. a rat, a mouse, a hamster or a guinea pig. Although any small-sized mammals can be useful in the generation of knock-in animals described herein, rodents are preferred, particularly mice (Mus musculus). Any murine species can be used for the preparation of the Fdg5 reporter mice. Commonly used mouse strains for experimental work include, but are not limited to: 129/SvJ, BALB/c, SWR/J, CBA/J, C57L/J, CH3/HeJ, C57BI/6J, CH3Heb/FeJ, AKR/, DBA/2J, A/J. As used herein, "hematopoietic stem cell identifier mammals," "Fdg5 knock-in hematopoietic stem cell identifier animals," and "Fdg5 knock-in animals" include progeny of such animals, such as the progeny of heterozygous crosses, including crosses with other reporter, transgenic, knock-out, or knock-in animals, as well as animal clones made from such Fdg5 knock-in hematopoietic stem cell identifier animals.

Embryonic stem cells are generated and maintained using methods well known to the skilled artisan such as those described by Doetschman et al. (1985) J. Embryol. Exp. Mol. Biol. 87:27-45). Any line of ES cells can be used; however, the line chosen is typically selected for the ability of the cells to integrate into and become part of the germ line of a developing embryo so as to create germ line transmission of the replacement cassette construct. Thus, any ES cell line that is believed to have this capability is suitable for use in the methods described herein. Several murine embryonic stem cell lines can be used, in embodiments of the aspects described herein, such as, for example, CB1-4 ES, CCE, 129/Ola, and TVB2 embryonic stem cells, isolated from 129SV/J mice, the murine cell line D3 (American Type Culture Collection, catalog no. CKL 1934), and the WW6 cell line (Ioffe et al. (1995) PNAS 92:7357-7361). The cells are cultured and prepared for replacement cassette insertion using methods well known to the skilled artisan, such as those set forth by Robertson in: Teratocarcinomas and Embryonic Stem Cells: A Practical Approach, E. J. Robertson, ed. IRL Press, Washington, D.C. (1987)); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)). ES cell transformation is carried out with a vector comprising a nucleic acid or replacement construct as described herein, which is linearized, purified and electroporated into the ES cells. Other transfection methods can be used, such as microinjection. Selection of embryonic stem cells having undergone homologous recombination at the Fdg5 locus is performed in a culture medium comprising one or more selection agents specific for or the selection marker(s) used in the nucleic acid or replacement construct at a suitable concentration. Other cloning and manipulation methods are described in, for example, Manipulating the Mouse Embryo: A Laboratory Manual, 3$^{rd}$ Edition, Cold Spring Harbor Laboratory Press; 3rd edition (Dec. 15, 2002).

In some embodiments of the aspects described herein, the ordinarily skilled artisan can further or also determine whether an ES cell has incorporated the nucleic acid construct by homologous recombination, using any technique known in the art, e.g., via Southern blot, PCR, other approaches known in the art, or combinations thereof.

Selected ES cells in which homologous recombination at the Fdg5 locus has been determined to occur, using any method known to one of skill in the art, such as, for example, Southern Blot analysis, are then transferred into a compatible recipient blastocyst and introduced into a surrogate mother to obtain chimeric animals. The resulting chimeric animals are bred to wild type animals to establish hybrid F1 animals. Some of the chimeric animals will harbor the targeted Fdg5 locus in the germinal cells and will transmit it to the offspring. By means of any appropriate method known to one of skill in the art, such as PCR genotyping and/or Southern blotting of DNA extracted from samples from the F1 progeny, such as tail specimens, it is possible to identify those animals that have the targeted Fdg5 locus (and can transmit it to the offspring). In some embodiments of the aspects described herein, the negative selection marker sequence is flanked by recombination sites, and can be excised by breeding the targeted animals with recombinase transgenic animals, for example, or by contacting a selected ES cells in which homologous recombination at the Fdg5 locus has been determined to occur with the recombinase in vitro.

The inventors have determined that mice with insertion of the nucleic acid constructs at each of the endogenous Fdg5 alleles are embryonic lethal. As demonstrated herein, mice that are heterozygous for the nucleic acid constructs, i.e., where the nucleic acid construct comprising the hematopoietic stem cell identifier molecule is inserted at only one of the endogenous Fdg5 alleles, are viable and fertile, and a breeding colony can be established. Accordingly, for use with the various aspects and embodiments described herein, it is preferred that the reporter knock-in animals are heterozygous for the targeted Fdg5 allele comprising the hematopoietic stem cell identifier molecule.

Isolated Hematopoietic Stem Cells, Clonal Cell Lines and Methods of Use Thereof

As demonstrated herein, the inventors have determined that expression of a single molecule, Fdg5, can be used to distinguish between hematopoietic stem cells and the most closely related population of multipotent progenitor cells, which are committed to the hematopoietic cell lineage but generally do not self-renew. This is in contrast to the existing schemes for identifying true HSCs from more differentiated populations, which rely on various combinations of positive and negative cell-surface markers. Accordingly, the hematopoietic stem cell identifier animals or Fdg5 knock-in animals described herein provide the ability, in some aspects, to isolate purified or substantially enriched hematopoietic stem cell populations having long-term multi-lineage repopulating activity and potent self-renewal activity. Also provided herein, in some aspects, are methods to specifically modulate, e.g., ablate, hematopoietic stem cell populations in vivo.

Hematopoietic tissues contain cells with long-term and short-term regeneration capacities, and committed multipotent, oligopotent, and unipotent progenitors. HSCs can be can be found in a variety of tissue sources, such as the bone marrow of adults, which includes femurs, hip, ribs, sternum, and other bones, as well as umbilical cord blood and placenta, and mobilized peripheral blood. Samples comprising HSCs can be obtained directly by removal from, for example, the hip using a needle and syringe, or from the blood following pre-treatment with cytokines, such as G-CSF (granulocyte colony-stimulating factors), that induce cells to be released from the bone marrow compartment.

Cellular differentiation is a complex process typically occurring through many cell divisions. Self-renewal is the classical part of the stem cell definition, and it is essential as used in this document in defining and identifying an HSC. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation".

In the context of cell ontogeny, the adjectives "differentiated", or "differentiating" are relative terms. The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at a previous point in their development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers. The term "lineages" as used herein refers to a term to describe cells with a common ancestry or cells with a common developmental fate.

Using a variety of confirmatory assays, including cell-surface phenotyping by flow cytometric analyses, and functional repopulating assays, as described herein in the Examples, the inventors have shown that hematopoietic cells, in both mice and humans, expressing high levels of Fdg5 are, in fact, true HSCs, and that Fdg5 expression or expression of an HSC identifier molecule from the Fdg5 locus can be used to even distinguish between self-renewing and multipotent hematopoietic stem cells and the most closely related population of multipotent progenitor cells, which are committed to the hematopoietic cell lineage but generally do not self-renew, in both mice and human.

Accordingly, HSCs isolated from the HSC identifier animals described herein provide novel tools and methods of characterizing, identifying, and modulating HSCs in vivo and for screening agents that modulate HSC activity.

Accordingly, in some aspects, provided herein are populations of hematopoietic stem cells enriched for or isolated from a biological sample taken from a hematopoietic stem cell identifier animal for use in the methods and uses described herein, using any method known to one of skill in the art.

In some embodiments of these aspects and all such aspects described herein, an isolated population is a substantially pure population of cells as compared to the heterogeneous population from which the cells were isolated or enriched from. In some embodiments of these aspects and all such aspects described herein, the isolated population is an isolated population of hematopoietic stem cells. In other embodiments of this aspect and all aspects described herein, the isolated population comprises a substantially pure population of hematopoietic stem cells as compared to a heterogeneous population of cells comprising various other cells types from which the hematopoietic stem cells were derived. In some embodiments, an isolated cell or cell population, such as a population of hematopoietic stem cells, is further cultured in vitro or ex vivo, e.g., in the presence of growth factors or cytokines, to further expand the number of cells in the isolated cell population or substantially pure cell population. Such culture can be performed using any method known to one of skill in the art.

As used herein, the term "population of hematopoietic cells" encompasses a heterogeneous or homogeneous population of hematopoietic stem cells and/or hematopoietic progenitor cells. In addition, differentiated hematopoietic cells, such as lymphocytes, can be present in a population of hematopoietic cells. A population of hematopoietic cells comprising at least two different cell types is referred to herein as a "heterogeneous population." A population of hematopoietic cells comprising only one cell type (e.g., hematopoietic stem cells expressing a hematopoietic stem cell identifier molecule under the operative control of the endogenous Fdg5 locus) is referred to herein as a "homogeneous population of cells."

The term "biological sample" as used herein refers to a cell or population of cells or a quantity of tissue or fluid from a hematopoietic stem cell identifier animal comprising one or more hematopoietic stem cells. Most often, the biological sample has been removed from the hematopoietic stem cell identifier animal, but the term "biological sample" can also refer to cells or tissue analyzed in vivo, i.e., without removal from the hematopoietic stem cell identifier animal. Biological samples include, but are not limited to, umbilical cord blood, placental samples, whole blood, bone marrow, tissue sample or biopsies, scrapes (e.g. buccal scrapes), plasma, serum, urine, saliva, cell culture, or cerebrospinal fluid. A biological sample or tissue sample can refer to any sample of tissue or fluid isolated from a hematopoietic stem cell identifier animal from which hematopoietic stem cells can be obtained, including but not limited to, for example, umbilical cord blood, peripheral blood, bone marrow, placental samples, thymus, lymph nodes, splenic tissue, liver tissue, plasma, sputum, serum, lung lavage fluid, tumor biopsy, urine, stool, spinal fluid, pleural fluid, nipple aspirates, lymph fluid, the external sections of the skin, respiratory, intestinal, and genitourinary tracts, tears, saliva, milk, cells (including but not limited to hematopoietic cells), tumors, organs, and also samples obtained from in vitro cell cultures.

In some embodiments of the aspects described herein, a biological sample comprising hematopoietic stem cells refers to a sample isolated from a hematopoietic stem cell identifier animal, such as, peripheral blood, thymus, or bone marrow, which is then further processed, for example, by cell sorting (e.g., FACS), to obtain a population of hematopoietic stem cells based on expression of the hematopoietic stem cell identifier molecule expressed under the control of the endogenous Fdg5 locus. In other embodiments of the aspects described herein, a biological sample comprising hematopoietic stem cells refers to an in vitro or ex vivo culture of expanded hematopoietic stem cells isolated or purified from a hematopoietic stem cell identifier animal.

The terms "isolate" and "methods of isolation," as used herein, refer to any process whereby a cell or population of cells, such as a population of hematopoietic stem cells, is removed from a subject, such as a hematopoietic stem cell identifier animal, or sample in which it was originally found, or a descendant of such a cell or cells. The term "isolated population," as used herein, refers to a population of cells that has been removed and separated from a biological sample, or from a mixed or heterogeneous population of cells found in such a sample. Such a mixed population includes, for example, a population of hematopoietic stem cells obtained from a cell suspension of a tissue sample.

The term "substantially pure," with respect to a particular cell population, such as an HSC population, refers to a population of cells that is at least about 75%, at least about 80%, at least about 85%, at least about 90%, at least about 95%, at least about 98%, or at least about 99% pure, with respect to the cells making up a total cell population. In other words, the terms "substantially pure" or "essentially purified," with regard to a population of hematopoietic stem cells isolated for use in the methods disclosed herein, refers to a population of hematopoietic stem cells that contain fewer than about 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 4%, fewer than about 3%, fewer than about 2%, fewer than about 1%, or less than 1%, of cells that are not hematopoietic stem cells, as defined by the terms herein. Some embodiments of these aspects further encompass methods to expand a population of substantially pure or enriched hematopoietic stem cells, wherein the expanded population of hematopoietic stem cells is also a substantially pure or enriched population of hematopoietic stem cells.

The terms "enriching" or "enriched" are used interchangeably herein and mean that the yield (fraction) of cells of one type, such as hematopoietic stem cells for use in the methods described herein, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

In some aspects and embodiments, any of a variety of methods to isolate a substantially pure population of hematopoietic stem cells from the Fdg5-knock-in animal described herein, depending on the nature of the hematopoietic stem identifier inserted into a Fdg5 locus, are available to a skilled artisan, including immunoselection techniques, such as high-throughput cell sorting using flow cytometric methods, affinity methods with antibodies labeled to magnetic beads, such as magnetic-activated cell separation (MACS), biodegradable beads, non-biodegradable beads, antibodies panned to surfaces, including dishes, automated single-cell sorting using dual-beam optical trapping, differential adhesion cell sorting, and micro-fabricated fluorescence-activated cell sorting, and any combination of such methods (Bonner W A, Hulett H R, Sweet R G: Fluorescence activated cell sorting, Rev Sci Instrument 1972, 43:404-409; Steinberg M: Reconstruction of tissues by dissociated cells, Science 1963, 141:401-408; and Fu A Y, et al.: A microfabricated fluorescence-activated cell sorter, Nature Biotech 1999, 17:1109-1111.

In some embodiments of the aspects described herein, markers previously identified as specific for hematopoietic stem cells can be used to confirm the HSC phenotype of cells isolated or enriched for from the hematopoietic stem cell identifier animals described herein. A "marker," as used herein, describes the characteristics and/or phenotype of a cell. Markers can be used for selection of cells comprising characteristics of interest. Markers will vary with specific cells. Markers are characteristics, whether morphological, functional or biochemical (enzymatic), particular to a cell type, or molecules expressed by the cell type. Preferably, such markers are proteins, and more preferably, possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, cellular shape, cellular size, cellular appearance (e.g., smooth, translucent), and cellular nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art.

Accordingly, as used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to.

A cell can be designated "positive" or "negative" for any given cell-surface marker. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell can express messenger RNA for a cell-surface marker, in order to be considered positive for the methods described herein, the cell must express it on its surface. Similarly, a cell is considered "negative" for a cell-surface marker if it does not express the marker on its cell-surface in amounts sufficient to be detected using methods known to those of skill in the art, such as contacting a cell with an antibody that binds specifically to that marker and subsequently performing flow cytometric analysis of such a contacted cell to determine whether the antibody is bound the cell. In some embodiments of the aspects described herein, where agents specific for cell-surface lineage markers used, the agents can all comprise the same label or tag, such as fluorescent tag, and thus all cells positive for that label or tag can be excluded or removed, to leave uncontacted the desired cell population, e.g., hematopoietic stem cells.

Accordingly, as defined herein, an "agent specific for a cell-surface marker" refers to an agent that can selectively react with or bind to that cell-surface marker, but has little or no detectable reactivity to another cell-surface marker or antigen. For example, an agent specific for CD34 will not identify or bind to CD35. Thus, agents specific for cell-surface markers recognize unique structural features of the markers. In some embodiments of the aspects described herein, an agent specific for a cell-surface marker binds to the cell-surface marker, but does not cause initiation of downstream signaling events mediated by that cell-surface marker, for example, a non-activating antibody. Agents specific for cell-surface molecules include, but are not limited to, antibodies or antigen-binding fragments thereof, natural or recombinant ligands, small molecules; nucleic acid sequence and nucleic acid analogues; intrabodies; aptamers; and other proteins or peptides.

In some embodiments of any of the aspects described herein, the preferred agents specific for cell-surface markers used for characterizing or isolating hematopoietic stem cells are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Such antibodies or antigen-binding fragments are available commercially from vendors such as R&D Systems, BD Biosciences, e-Biosciences and Miltenyi, or can be raised against these cell-surface markers by methods known to those skilled in the art.

In some embodiments of the aspects described herein, an agent specific for a cell-surface molecule, such as an antibody or antigen-binding fragment, is labeled with a tag. The terms "label" or "tag", as used herein, refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods to isolate and enrich endothelial cell progenitor cells.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable tag, such as c-Myc, HA, VSV-G, HSV, FLAG, V5, or HIS, which can be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the methods of invention include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5, Cy7, nanoparticles, or quantum dots.

In some embodiments of these aspects and all such aspects described herein, isolation of and enrichment for populations of hematopoietic stem cells can be performed using flow cytometric methods, alone or in combination with magnetic bead based methods, to isolate or enrich for hematopoietic stem cells. As defined herein, "flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies, and can more precisely identify a target population by their phenotypic markers. Certain flow cytometric instruments can take digital images of individual cells, allowing for the analysis of fluorescent signal location within or on the surface of cells.

A common variation of flow cytometric techniques is to physically sort particles based on their properties, so as to purify populations of interest, using "fluorescence-activated cell sorting." As defined herein, "fluorescence-activated cell sorting" or "flow cytometric based sorting" methods refer to flow cytometric methods for sorting a heterogeneous mixture of cells from a single biological sample into one or more containers, one cell at a time, based upon the specific light scattering and fluorescent characteristics of each cell and provides fast, objective and quantitative recording of fluorescent signals from individual cells as well as physical separation of cells of particular interest. For example, as demonstrated herein using the mCherry reporter molecule expressed under the control of the endogenous Fdg5 locus, hematopoietic stem cells can be sorted and isolated based on expression of a reporter molecule, such as mCherry, expressed under the operative control of the Fdg5 locus. In some embodiments of the methods described herein, when the hematopoietic stem cell identifier molecule is a fluorescent reporter molecule, HSCs can be directly sorted based on expression of the fluorescent reporter molecule. In some embodiments of the methods described herein, when the hematopoietic stem cell identifier molecule is a cell surface molecule, HSCs can be sorted based on using an agent specific for the cell-surface molecule, such as an antibody or antigen-binding fragment, labeled with a tag, such as a fluorescent molecule, that can be detected by a flow cytometer, to isolate and enrich for populations of hematopoietic stem cells.

In some embodiments of these aspects and all such aspects described herein, isolation of and enrichment for populations of hematopoietic stem cells can be performed using bead based sorting mechanisms, such as magnetic beads. In some embodiments, the biological sample from a hematopoietic stem cell identifier animal is contacted with magnetic beads coated with an antibody specific for the hematopoietic stem cell identifier molecule, such that only HSCs are selected. This causes the cells in the sample expressing the hematopoietic stem cell identifier molecule to attach to the magnetic beads. Afterwards the contacted cell solution is transferred to a strong magnetic field, such as a column or rack having a magnet. The cells attached to the beads (expressing the cell-surface marker) stay on the column or sample tube, while other cells (not expressing the cell-surface marker) flow through or remain in solution. Using bead based sorting methods, cells can be separated positively or negatively, or using a combination therein, with respect to the particular cell-surface markers. In some embodiments of these aspects and all such aspects described herein, magnetic activated cell sorting (MACS) strategies are used for isolation and preselection of hematopoietic stem cells.

In other embodiments of the aspects described herein, one or more additional cell-surface markers are used for isolating and/or enriching for HSCs, using positive or negative selection methods, or a combination therein. Such additional cell-surface markers include, but are not limited to, CD133, lineage markers, KLS, Flk2, CD150, CD48, CD244, CD44, SCA-1, CD117 (c-kit), CD16/32, CD150, CD48, and CD244.

As defined herein, "positive selection" refers to techniques that result in the isolation or enrichment of cells expressing specific cell-surface markers, while "negative selection" refers techniques that result in the isolation or enrichment of cells not expressing specific cell-surface markers. In some embodiments, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select hematopoietic stem cells expressing one or more specific cell-surface markers. For example, in a negative selection protocol, a biological sample, such as a cell sample, is first contacted with labeled antibodies specific for cell-surface markers of interest, such as CD2, CD3, CD14, CD16, CD19, CD56, and CD235a and the sample is then contacted with beads that are specific for the labels of the antibodies, and the cells expressing any of the markers CD2, CD3, CD14, CD16, CD19, CD56, and CD235a are removed using immunomagnetic lineage depletion.

A number of different cell-surface markers have specific expression on specific differentiated cell lineages, and are not expressed by the hematopoietic stem cells isolated for the methods described herein. Accordingly, when agents specific for these lineage cell-markers are contacted with hematopoietic stem cells, the cells will be "negative." Lineage cell-markers that are not expressed by the hematopoietic stem cells contemplated for use in the methods described herein include, but are not limited to, CD13 and CD33 (expressed on myeloid cells); CD71 (expressed on erythroid cells); CD19 and B220 (expressed on B cells); CD61 (expressed on human megakaryocytic cells); Mac-1 (CD11b/CD18) (expressed on monocytes); Gr-1 (expressed on granulocytes); Ter119 (expressed on erythroid cells); and Il7Ra, CD2, CD3, CD4, CD5, CD8 (expressed on T cells); CD14, CD56, and CD235a. In some embodiments of the aspects described herein, the lineage markers used can be dependent on the species from which the hematopoietic stem cells are being isolated, as determined by one of skill in the art. For example, when isolating human hematopoietic stem cells the combination of lineage markers to be excluded can comprise CD2, CD3, CD16, CD19, CD56, and CD235a. One can further enrich the cell population for the methods and uses described herein by removing cells that express the markers set forth in this paragraph.

In some embodiments of the aspects, the substantially pure or enriched for population of isolated hematopoietic stem cells obtained from a HSC identifier animal or Fdg5 knock-in animal are further expanded or increased in numbers prior to their use in the methods described herein.

In some embodiments, hematopoietic stem cells isolated or enriched for using the methods and techniques described herein are expanded in culture, i.e., the cell numbers are increased, using methods known to one of skill in the art, prior to administration to a subject in need. In some embodiments, such expansion methods can comprise, for example, culturing the hematopoietic stem cells in serum-free medium supplemented with factors and/or under conditions that cause expansion of hematopoietic stem cells, such as stem cell factor, IL-3, and GM-CSF. In some embodiments of the methods described herein, hematopoietic stem cells are expanded in the presence of deaxmethasone.

In other embodiments of the aspects described herein, hematopoietic stem cells isolated or enriched for use in the methods and techniques described herein are expanded using nanotechnological or nanoengineering methods, as reviewed in Lu J et al., "A Novel Technology for Hematopoietic Stem Cell Expansion using Combination of Nanofiber and Growth Factors." Recent Pat Nanotechnol. 2010 Apr. 26.

As used herein, the terms "proliferating", "proliferation", "expanding", and "expansion" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The terms "increased," "increase," "enhance," or "expand" are all used herein to generally mean an increase in the number of hematopoietic stem cells by a statically significant amount; for the avoidance of any doubt, the terms "increased," "increase," "expand," "expanded," or "enhance" mean an increase, as compared to a reference level, of at least about 10%, of at least about 15%, of at least about 20%, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, at least about a 10-fold increase, at least about a 25-fold increase, at least about a 50-fold increase, at least about a 100-fold increase, or any increase of 100-fold or greater, as compared to a control or reference level. A control sample or control level is used herein to describe a population of cells obtained from the same biological source that has, for example, not been expanded using the methods described herein.

The term "regeneration" means regrowth of a cell population, organ or tissue after disease or trauma. For example, blood regeneration refers to the regrowth or repopulation of blood cells following disease or trauma to blood cells, e.g., following radiation treatment or chemotherapy.

In some embodiments of the aspects described herein, cancer stem cells can be identified using the expression from the Fdg5 locus, as described herein. It has been recently discovered that stem-like cells are present in some human tumors and, while representing a small minority of the total cellular mass of the tumor, are the subpopulation of tumor cells responsible for growth of the tumor. In contrast to normal stem cells, "tumor stem cells" or "cancer stem cells" are defined as cells that can undergo self-renewal, as well as abnormal proliferation and differentiation to form a tumor. Functional features of tumor stem cells are that they are tumorigenic; they can give rise to additional tumorigenic cells by self-renewal; and they can give rise to non-tumorigenic tumor cells. As used herein, particularly in reference to an isolated cell or isolated cell population, the term "tumorigenic" refers to a cell derived from a tumor that is capable of forming a tumor, when dissociated and transplanted into a suitable animal model such as an immunocompromised mouse. The developmental origin of tumor stem cells can vary among different types of cancers. It is believed, without wishing to be bound or limited by theory, that tumor stem cells may arise either as a result of genetic damage that deregulates normal mechanisms of proliferation and differentiation of stem cells (Lapidot et al., Nature 367(6464): 645-8 (1994)), or by the dysregulated proliferation of populations of cells that acquire stem-like properties. For example, it was shown that leukemia stem cells maintain the global identity of the progenitor cell from which they arose, while activating a limited stem cell or self-renewal-associated program. Further, it was shown that leukemia stem cells express a self-renewal program normally associated with HSCs (A. V. Krivtsov et al., "Transformation from committed progenitor leukaemia stem cell initiated by MLL-AF9," Nature, August 2006, 442:17, pp. 818-822).

Examples of tumors from which samples containing cancer stem cells can be isolated from or enriched for using the replacement constructs and Fdg5 animal models described herein, include leukemias, and other cancers, such as, but not limited to: fibrosarcoma, myxosarcoma, liposarcoma, chondrosarcoma, osteogenic sarcoma, chordoma, angiosarcoma, endotheliosarcoma, lymphangiosarcoma, mesothelioma, Ewing's tumor, lymphangioendotheliosarcoma, synovioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytic tumors (e.g., diffuse, infiltrating gliomas, anaplastic astrocytoma, glioblastoma, gliosarcoma, pilocytic astrocytoma, pleomorphic xanthoastrocytoma), oligodendroglial tumors and mixed gliomas (e.g., oligodendroglioma, anaplastic oligodendroglioma, oligoastrocytoma, anaplastic oligoastrocytoma), ependymal tumors (e.g., ependymoma, anaplastic ependymoma, myxopapillary ependymoma, subependymoma), choroid plexus tumors, neuroepithelial tumors of uncertain origin (astroblastoma, chordoid glioma, gliomatosis cerebri), neuronal and mixed-neuronal-glial tumors (e.g., ganglioglioma and gangliocytoma, desmoplastic infantile astrocytoma and ganglioglioma, dysembryoplastic neuroepithelial tumor, central neurocytoma, cerebellar liponeurocytoma, paraganglioglioma), pineal parenchymal tumors, embryonal tumors (medulloepithelioma, ependymoblastoma, medulloblastoma, primitive neuroectodemmal tumor, atypical teratoid/rhabdoid tumor), peripheral neuroblastic tumors, tumors of cranial and peripheral nerves (e.g., schwannoma, neurinofibroma, perineurioma, malignant peripheral nerve sheath tumor), meningeal tumors (e.g., meningeomas, mesenchymal, non-meningothelial tumors, haemangiopericytomas, melanocytic lesions), germ cell tumors, tumors of the sellar region (e.g., craniopharyngioma, granular cell tumor of the neurohypophysis), hemangioblastoma, melanoma, and retinoblastoma.

In some aspects, cancer stem cell identifier models can be generated using the Fdg5 knock-in animals described herein. In such aspects, a mouse model of cancer can be crossed or bred with any of the Fdg5 knock-in animals described herein, and any progeny mice selected or screened for having one of the two Fdg5 loci replaced with the hematopoietic stem cell identifier molecule of the Fdg5 knock-in animal, e.g., such as a fluorescent reporter molecule or toxic molecule. Using such cancer stem cell identifier models, any cancer stem cell expressing the hematopoietic stem cell identifier molecule from the Fdg5 locus can be identified, isolated, and/or further characterized, as described for the Fdg5 knock-in animals.

Non-limiting examples of mouse cancer models useful in such aspects include genetically engineered mouse models of cancer, such as, for example, mouse leukemia models, such as the primary human AML xenotransplantation model using newborn mice of the NOD.Cg-Prkdc$^{scid}$ Il2rg$^{tm1Wjl}$/SzJ strain; AKR/J mice having high leukemia incidence (60-90%); CBA/Ca mice, which have high inducibility of myeloid leukemia in response to benzene and radiation exposure; C57L/J mice, which have a high incidence of Hodgkin's-like reticulum cell neoplasm at 18 months of age and pituitary tumors in old multiparous females; B6.Cg-Tg (BCR/ABL)623Hkp/J transgenic mice, which contain the truncated murine metallothionein-1 (Mt1) promoter driving expression of the human p190 form of the BCR/ABL1 fusion protein cDNA, and develop hematologic malignancies at 3 months of age; C58/J mice, which exhibit a high incidence of leukemia (>90% by one year of age); P/J mice, which exhibit a high incidence of lymphatic leukaemia; Mll1$^{tm2(MLLT3)Thr}$/KsyJ, which have a Mll-AF9 knock-in allele encoding a MLL-AF9 fusion protein that mimics the t(9;11)(p22;q23) translocation identified in acute myeloid leukemia (AML) patients; and B6.129S1-Is(14)2Rdf mice, which carry the conditional (floxed) MDR (minimal deleted region) allele, 14qC3-MDR, and when bred to a strain with Cre recombinase expression in B lymphocytes is useful in studies of chronic lymphocytic leukemia (CLL); lung cancer mouse models resulting from targeted activation of the K-RAS proto-oncogene and simultaneous inactivation of retinoblastoma gene and p53 in the mouse lung; breast cancer mouse models involving overexpression of oncogenes via the long-terminal repeat of the mouse mammary tumor virus, including c-Myc, cyclin D1, Her2, and Wnt-1; prostate cancer mouse models, such as prostate-specific conditional knockouts of the NKX3.1, PTEN, P27, and P53 tumor suppressors; mouse models of colon cancer, such as the APCMin/+ model of intestinal tumorigenesis, and SMAD3$^{-/-}$ mice, which develop colonic adenocarcinoma and metastases, in an APC-independent manner; ovarian cancer mouse models, such as the RCAS-TVA system to overexpress oncogenes in ovarian epithelial cells ex vivo, followed by implantation within the ovarian bursa, the virally induced model of simultaneous, Cre-mediated P53, and RB inactivation, and K-RASLSLG12D/+ mice, which develop peritoneal endometriosis; mouse models of pancreatic cancer, such as KC mice, which is based on mutation of the endogenous murine Kras gene specifically in pancreatic progenitor cells, and KPC mice in which PdxCre-expressing compound mutant animals were generated with conditional mutations in both Kras and Trp53

The Fdg5 knock-in animals described herein further provide essential tools in the understanding of HSC biology, development, and differentiation, and also provide unique tools in drug screening for evaluating the therapeutic potential of putative HSC modulators or agents, including small molecule compounds, such as HSC expander agents. Accordingly, the Fdg5 knock-in animals and HSCs isolated from such animals are useful in, for example: (i) identifying HSC proliferation modulating candidate compounds, particularly compounds or agents that promote HSC proliferation without promoting HSC differentiation; (ii) identifying agents that modulate (increase or decrease) HSC differentiation; (iii) identifying HSC migration modulating candidate compounds; and (iv) identifying HSC survival modulating candidate compounds, i.e., agents that maintain the number and hematopoietic stem cell activity of a population of HSCs. Because the inventors have determined that FDG5 serves as a specific and unique marker of human HSCs as well, HSC activity modifying agents identified using the animal models described herein and cells isolated from such animals are applicable to human HSC modulation as well. Characterization of candidate agents can include aspects such as compound development, identifying HSC-specific toxicity and HSC-specific survival, and assessments of compound safety, compound efficacy, and dose-response parameters. In some embodiments, HSC parameters and functional activities that can be assayed for modulation by a candidate agent, using the screening methods described herein include, but are not limited to, agents that promote growth, expansion, potency, differentiation, proliferation, survival, regeneration, maintenance of the HSCs in an undifferentiated state, and/or inhibit or negatively affect HSC differentiation.

The screening methods described herein are useful, in some aspects, in screening for agents to maintain HSCs in an undifferentiated state, that is, in a multipotent, self-renewing state. In some embodiments of these aspects and all such aspects described herein, the methods are useful in screening for agents to promote the proliferation of HSCs, and in other embodiments, the screening methods can be used for screening agents that increase survival of HSCs. The HSC screening methods described herein are also useful, in some aspects, for in vitro assays and screening assays to detect agents that are active on HSCs, for example, to screen for agents that affect the differentiation of HSCs, including differentiation of HSCs along the lymphocyte or granulocyte lineages, for example. A wide variety of assays may be used for this purpose, including immunoassays for protein binding; determination of cell growth, differentiation and functional activity; production of factors; and the like.

Typically, in the in vitro and ex vivo aspects of the screening methods described herein, HSCs isolated or enriched from one or more Fdg-5 knock-in animals as described herein are contacted with the agent of interest, and the effect of the agent assessed by monitoring output parameters, such as expression of markers, cell viability, differentiation characteristics, hematopoietic multipotency and self-renewal capacity and the like. In some embodiments of these aspects, the screening methods described herein can be used to screen for agents in which some HSCs comprising a particular mutation and/or polymorphism respond differently compared with stem cells without the mutation and/or polymorphism, therefore the methods can be used for example, to asses an effect of a particular drug and/or agent on stem cells from a defined subpopulation of cells, therefore acting as a high-throughput screen for personalized medicine and/or pharmacogenetics. The manner in which cells respond to an agent, particularly a pharmacologic agent, including the timing of responses, for example, is an important reflection of the physiologic state of the cell.

Candidate agents can, in some embodiments of the screening methods described herein, be applied to a media, where it contacts the HSC and induces its effects. Alternatively, the agent can act in an intracellular manner within the HSC, as a result of introduction of the nucleic acid sequence into the cell and its transcription resulting in the production of the nucleic acid and/or protein agent within the cell. The exposure to a candidate agent can be continuous or non-continuous, in some embodiments. In those embodiments where a candidate agent is added or applied to the media, the agent can be added in a solution, or readily soluble form, to the medium of cells in culture. The agents can be added, in some embodiments, in a flow-through system, as a stream, intermittent or continuous, or alternatively, adding a bolus of the compound, singly or incrementally, to an otherwise static solution. In those embodiments employing a flow-through system, for example, two fluids are used, where one is a physiologically neutral solution, and the other is the same solution with the candidate agent added. The first fluid is passed over the cells, followed by the second. In those embodiments employing a single solution method, a bolus of the test compound is added to the volume of medium surrounding the HSCs. The overall concentrations of the components of the culture medium should not change significantly with the addition of the bolus, or between the two solutions in a flow through method. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

Candidate agents can, in some embodiments of the screening methods described herein, be screened for effect on the HSC by adding the agent to at least one and usually a plurality of HSC samples, usually in parallel with cells lacking the agent. The change in parameters in response to the agent is measured, and the result evaluated by comparison to reference cultures, e.g. in the presence and absence of the agent, obtained with other agents, etc. A plurality of assays can be run in parallel with different candidate agent concentrations to obtain a differential response to the various concentrations. As known in the art, determining the effective concentration of an agent typically uses a range of concentrations resulting from 1:10, or other log scale, dilutions. The concentrations can be further refined with a second series of dilutions, if necessary. Typically, one of these concentrations serves as a negative control, i.e. at zero concentration or below the level of detection of the agent or at or below the concentration of agent that does not give a detectable change in the phenotype.

Accordingly, provided herein, in some aspects, are methods for screening a candidate agent for the ability to modulate hematopoietic stem cell activity using a hematopoietic stem cell identifier animal or cells isolated from a hematopoietic stem cell identifier animal, wherein the hematopoietic stem cell identifier animal comprises a HSC identifier molecule, such as a reporter molecule, under the regulation of an endogenous Fdg5 locus. Such methods include administering to a hematopoietic stem cell identifier animal a candidate agent in vivo, or in vitro or ex vivo contacting a hematopoietic stem cell isolated and/or purified from a hematopoietic stem cell identifier animal, and comparing a desired hematopoietic stem cell activity, such as proliferation, hematopoietic multipotency, and/or self-renewal, with the hematopoietic stem cell activity of a hematopoietic stem cell identifier animal or a hematopoietic stem cell isolated or purified from a hematopoietic stem cell identifier animal not administered or contacted with the candidate agent. A difference, whether an increase or decrease, in the desired hematopoietic stem cell activity in the hematopoietic stem cell identifier animal administered the candidate agent compared to the hematopoietic stem cell identifier animal not administered the candidate agent is indicative of a candidate agent that modulates the desired HSC activity. For example, in some embodiments, where a candidate agent maintains hematopoietic stem cell activity, e.g., self-renewal or the number of cells, the hematopoietic stem cell isolated or purified from a hematopoietic stem cell identifier animal not administered or contacted with the candidate agent has decreased number of cells or self-renewal activity relative to the hematopoietic stem cell isolated or purified from a hematopoietic stem cell identifier animal that has been administered or contacted with the candidate agent.

In some aspects, provided herein are ex vivo methods for screening agents to expand hematopoietic stem cells, such methods comprising the steps of: exposing a population of cells isolated or selected from a heterozygous Fdg5 knock-in mouse expressing a hematopoietic stem cell identifier to a candidate agent ex vivo; and comparing cell growth rate of the population of cells expressing the hematopoietic stem cell identifier exposed to the candidate agent to a population of cells expressing the hematopoietic stem cell identifier that has not been exposed to the candidate agent, wherein if the cell growth rate is increased in the population of cells expressing the hematopoietic stem cell identifier exposed to the candidate agent compared to the population of cells expressing the hematopoietic stem cell identifier that has not been exposed to the candidate agent, the agent is indicated as an agent that expands hematopoietic stem cells.

As used herein, "cellular parameter," HSC parameter," or "hematopoietic stem cell activity" refer to measurable components or qualities of HSCs, particularly components that can be accurately measured, most desirably in a high-throughput system. A cellular parameter can be any measurable parameter related to a phenotype, function, or behavior of a cell. Such cellular parameters include, changes in characteristics and markers of an HSC or HSC population, including but not limited to changes in viability, cell growth, expression of one or more or a combination of markers, such as cell surface determinants, such as receptors, proteins, including conformational or posttranslational modification thereof, lipids, carbohydrates, organic or inorganic molecules, nucleic acids, e.g. mRNA, DNA, global gene expression patterns, etc. Such cellular parameters can be measured using any of a variety of assays known to one of skill in the art. For example, viability and cell growth can be measured by assays such as Trypan blue exclusion, CFSE dilution, and $^3$H incorporation. Expression of protein or polypeptide markers can be measured, for example, using flow cytometric assays, Western blot techniques, or microscopy methods. Gene expression profiles can be assayed, for example, using microarray methodologies and quantitative or semi-quantitative real-time PCR assays.

A cellular parameter can also refer to a functional parameter or functional activity. While most cellular parameters will provide a quantitative readout, in some instances a semi-quantitative or qualitative result can be acceptable. Readouts can include a single determined value, or can include mean, median value or the variance, etc. Characteristically a range of parameter readout values can be obtained for each parameter from a multiplicity of the same assays. Variability is expected and a range of values for each of the set of test parameters will be obtained using standard statistical methods with a common statistical method used to provide single values.

As used here the term "increased growth rate" refers to a decrease in the doubling time of an HSC isolated from a Fdg5 knock-in mouse expressing a hematopoietic stem cell identifier described herein of at least 2 hours (h) compared to the doubling time of a corresponding HSC cultured in substantially similar growth conditions, except for the presence of the candidate agent. In some embodiments of these aspects and all such aspects described herein, it is preferred that the doubling time of the cell is at least 3 hours less, at least 4 hours less, at least 5 hours less, at least 6 hours less, at least 7 hours less, at least 8 hours less, at least 9 hours less, at least 10 hours less, at least 11 hour less, at least 12 hours less, at least 13 hours less, at least 14 hours less, at least 15 hours less, at least 16 hours less, at least 17 hours less, at least 18 hours less, at least 19 hours less, at least 20 hours less, at least 21 hour less, at least 22 hours less, at least 23 hours less, at least 24 hours less, or more compared to the doubling time of a corresponding HSC cultured in substantially similar growth conditions, except for the presence of the candidate agent.

In some embodiments, to determine doubling time, one can simply count the number of cells at two or more time points (e.g., using Trypan Blue staining) and optionally plot the relationship between number of cells and time on a graph. The slope of the linear portion of the graph can be used to determine the doubling time of a cell culture during the active growth phase. Other methods for determining doubling time are known in the art and can be used with the methods and cells described herein.

Also provided herein, in some aspects, are ex vivo methods for screening agents to modulate hematopoietic stem cell activity, such methods comprising the steps of: exposing a population of cells isolated from a heterozygous Fdg5 knock-in mouse expressing a hematopoietic stem cell identifier to a candidate agent ex vivo; and comparing hematopoietic stem cell activity of the population of cells expressing the hematopoietic stem cell identifier exposed to the candidate agent to a population of cells expressing the hematopoietic stem cell identifier that has not been exposed to the candidate agent, wherein if the hematopoietic stem cell activity is increased or decreased in the population of cells expressing the hematopoietic stem cell identifier exposed to the candidate agent compared to the population of cells expressing the hematopoietic stem cell identifier that has not been exposed to the candidate agent, the agent is indicated as an agent that modulates hematopoietic stem cell activity.

In some embodiments of these aspects, and all such aspects described herein, the hematopoietic stem cell activity is self-renewal activity. In other words, the screening methods described herein are useful for identifying agents or compounds that increase hematopoietic stem cell self-renewal or hematopoietic stem cell differentiation, promote hematopoietic stem cell maturation, or enhance hematopoietic stem cell survival.

Functional aspects of HSC phenotypes, or hematopoietic stem cell activities, such as the ability of an HSC to give rise to long-term, multi-lineage reconstitution in a recipient, can be easily determined by one of skill in the art using routine methods known in the art, and as described herein, for example, in the Examples.

The in vitro or ex vivo assays described herein can, in some embodiments, be performed on cells isolated from Fdg5 knock-in animals, as well as, in some embodiments, on tissue preparations or extracts from such animals, such as bone marrow, spleen or lymph node preparations. In particular, rapid, high throughput screening, of, for example, small molecule libraries, to identify candidate agents can be carried out using HSCs isolated from Fdg5 knock-in animals and incubating such cells with a candidate agent, or plurality of candidate agents, and assaying cellular proliferation, multipotent differentiation potential, survival, and the like. In some embodiments of these aspects and all such aspects described herein, screening of multiple or a plurality of candidate compounds, such as libraries of compounds, using high-throughput methods can be performed.

Figure 14:
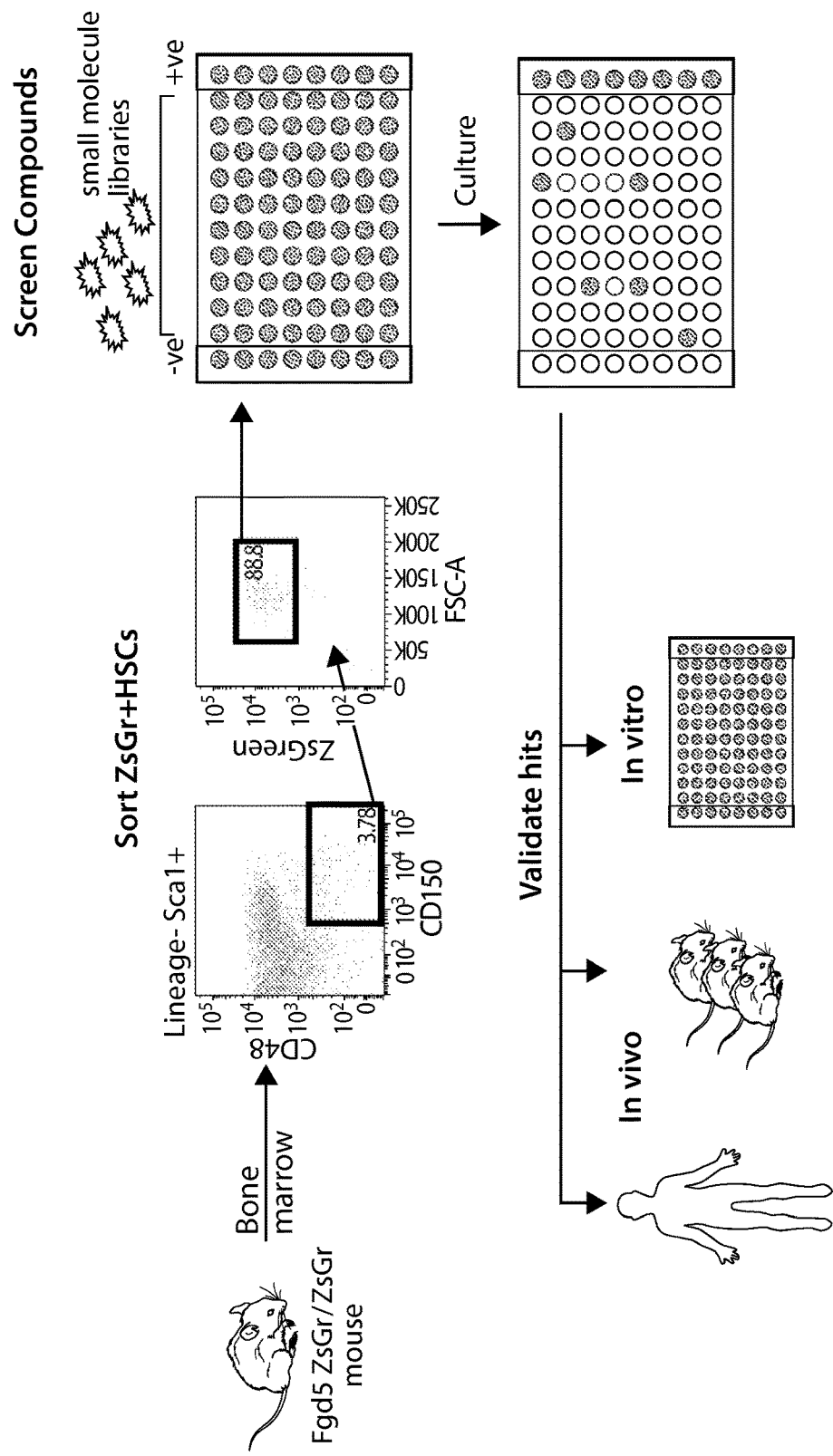
FIG. 14 depicts an exemplary embodiment of a small molecule screening strategy. ZsGreen$^+$ HSCs from the Fgd5 reporter mice are used to discover small molecules that can maintain and/or expand HSC during ex vivo culture. Hits are validated in vitro and in vivo using both mouse and human HSCs. Molecules for screening include, for example, 5000-7000 small molecule compounds targeting kinases, epigenetic molecules, growth factors, G-protein coupled receptors etc.
Figure 15A:
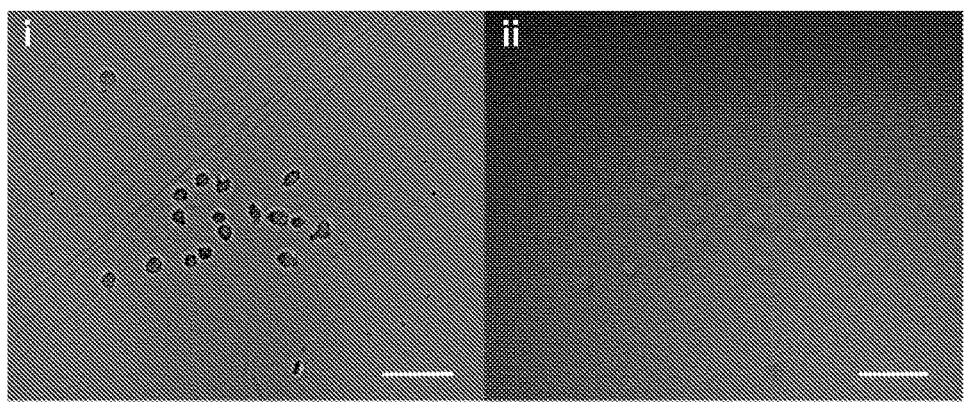
FIGS. 15A-15B show detection of ZsGreen$^+$ cells at day 2 post seeding of 15ZsGreen HSCs/well (FIG. 15A) or 15 ZsGreen$^+$HSCs/well (FIG. 15B) into a round bottom 96 well plate. HSCs defined as Lineage$^-$Sca1$^+$CD150$^+$CD48$^-$. Scale bar=50 μM; i) Brightfield; ii) ZsGreen.
Figure 15B:
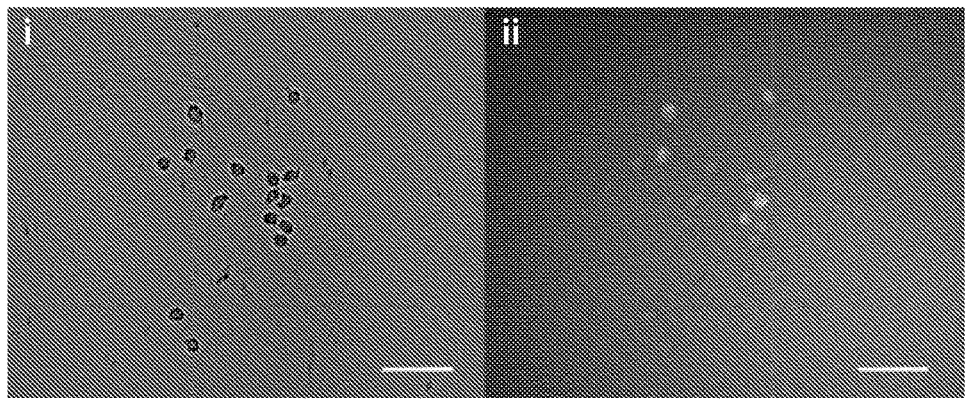
Figure 16A:
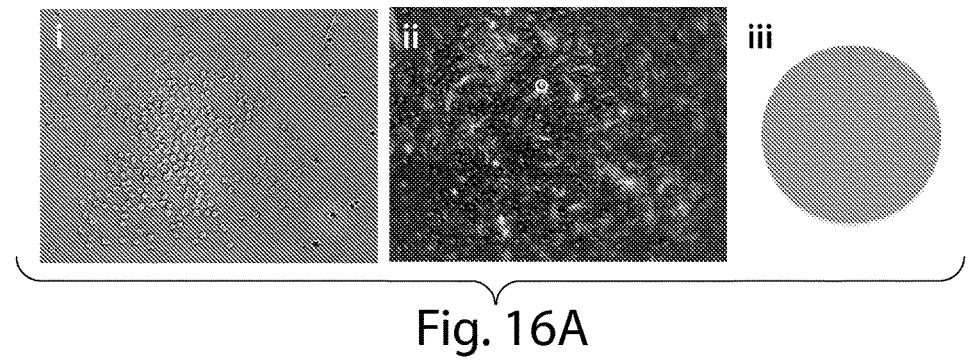
FIGS. 16A-16C demonstrate validity of screening approach. Day 6 post-seeing of ZsGreen$^+$HSCs into 0.1% DMSO alone (negative control) (FIG. 16A) or with small molecules X and Y respectively (FIGS. 16B-16C). i) Brightfield; ii) ZsGreen. Circles indicate ZsGreen+ cells; iii) % GFP at day 6 of indicated wells. Green=% ZsGreen+ cells; Grey=% ZsGreen− cells.
Figure 16B:
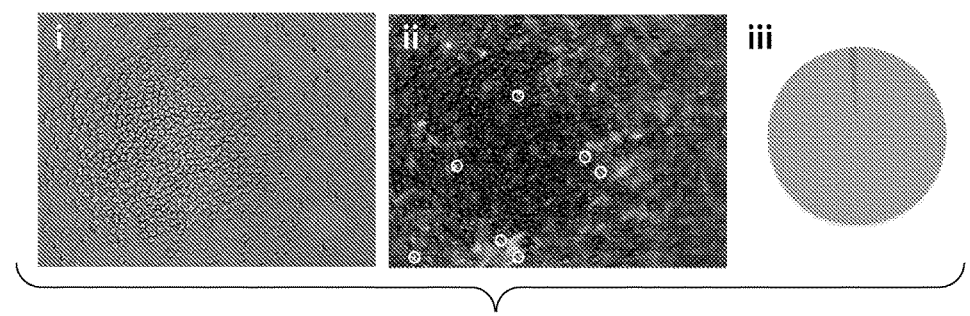
Figure 16C:
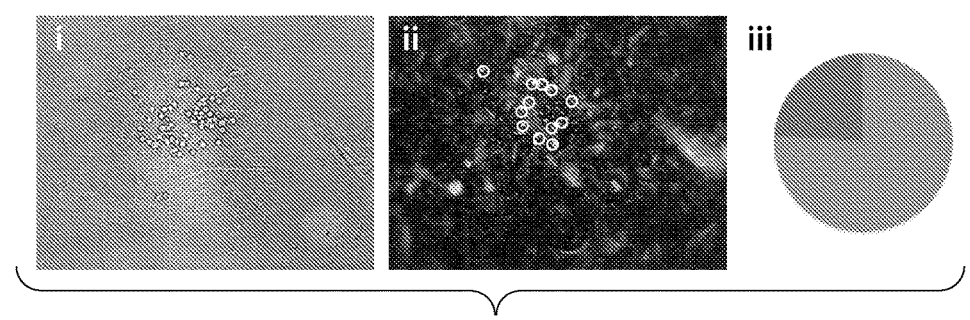
Figure 17A:
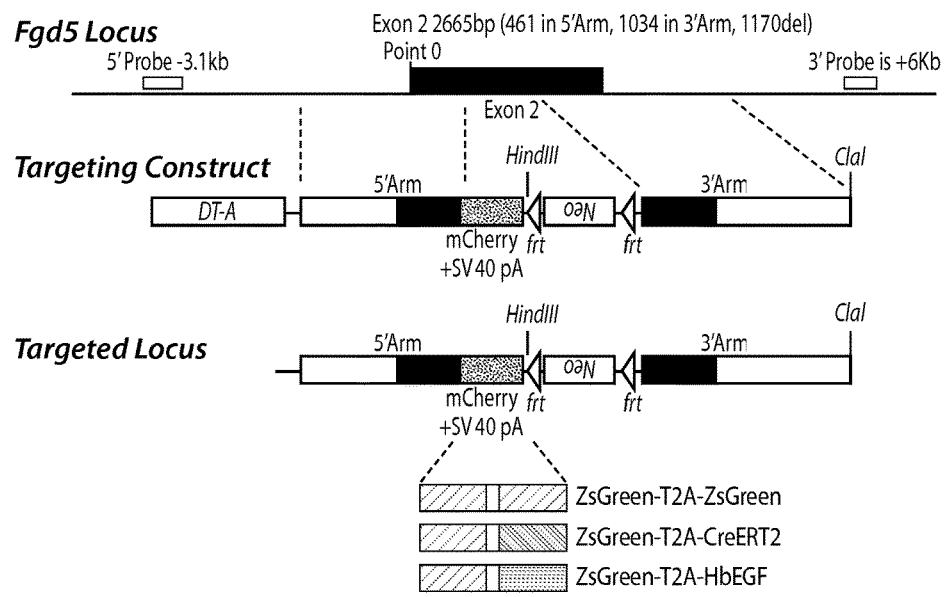
FIGS. 17A-17B demonstrate generation of Fgd5 Knock-in mice with multiple cassettes.
Figure 17B:
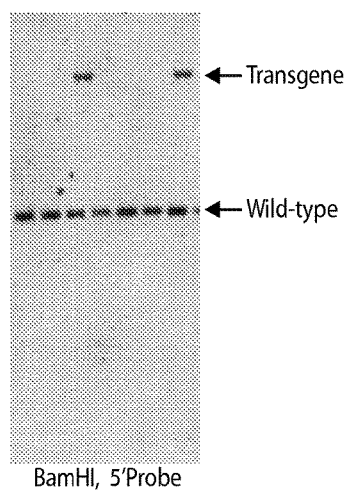
Figure 18A:
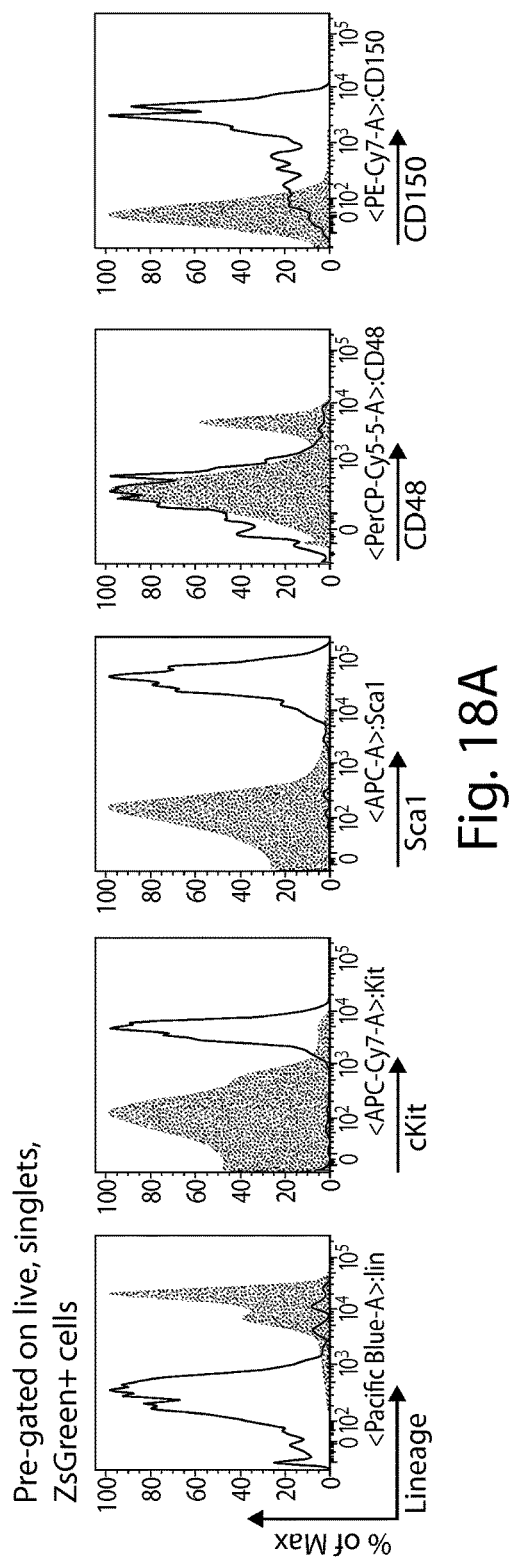
FIGS. 18A-18B demonstrate that ZsGreen marks hematopoietic stem and progenitor cells in Fgd5-ZsGreen reporter mice.
Figure 18B:
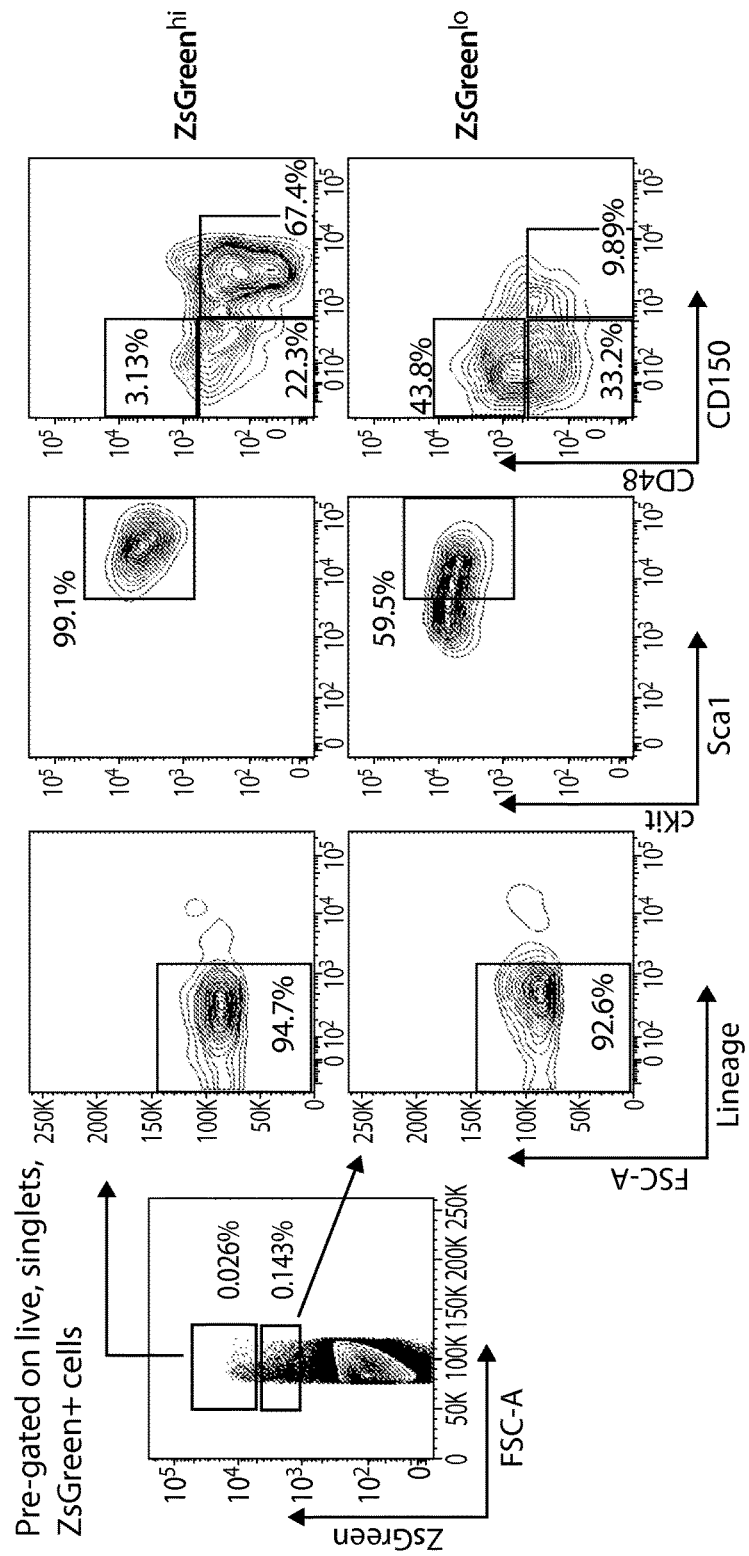

For example, as described herein at FIGS. 14-16C, a library of small molecule compounds can be screened using HSCs isolated from Fdg5 knock-in animals in a high-throughput screening method. For example, as depicted at FIG. 14, cells, such as bone marrow cells, can be isolated from an Fdg5 knock-in animal expressing a reporter molecule, such as ZsGreen or GFP, under the control of the endogenous Fdg5 locus. The isolated cells can then, in some embodiments, be sorted using, for example, a flow cytometric cell sorter, or a magnetic bead based sorting mechanism, on the basis of expression or lack of expression of cell surface molecules, and on the basis of the reporter molecule expressed by the Fdg5 knock-in animal. For example, in some embodiments, the isolated cells can be sorted on the basis of being Lineage$^-$Sca1$^+$CD48$^-$CD150$^+$Reporter$^+$. The isolated cells or sorted isolated cells can then be cultured, for example, in a multi-well format, such that individual wells are exposed to one or more small molecule compounds from, for example, a plurality of small molecule compounds, such as a library of small molecules, or a plurality of libraries of small molecules. Positive and negative control wells are also included to ensure validity of the screening method. The HSCs isolated from Fdg5 knock-in animals are then cultured with the small molecule compound and cultured for a suitable period of time, in order to measure a change in a desired HSC parameter or hematopoietic stem cell activity in the presence of the small molecule compounds, and are typically compared to cells that are cultured, for example, in parallel without exposure or contacting with the small molecule compound. An example of experimental data demonstrating such a screening method is found, for example, at FIGS. 15A, 15B, 16A, 16B, and 16C, which show results of small molecules X and Y on cell growth of isolated and sorted bone marrow HSCs obtained from Fdg5 knock-in animals expressing the reporter molecule ZsGreen.

Small molecule compounds identified using such screening methods can then further be validated in vitro or in vivo. For example, in vivo validation can involve administering the candidate small molecule compound to a test animal or test subject, and desired HSC parameters are evaluated before and after administration. The response of the treated test animal or test subject is compared to those of untreated test animals or subjects, and statistical analyses are performed to identify any differences in the desired HSC parameter. In other embodiments, in vivo validation can involve a "transplantation model" in which HSC cells treated with the candidate small molecule agent are transplanted to an animal, and the functional potential of the transplanted cells, such as the ability to self-renew in vivo, is determined and measured.

Accordingly, provided herein in some aspects are the screening methods described herein are methods of high-throughput screening of a plurality of small molecule compounds, such as a libraries of small molecule compounds, for identifying small molecules that modulate, e.g., increase or decrease, HSC activity or function comprising:

(i) Exposing or contacting, in vitro or in vivo, a plurality of HSC cells or cell populations isolated from a heterozygous Fdg5 knock-in animal expressing an HSC identifier to a small molecule compound, or a combination of small molecule compounds, for example, obtained from a small molecule library comprising a plurality of small molecule compounds; and (ii) Measuring an HSC activity or function of each of the exposed or contacted plurality of HSC cells or cell populations, and measuring an HSC activity of HSC cells or cell populations isolated from a heterozygous Fdg5 knock-in animal expressing a HSC identifier that have not been exposed to a small molecule compound, wherein when the HSC activity or function is increased or decreased in any of the exposed or contacted plurality of HSC cells or cell populations compared to the HSC cells or cell populations that have not been exposed to a small molecule compound, the small molecule compound is identified as small molecule that modulates HSC activity or function.

In some embodiments of these methods and all such methods described herein, the plurality of HSC cells or cell populations isolated from a heterozygous Fdg5 knock-in animal are plated in parallel on, for example one or more multiwall cell culture plates.

In some embodiments of these methods and all such methods described herein, the plurality of HSC cells or cell populations isolated from a heterozygous Fdg5 knock-in animal are bone marrow cells.

In some embodiments of these methods and all such methods described herein, the plurality of HSC cells or cell populations isolated from a heterozygous Fdg5 knock-in animal are sorted prior to the exposing or contacting step. In some embodiments, the plurality of HSC cells or cell populations isolated from a heterozygous Fdg5 knock-in animal are sorted on the basis of being Lineage$^-$Sca1$^+$CD48$^-$CD150$^+$HSC identifier$^+$.

In some embodiments of these methods and all such methods described herein, the HSC activity or function is selected from HSC proliferation, HSC differentiation, HSC migration, HSC survival or maintenance, and HSC self-renewal activities.

In some embodiments of these methods and all such methods described herein, the plurality of HSC cells or cell populations isolated from a heterozygous Fdg5 knock-in animal expressing an HSC identifier are exposed or contacted with the different small molecule compounds for at least 30 minutes.

In some embodiments of these methods and all such methods described herein, the plurality of HSC cells or cell populations isolated from a heterozygous Fdg5 knock-in animal expressing an HSC identifier are exposed or contacted in a media solution.

In some embodiments of these methods and all such methods described herein, the method further comprises a step of in vitro validation, in vivo validation, or both, of each of small molecules that modulates HSC activity or function identified in step (ii).

In some aspects, a test compound or test agent is screened in vivo using the Fdg5 knock-in animals described herein. A test compound is typically administered one or more Fdg5 knock-in animals and desired HSC parameters are evaluated before and after administration. The response of treated Fdg5 knock-in animals is compared to those of untreated Fdg5 knock-in animals, and statistical analyses are performed to identify any differences in the desired HSC parameter.

As used herein, a "non-knock-in," "normal mouse," or "control mouse" refers to a wild-type mouse or a mouse in which the nucleic acid sequence, activity or expression of the Fdg5 gene has not been manipulated.

HSCs isolated from Fdg5 knock-in animals described herein can be exposed to or cultured with a candidate agent for various times. Suitable times can be determined by those of skill in the art by monitoring stem cell morphology, or other phenotypic characteristics of HSCs, including but not limited to, increase in the growth rate (e.g., decrease in doubling time), ability to expand from a single cell, etc. For example, cells can be treated for 10 minutes, 15 minutes, 30 minutes etc., or more often, treated for hours or days, e.g., 1 hour, 2 hours, 3 hours, 4 hours, up to 24 hours, days (e.g., 1 day, 2 days, 3 days, 4 days, 5, days 6 days, 7 days), or even weeks (e.g., 2 weeks, 3 weeks, 4 weeks, 5 weeks, 6 weeks, 7 weeks, 8 weeks, 9 weeks, 10 weeks, 11 weeks, 12 weeks or more). The duration of exposure or treatment with a candidate agent will be that treatment necessary to achieve at least, the ability to expand from a single cell and decreased doubling time and the ability to be passaged via trypsin digest. In some embodiments of the aspects described herein, HSC cells or cell populations isolated from a heterozygous Fdg5 knock-in animal expressing an HSC identifier are first cultured prior to the exposure to the candidate agent. In some embodiments of the aspects described herein, HSC cells or cell populations isolated from a heterozygous Fdg5 knock-in animal expressing an HSC identifier are cultured subsequent to a given timeframe of exposure to the candidate agent in the absence of the candidate agent, i.e., the candidate agent is removed from the cells after a desired period of exposure.

The term "candidate agent" is used herein to mean any agent that is being examined for ability to modulate one or more HSC activities, as the term is used herein. Although the method generally is used as a screening assay to identify previously unknown molecules that can act as a therapeutic agent, the screening described herein can also be used to confirm that an agent known to have such activity, in fact has the activity, for example, in standardizing the activity of the therapeutic agent.

A candidate agent can be any type of molecule, including, for example, a peptide, a peptidomimetic, a polynucleotide, or a small organic molecule, that one wishes to examine for the ability to modulate a desired HSC activity, such as, for example, HSC proliferation. It will be recognized that the methods described herein are readily adaptable to a high throughput format and, therefore, the methods are convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. Nos. 5,622,699; 5,206,347; Scott and Smith, Science 249:386-390, 1992; Markland et al., Gene 109:1319, 1991; each of which is incorporated herein by reference in their entireties); a peptide library (U.S. Pat. No. 5,264,563, which is incorporated herein by reference); a peptidomimetic library (Blondelle et al., Trends Anal. Chem. 14:8392, 1995; a nucleic acid library (O'Connell et al., supra, 1996; Tuerk and Gold, supra, 1990; Gold et al., slpra, 1995; each of which is incorporated herein by reference in their entireties); an oligosaccharide library (York et al., Carb. Res., 285: 99128, 1996; Liang et al., Science, 274:1520-1522, 1996; Ding et al., Adv. Expt. Med. Biol., 376:261-269, 1995; each of which is incorporated herein by reference in their entireties); a lipoprotein library (de Kruif et al., FEBS Lett., 399:232-236, 1996, which is incorporated herein by reference in their entireties); a glycoprotein or glycolipid library (Karaoglu et al., J. Cell Biol., 130:567-577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference in their entireties).

Accordingly, the term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. A candidate agent also includes any chemical, entity or moiety, including without limitation synthetic and naturally-occurring non-proteinaceous entities. In certain embodiments, the candidate agent is a small molecule having a chemical moiety. Such chemical moieties can include, for example, unsubstituted or substituted alkyl, aromatic, or heterocyclyl moieties and typically include at least an amine, carbonyl, hydroxyl or carboxyl group, frequently at least two of the functional chemical groups, including macrolides, leptomycins and related natural products or analogues thereof. Candidate agents can be known to have a desired activity and/or property, or can be selected from a library of diverse compounds.

Also included as candidate agents are pharmacologically active drugs, genetically active molecules, etc. Such candidate agents of interest include, for example, chemotherapeutic agents, hormones or hormone antagonists, growth factors or recombinant growth factors and fragments and variants thereof. Exemplary of pharmaceutical agents suitable for use with the screening methods described herein are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all of which are incorporated herein by reference in their entireties. Also included are toxins, and biological and chemical warfare agents, for example see Somani, S. M. (Ed.), "Chemical Warfare Agents," Academic Press, New York, 1992), the contents of which is herein incorporated in its entirety by reference.

Candidate agents, such as chemical compounds, can be obtained from a wide variety of sources including libraries of synthetic or natural compounds, such as small molecule compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Synthetic chemistry transformations and protecting group methodologies (protection and deprotection) useful in synthesizing the candidate compounds for use in the screening methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof, the contents of each of which are herein incorporated in their entireties by reference.

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233, the contents of each of which are herein incorporated in their entireties by reference.

Libraries of candidate agents can also, in some embodiments, be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310; Ladner supra.), the contents of each of which are herein incorporated in their entireties by reference.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "drug" or "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The route of administration of a candidate agent will depend, in part, on the chemical structure of the candidate agent. Peptides and polynucleotides, for example, are not particularly useful when administered orally because they can be degraded in the digestive tract. However, methods for chemically modifying peptides, for example, to render them less susceptible to degradation by endogenous proteases or more absorbable through the alimentary tract are well known (see, for example, Blondelle et al., Trends Anal. Chem. 14:83-92, 1995; Ecker and Crooke, Bio/Technology, 13:351-360, 1995; each of which is incorporated herein by reference). In addition, a peptide agent can be prepared using D-amino acids, or can contain one or more domains based on peptidomimetics, which are organic molecules that mimic the structure of peptide domain; or based on a peptoid such as a vinylogous peptoid.

When a candidate agent is being administered in vivo to an Fdg5 knock-in animal, it can be administered in vivo by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the candidate agent can be administered by injection, intubation, orally or topically, the latter of which can be passive, for example, by direct application of an ointment, or active, for example, using a nasal spray or inhalant, in which case one component of the composition is an appropriate propellant.

The total amount of a candidate agent to be administered in practicing a method of the invention can be administered to a subject as a single dose, either as a bolus or by infusion over a relatively short period of time, or can be administered using a fractionated treatment protocol, in which multiple doses are administered over a prolonged period of time. The candidate agent can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

Administration of candidate agents in vivo is typically performed via parenteral route or administration, or by intraperitoneal, oral, intravenous, spray, or intradermal routes. The response and the parameters measured for the treated Fdg5 knock-in animals are compared to the ones of Fdg5 knock-in animals in the absence of such treatment, or using a control agent, using standard statistical methods (i.e. one way ANOVA, Bonferroni test).

Data obtained from cell based assays and animal studies can be used in formulating a range of dosage of the candidate agent for use in humans, for example. The dosage of the drug candidate, homologue, analogue, or derivative, lies preferably within a range of concentrations that, following administration by a particular route, produce a circulating concentration consistent with the ED50 and having little or no toxicity.

Embodiments of the various aspects described herein can be illustrated by the following paragraphs:

A. A nucleic acid construct comprising, in a 5' to 3' direction, a 5' sequence of an Fgd5 gene of SEQ ID NO: 1, a hematopoietic stem cell identifier sequence, and a 3' sequence of an Fgd5 gene of SEQ ID NO: 1.

B. The nucleic acid construct of paragraph A, wherein the hematopoietic stem cell identifier is a fluorescent reporter sequence.

C. The nucleic acid construct of paragraph B, wherein the fluorescent reporter sequence is an mCherry fluorescent reporter sequence of SEQ ID NO: 5

D. The nucleic acid construct of any one of paragraphs A-C, wherein the 5' sequence of an Fgd5 gene of SEQ ID NO: 1 comprises SEQ ID NO: 3.

E. The nucleic acid construct of any one of paragraphs A-D, wherein the 3' sequence of an Fgd5 gene of SEQ ID NO: 1 comprises SEQ ID NO: 4.

F. The nucleic acid construct of any one of paragraphs A-E, further comprising a sequence encoding a positive selection marker, or a sequence encoding a negative selection marker or both.

G. A vector comprising the nucleic acid construct of any one of paragraphs A-F.

H. A heterozygous hematopoietic stem cell identifier knock-in mouse comprising the nucleic acid construct of any one of paragraphs A-F at an endogenous Fgd5 gene locus, wherein the nucleic acid construct is/has been introduced into the endogenous Fgd5 gene locus by homologous recombination, wherein the expression of the hematopoietic stem cell identifier sequence is operably linked to the endogenous Fgd5 gene locus, and wherein said hematopoietic stem cell identifier sequence replaces a portion of a sequence of the endogenous Fgd5 gene locus.

I. An isolated hematopoietic stem cell comprising a hematopoietic stem cell identifier sequence operably linked to the endogenous Fgd5 gene locus obtained from the heterozygous reporter knock-in mouse of paragraph H.

J. A method of isolating hematopoietic stem cells comprising selecting or removing cells from the heterozygous reporter knock-in mouse of paragraph H expressing the hematopoietic stem cell identifier sequence.

K. The method of paragraph J, wherein the selecting or removing comprises physical sorting of cells from the heterozygous reporter knock-in mouse of paragraph H.

L. The method of paragraph K, wherein the physical sorting comprises flow cytometric based sorting.

M. The method of paragraph K, wherein the physical sorting comprises magnetic-bead based sorting.

N. An ex vivo method for screening agents to expand hematopoietic stem cells comprising the steps of: exposing a population of cells isolated or selected from the heterozygous hematopoietic stem cell identifier knock-in mouse of paragraph H expressing the hematopoietic stem cell identifier to a candidate agent ex vivo; and comparing cell growth rate of the population of cells expressing the hematopoietic stem cell identifier exposed to the candidate agent to a population of cells expressing the hematopoietic stem cell identifier that has not been exposed to the candidate agent, wherein if the cell growth rate is increased in the population of cells expressing the hematopoietic stem cell identifier exposed to the candidate agent compared to the population of cells expressing the hematopoietic stem cell identifier that has not been exposed to the candidate agent, the agent is indicated as an agent that expands hematopoietic stem cells.

O. An ex vivo method for screening agents to modulate hematopoietic stem cell activity comprising the steps of: exposing a population of cells isolated from the heterozygous hematopoietic stem cell identifier knock-in mouse of paragraph H expressing the hematopoietic stem cell identifier to a candidate agent ex vivo; and comparing hematopoietic stem cell activity of the population of cells expressing the hematopoietic stem cell identifier exposed to the candidate agent to a population of cells expressing the hematopoietic stem cell identifier that has not been exposed to the candidate agent, wherein if the hematopoietic stem cell activity is increased or decreased in the population of cells expressing the hematopoietic stem cell identifier exposed to the candidate agent compared to the population of cells expressing the hematopoietic stem cell identifier that has not been exposed to the candidate agent, the agent is indicated as an agent that modulates hematopoietic stem cell activity.

P. The ex vivo method for screening agents of paragraph O, wherein the hematopoietic stem activity is self-renewal.

Q. A method or assay for large-scale screening and identification of small molecule compounds that modulate hematopoietic stem cell activity comprising the steps of: exposing one or more populations of cells isolated from a heterozygous hematopoietic stem cell identifier knock-in mouse of paragraph H expressing the hematopoietic stem cell identifier to a library of small molecule candidate agents ex vivo or in vitro; and comparing hematopoietic stem cell activity of the population of cells expressing the hematopoietic stem cell identifier exposed to the library of small molecule candidate agents to the population of cells expressing the hematopoietic stem cell identifier that have not been exposed to the library of small molecule candidate agents, wherein if the hematopoietic stem cell activity is increased or decreased in the populations of cells expressing the hematopoietic stem cell identifier exposed to the library of small molecule candidate agents compared to the populations of cells expressing the hematopoietic stem cell identifier that have not been exposed to the library of small molecule candidate agents, the small molecule agent is identified as an agent that modulates hematopoietic stem cell activity.

R. The method or assay of paragraph Q, wherein the hematopoietic stem cell activity is self-renewal.

S. The method or assay of any one of paragraphs Q or R, wherein the hematopoietic stem cell activity is hematopoietic stem cell activity expansion.

T. The method or assay of any one of paragraphs Q-S, wherein the cells isolated from the heterozygous hematopoietic stem cell identifier knock-in mouse are bone marrow cells.

U. The method or assay of any one of paragraphs Q-T, wherein the cells isolated from a heterozygous hematopoietic stem cell identifier knock-in mouse are pre-sorted prior to the exposing step to identify cells expressing the hematopoietic stem cell identifier.

V. The method or assay of any one of paragraphs Q-U, wherein the cells or populations of cells exposed to the candidate agent or library of small molecule candidate agents are cultured.

W. The method or assay of any one of paragraphs Q-V, wherein the candidate agent(s) or small molecule candidate agent(s) identified using the screening methods and assays described herein are further subjected to an in vivo or in vitro validation step.

X. The method or assay of paragraph W, wherein the in vivo validation step evaluates functional potential of cells exposed to the candidate agent(s) or small molecule candidate agent(s) in a transplantation model.

Y. A method of high-throughput screening of a plurality of small molecule compounds for identifying small molecules that modulate HSC activity or function comprising:
(i) Exposing or contacting a plurality of HSC cells or cell populations isolated from a heterozygous Fdg5 knock-in animal expressing an HSC identifier to a small molecule compound, or combination of small molecule compounds; and
(ii) Measuring an HSC activity or function of each of the exposed or contacted plurality of HSC cells or cell populations, and measuring the HSC activity of HSC cells or cell populations isolated from a heterozygous Fdg5 knock-in animal expressing a HSC identifier that have not been exposed to a small molecule compound obtained from the small molecule library, wherein when the HSC activity or function is increased or decreased in any of the exposed or contacted plurality of HSC cells or cell populations compared to the HSC cells or cell populations that have not been exposed to a small molecule compound, the small molecule compound is identified as small molecule that modulates HSC activity or function.

Z. The method of paragraph Y, wherein the plurality of HSC cells or cell populations isolated from a heterozygous Fdg5 knock-in animal are bone marrow cells.

AA. The method of any one of paragraphs Y-Z, wherein the plurality of HSC cells or cell populations isolated from a heterozygous Fdg5 knock-in animal are sorted prior to the exposing or contacting step.

BB. The method of paragraph AA, wherein the plurality of HSC cells or cell populations isolated from a heterozygous Fdg5 knock-in animal are sorted on the basis of being Lineage $Sca1^+CD48^-CD150^+$HSC identifier$^+$.

CC. The method of any one of paragraphs Y-BB, wherein the HSC activity or function is selected from HSC proliferation, HSC differentiation, HSC migration, HSC survival, and HSC self-renewal activities.

DD. The method of any one of paragraphs Y-CC, wherein the plurality of HSC cells or cell populations isolated from a heterozygous Fdg5 knock-in animal expressing an HSC identifier are exposed or contacted with the different small molecule compounds for at least 30 minutes.

EE. The method or assay of any one of paragraphs Y-DD, wherein the plurality of HSC cells or cell populations isolated from a heterozygous Fdg5 knock-in animal expressing an HSC identifier are exposed or contacted in a media solution.

FF. The method of any one of paragraphs Y-EE, wherein the method further comprises a step of in vitro validation, in vivo validation, or both, of each of small molecules that modulates HSC activity or function identified in step (ii).

GG. The method of paragraph FF, wherein the in vivo validation step evaluates functional potential of HSCs exposed to the small molecule(s) in a transplantation model.

HH. An ex vivo method for screening agents that maintain or increase hematopoietic stem cell activity comprising the steps of: exposing a population of cells isolated from the heterozygous hematopoietic stem cell identifier knock-in mouse of paragraph H expressing the hematopoietic stem cell identifier to a candidate agent ex vivo; and comparing hematopoietic stem cell activity of the population of cells expressing the hematopoietic stem cell identifier exposed to the candidate agent to a population of cells expressing the hematopoietic stem cell identifier that has not been exposed to the candidate agent, wherein if the hematopoietic stem cell activity is increased or maintained in the population of cells expressing the hematopoietic stem cell identifier exposed to the candidate agent compared to the population of cells expressing the hematopoietic stem cell identifier that has not been exposed to the candidate agent, the agent is indicated as an agent that maintains hematopoietic stem cell activity.

II. The ex vivo method for screening agents of paragraph HH, wherein the hematopoietic stem activity is self-renewal.

JJ. The ex vivo method for screening agents of paragraph HH, wherein the hematopoietic stem activity is hematopoietic multipotency.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. Other than in the operating examples, or where otherwise indicated, all numbers expressing quantities of ingredients or reaction conditions used herein should be understood as modified in all instances by the term "about." The term "about" when used in connection with percentages can mean±1%.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

EXAMPLES

Hematopoietic stem cells (HSCs) function to maintain blood homeostasis throughout life by their unique ability to differentiate into all blood cell types and to self-renew. These properties, along with the robust ability of HSCs to engraft myeloablated recipients in the setting of bone marrow transplantation, have established the clinical paradigm for therapeutic stem cell use (Weissman, 2000).

Originally described in the 1960s by Till and McCulloch and colleagues, HSCs were first experimentally defined by their ability to form macroscopic colonies in the spleens (CFU-S) of irradiated recipients after bone marrow transplantation that histological examination revealed contained multiple blood lineages (Till and Mc, 1961), and cytological examination revealed were clonally-derived (Becker et al., 1963). Together with the demonstration that a subset of CFU-S colonies had the potential to reform colonies when transplanted into secondary recipients (Siminovitch et al., 1963), the defining properties of hematopoietic stem cells—multi-potency and self-renewal—were established. In the fifty years since these seminal studies were conducted, the experimental study of HSCs has progressed and led to an understanding of the biology of HSCs. These efforts included, in part, the development of a number of in vivo and in vitro assays that permitted evaluation of HSC self-renewal and multi-lineage potential, and methods that allowed purification of HSCs by fluorescence-activated cell sorting (FACS).

HSCs were initially reported to be enriched within the $Thy1^{low}Lineage^-$ fraction of the murine bone marrow (Muller-Sieburg et al., 1986), and subsequently cells with a $Thy1^{low}Lineage^- Sca1^+$ immunophenotype were shown to possess long-term multi-lineage repopulating activity (Spangrude et al., 1988). The immunophenotype of HSCs was further refined culminating with the demonstration that single cells purified from the $Lineage^-Sca1^+ckit^+CD34^{-/low}$ fraction of the bone marrow of adult mice could function to long-term multi-lineage reconstitute irradiated recipients at the clonal level (Osawa et al., 1996). Additional cell surface markers that have also been used to enrich for HSC activity include; CD105 (Chen et al., 2002), Flk2/Flt3 (Christensen and Weissman, 2001), CD201/Procr (Balazs et al., 2006), Esam (Ooi et al., 2009; Yokota et al., 2009)) and CD150, CD48, CD244 (Kiel et al., 2005) amongst others. In addition to immunophenotype, intravital dye efflux activity has also proven to be an effective strategy for enriching for HSC activity (Bertoncello et al., 1985; Goodell et al., 1996; Wolf et al., 1993).

While immunophenotype combined with flow cytometry has become the principle technique used for identifying and studying diverse cells types, genetically engineered reporter mice have also enabled the identification and study of other cell types, including tissue-specific stem cells from other organs. For example, rapidly cycling intestinal stem cells were identified with the use of an Lgr5 reporter (Barker et al., 2007), whereas a population of more slowly cycling stem cells in the intestinal crypt were marked with a reporter for telomerase (Montgomery et al.). In the developing embryo, reporter strains for Isl1 (Laugwitz et al., 2005) and WT1 (Zhou et al., 2008) have been combined with lineage-tracing experiments to identify cardiac progenitors in the developing heart. In the skin, a Tet-inducible H2B-GFP reporter stain was used in conjunction with a keratinocyte-specific driver to isolate label-retaining stem cells in the epidermis (Tumbar et al., 2004). A similar H2B-GFP label retention strategy was later utilized by two independent groups to explore the turn-over of HSCs, showing that a label-retaining population of cells with potent HSCs activity reside in a state of prolonged dormancy during steady-state homeostasis (Foudi et al., 2009; Wilson et al., 2008). Importantly, depending upon vector design, introducing reporter cassettes into specific genomic loci (knock-in) can also lead to the disruption of the targeted gene permitting analysis of the null (knock-out) genotype when targeted alleles are crossed to homozygosity.

In order to identify novel genes that could be used to specifically report on HSC activity within the murine bone marrow, we performed a system-wide microarray screen of hematopoietic stem, progenitor and effector cells, and found a number of genes whose expression was highly restricted to the HSC compartment. Generation of mice with targeted reporter knock-in/knock-out alleles at three of the identified genes, Sult1a1, Clec1a and Fgd5 revealed that whereas knockout of Sult1a1 and Clec1a were viable and had normal HSC function, nullizygosity of Fgd5 was embryonic lethal at mid-gestation, although the generation and function of definitive HSCs was not affected by loss of Fgd5. Of the 3 reporter alleles, only Fgd5 explicitly marked immunophenotypic HSCs in the adult marrow at steady state, and after transplantation. Fgd5 explicitly marked immunophenotypic HSCs in the adult marrow at steady state, and after transplantation. Bone marrow cells isolated based solely on reporter signal of the Fgd5-reporter mice showed robust HSC activity, with all stem cell activity residing within the labeled fraction. These results demonstrate that HSCs can be identified and purified from the bone marrow of Fgd5-reporter mice by single color fluorescence, and that expression from the Fgd5 locus explicitly mark immunophenotypic and functional HSCs.

Figure 1B:
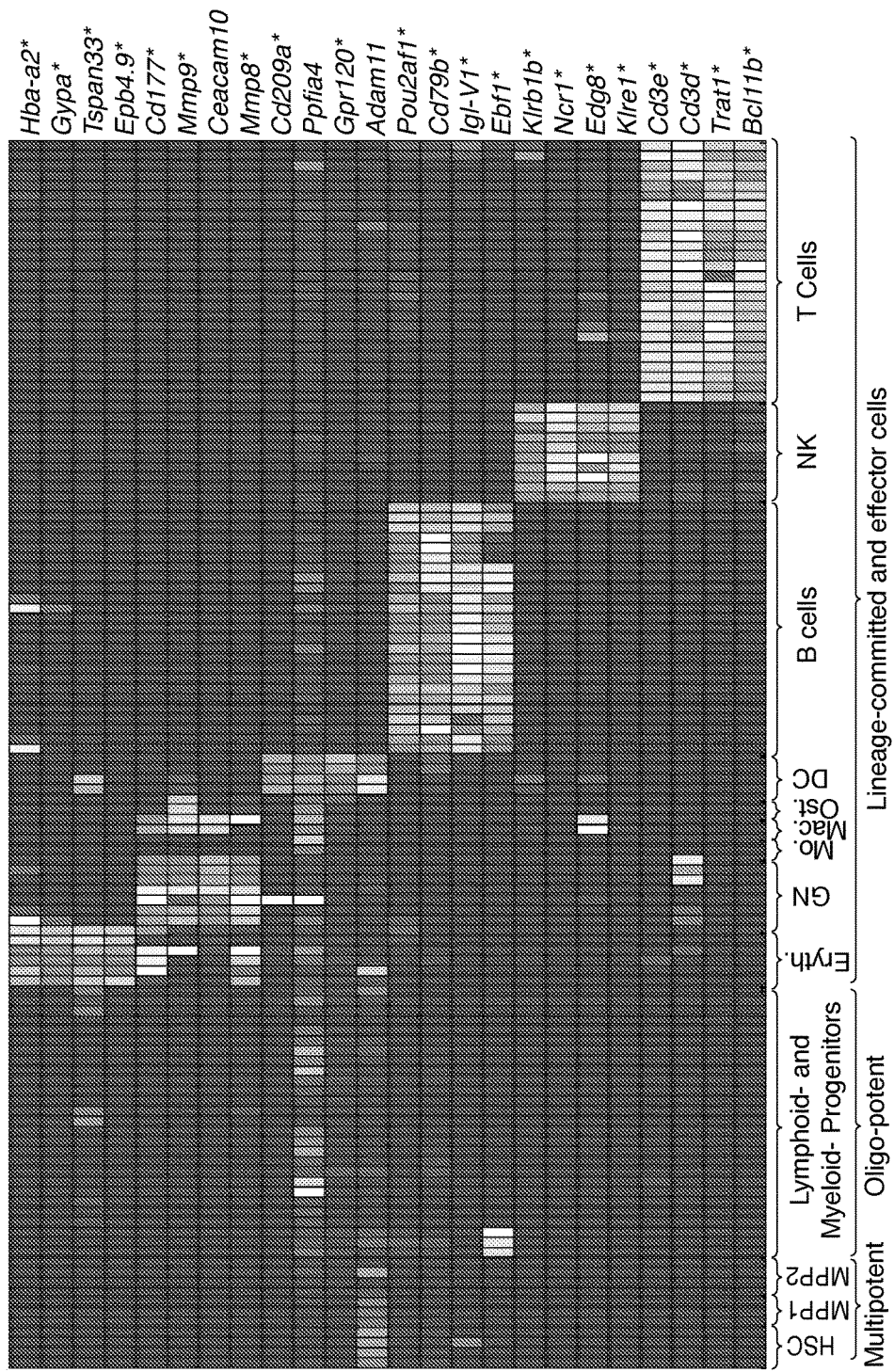

Systems-Wide Microarray Screen Identifies Genes with HSC-Restricted Expression in the Adult Hematopoietic System In order to identify genes specifically expressed in HSCs within the hematopoietic system we compiled the expression profiles of 37 different hematopoietic cell types comprising the vast majority of hematopoietic progenitor and effector cells (FIG. 1A). These data sets include published microarray data that were carefully curated from publicly available databases in addition to previously unpublished data of our own. As many of these data sets were generated in different labs we subjected them to number of quality control (QC) measures in accordance with current standards using the ArrayQualityMetrics package of R/Bioconductor (on the worldwide web at bioconductor.org). In total, 122 expression profiles passed QC were normalized together in a single database. Using this database we were readily able to identify genes that showed highly restricted expression in diverse hematopoietic cell types (FIG. 1B). Analysis of such cell type-specific gene lists indicated that previously established and validated cell-type-specific genes can be identified (FIG. 1B). These included genes known to mediate critical functions in specific cell types, as well as genes whose products are routinely used to phenotypically define different cell types with no known function in the specific cell type (FIG. 1B). For example, Ncr1, which is critical in NK cells (Gazit et al., 2006), Bcl11b that is involved in specifying T-cell identity (Wakabayashi et al., 2003), and the adult alpha-globin in erythroblasts (Paszty et al., 1995) were highly restricted to these cells in our database (FIG. 1B). Similar results were obtained for other hematopoietic cell types, and in all cases the cell type-specific genes were associated with a very high degree of statistical confidence, due to the fact that only FACS purified cells were used in the generation of the data, and also because of the large number of samples and biological replicates analyzed (Table 1). These results indicate that our database can be used as an effective discovery tool for genes specifically expressed in diverse hematopoietic cell types.

Figure 1C:
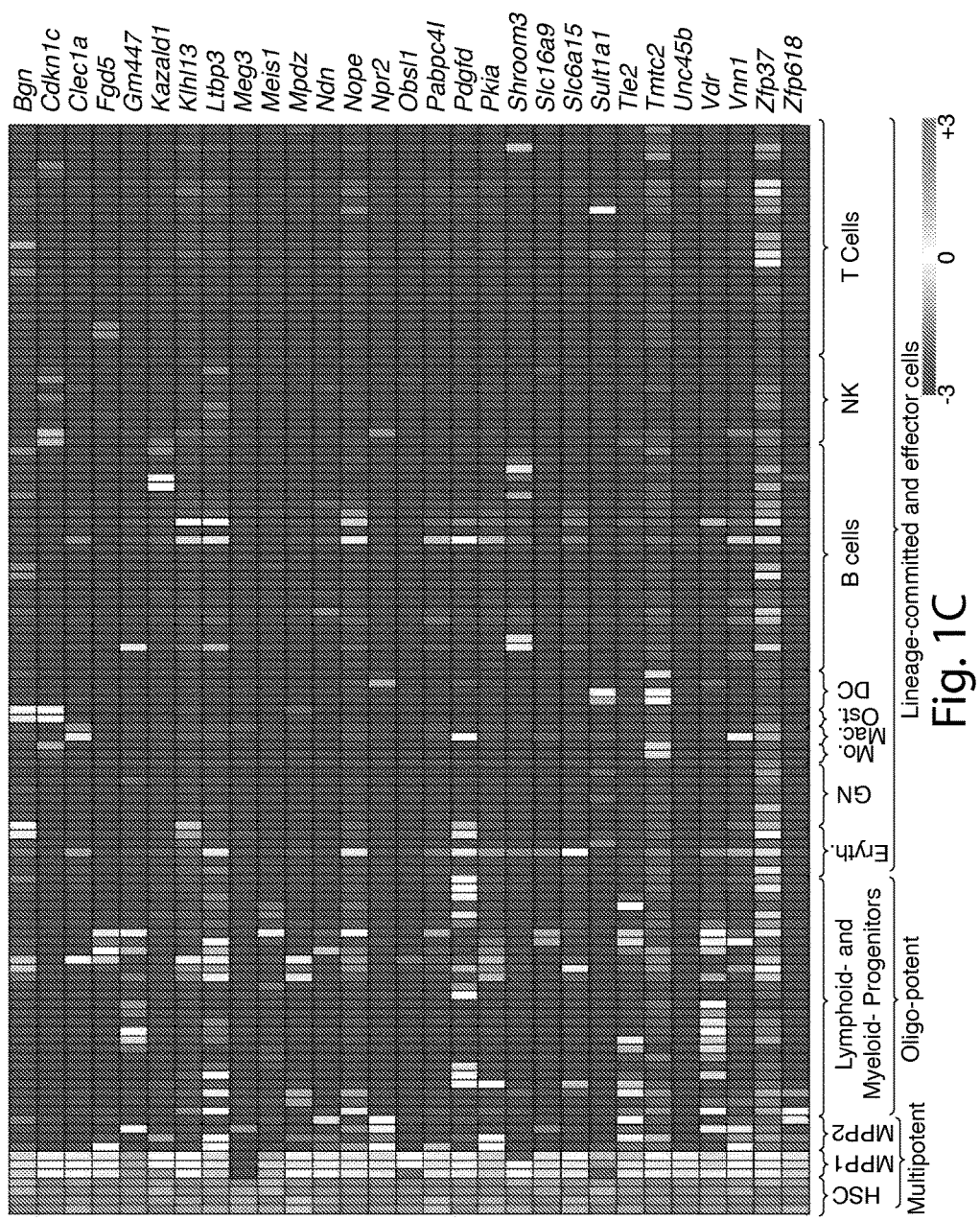
Figures 1, 8A:
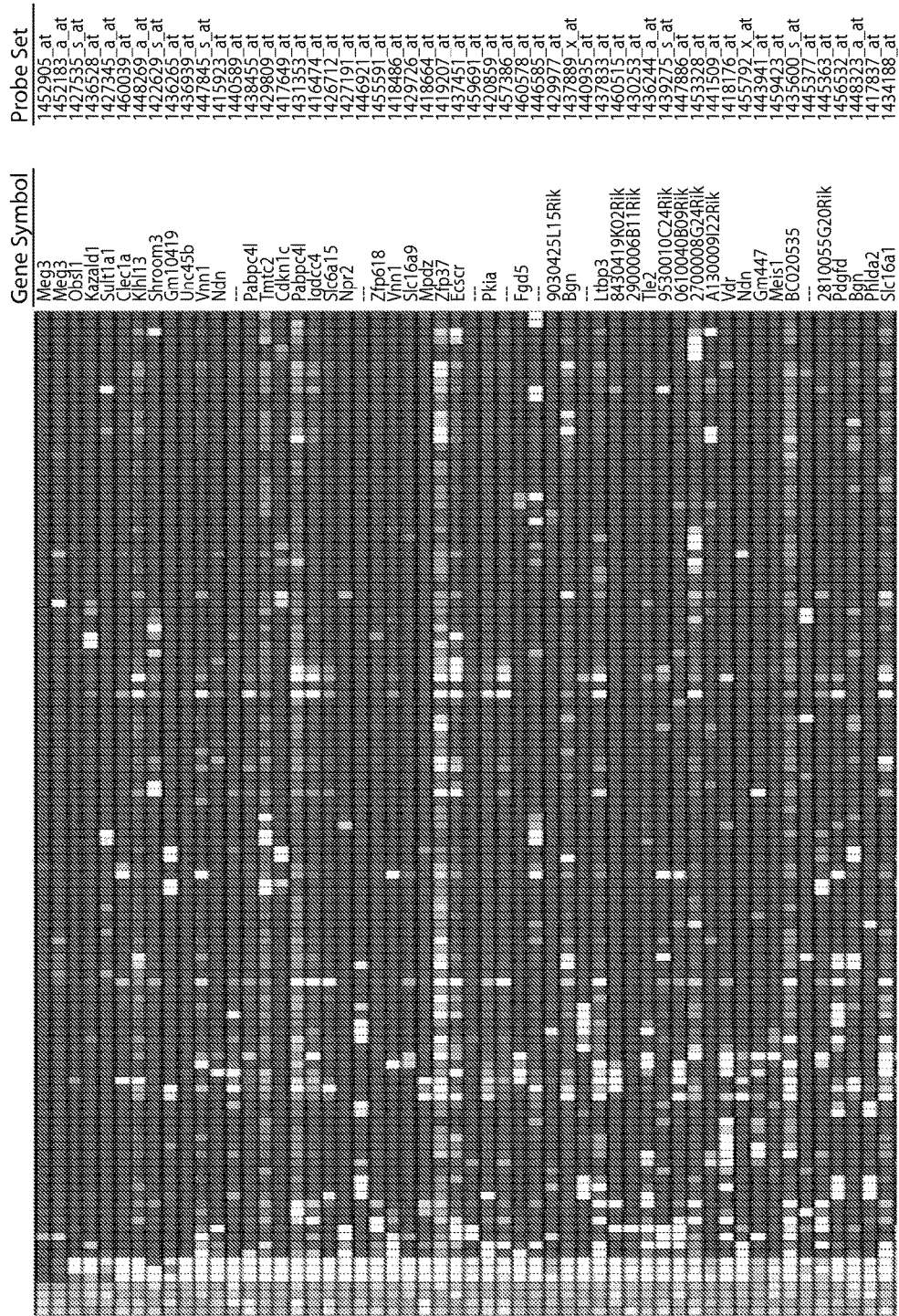
FIGS. 8A-8B depict heatmaps of HSC-specific genes.
Figures 2, 8A:
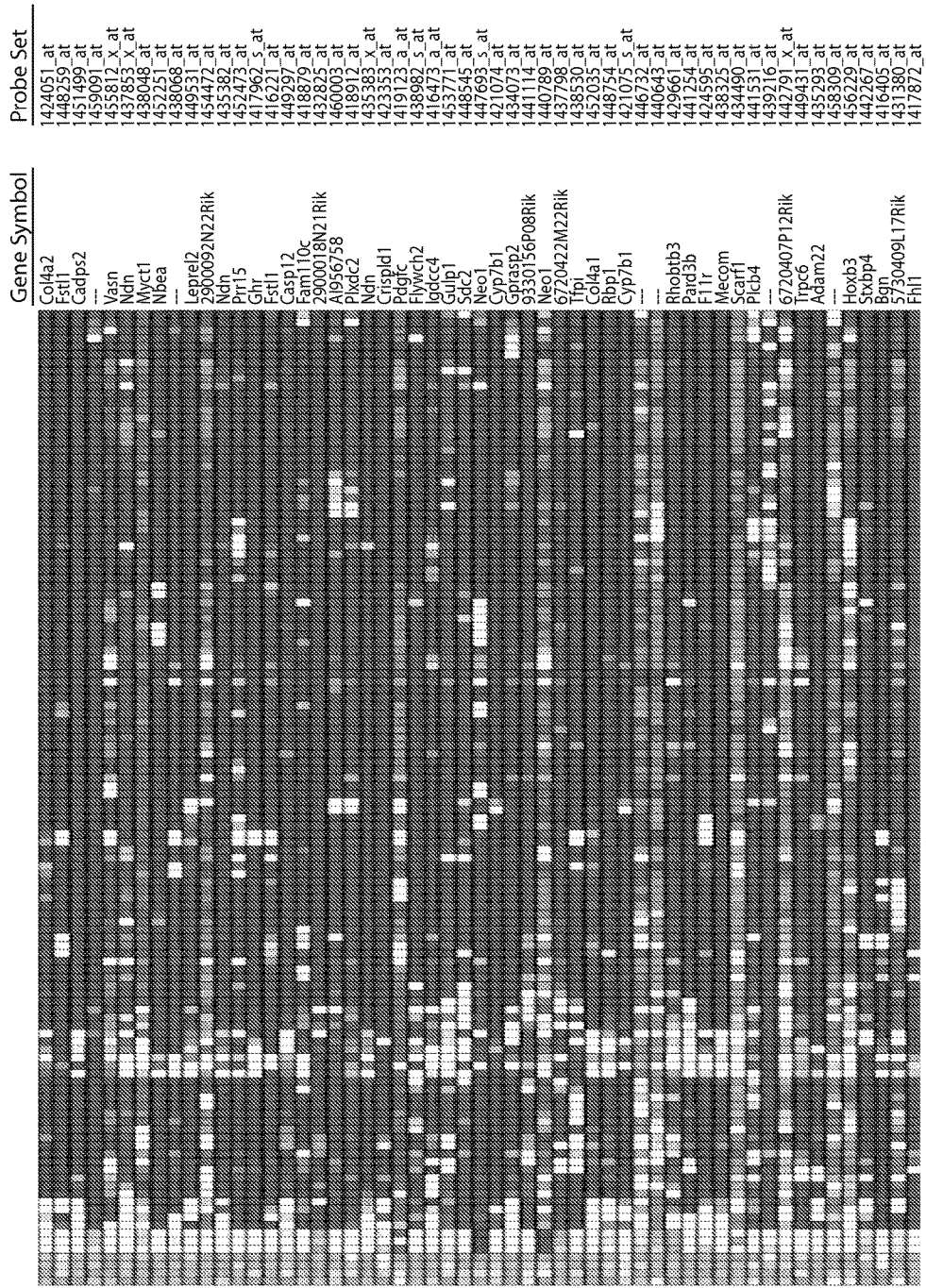
Figures 3, 8A:
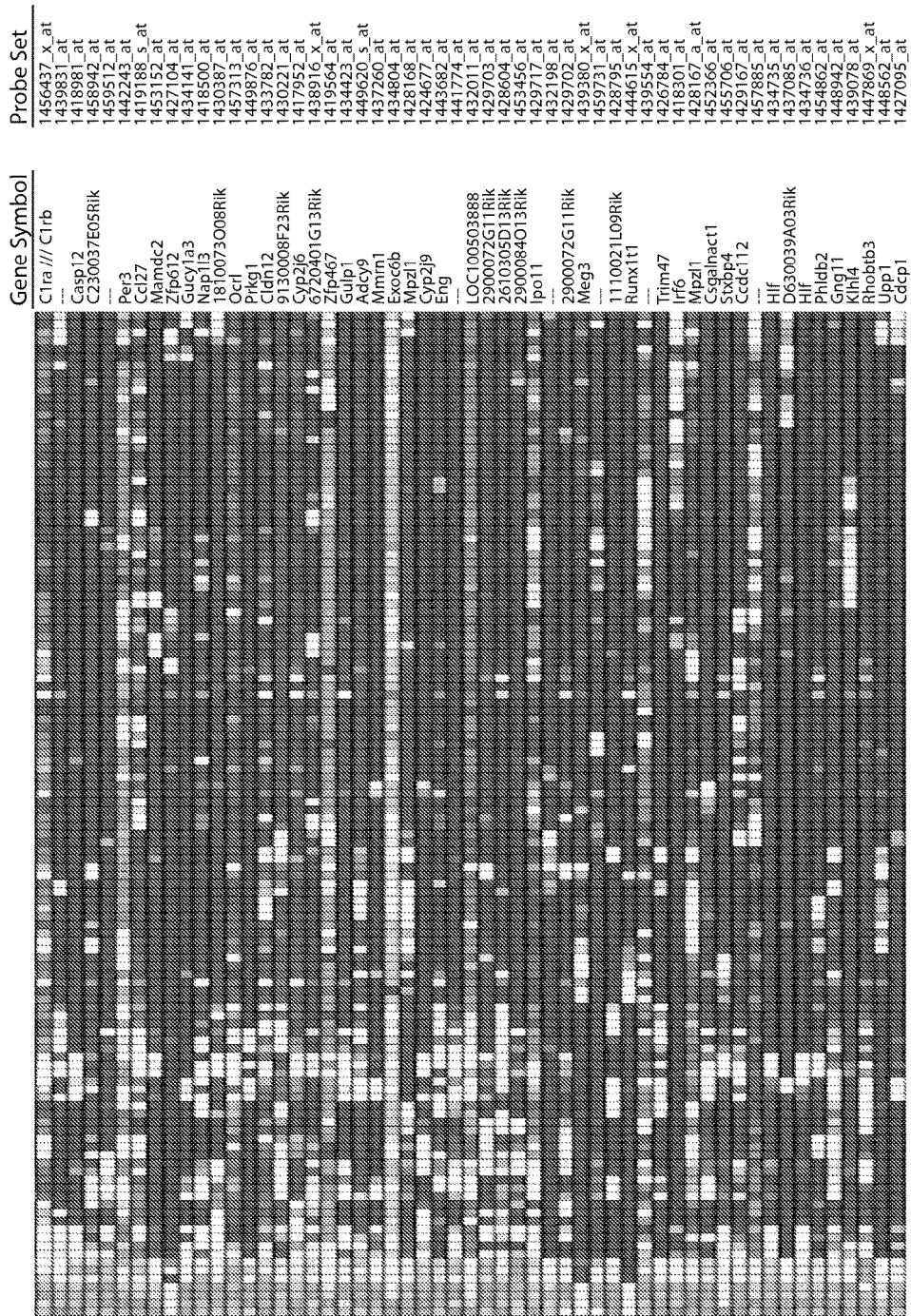
Figures 4, 8A:
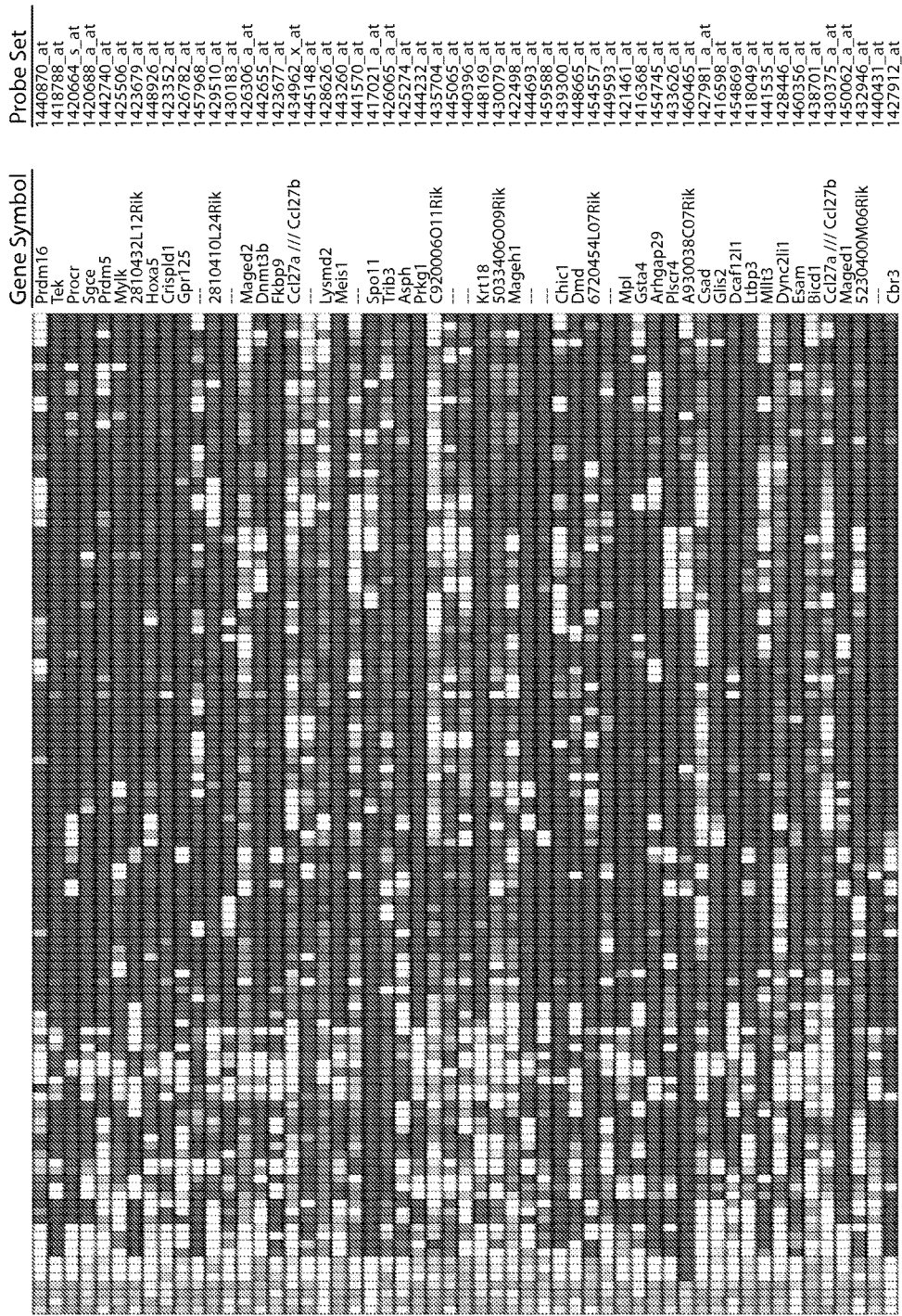
Figures 5, 8A:
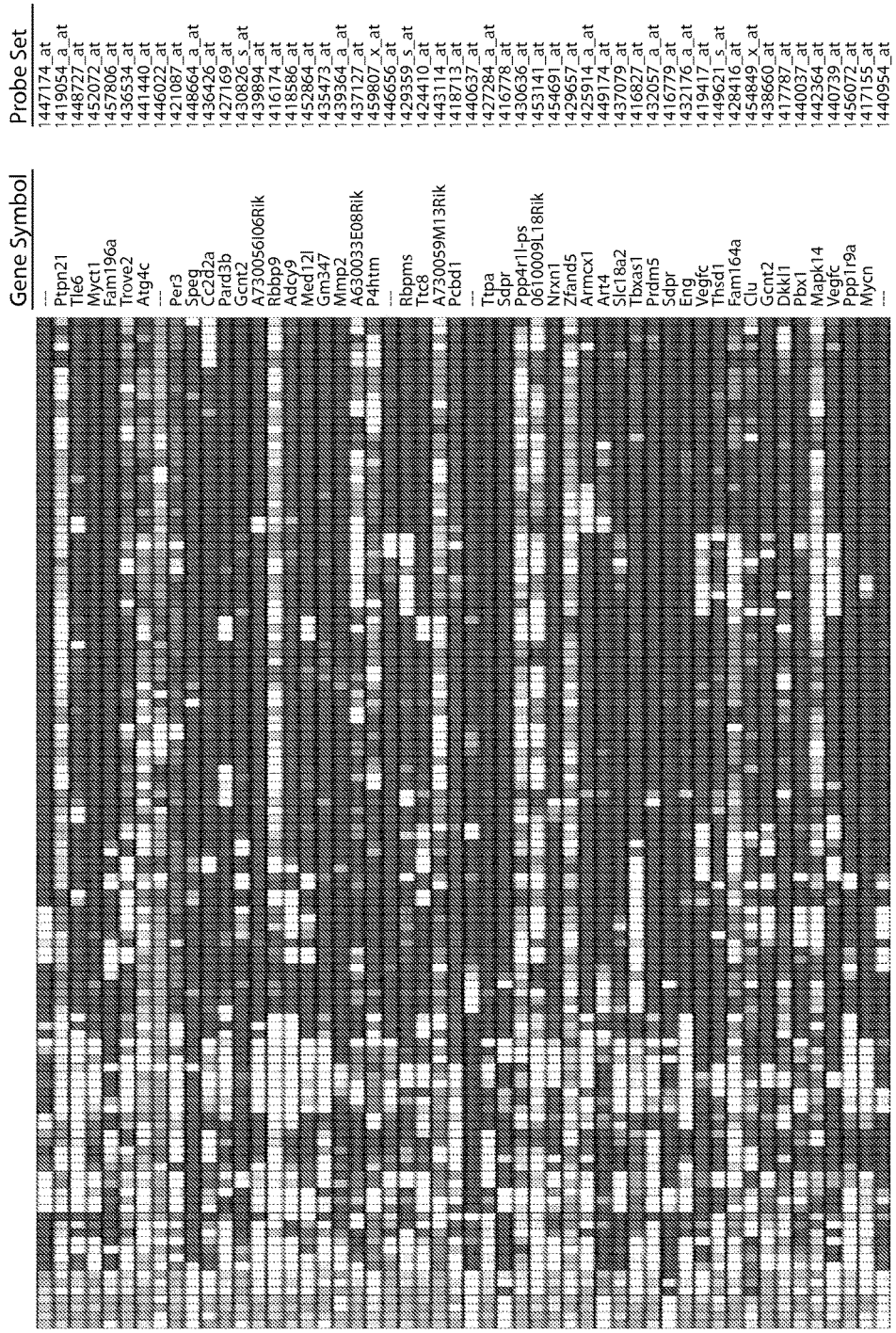
Figures 6, 8A:
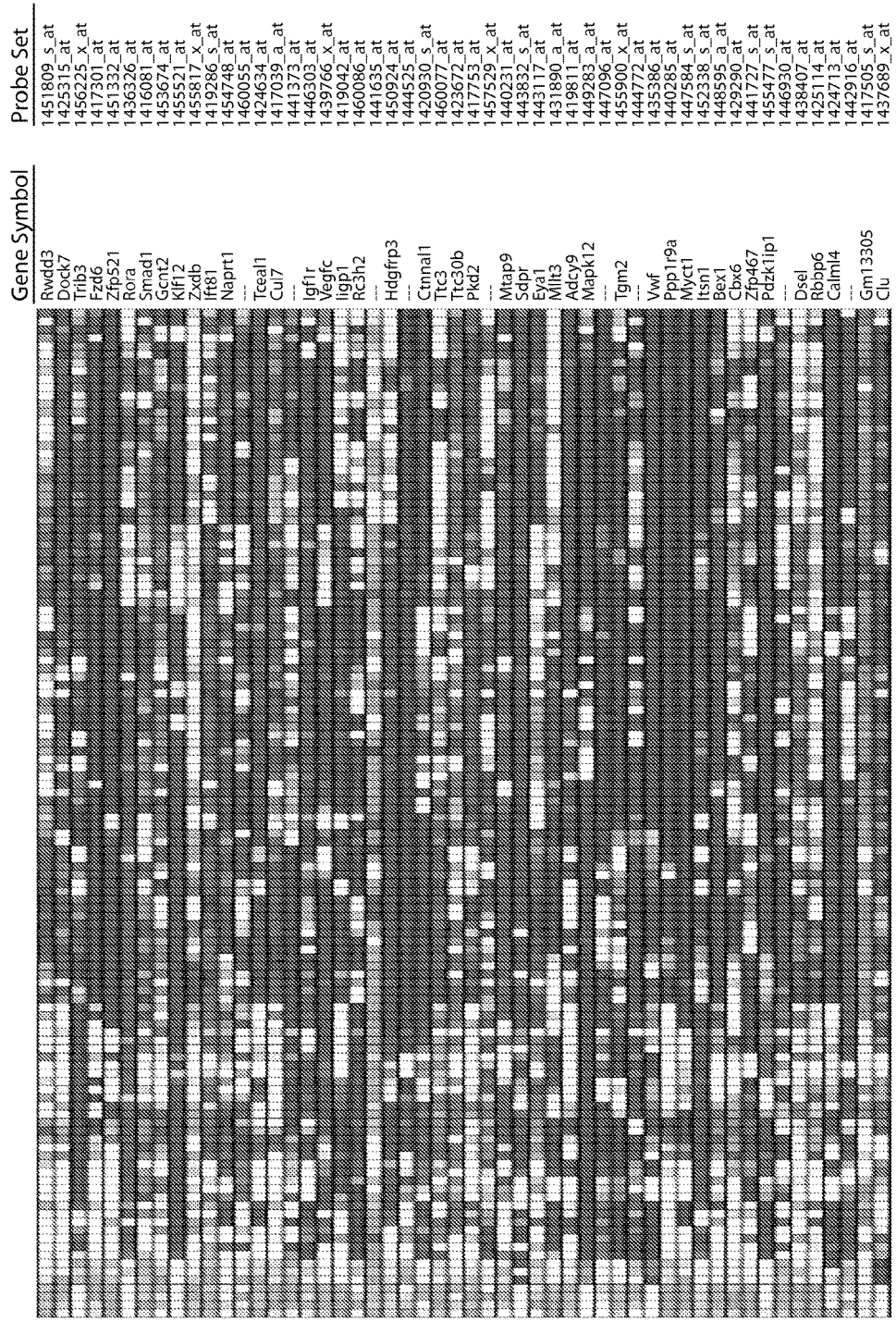
Figure 8B:
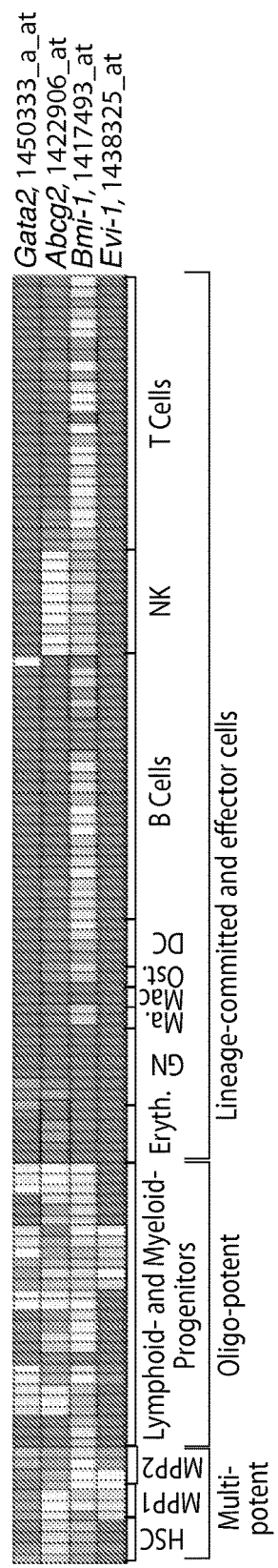
Figure 9D:
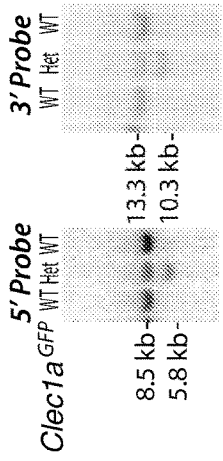
FIGS. 9A-9F depict schematics of targeting reporters into HSC-specific genes and Targeting Clec1a, Sult1a1 and Fgd5 in ES cells by homologous recombination. Schematic of targeting strategies are shown for Clec1a (FIG. 9A), Sult1a1 (FIG. 9B) and Fgd5 (FIG. 9C) showing endogenous locus, targeting vectors, targeted loci, and Southern blot confirmation using 5' and 3' probes. Endogenous loci shown with exons (empty for non-coding and gray-filled for coding region), restriction sites and Southern probes locations (bold black line). Targeting vectors shown with Diphtheria-Toxin (DTA), Neomycin-Resistance (Neo), flpe-sites (gray triangles) and the fluorescent reporter gene (box). Targeted loci shown with inserted reporter, diagnostic restriction sites and expected size of digested-fragments.
Figure 9E:
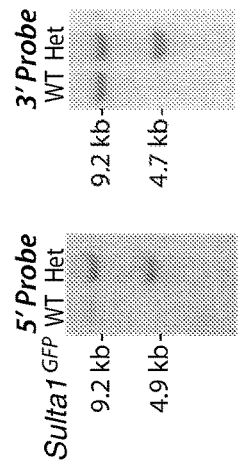
Figure 9F:
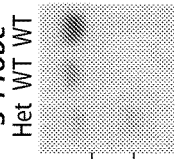
Figure 9F:
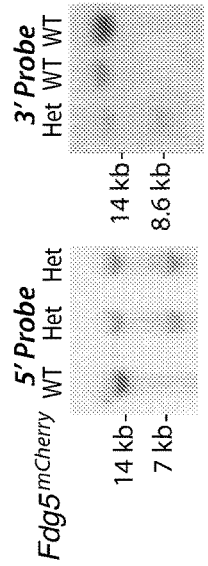
Figure 9A:
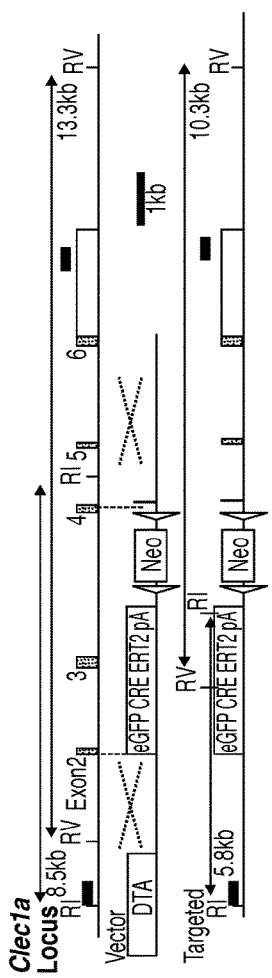
Figure 9B:
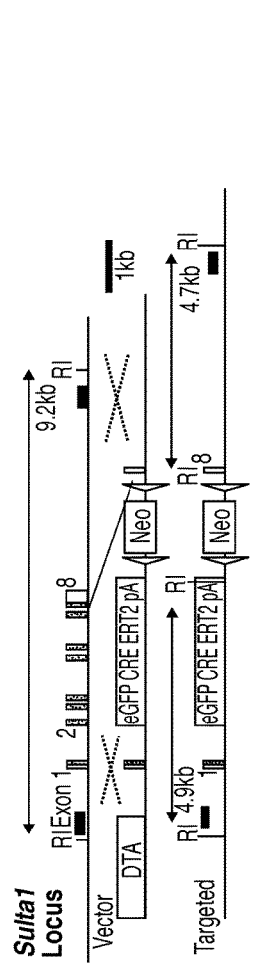
Figure 9C:
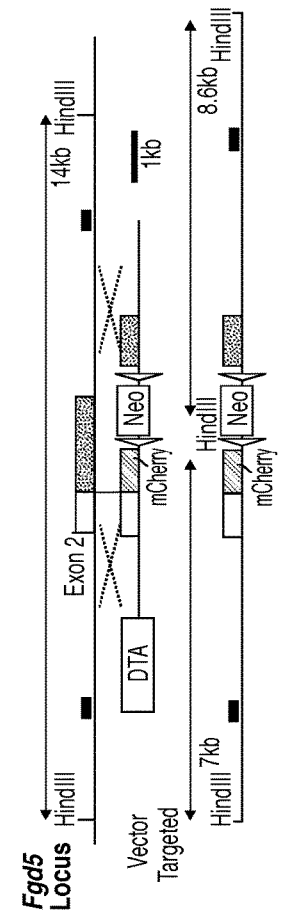

We next sought to identify genes predominantly expressed in HSCs in comparison to their downstream progenitor and effector progeny. These analyses identified 323 probe sets corresponding to 235 unique annotated genes with highly restricted expression in HSCs (FIG. 1C, FIGS. 8A-8B, Table 2). Interestingly, many of these genes were also expressed at low levels in multi-potent progenitors (MPP1s), which represent the most proximal progenitor to HSCs and have previously been referred to in the literature as short-term HSCs (ST-HSCs) (FIG. 1C). Amongst the HSC-enriched genes were several that encode proteins with well-established functional roles in HSC biology such as Cdkn1c (Matsumoto et al., 2011; Zou et al., 2011), Meis1 (Pineault et al., 2002) and Ndn (Kubota et al., 2009), in addition to many genes that have not yet been reported to have a functional role in HSC biology. We chose to focus on three genes of this latter group, Clec1a, Fgd5, and Sult1a1, which showed highly restricted expression in our database (FIG. 1C). In addition to expression specificity, these genes were selected, in part, based on consideration of their genomic structure (intron/exon, repetitive elements), which suggested that they would be amenable to targeting by homologous recombination. Of these, Clec1a encodes a C-type lectin type II transmembrane receptor that has been shown to be expressed in human and rat dendritic and endothelial cells (Colonna et al., 2000; Sobanov et al., 2001; Thebault et al., 2009), and has been reported to play an immuno-modulatory role in allograft tolerance in rats (Thebault et al., 2009). Sult1a1 encodes a cytosolic transferase studied in human cells for its ability to conjugate sulfate to various phenolic substrates (Hildebrandt et al., 2009; Raftogianis et al., 1997; Wilborn et al., 1993). Fgd5 encodes a protein predicted to have GTP-exchange (GEF) activity that has been studied exclusively in the context of endothelial cell biology (Cheng et al., 2012; Kurogane et al.). Fgd5, Clec1a and Sult1a1 have not been studied in the context of HSC biology previously.

Figure 1D:
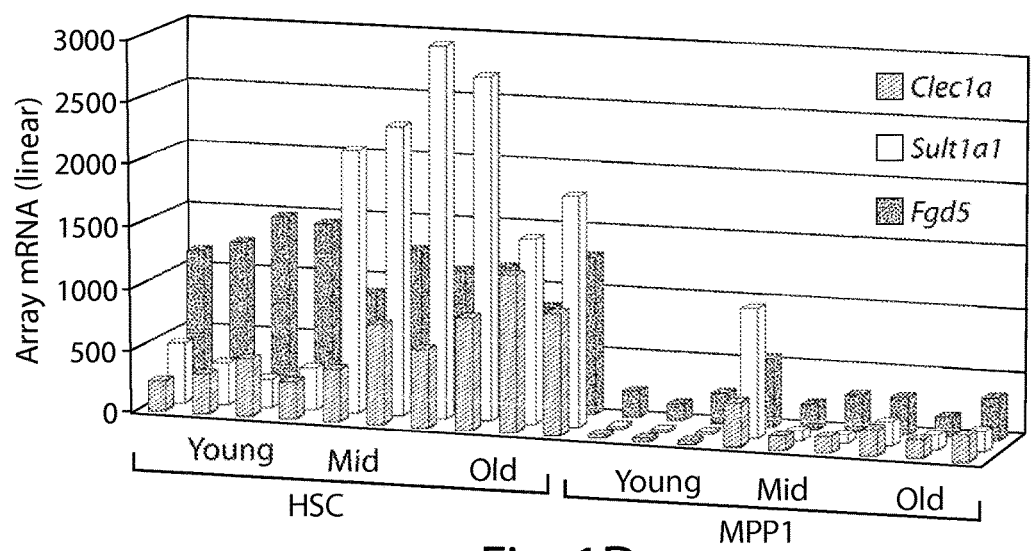

Since we and others have found that gene expression changes during HSC ontogeny (Chambers et al., 2007; Rossi et al., 2005), we wanted to examine the expression of Fgd5, Clec1a and Sult1a1 during aging. Towards this we generated expression data for HSCs and MPP1s from mid-aged (12 months), and old (24 months) mice and normalized this to the data we had generated for young (4 months) mice (FIG. 1D). Interestingly, whereas Fgd5 was highly and relatively stably expressed in HSCs during aging, the expression of Clec1a and Sult1a1 showed an expression pattern that dynamically changed during aging. Clec1a showed low relative expression in young HSCs that remained unchanged at mid-age and increased in HSCs of old mice. Sult1a1 expression however was also lowest in HSCs from young mice, but was substantially upregulated in HSCs from mid-aged mice, and remained high in mice with advanced age. All three genes were expressed at much lower levels in MPP1s/ST-HSCs independent of the age of the mice. These results demonstrate that expression of Fgd5, Clec1a and Sult1a1 is predominantly confined to HSCs in the adult hematopoietic system, and each of these genes is differentially expressed in HSCs during aging. Taken together, these results demonstrate that expression of Fgd5, Clec1a and Sult1a1 is predominantly confined to HSCs in the adult hematopoietic system.

Immunophenotypic HSCs are Labeled by mCherry in Fgd5$^{mCherry}$/+ Mice

In order to generate reporter mice and explore the roles for Clec1a, Sult1a1 and Fgd5 in HSC biology, constructs were made to target each locus by homologous recombination in embryonic stem (ES) cells using a knock-in/knock-out strategy. In all cases, constructs were designed to place a fluorescence reporter cassette (either mCherry into Fgd5, or eGFP•CreERT2 into Clec1a and Sult1a1) in-frame with the protein coding sequence at the endogenous locus that would be expected to be expressed under the regulatory control of the promoter of Clec1a, Sult1a1 or Fgd5 (FIGS. 9A-9F). At the same, correct targeting of the loci is expected to generate null alleles for each of the genes. Sequence verified targeting constructs were introduced into ES cells derived from C57/B16 mice; correctly targeted ES cell clones were identified by Southern blotting; and germline transmission of the targeted alleles was established (FIGS. 9A-9F).

In order to characterize the utility of the targeted alleles to label HSCs, we isolated bone marrow (BM) cells from young adult Fgd5$^{mCherry}$/+, Sult1a1$^{GFP}$/+ and Clec1a$^{GFP}$/+ mice and control littermates and immuno-stained for HSCs using a panel of well-defined markers (lineage Sca1$^+$cKit$^+$ CD48$^-$CD150$^+$), and then analyzed BM cells to visualize reporter signal by flow cytometry. The BM of young adult Clec1a$^{GFP}$/+ mice showed almost negligible expression in HSCs, while HSCs identified from the BM of Sult1a1$^{GFP}$/+ mice were completely negative for reporter fluorescence (FIG. 2A). In contrast, immunophenotypic HSCs from the Fgd5$^{mCherry}$/+ mice were almost uniformly positive for reporter signal (mCherry) (FIG. 2A). We focused on the Fgd5$^{mCherry}$/+ mice for further characterization.

While Fgd5$^{mCherry}$/+ mice clearly showed labeling of immunophenotypic HSCs, we sought to determine the spectrum of BM cells expressing mCherry. To address this we gated BM cells from the Fgd5$^{mCherry}$/+ mice into mCherry positive and negative (mCherry$^+$, mCherry$^-$) fractions, and then determined the immunophenotype of these cells by co-staining with a panel of markers. This analysis revealed that in contrast to mCherry$^-$ cells, a significant fraction of the mCherry$^+$ cells were: negative for the lineage markers associated with mature blood cells (B220, Mac1, GR-1, Ter119, CD3, CD4, CD8); positive for c-Kit, and Sca1; negative for CD48; and positive for CD150$^+$ (FIG. 2B). By gating sequentially through these markers, the vast majority of the mCherry$^+$ cells of Fgd5$^{mCherry}$/+ BM co-stained with markers of immunophenotypic HSCs (lineage$^-$Sca1$^-$cKit$^+$ CD48$^-$CD150$^+$) (FIG. 2B).

Figure 2C:
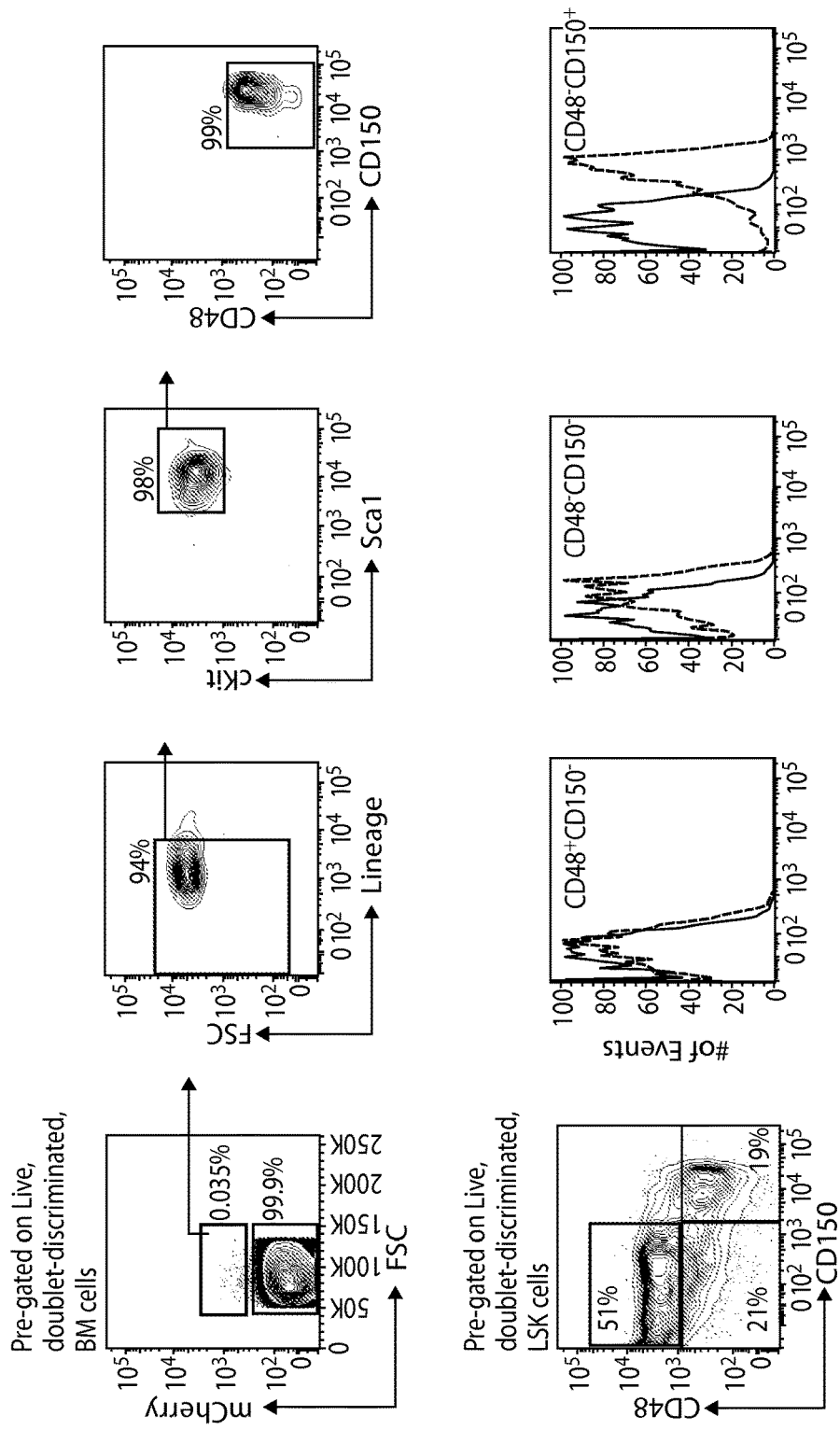
Figure 2D:
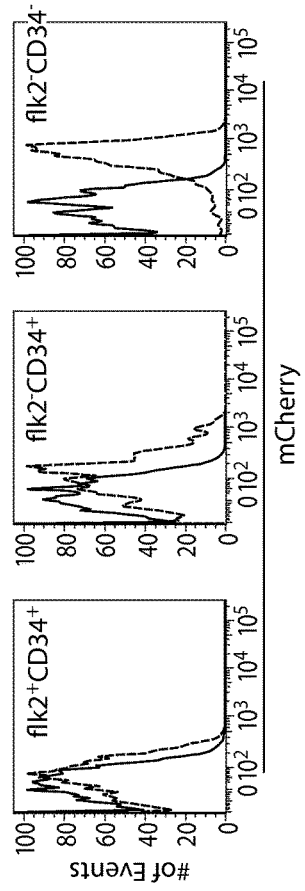
Figure 2D:
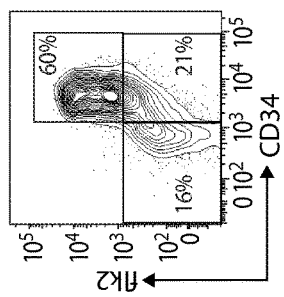
Figure 2E:
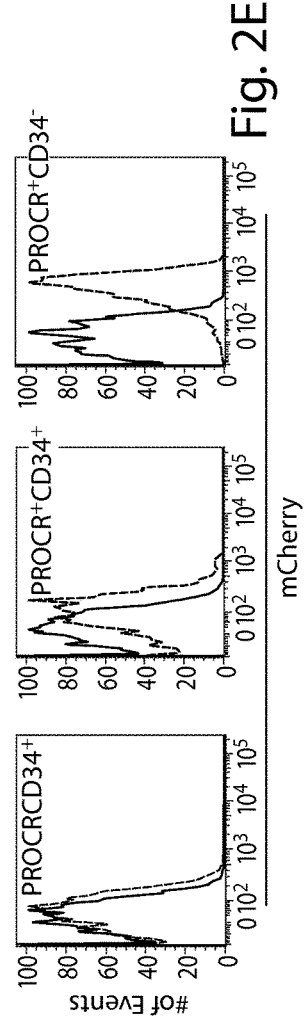
Figure 2E:
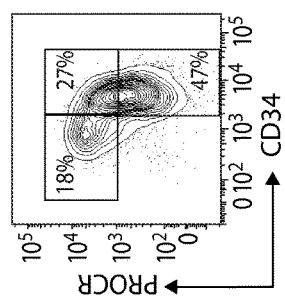
Figure 2F:
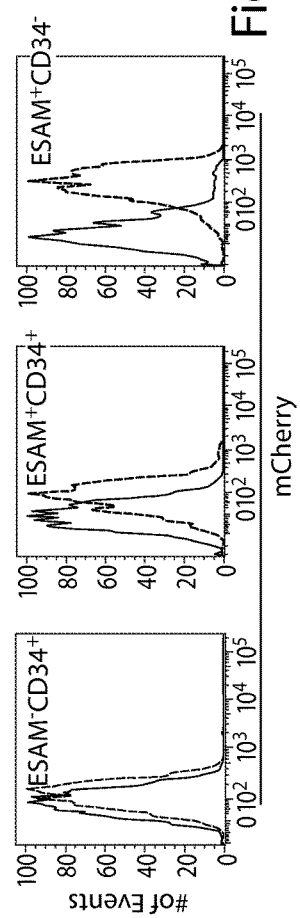
Figure 2F:
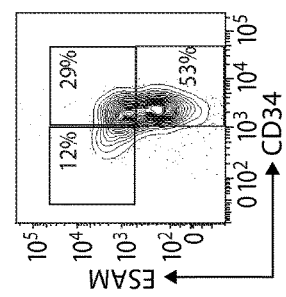

Our expression profiling data showed that whereas Fgd5 expression in the murine BM was almost exclusively restricted to HSCs, low-level expression was also detected in multi-potent progenitor cells. To examine this, we stained the BM of Fgd5$^{mCherry}$/+ mice with a number of different marker combinations that are used by many labs to identify HSCs and discriminate them from multi-potent progenitor cell subsets within the primitive Lineage$^-$Sca1$^+$c-Kit$^+$ (LSK) fraction of the murine BM. Using markers associated with the "Slam code" (Kiel et al., 2005) revealed that as we had previously observed (FIGS. 2A-2B), the vast majority of HSCs (LSKCD150$^+$CD48$^-$) were fluorescently labeled (FIG. 2C). In contrast, the most proximal multi-potent progenitors (LSKCD150-CD48) were predominantly negative except for a small fraction of this population that showed low-level expression of the reporter, whereas the more distal LSKCD150$^-$CD48$^+$ progenitors were essentially negative. Similarly, when CD34 and Flk2 were used to immunophenotypically define HSCs and multi-potent progenitors (Christensen and Weissman, 2001; Osawa et al., 1996; Rossi et al., 2005), HSCs (LSKFlk2$^-$CD34$^-$) were predominantly positive for label, while a minor fraction of LSKFlk2$^-$CD34$^+$ MPP1s/ST-HSCs expressed low-levels of signal, while very little signal was detected in the LSKFlk2$^+$ CD34$^+$ MPP2 fraction (FIG. 2D), consistent with our microarray data (FIGS. 1A-1D). Similar results were found using other marker strategies to identify HSCs and multi-potent progenitors including ESAM (Ooi et al., 2009; Yokota et al., 2009) (FIG. 2F), and PROCR/CD201 (Balazs et al., 2006) (FIG. 2C, 2E). Taken together, these results indicate that immunophenotypic HSCs are almost exclusively labeled in the BM of Fgd5$^{mCherry}$/+ mice.

Fgd5-Deficiency does not Impair HSC Function and is not Required for Definitive Hematopoiesis.

Since the targeting of the Fgd5 locus places a mCherry cassette into the first exon of the Fgd5 coding region and is predicted to generate a null allele, we wanted to determine if inactivation of one or both Fgd5 alleles would affect HSC function. To address this in the setting of Fgd5 heterozygosity, we competitively transplanted 1×10$^6$ BM cells from Fgd5$^{mCherry}$/+ or wild-type (Fgd5$^{+/+}$) control littermates (CD45.2) against 1×10$^6$ wild type BM cells (CD45.1) into lethally irradiated congenic recipients (CD45.1). Transplant recipients were bled at monthly intervals and reconstitution of CD45.2 test cells (FIG. 3A), and their contribution to myeloid lineage granulocytes and monocytes, and lymphoid lineage B-, and T-cells, was determined (FIG. 3B). This showed that Fgd5 heterozygosity had no adverse effect on HSC function with respect to total repopulating, or lineage potential in primary (1°) transplant recipients. To further challenge the Fgd5$^{mCherry}$/+ and wildtype HSCs, serial transplantation into secondary (2°) recipients was performed. Peripheral blood analysis out to 20 weeks post-transplant revealed that HSCs derived from both Fgd5$^{mCherry}$/+ and Fgd5$^{+/+}$ mice robustly reconstituted 2° hosts showing comparable repopulating activity (FIG. 3C), and no differences in lineage output (FIG. 3D). Thus inactivation of one Fgd5 allele has no adverse consequence on the long-term functional potential of HSCs.

We next sought to determine if Fgd5 nullizygosity would have an impact on HSC function. To address this we set Fgd5$^{mCherry}$/+×Fgd5$^{mCherry}$/+ crosses but were unable to identify any viable Fgd5$^{mCherry/mCherry}$ offspring indicating that ablation of Fgd5 is embryonic lethal. We therefore examined the requirement for Fdg5 during embryonic development and found that whereas no Fgd5$^{mCherry/mCherry}$ embryos could be identified at embryonic day 13.5 (E13.5) or later, null embryos could be obtained at sub-Mendelian numbers at E12.5, and at Mendelian numbers at E11.5 (FIG. 3E).

Figure 3F:
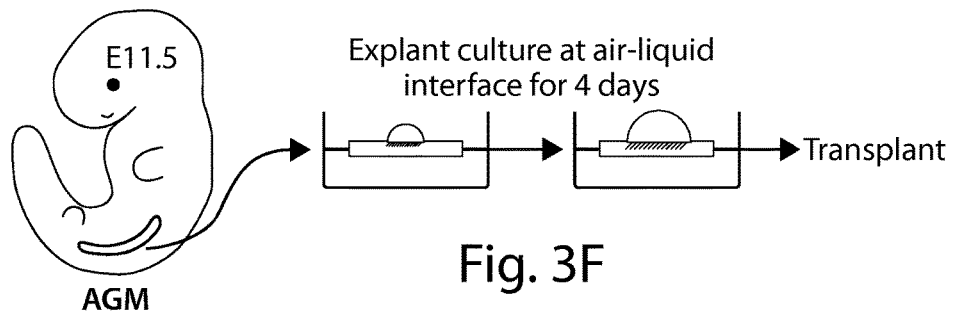
Figure 3G:
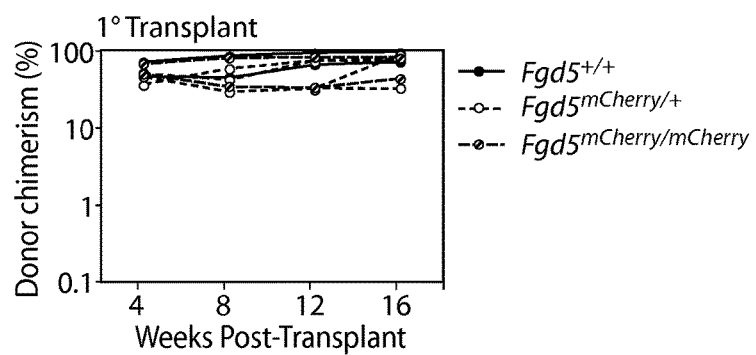
Figure 3H:
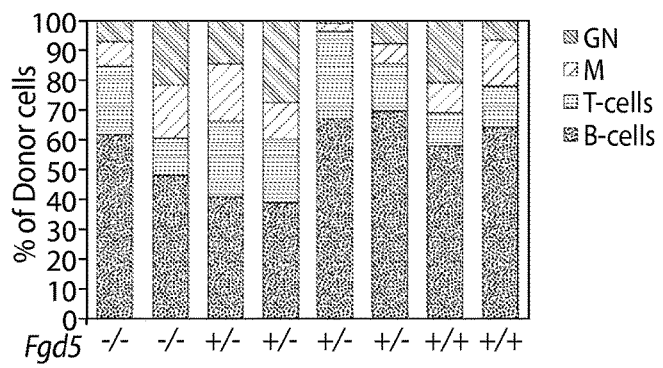
Figure 3I:
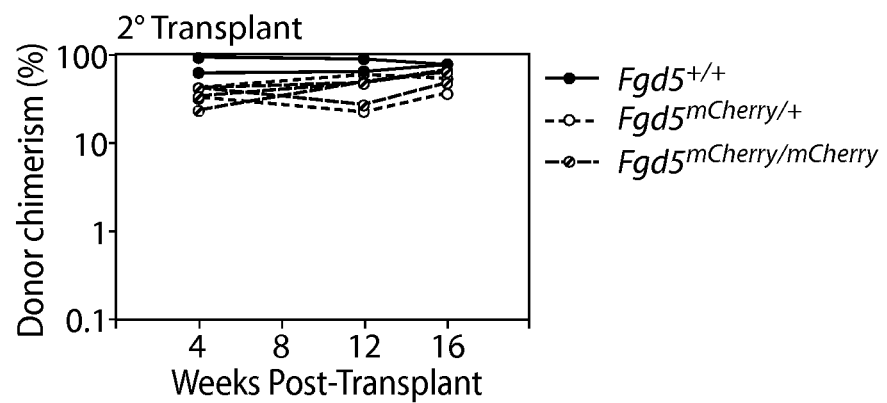
Figure 3J:
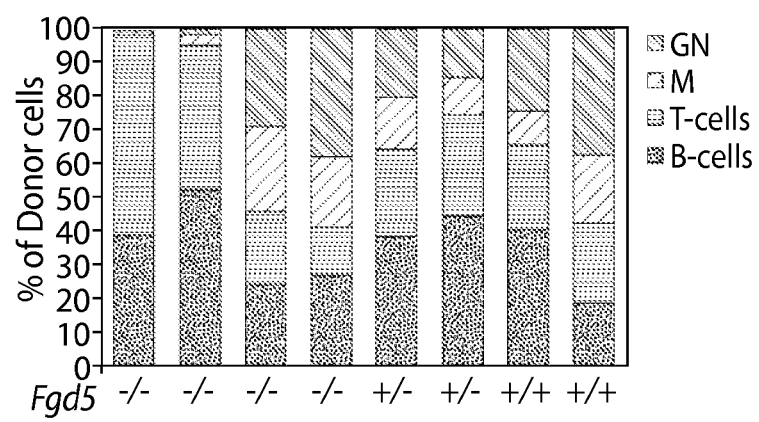
Figure 4A:
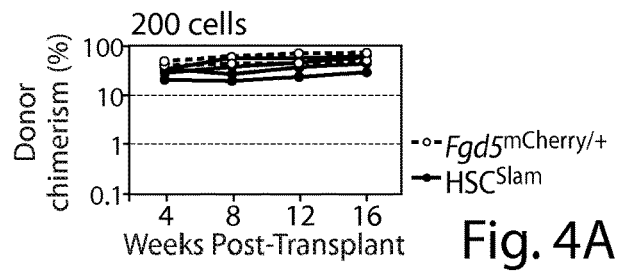
FIGS. 4A-4K demonstrate that Fgd5$^{mCherry}$ identifies cells with potent HSC activity.
Figure 4B:
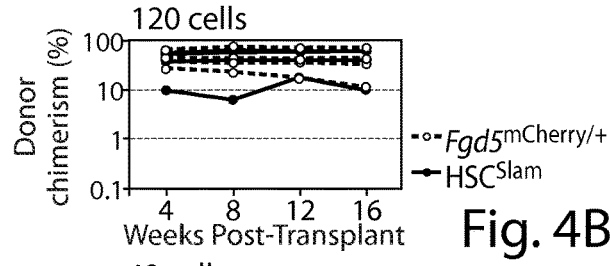
Figure 4C:
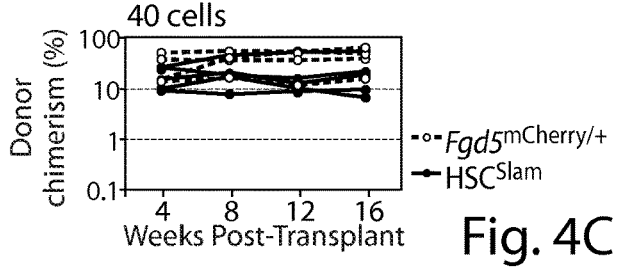
Figure 4D:
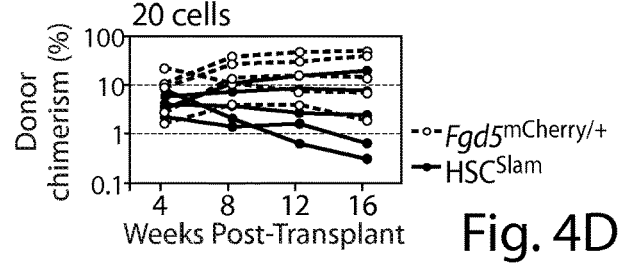
Figure 4E:
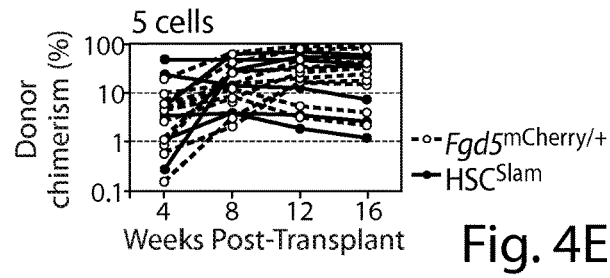
Figure 4F:
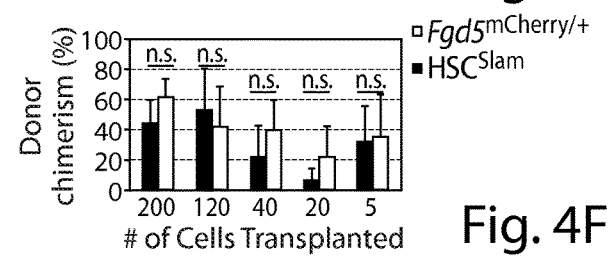
Figure 4G:
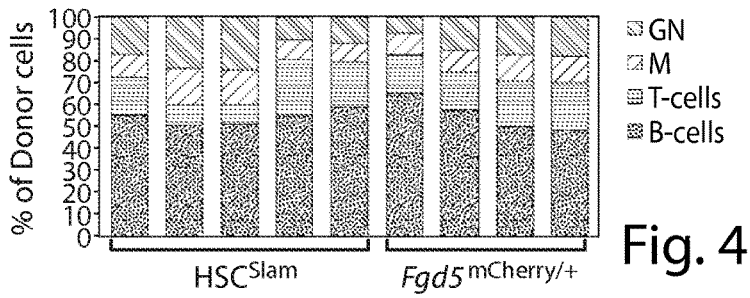
Figure 4H:
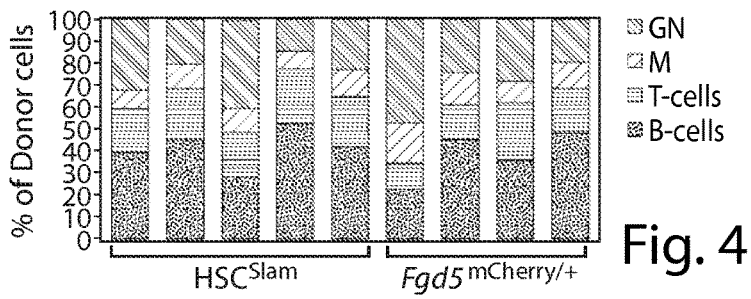
Figure 4I:
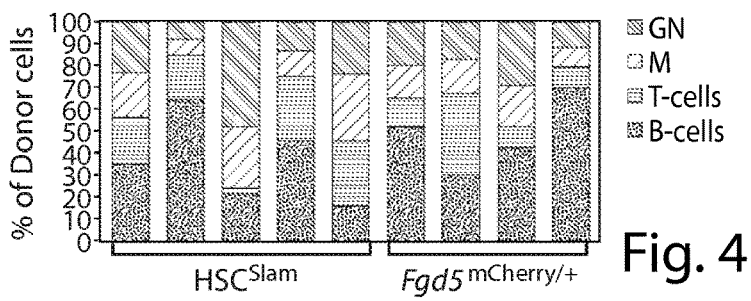
Figure 4J:
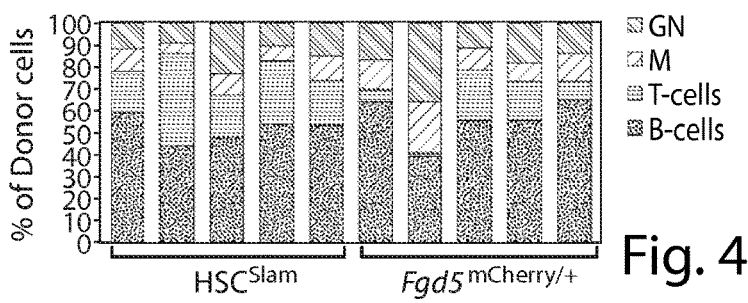
Figure 4K:
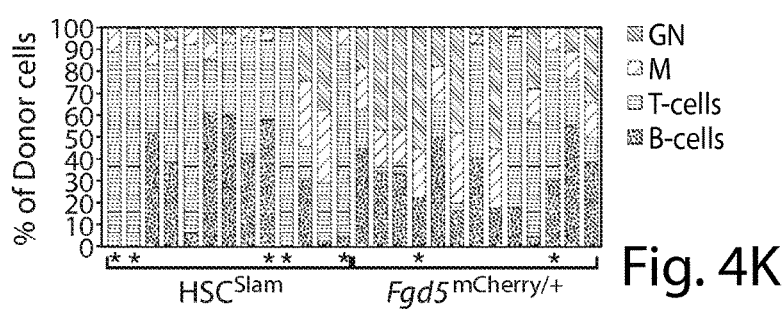
Figure 13:
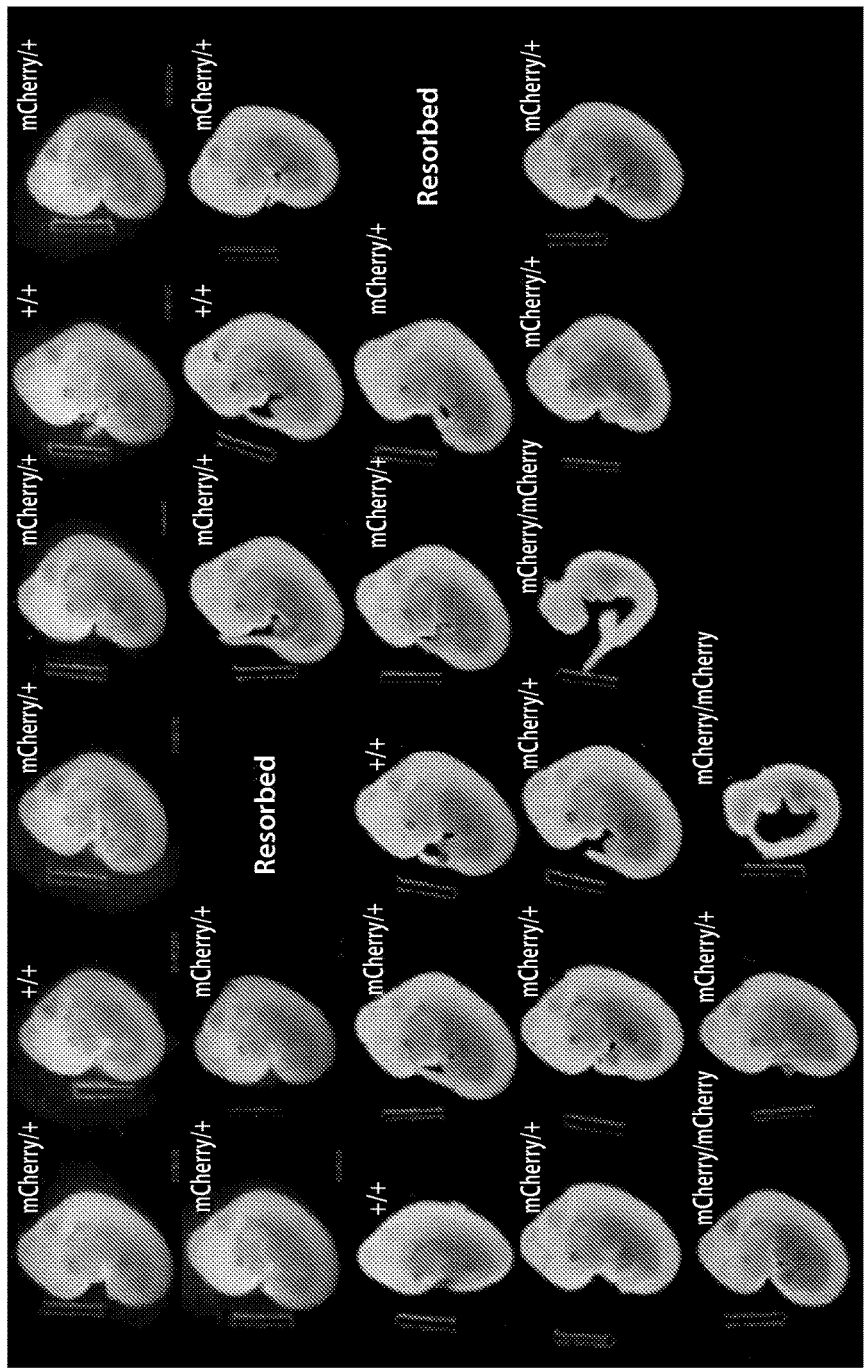
FIG. 13 demonstrates that Fgd5 is required for embryonic development.

Gross examination of embryos at E11.5 showed that while many embryos Fgd5 null embryos appeared morphological normal at E11.5, the presence of resorbed embryos and Fgd5$^{mCherry/mCherry}$ embryos with clear morphological abnormalities at E12.0 indicate that most Fgd5 null embryos die around E11.5-E12.0 (FIG. 3E, FIG. 13). These results indicate that FDG5 is required for late gestation, and suggest that Fgd5$^{mCherry/mCherry}$ embryos die at or shortly after E11.5 of development. Since this time point is close to the developmental timepoint at which definitive HSCs first emerge in the developing embryo at the aorta-gonad mesonephros (AGM) (E10.5) (Dzierzak and Speck, 2008), this raised the possibility that definitive hematopoiesis may be defective or impaired in absence of FGD5. To test this possibility directly, we dissected the AGM region of E11.5 embryos derived from Fgd5$^{mCherry}$/+×Fgd5$^{mCherry}$/+crosses and cultured them for 4 days at an air/liquid interface using a protocol adapted from Medvinsky and colleagues (Medvinsky and Dzierzak, 1996; Taoudi et al., 2008), and then competitively transplanted all the cells from the AGM explants into irradiated recipients (FIG. 3F). These experiments showed that although there were some variability in lineage output as might be expected with this protocol, AGM explants arising from $Fgd5^{+/+}$, $Fgd5^{mCherry/+}$, or $Fgd5^{mCherry/mCherry}$ embryos all gave rise to HSCs capable of long-term multi-lineage reconstitution in 1° recipients (FIGS. 3G-3H). To further test the functional capacity of the AGM-derived HSCs, $2\times10^6$ BM cells from the 1 hosts were serially transplanted into 2° recipients. These experiments showed that AGM-derived HSCs of all Fgd5 genotypes were able to give rise to long-term, multi-lineage reconstitution in 2° hosts (FIGS. 3I-3J).

Taken together, these results indicate that Fgd5 is required for embryonic development, but is not required for the generation of definitive HSCs, and further that loss of one or both Fgd5 alleles does not impair the long-term self-renewal or multi-lineage differentiation potential of HSCs.

Figure 10A:
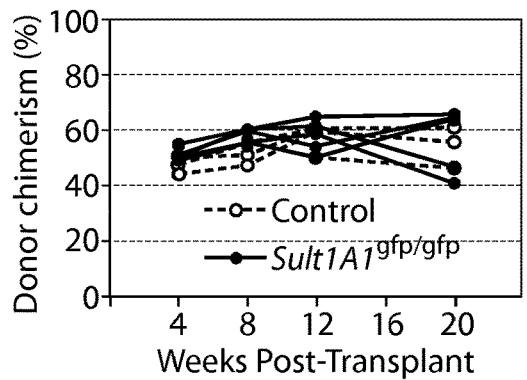
FIGS. 10A-10C demonstrate that Sult1A1 or Clec1a are dispensable for HSC activity in competitive transplantation. Transplantation of whole bone marrow cells from Sult1a1$^{gfp/gfp}$ or control mice, and Clec1a$^{gfp/gfp}$ or control mice showing total donor reconstitution over the time course of transplantation, and average lineage breakdown of donor cells at 16 weeks post-transplant is shown. Granulocytes (GN), macrophage/monocytes (M), B-cells and T-cells are indicated. Error bars indicate standard deviation.
Figure 10B:
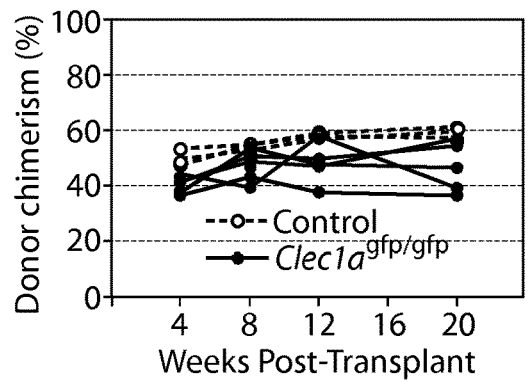
Figure 10C:
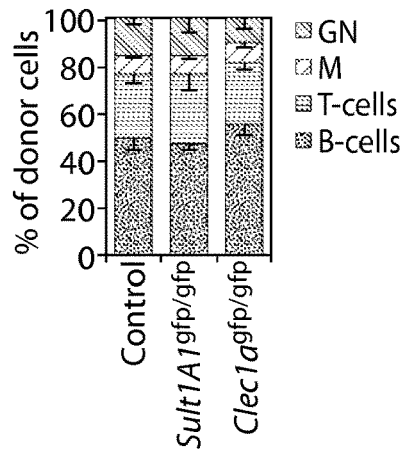
Figures 1, 11:
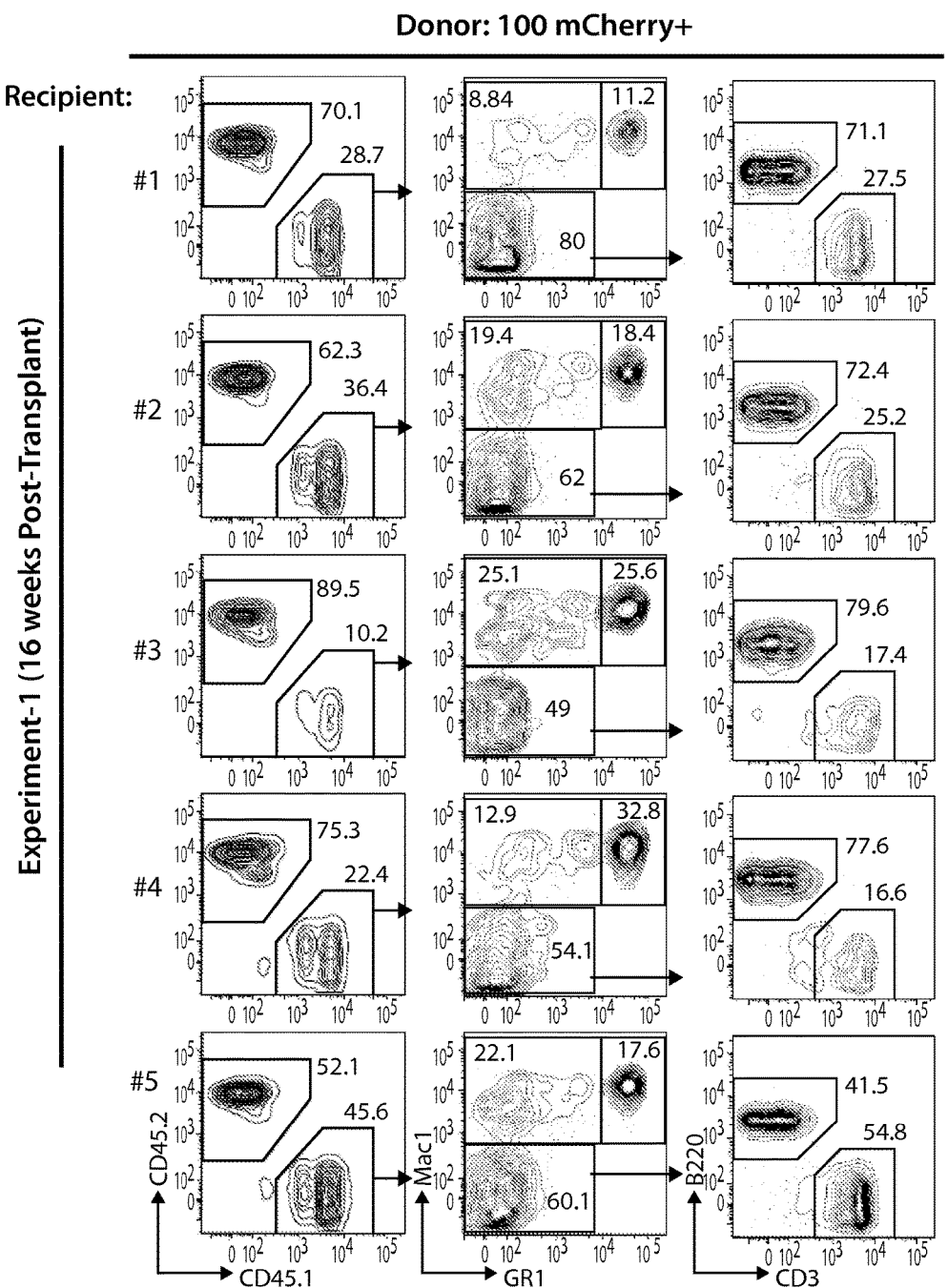
FIG. 11 demonstrates that mCherry$^-$ cells have no HSC-activity. FACS plots of late time point bleed data from the 100 mCherry+ (top) or 100,000 mCherry− (bottom), where donor cells are CD45.2 and lineage composition analyzed for Granulocytes (Mac1+Gr1$^+$), Myeloids (Mac1$^+$Gr1$^-$), B cells (Mac1$^-$, B220$^+$CD3$^-$) and T cells (Mac1$^+$, B220$^-$CD3$^+$).
Figures 2, 11:
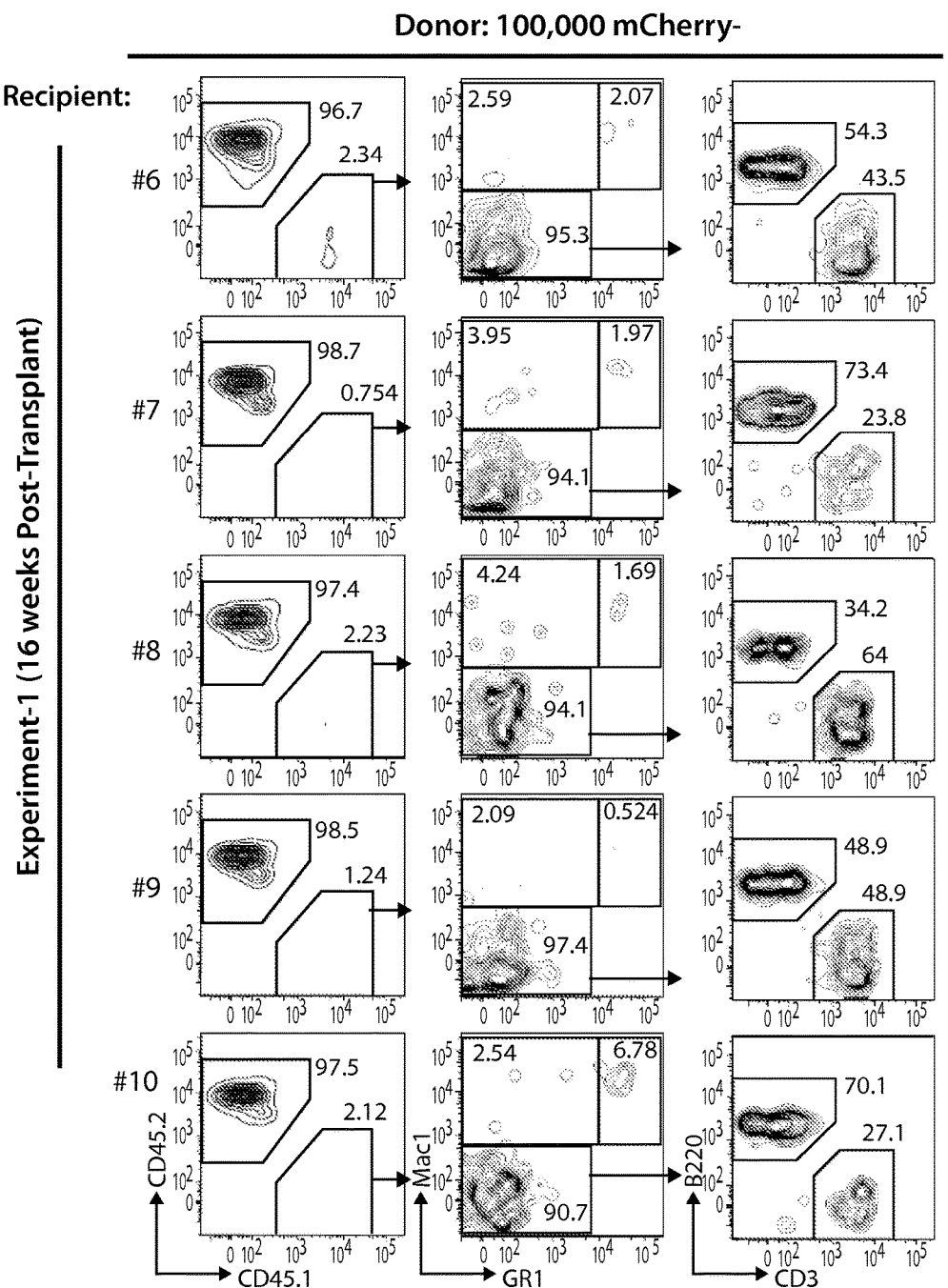
Figures 3, 11:
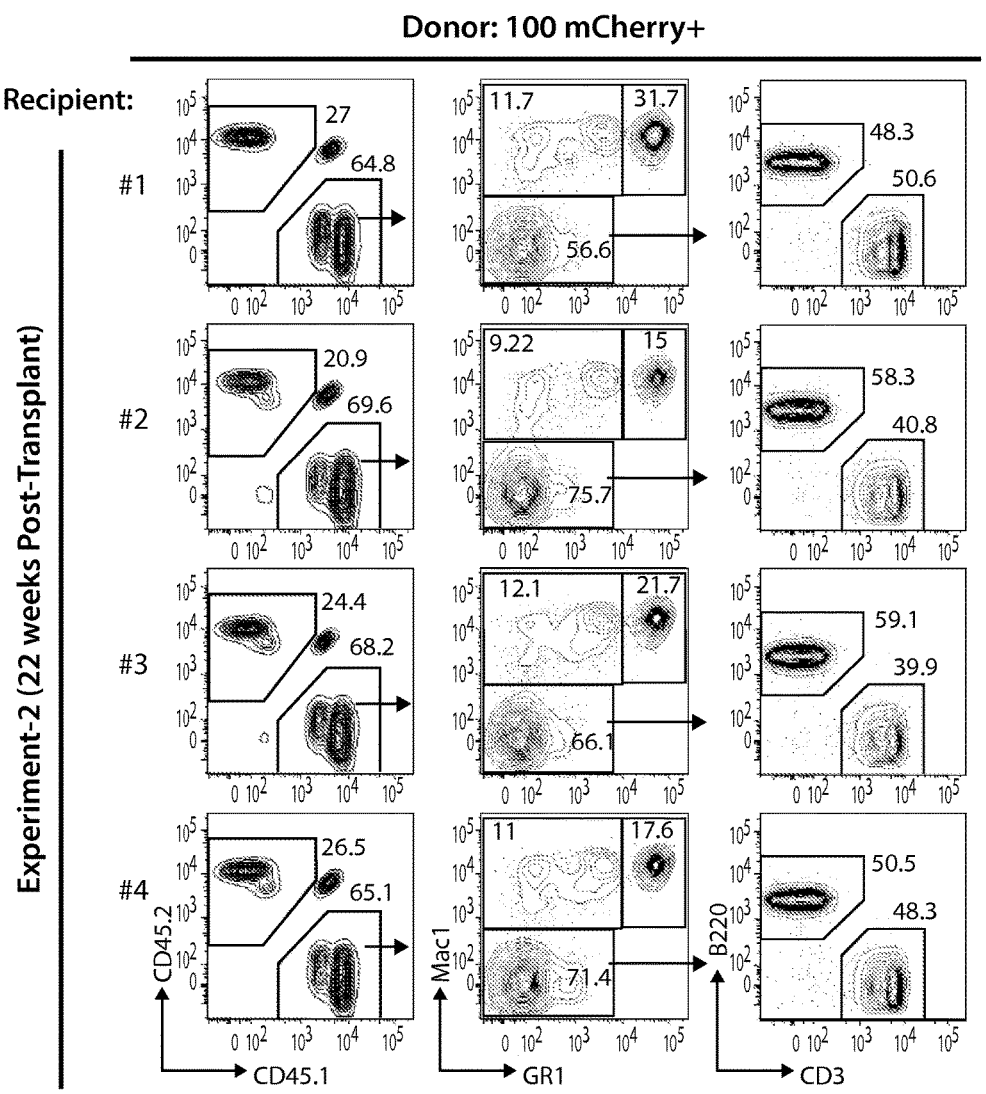
Figures 4, 11:
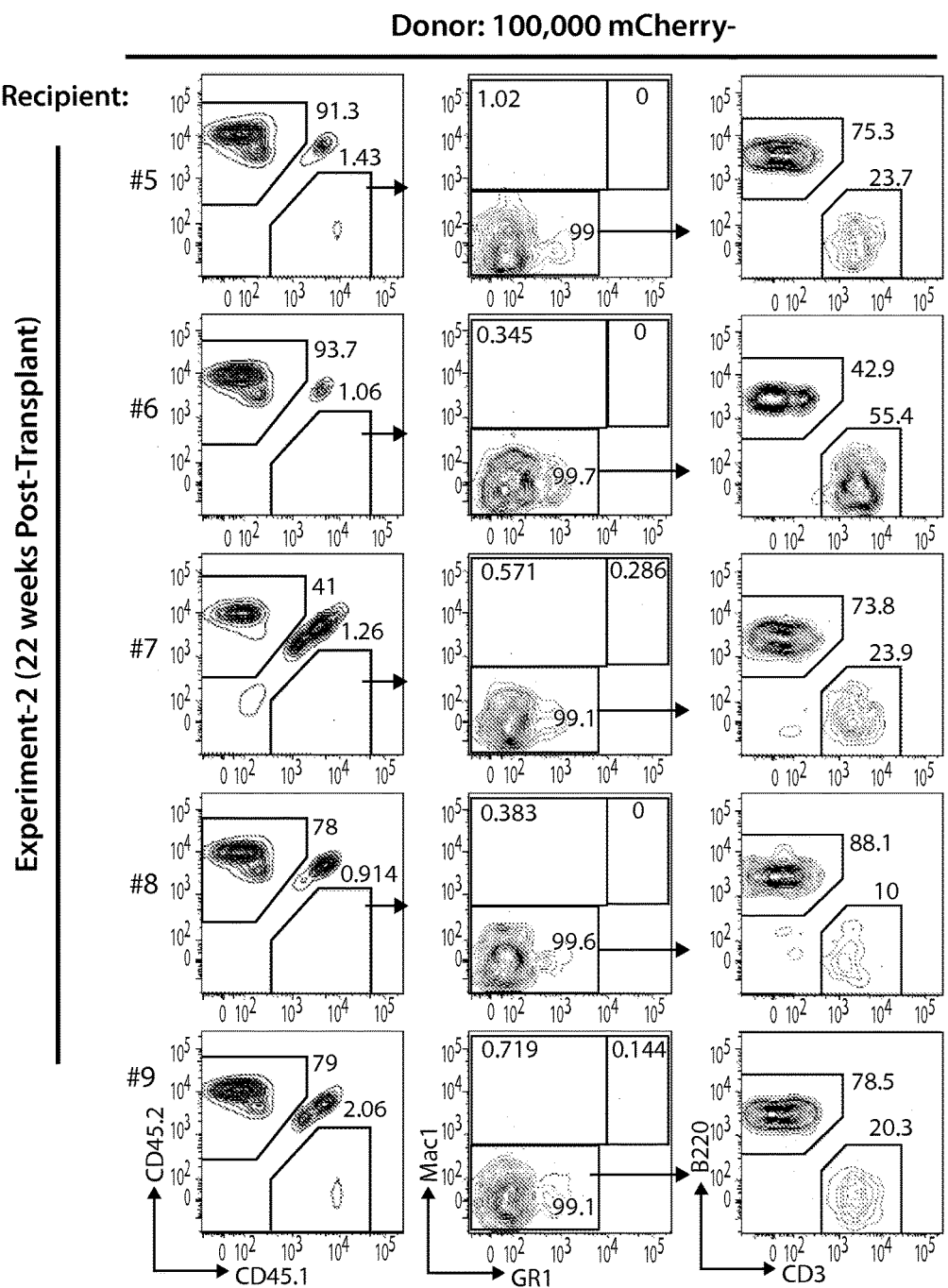
Figure 12:
FIG. 12 depicts a whole transcriptome microarray data of human hematopoietic cell types, demonstrating that Fgd5 expression is largely restricted to cord blood (CB) HSCs, and adult bone marrow hematopoietic stem cells (lineage$^-$CD90$^+$CD38-CD34$^+$) in comparison to proximal CD38+ CD34+ progenitors or downstream effector cells where it is not expressed.

Due to the knock-in/knock-out strategy that we used, we determined that neither Clec1a nor Sult1a1 were required for embryonic development as homozygous null mice were born at Mendelian numbers and appeared phenotypically normal. Moreover, HSCs from mice harboring Clec1a or Sult1a1 alleles functioned normally in transplantation assays indicating that neither gene was required for HSC activity (FIGS. 10A-10C).

$Fgd5^{mCherry}$ Identifies Bone Marrow Cells with Potent Hematopoietic Stem Cell Activity Having determined that the mCherry$^+$ BM fraction of $Fgd5^{mCherry/+}$ mice labels cells that express markers consistent with immunophenotypic HSCs (FIGS. 2A-2C), and also that the targeted allele had no adverse effect on HSC function (FIGS. 3A-3J), we next sought to test the functional activity of the labeled cells directly. Towards this we sorted defined numbers of cells based solely on mCherry-positivity from the BM of $Fgd5^{mCherry/+}$ mice (CD45.2), and competitively transplanted them into lethally irradiated congenic recipients (CD45.1). In parallel, we also sorted immunophenotypic HSCs (LSKCD150$^+$CD48$^-$, hereafter referred to as "HSC$^{Slam}$") and competitively transplanted these into different recipients. In a series of independent experiments, mCherry$^+$ cells, and HSC$^{Slam}$ were transplanted at 200, 120, 40, 20 or 5 cell doses, and recipient mice were monitored for peripheral blood reconstitution for 16 weeks (FIGS. 4A-4K). At all transplant doses, the mCherry$^+$ cells, and HSC$^{Slam}$ gave rise to long-term donor chimerism that was statistically comparable (FIGS. 4A-4F). In each of the 200, 120, 40 and 20 cell transplants, all recipient mice transplanted with either mCherry$^+$ cells or HSC$^{Slam}$ showed donor-derived multi-lineage reconstitution 16 weeks post-transplant, whereas at the 5-cell dose, 11/13 and 8/13 recipients were multi-lineage reconstituted when mCherry$^+$ cells or HSC$^{Slam}$ were transplanted, respectively (FIGS. 4G-4K). These results demonstrate that the mCherry$^+$ fraction of $Fgd5^{mCherry/+}$ BM is highly enriched with potent repopulating activity that is functionally comparable, on a per cell basis, to HSCs sorted by rigorous immunophenotypic markers.

Figure 5A:
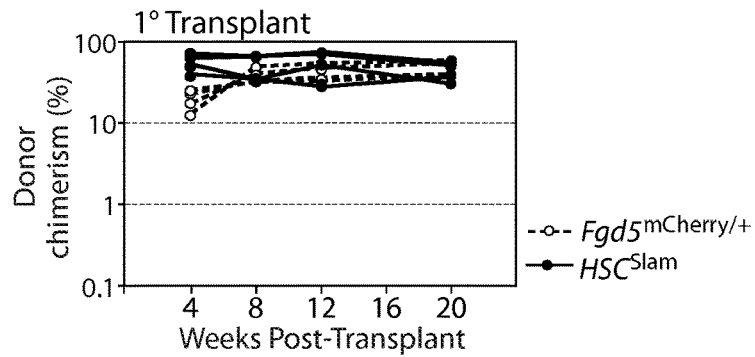
FIGS. 5A-5D demonstrate that Fgd5$^{mCherry}$ labeled HSCs have extensive self-renewal and repopulating potential.
Figure 5B:
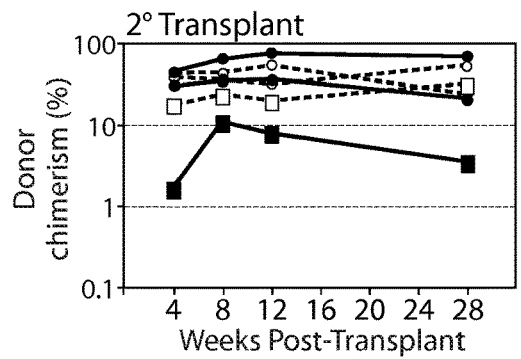
Figure 5C:
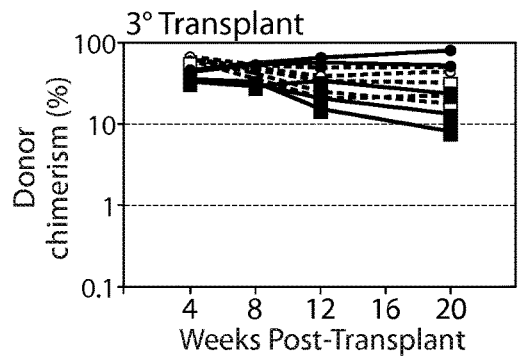
Figure 5D:
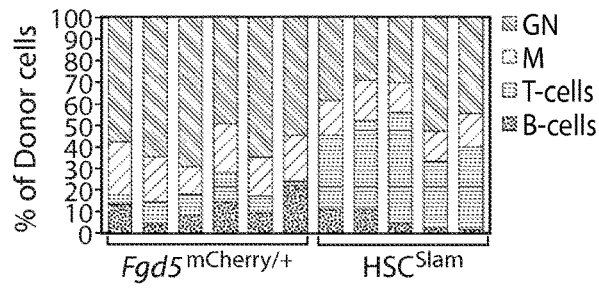

In addition to the ability to give rise to long-term multi-lineage reconstitution in 1 transplant recipients, HSCs are most rigorously experimentally defined by their ability to sustain activity during serial transplantation. To address this, we again isolated mCherry$^+$ cells or HSC$^{Slam}$ from $Fgd5^{mCherry/+}$ or $Fgd5^{+/+}$ mice (CD45.2) respectively, and competitively transplanted 250 cells of each into irradiated congenic (CD45.1) recipients. Analysis of 1 recipients revealed, as before, that the mCherry$^+$ cells and HSC$^{Slam}$ performed comparably (FIG. 5A). Twenty-one weeks post-transplant, $2\times10^6$ BM cells derived from the 1° recipients were transplanted into 2° hosts (CD45.1). Throughout the 28 weeks that the experiment was followed, all 2° hosts showed donor-derived multi-lineage reconstitution (FIG. 5B). Thirty-one weeks post-transplant, BM cells were harvested from the 2° hosts and $5\times10^6$ cells were transplanted into tertiary (3°) recipients (CD45.1). As we had observed in the 2° hosts, both the mCherry$^+$ cells and HSC$^{Slam}$ continued to show potent long-term multi-lineage repopulating activity in all the 3° recipients (FIGS. 5C-5D). These experiments demonstrate that the mCherry$^+$ fraction of $Fgd5^{mCherry/+}$ BM contains potent multi-lineage repopulating potential, and extensive self-renewal potential.

Figure 6C:
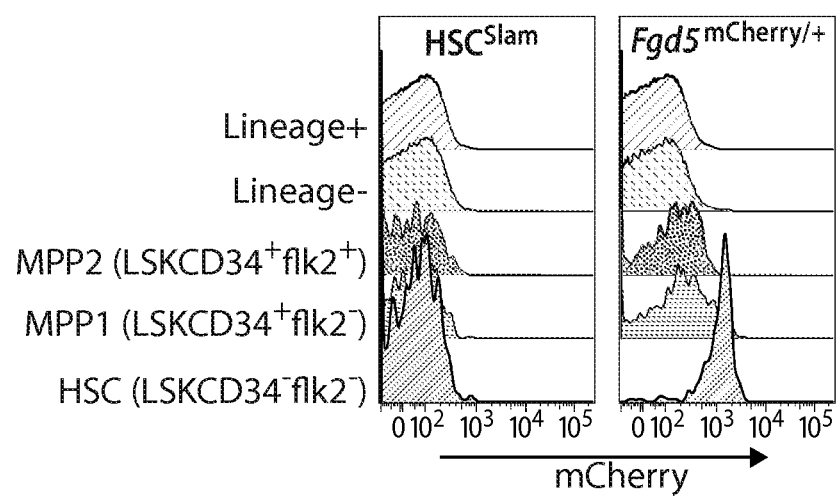

We next analyzed the BM reconstitution of recipients that had been transplanted with either mCherry$^+$ cells or HSC$^{Slam}$. Similar to the chimerism observed in the peripheral blood (FIGS. 4A-4K), the BM was robustly reconstituted with CD45.2 donor-derived cells regardless of whether mCherry$^+$ cells or HSC$^{Slam}$ had been transplanted (FIG. 6A). Co-staining the BM with a panel of markers showed as we had observed in the steady state (FIGS. 2A-2C), the mCherry+ signal was primarily restricted to the immunophenotypic HSC (LSKFlk2$^-$CD34$^-$) compartment, with only a minor fraction of the LSK multi-potent progenitors expressing lower levels of label FIG. 6A-6B). These results demonstrate that the mCherry$^+$ cells are able to self-renew to give rise to immunophenotypic HSCs in vivo, and further that the near exclusive labeling of HSCs observed in the BM of $Fgd5^{mCherry/+}$ mice is faithfully maintained even after the extensive challenge of primary transplantation.

Figure 7A:
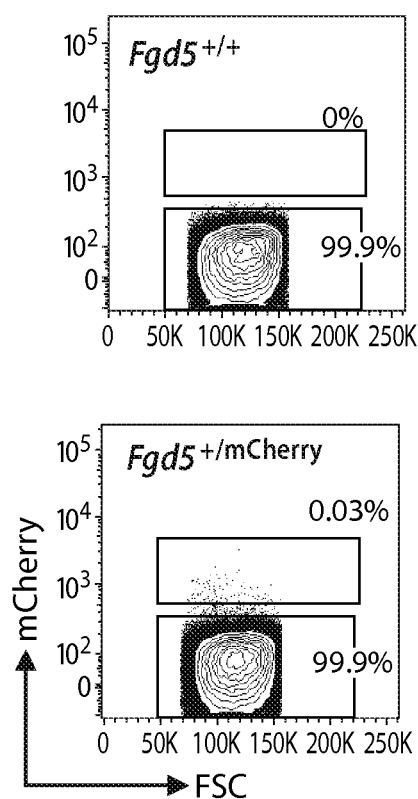
FIGS. 7A-7F demonstrate that all HSCs are labeled by Fgd5$^{mCherry}$.
Figure 7B:
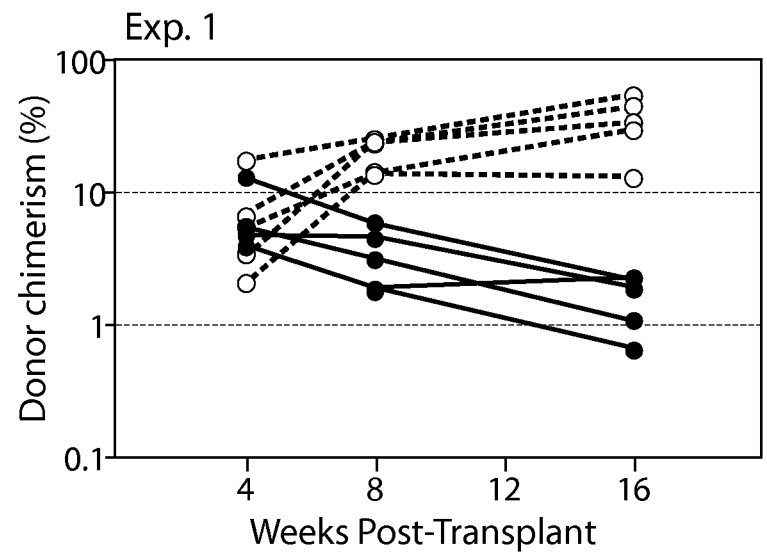
Figure 7C:
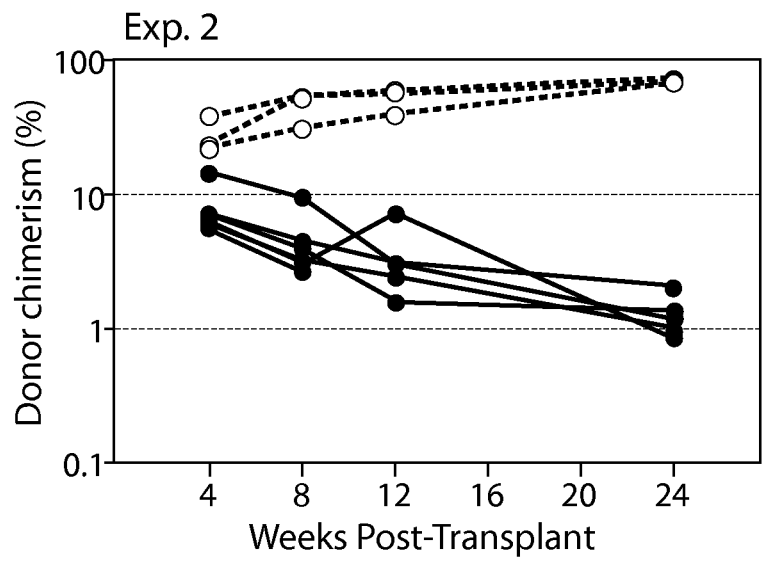
Figure 7D:
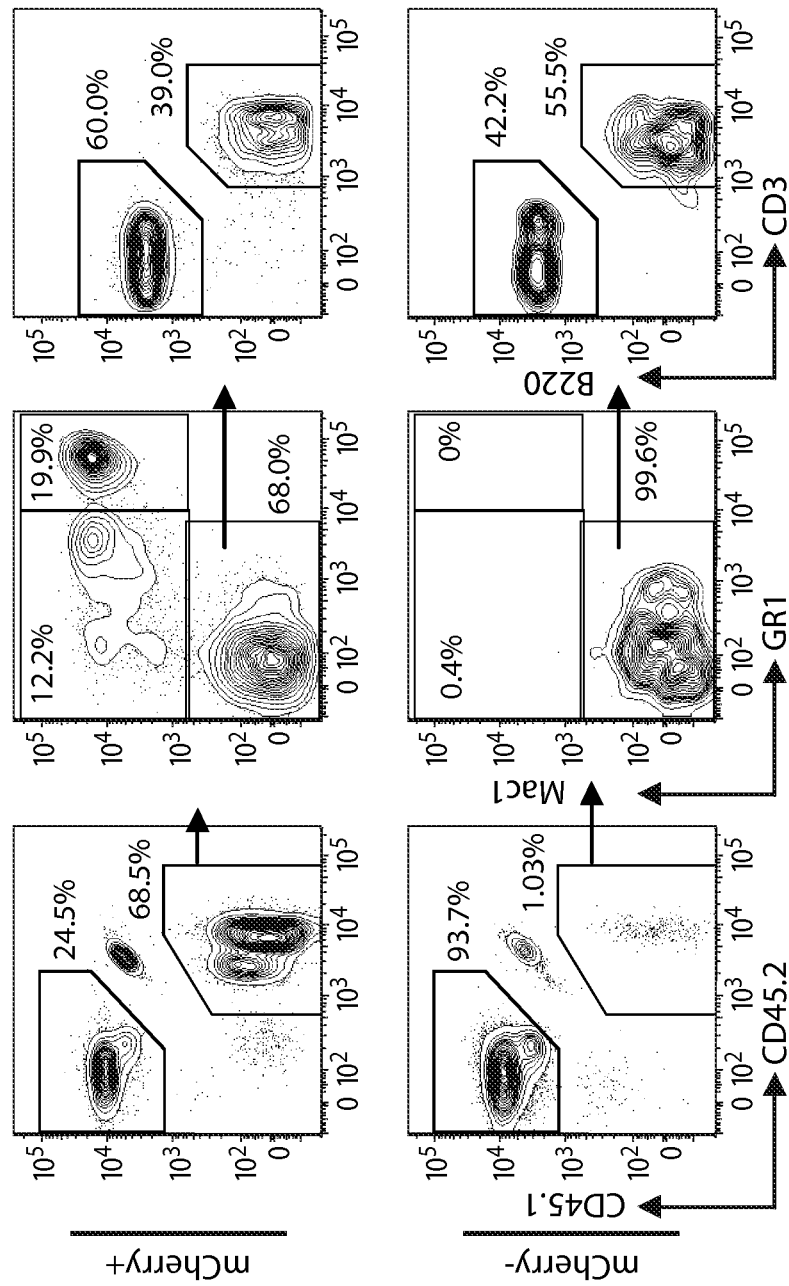
Figure 7E:
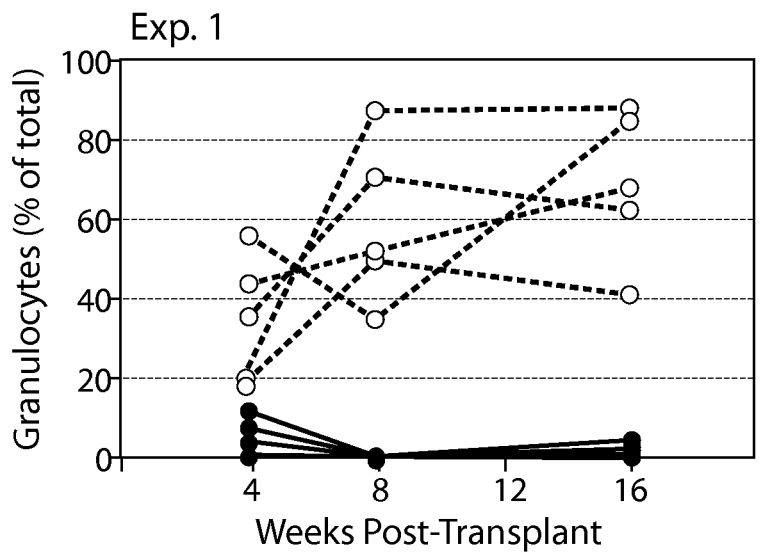
Figure 7F:
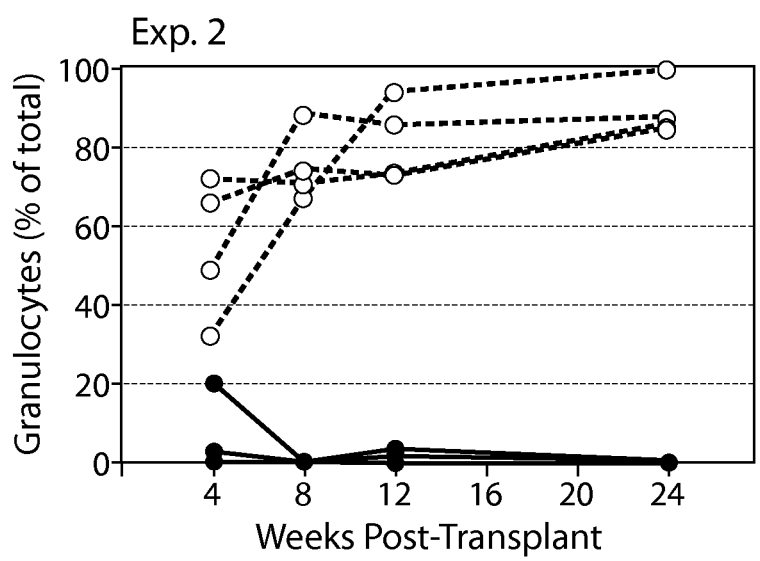

All HSC Activity Resides within the mCherry$^+$ Fraction of $Fgd5^{mCherry/+}$ BM We next sought to determine if all HSC activity was confined to the mCherry$^+$ fraction of the $Fgd5^{mCherry/+}$ BM. To address this we sorted the BM of $Fgd5^{mCherry/+}$ mice into mCherry$^+$ and mCherry$^-$ fractions, and competitively transplanted either 100 or 100,000 cells, respectively, into irradiated recipients in two independent experiments (FIGS. 7A-7B). As we had previously observed (FIGS. 4A-4K, 5A-5D), the 100-mCherry$^+$ cell transplants all yielded robust long-term, multi-lineage reconstitution in both experiments (FIGS. 7B-7D). In contrast, the 100,000-mCherry$^-$ cell transplants yielded short-term reconstitution that gradually diminished to very low levels at later time-points (FIGS. 7B-7D). Peripheral blood analysis of the few remaining donor-derived cells at 16-weeks (experiment #1) or 24-weeks (experiment #2) post-transplant revealed that virtually all were B- and T-cells, which can be long-lived (FIG. 7C). Importantly, while the mCherry$^+$ cell transplants all gave rise to sustained and high levels of granulocyte chimerism indicating robust, ongoing HSC activity (Bhattacharya et al., 2006; Bryder et al., 2006), granulocyte reconstitution was progressively extinguished in the recipients transplanted with the Cherry$^-$ fraction indicating an absence of HSC activity (FIGS. 7E-7F). The sole exception to this was one of the recipients of 100,000 mCherry– cells in experiment #1 that showed very low donor-derived granulocyte reconstitution 16 weeks post-transplant (FIG. 7E). Although we cannot exclude the possibility that a HSC activity resides in the mCherry$^-$ fraction of the bone marrow at very low frequency, the fact that only 1 out of 10 independent recipients transplanted with 100,000 mCherry$^-$ cells showed minor granulocyte reconstitution 16 weeks post-transplant, suggests that the vast majority, if not all, of HSC activity resides in the mCherry+ fraction of the Fgd5$^{mCherry/+}$ mice.

As described herein, we set out to identify genes with restricted expression in the HSC compartment of the murine bone marrow, and then target the endogenous loci of a number of identified genes in mouse ES cells to generate reporter knock-in/knock-out alleles. Mice bearing such alleles could be used to identify HSCs by single-color fluorescence without the need for immunostaining, which has great utility for addressing outstanding questions related to HSC biology. At the same time, our knock-in/knock-out approach allows us to examine the requirement of the targeted genes for HSC development and function. To achieve these goals, we employed a microarray approach in which we compared the expression profiles of highly purified HSCs to that of 36 downstream progenitor and effector cells. Previous studies using related approaches have been successful in identifying genes that function in HSCs or in downstream populations (Balazs et al., 2006; Chambers et al., 2007; Forsberg et al., 2010; Forsberg et al., 2005; Ivanova et al., 2002; Kiel et al., 2005; Luckey et al., 2006; Park et al., 2002; Shojaei et al., 2005), as well as genes whose products serve as antigens that have been used to facilitate identification of HSCs such as Esam (Forsberg et al., 2005), the Slam code (CD150, CD48, CD244) (Kiel et al., 2005), Procr/CD201 (Balazs et al., 2006). Mindful of the fact that HSCs share a number of functional attributes with their proximal multi-potent progenitor progeny, and also, to a lesser degree, with more downstream oligo-potent and lineage-restricted progenitors, we included such populations in our microarray screen reasoning that this would allow us to more precisely identify genes with HSC-restricted expression. With this said, it must be recognized that identifying a gene as "specific" to any cell type is ultimately limited by the spectrum and comprehensiveness of the samples studied. Using the hematopoietic database assembled for this study, we were able to identify 323 probe sets with highly restricted expression in HSCs, many of which have not been previously studied in the context of HSC biology.

To assess the functional role(s) that such identified genes play in HSCs, and to increase the likelihood of identifying a genomic locus that upon targeting would lead to faithful HSC labeling, we focused on 3 genes with highly HSC-restricted expression. The knock-in/knock-out targeting strategy we employed allowed us to determine that neither Clec1a nor Sult1a1 are required for normal mammalian development, and both appeared to be dispensable for HSC function in transplantation experiments (FIGS. 10A-10C). By contrast, whereas Fgd5 heterozygotes developed normally and showed no deficit in HSC function, Fgd5 nullizygosity was embryonic lethal at mid-gestation indicating a critical, non-redundant function for FGD5 during development. Recent studies have suggested that Fgd5 expression was highly restricted to endothelial precursors in developing mice and the vasculature of zebrafish embryos and adult mice (Cheng et al., 2012). Fgd5 also expressed in a number of human endothelial cell lines where it has been suggested to play a role regulating CDC42 activity during capillary formation (Kurogane et al.). The importance of Fgd5 in endothelial cell biology was recently confirmed in a study in which murine Fgd5 was knocked-down by siRNA, and over-expressed, showing that FGD5 regulates vascular pruning during endothelial cell remodeling (Cheng et al., 2012). These studies indicate that the embryonic lethality associated with loss of FGD5 may result from defective vasculogenesis, and though beyond the scope of the work presented herein, the Fgd5 null allele generated herein could represent an important genetic tool for addressing this, in some aspects. With regard to hematopoiesis, we showed that despite the mid-gestation lethality, Fgd5-deficiency did not impair the formation or function of definitive HSCs (FIGS. 3A-3J), which retained extensive self-renewal and multi-lineage differentiation potential.

A number of previous studies have targeted a variety of loci with the intent of establishing a faithful HSC reporter. Mice bearing a reporter for the Gata2 transcription factor that is not specifically expressed in HSCs (FIGS. 8A-8B) were found to be useful for enriching for HSC activity when sorted in combination with immuno-staining for Sca1 (Suzuki et al., 2006). Similarly, although mice bearing a reporter allele at the Abcg2 locus predominantly labeled Ter119+ erythroid cells in the murine BM as expected from expression analysis (FIGS. 8A-8B), HSCs could be identified when used in combination with side-population activity, and antibody staining to exclude lineage positive cells (Tadjali et al., 2006). Interestingly, although Bmi-1 is broadly expressed throughout hematopoiesis (FIGS. 8A-8B), mice bearing a GFP knock-in allele at the Bmi-1 locus, which is critical for HSC function (Park et al., 2003), were used to demonstrate that BM cells expressing the highest levels of GFP contained HSC activity when sorted in combination with additional HSC markers (Hosen et al., 2007). In a recent study, Kurokawa and colleagues targeted the Evi-1 locus, which is required for HSC function (Goyama et al., 2008), by cleverly knocking-in an Evi-1 cDNA-IRES-GFP rescue/reporter cassette, which largely rescued HSC activity (Kataoka et al., 2011). This study showed that while the majority of cells of the primitive LSK compartment were GFP-labeled in these mice, only the GFP+ fraction when sorted in combination with the LSK or other HSC markers exhibited HSC activity (Kataoka et al., 2011). Thus, although a number of reporter mice have been developed that label hematopoietic stem and progenitors, the goal of establishing a reporter strain that faithfully and specifically labels HSCs has not been previously achieved.

Although Clec1a and Sult1a1 were identified as being amongst the most HSC-restricted from our expression screen, targeting expression reporter cassettes into the coding region of these genes did not lead to expression in the HSC compartment. We have noted that both Clec1a and Sult1a1 are dynamically age-regulated, with relatively low expression in HSCs isolated from young mice, and elevated expression with advancing age (FIG. 1d). Without wishing to be limited or restricted by theory, several reasons could underlie this outcome, including the possibility that targeting the loci in the manner that we did sufficiently disrupted regulatory elements necessary for expression in HSCs. In contrast to Clec1a and Sult1a1, targeting of the Fgd5 locus yielded a reporter that almost exclusively labels HSCs in the murine BM. In addition to being essentially synonymous with a myriad of markers that are used to immunophenotypically identify HSCs (Balazs et al., 2006; Bryder et al., 2006; Kiel et al., 2005; Ooi et al., 2009; Osawa et al., 1996), cells sorted solely on reporter signal from the Fgd5$^{mCherry/+}$ mice had potent HSC activity that matched the functional potential of rigorously immuno-purified HSCs (Kiel et al., 2005). We demonstrated that the Fgd5-reporter effectively marked all HSC activity in the steady state BM, which is remarkable in light of evidence showing that even widely used protocols that have proven very effective in identifying HSCs such as side population activity (Goodell et al., 1996) do not strictly identify all cells with HSC activity (Morita et al., 2006). Moreover, the demonstration that Fgd5-reporter activity exclusively identified immunophenotypic HSCs in the BM of transplanted mice suggests that even under experimental settings requiring extensive HSC activity and self-renewal, Fgd5-reporter expression remained a powerful tool for identifying HSCs. These properties therefore indicate that the Fgd5-reporter is a useful tool for studying the pathways and molecules that govern the central properties of HSCs. Moreover, our data described herein identifies Fgd5 as an ideal locus for the construction of a repertoire of additional strains designed to specifically study the functional, molecular and therapeutic properties of HSCs.

Experimental Procedures

Hematopoietic Expression Database

AFFYMETRIX microarrays 430.2 were used to detect genome-wide expression of sorted cells from C57BL/6 mice. We have generated some of the arrays data including the HSCs and MPPs of young, mid aged and old mouse. Additional arrays data included data curated from GEO (complete list of accession numbers in Table 1). All of the arrays were normalized together using the gcRMA using R. To identify cell-type specific genes we applied several filters: 1. Only probe sets that had expression values ≥Log 7.0 were included. 2. Ratio of expression difference for the cell type of interest to all others had to be greater than 4-fold; 3. Statistical significance for the cell type of interest to all others had to be $P<10^{-6}$ by student's t-test.

Gene Targeting

The targeting constructs (FIGS. 9A-9C) were generated using the W vector. Homologous-arms were cloned by PCR from genomic DNA of C57Bl/6 and reporter-genes cassettes were fitted with adequate restriction sites using PCR. Constructs were sequenced and validated to be correct. ES cells (B6/3) derived from C57Bl/6 mice were electroporated with linearized constructs and selected with G418 on Neo-resistant feeders. Clones were manually picked, expanded and screened by southern blot. Positive clones were further expanded, validated, and injected into blastocysts, and germline transmission confirmed.

FACS Analysis and Cell Sorting

Adult mouse bone marrow was obtained from the tibia, femur and pelvic bones by crashing and isolating over HISTOPAQUE 1083 (Sigma). Cells were stained for 1.5 hours in PBS 2 mM EDTA, 2% FBS at 4° C. with some combinations of the following antibodies: Lineages markers; Ter119 (Ter119), Mac-1 (ml/70), Gr-1 (8C5), CD3 (17A2), CD4 (RM4-5), CD8 (53-6.7), B220 (RA3-6B2), IL7Ra (A7R34); CD34 (RAM34), Flk2 (A2F10), cKit (2B8), Sca1 (D7), CD150 (TC15-12F12.2), CD48 (HM48-1), CD201 (eBiol560), ESAM (1G8); all from BIOLEGEND or EBIOSCIENCE. After staining, cells were washed and suspended with DAPI (1 µg/ml), and kept on ice. Cells were sorted on an ARIAII (BD BIOSCIENCES) or MOFLO® ASTRIOS™ (BECKMAN COULTER), equipped with 590 nm laser for optimal detection of the mCherry signal. Transplanted cells were double sorted for purity. Additional strains used included; 129Sv/SvImJ, Balb/cJ, C3H/HeJ and CBA/J from Jackson Laboratories, Bar Harbor, Me., USA.

Transplantations and Peripheral Blood Analysis

Congenic recipient mice were lethally irradiated (900 rad). Donor cells were mixed with competitors and injected in 200 µl PBS, 2 mM EDTA, 2% FBS into the tail-vain. At the indicated time points, 2-3 drops of blood were collected from the tail into 150 µl Alsever's solution (SIGMA). Blood samples were treated with 10 ml ACK solution (0.15M $NH_4Cl$, 1 mM $KHCO_3$, 0.1 mM EDTA) for 5 minutes at room temperature and washed 2× with PBS. Leukocytes were stained with PerCP/Cy5.5-Ter119 (Ter119), PE/Cy7-Mac1 (ml/70), Fitc-Gr1 (8C5), PE-CD3 (17A2), APC/Cy7-B220 (RA3-6B2), A647-CD45.1 (A20) and PacBlue-CD45.2 (104); all from BIOLEGEND. Cells were washed and suspended with Propidium Iodide (1 µg/ml) before reading on FACS CANTO II (BD BIOSCIENCES). Analysis was done using FLOWJO software. For serial-transplants (secondary and tertiary), whole bone marrow of recipients was harvested and $2×10^6$ cells injected into lethally irradiated congenic recipients.

AGM Explants, Culturing, and Imaging

Procedure was adapted from (Medvinsky and Dzierzak, 1996; Taoudi et al., 2008). Briefly, the Aorta-Gonad-Mesonephrous (AGM) with some of surroundings tissues (but strictly no somites) of E11.5 embryos (CD45.2) were individually dissected and cultured on top of DURAPORE 0.65 m filters (Millipore) at the air-liquid interface with IMDM media containing 20% serum and 100 ng/ml SCF, IL3 and flt3L (all from PEPROTECH). After 4 days, cells were dissociated with Collagenase I (Worthington), filtered, and mixed with whole bone marrow competitor cells (CD45.1) and transplanted into lethally irradiated congenic recipients (CD45.1).

TABLE 1

List of Accession Numbers

| # | Population (and GSM accesion number) | Common name |
|---|---|---|
| 1 | HSC#1 | Hematopoietic Stem Cell |
| 2 | HSC#2 | Hematopoietic Stem Cell |
| 3 | HSC#3 | Hematopoietic Stem Cell |
| 4 | HSC#4 | Hematopoietic Stem Cell |
| 5 | MPP#1 | Multipotent Progenitors |
| 6 | MPP#2 | Multipotent Progenitors |
| 7 | MPP#3 | Multipotent Progenitors |
| 8 | Flk2+_Mansson_GSM303313 2.CEL | flk2+ Multipotent progenitors |
| 9 | Flk2+_mansson1_GSM303312.CEL | flk2+ Multipotent progenitors |
| 10 | Flt3+ GSM175732.CEL | flk2+ Multipotent progenitors |
| 11 | Flt3+ GSM175734.CEL | flk2+ Multipotent progenitors |
| 12 | CLP GSM207676.CEL | Common Lymphoid Progenitors |
| 13 | CLP GSM207677.CEL | Common Lymphoid Progenitors |
| 14 | CLP GSM207678.CEL | Common Lymphoid Progenitors |
| 15 | CMP_1R_Kumar_GSM267848.CEL | Common Myeloid Progenitors |
| 16 | CMP_2R_Kumar_GSM267850.CEL | Common Myeloid Progenitors |

TABLE 1-continued

List of Accession Numbers

| # | Population (and GSM accesion number) | Common name |
|---|---|---|
| 17 | CMP_3R_Kumar_GSM267852.CEL | Common Myeloid Progenitors |
| 18 | CMP_novartis_2_GSM258642.CEL | Common Myeloid Progenitors |
| 19 | CMP_novartis_GSM258641.CEL | Common Myeloid Progenitors |
| 20 | GMP_kumar_1_GSM267842.CEL | Granulocyte-Macrophage Progenitors |
| 21 | GMP_kumar_2_GSM267843.CEL | Granulocyte-Macrophage Progenitors |
| 22 | GMP_kumar_3_GSM267844.CEL | Granulocyte-Macrophage Progenitors |
| 23 | GMP_novartis_2_GSM258666.CEL | Granulocyte-Macrophage Progenitors |
| 24 | GMP_novartis_GSM258665.CEL | Granulocyte-Macrophage Progenitors |
| 25 | MEP_novartis_2_GSM258720.CEL | Megakaryocyte-Erythrocyte Progenitors |
| 26 | MEP_novartis_GSM258719.CEL | Megakaryocyte-Erythrocyte Progenitors |
| 27 | MkP GSM207687.CEL | Megakaryocyte-Erythrocyte Progenitors |
| 28 | MkP GSM207688.CEL | Megakaryocyte-Erythrocyte Progenitors |
| 29 | MkP GSM207689.CEL | Megakaryocyte-Erythrocyte Progenitors |
| 30 | PreGM GSM207679.CEL | Pre Granulocyte-Macrophage |
| 31 | PreGM GSM207680.CEL | Pre Granulocyte-Macrophage |
| 32 | PreGM GSM207681.CEL | Pre Granulocyte-Macrophage |
| 33 | PreMegE GSM207682.CEL | Pre Megakaryocyte-Erythrocyte |
| 34 | PreMegE GSM207683.CEL | Pre Megakaryocyte-Erythrocyte |
| 35 | PreMegE GSM207684.CEL | Pre Megakaryocyte-Erythrocyte |
| 36 | PreCFU-E GSM207690.CEL | Pre Colony Forming Units Erythrocyte |
| 37 | PreCFU-E GSM207691.CEL | Pre Colony Forming Units Erythrocyte |
| 38 | PreCFU-E GSM207692.CEL | Pre Colony Forming Units Erythrocyte |
| 39 | Erythroblast_Orkin_1_GSM245460.CEL | Erythroblast |
| 40 | Erythroblast_Orkin_2_GSM245462.CEL | Erythroblast |
| 41 | Erythroblast_Orkin_3_GSM245464.CEL | Erythroblast |
| 42 | Erythroblasts_GSM315615.CEL | Erythroblast |
| 43 | NucErythro_GSM149597.CEL | Nucleated Eryth. |
| 44 | NucErythro_GSM149598.CEL | Nucleated Eryth. |
| 45 | Granulocyte GSM149595.CEL | Granulocyte |
| 46 | Granulocyte GSM149596.CEL | Granulocyte |
| 47 | Granulocytes_mac1+_gr1+_2_GSM258668.CEL | Granulocyte |
| 48 | Granulocytes_mac1+_gr1+_GSM258667.CEL | Granulocyte |
| 49 | Neutrophil_2_GSM303490.CEL | Granulocyte |
| 50 | Neutrophil_3_GSM303491.CEL | Granulocyte |
| 51 | Neutrophil_GSM303489.CEL | Granulocyte |
| 52 | Macrophage_BM_novartis_2_GSM258694.CEL | Macrophage |
| 53 | Macrophage_BM_novartis_GSM258693.CEL | Macrophage |
| 54 | Monocytes GSM149593.CEL | Monocyte |
| 55 | Monocytes GSM149594.CEL | Monocyte |
| 56 | Osteoclasts_novartis_2_GSM258744.CEL | Osteoclast |
| 57 | Osteoclasts_novartis_GSM258743.CEL | Osteoclast |
| 58 | cDC CD11b GSM247589.CEL | Dendritic Cell |
| 59 | cDC CD11b' GSM247590.CEL | Dendritic Cell |
| 60 | pDC GSM247591.CEL | Plasmacytoid DC |
| 61 | pDC' GSM247592.CEL | Plasmacytoid DC |
| 62 | Pro-B cells (CD19+B220+CD43−IgM−)_2_GSM280474.CEL | Pro-B |
| 63 | Pro-B cells (CD19+B220+CD43−IgM−)_GSM280473.CEL | Pro-B |
| 64 | Pro-B_(CD19+AA4.1+CD43low)_GSM280471.CEL | ProB |
| 65 | Pro-B_(CD19+AA4.1+CD43low)_GSM280471GSM280472.CEL | Pro-B |
| 66 | naiveB#1_GSM94741.CEL | B cell |
| 67 | naiveB#2_GSM94744.CEL | B cell |
| 68 | naiveB#3_GSM94745.CEL | B cell |
| 69 | B lympho GSM247595.CEL | |
| 70 | B lympho_1GSM247596.CEL | |
| 71 | B lympho_2 GSM247597.CEL | |
| 72 | GSM149591.CEL | |
| 73 | GSM149592.CEL | |
| 74 | Follicular_b-cells_novartis_2_GSM258664.CEL | |
| 75 | Follicular_b-cells_novartis_GSM258663.CEL | |
| 76 | Mature B cells (CD19+IgM+)_2_GSM280476.CEL | |
| 77 | Mature B cells (CD19+IgM+)_GSM280475.CEL | |
| 78 | Germinal Center#1 GSM94765.CEL | Germinal Center B cell |
| 79 | Germinal Center#2 GSM94766.CEL | Germinal Center B cell |
| 80 | Germinal Center#3 GSM94767.CEL | Germinal Center B cell |
| 81 | PlasmaB #1_GSM94747.CEL | Plasma Cell |
| 82 | PlasmaB#2_GSM94762.CEL | Plasma Cell |
| 83 | PlasmaB#3_GSM94763.CEL | Plasma Cell |
| 84 | MemoryB#1_GSM94768.CEL | Memory B cell |
| 85 | MemoryB#2_GSM94769.CEL | Memory B cell |
| 86 | MemoryB#3_GSM94771.CEL | Memory B cell |
| 87 | NK_2_dembele_GSM247594.CEL | NK cell |
| 88 | NK_Dembele_GSM247593.CEL | NK cell |
| 89 | NK_IL-15_active_2_GSM188005.CEL | Activated NK |
| 90 | NK_IL-15_active_meyer_GSM188002.CEL | Activated NK |

TABLE 1-continued

List of Accession Numbers

| # | Population (and GSM accesion number) | Common name |
|---|---|---|
| 91 | NK_il-15_active_3_GSM188006.CEL | Activated NK |
| 92 | NK_novartis_2_GSM258732.CEL | NK cell |
| 93 | NK_novartis_GSM258731.CEL | NK cell |
| 94 | NK_resting_meyer_2_GSM188003.CEL | NK cell |
| 95 | NK_resting_meyer_3_GSM188004.CEL | NK cell |
| 96 | NK_resting_meyer_GSM188001.CEL | NK cell |
| 97 | thymocyte_DP_CD4+CD8+_novartis_2_GSM258782.CEL | Double-positive Thymocyte |
| 98 | thymocyte_DP_CD4+CD8+_novartis_GSM258781.CEL | Double-positive Thymocyte |
| 99 | thymocyte_SP_CD4+_novartis_2_GSM258784.CEL | Single Positive CD4 |
| 100 | thymocyte_SP_CD4+_novartis_GSM258783.CEL | Single Positive CD4 |
| 101 | thymocyte_SP_CD8+_novartis_2_GSM258786.CEL | Single Positive CD8 |
| 102 | thymocyte_SP_CD8+_novartis_GSM258785.CEL | Single Positive CD8 |
| 103 | T CD8 GSM247598.CEL | CD8 T cell |
| 104 | T CD8' GSM247599.CEL | CD8 T cell |
| 105 | T-cell_CD8+_novartis_2_GSM258776.CEL | CD8 T cell |
| 106 | T-cell_CD8+_novartis_GSM258775.CEL | CD8 T cell |
| 107 | CD8naive GSM149585.CEL | CD8 T cell |
| 108 | CD8naive GSM149586.CEL | CD8 T cell |
| 109 | CD8act GSM149589.CEL | Activated CD8 |
| 110 | CD8act GSM149590.CEL | Activated CD8 |
| 111 | T-cell_CD4+_novartis_2_GSM258774.CEL | CD4 T cell |
| 112 | T-cell_CD4+_novartis_GSM258773.CEL | CD4 T cell |
| 113 | CD4naive GSM149583.CEL | CD4 T cell |
| 114 | CD4naive GSM149584.CEL | CD4 T cell |
| 115 | CD4act GSM149587.CEL | Activated CD4 |
| 116 | CD4act GSM149588.cel | Activated CD4 |
| 117 | NEG-Foxp3_Carls_2_GSM158527.CEL | regulatory T cell |
| 118 | NEG-Foxp3_Carls_GSM158520.CEL | regulatory T cell |
| 119 | Foxp3_Rud_2_GSM154373.CEL | regulatory T cell |
| 120 | Foxp3_rud_GSM154369.CEL | regulatory T cell |
| 121 | T-cell_FOXp3+_novartis_2_GSM258778.CEL | regulatory T cell |
| 122 | T-cell_FOXp3+_novartis_GSM258777.CEL | regulatory T cell |

TABLE 2

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1455792_x_at | Ndn | 12.59 | 9.34 | 1.39E−21 |
| 1434736_at | Hlf | 13.23 | 8.98 | 9.04E−12 |
| 1438325_at | Evi1 | 12.32 | 8.92 | 6.77E−16 |
| 1434735_at | Hlf | 11.95 | 8.81 | 7.29E−12 |
| 1435383_x_at | Ndn | 12.72 | 8.77 | 1.80E−18 |
| 1430253_at | 2900006B11Rik | 11.55 | 8.75 | 1.98E−22 |
| 1435382_at | Ndn | 12.61 | 8.72 | 3.58E−19 |
| 1421461_at | Mpl | 11.81 | 8.47 | 8.81E−10 |
| 1448595_a_at | Bex1 | 14.16 | 8.30 | 6.98E−07 |
| 1437260_at | Mmrn1 | 12.00 | 8.27 | 3.42E−13 |
| 1443260_at | Meis1 | 11.65 | 8.20 | 1.72E−10 |
| 1440431_at | — | 12.95 | 7.96 | 2.11E−09 |
| 1459091_at | — | 10.81 | 7.81 | 3.66E−20 |
| 1446656_at | — | 12.78 | 7.77 | 9.61E−09 |
| 1417872_at | Fhl1 | 10.73 | 7.76 | 4.60E−15 |
| 1453152_at | Mamdc2 | 11.06 | 7.55 | 1.62E−14 |
| 1460578_at | Fgd5 | 10.36 | 7.34 | 2.62E−25 |
| 1420664_s_at | Procr | 11.48 | 7.27 | 4.10E−11 |
| 1417155_at | Mycn | 11.73 | 7.24 | 8.49E−08 |
| 1434141_at | Gucy1a3 | 11.10 | 7.21 | 2.67E−14 |
| 1447174_at | — | 10.95 | 7.17 | 2.46E−09 |
| 1459731_at | — | 11.72 | 7.16 | 4.23E−12 |
| 1455900_x_at | Tgm2 | 13.37 | 7.05 | 4.44E−07 |
| 1415923_at | Ndn | 10.20 | 7.02 | 4.38E−34 |
| 1432825_at | 2900018N21Rik | 10.05 | 7.02 | 1.06E−18 |
| 1451499_at | Cadps2 | 10.19 | 7.00 | 3.19E−20 |
| 1444232_at | Prkg1 | 10.26 | 6.93 | 3.06E−10 |
| 1459423_at | Meis1 | 10.66 | 6.80 | 1.91E−21 |
| 1440037_at | Pbx1 | 11.33 | 6.76 | 7.00E−08 |
| 1436939_at | Unc45b | 9.52 | 6.73 | 6.38E−38 |
| 1459512_at | — | 9.54 | 6.73 | 8.26E−15 |

TABLE 2-continued

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1417649_at | Cdkn1c | 9.24 | 6.63 | 5.28E−33 |
| 1429726_at | Slc16a9 | 8.79 | 6.60 | 1.42E−30 |
| 1455477_s_at | Pdzk1ip1 | 11.75 | 6.57 | 7.96E−07 |
| 1452366_at | Csgalnact1 | 10.18 | 6.53 | 6.31E−12 |
| 1416778_at | Sdpr | 9.85 | 6.43 | 1.69E−08 |
| 1448169_at | Krt18 | 10.40 | 6.40 | 4.26E−10 |
| 1435386_at | Vwf | 10.70 | 6.40 | 5.30E−07 |
| 1440637_at | — | 9.80 | 6.37 | 1.50E−08 |
| 1438660_at | Gcnt2 | 10.83 | 6.33 | 5.77E−08 |
| 1446921_at | — | 8.94 | 6.30 | 3.42E−31 |
| 1456072_at | Ppp1r9a | 10.37 | 6.25 | 8.03E−08 |
| 1448754_at | LOC100045055 /// Rbp1 | 9.16 | 6.25 | 2.23E−16 |
| 1444525_at | — | 10.08 | 6.24 | 2.16E−07 |
| 1416221_at | Fstl1 | 9.49 | 6.24 | 4.22E−19 |
| 1421074_at | Cyp7b1 | 8.97 | 6.23 | 2.65E−17 |
| 1418301_at | Irf6 | 9.34 | 6.09 | 5.65E−12 |
| 1427345_a_at | Sult1a1 | 8.38 | 6.06 | 2.18E−53 |
| 1444693_at | — | 9.26 | 6.04 | 5.87E−10 |
| 1438068_at | — | 9.49 | 6.01 | 8.72E−20 |
| 1435293_at | Adam22 | 8.96 | 6.00 | 1.91E−15 |
| 1440285_at | Ppp1r9a | 10.11 | 6.00 | 5.60E−07 |
| 1451332_at | Zfp521 | 9.67 | 5.98 | 1.19E−07 |
| 1452251_at | Nbea | 8.94 | 5.98 | 5.54E−20 |
| 1437079_at | Slc18a2 | 10.05 | 5.98 | 3.11E−08 |
| 1424677_at | Cyp2j9 | 9.78 | 5.97 | 7.28E−13 |
| 1439380_x_at | Meg3 | 9.37 | 5.97 | 4.23E−12 |
| 1439078_at | Klhl4 | 9.62 | 5.96 | 1.74E−11 |
| 1416405_at | Bgn | 8.28 | 5.95 | 3.05E−15 |
| 1452338_s_at | Itsn1 | 9.97 | 5.95 | 6.39E−07 |
| 1423679_at | 2810432L12Rik | 9.22 | 5.94 | 4.84E−11 |
| 1447886_at | 0610040B09Rik | 8.21 | 5.92 | 5.52E−22 |
| 1439831_at | — | 10.35 | 5.91 | 5.09E−15 |
| 1452905_at | Meg3 | 8.40 | 5.91 | 6.38E−112 |
| 1452183_a_at | Meg3 | 8.18 | 5.90 | 2.00E−74 |
| 1429702_at | 2900072G11Rik | 10.44 | 5.89 | 3.45E−12 |
| 1439766_x_at | Vegfc | 11.10 | 5.88 | 1.96E−07 |
| 1448942_at | Gng11 | 11.01 | 5.87 | 1.60E−11 |
| 1418486_at | Vnn1 | 8.64 | 5.87 | 7.07E−31 |
| 1430183_at | — | 9.30 | 5.86 | 8.60E−11 |
| 1441774_at | — | 9.45 | 5.85 | 8.79E−13 |
| 1417962_s_at | Ghr | 8.24 | 5.83 | 4.18E−19 |
| 1440954_at | — | 9.89 | 5.82 | 8.92E−08 |
| 1449876_at | Prkg1 | 8.71 | 5.81 | 7.70E−14 |
| 1432176_a_at | Eng | 10.27 | 5.81 | 4.57E−08 |
| 1418664_at | Mpdz | 8.62 | 5.80 | 2.26E−30 |
| 1457968_at | — | 10.71 | 5.80 | 6.06E−11 |
| 1438982_s_at | Flywch2 | 8.69 | 5.79 | 5.63E−18 |
| 1416473_a_at | Nope | 9.37 | 5.79 | 8.72E−18 |
| 1447693_s_at | Neo1 | 9.42 | 5.76 | 1.79E−17 |
| 1426712_at | Slc6a15 | 8.58 | 5.73 | 1.33E−31 |
| 1429977_at | 9030425L15Rik | 8.13 | 5.73 | 4.68E−24 |
| 1460515_at | 8430419K02Rik | 8.32 | 5.72 | 1.69E−22 |
| 1460039_at | Clec1a | 8.34 | 5.71 | 2.16E−46 |
| 1427095_at | Cdcp1 | 8.69 | 5.69 | 2.30E−11 |
| 1447584_s_at | Myct1 | 9.72 | 5.68 | 6.13E−07 |
| 1424051_at | Col4a2 | 8.58 | 5.68 | 2.02E−20 |
| 1421075_s_at | Cyp7b1 | 9.25 | 5.67 | 2.95E−16 |
| 1420688_a_at | Sgce | 9.43 | 5.67 | 4.15E−11 |
| 1427535_s_at | Obsl1 | 7.71 | 5.66 | 2.66E−67 |
| 1440870_at | Prdm16 | 9.78 | 5.66 | 2.92E−11 |
| 1439275_s_at | 9530010C24Rik | 8.55 | 5.65 | 3.72E−22 |
| 1447096_at | — | 11.24 | 5.64 | 3.80E−07 |
| 1426784_at | Trim47 | 8.94 | 5.64 | 5.11E−12 |
| 1437853_x_at | Ndn | 10.31 | 5.64 | 4.48E−20 |
| 1455706_at | — | 9.69 | 5.63 | 6.66E−12 |
| 1430387_at | 1810073O08Rik | 9.38 | 5.63 | 3.65E−14 |

TABLE 2-continued

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1418981_at | Casp12 /// LOC100044205 | 8.38 | 5.63 | 5.83E−15 |
| 1427191_at | Npr2 | 7.90 | 5.61 | 3.04E−31 |
| 1448259_at | Fstl1 | 8.42 | 5.56 | 2.23E−20 |
| 1425914_a_at | Armcx1 | 9.87 | 5.56 | 3.01E−08 |
| 1434423_at | Gulp1 | 9.19 | 5.55 | 2.30E−13 |
| 1452035_at | Col4a1 | 8.60 | 5.55 | 1.83E−16 |
| 1433626_at | Plscr4 | 9.50 | 5.53 | 1.04E−09 |
| 1448323_a_at | Bgn | 8.66 | 5.53 | 1.02E−20 |
| 1427284_a_at | Ttpa | 8.84 | 5.52 | 1.61E−08 |
| 1454869_at | Wdr40b | 10.11 | 5.48 | 1.27E−09 |
| 1417301_at | Fzd6 | 9.29 | 5.47 | 1.18E−07 |
| 1418912_at | Plxdc2 | 9.00 | 5.47 | 1.38E−18 |
| 1456532_at | Pdgfd | 9.09 | 5.46 | 8.02E−21 |
| 1459691_at | — | 8.10 | 5.46 | 1.97E−26 |
| 1452864_at | Med12l | 9.48 | 5.45 | 5.94E−09 |
| 1449297_at | Casp12 /// LOC100044205 | 8.31 | 5.44 | 6.36E−19 |
| 1437085_at | D630039A03Rik | 8.49 | 5.42 | 7.49E−12 |
| 1453456_at | 2900084O03Rik | 8.52 | 5.42 | 1.77E−12 |
| 1423677_at | Fkbp9 | 8.39 | 5.40 | 1.14E−10 |
| 1428795_at | 1110021L09Rik | 8.44 | 5.39 | 4.50E−12 |
| 1447869_x_at | Rhobtb3 | 9.05 | 5.37 | 1.91E−11 |
| 1457386_at | — | 9.09 | 5.37 | 2.41E−25 |
| 1460003_at | AI956758 | 8.35 | 5.37 | 1.35E−18 |
| 1440739_at | Vegfc | 8.50 | 5.36 | 7.71E−08 |
| 1442655_at | Dnmt3b | 9.49 | 5.34 | 9.80E−11 |
| 1428167_a_at | Mpzl1 | 10.51 | 5.33 | 5.80E−12 |
| 1449431_at | Trpc6 | 9.08 | 5.33 | 1.50E−15 |
| 1459588_at | — | 8.49 | 5.33 | 6.20E−10 |
| 1442267_at | Stxbp4 | 8.11 | 5.29 | 2.40E−15 |
| 1441509_at | A130009I22Rik | 7.94 | 5.29 | 1.19E−21 |
| 1436265_at | ENSMUSG00000072769 | 7.64 | 5.28 | 4.22E−41 |
| 1428168_at | Mpzl1 | 8.32 | 5.26 | 4.98E−13 |
| 1441535_at | Mllt3 | 9.33 | 5.24 | 1.47E−09 |
| 1438455_at | Pabpc4l | 8.09 | 5.23 | 9.18E−34 |
| 1448269_a_at | Klhl13 | 8.12 | 5.23 | 3.18E−46 |
| 1441727_s_at | Zfp467 | 10.86 | 5.22 | 7.38E−07 |
| 1429703_at | 2900072G11Rik | 8.75 | 5.22 | 1.30E−12 |
| 1440589_at | — | 8.12 | 5.19 | 6.80E−34 |
| 1419042_at | Iigp1 /// LOC100044196 | 10.37 | 5.16 | 2.05E−07 |
| 1419417_at | Vegfc | 9.55 | 5.16 | 4.58E−08 |
| 1448562_at | Upp1 | 7.97 | 5.15 | 2.26E−11 |
| 1436528_at | Kazald1 | 7.55 | 5.13 | 6.40E−57 |
| 1423353_at | Crispld1 | 7.64 | 5.11 | 4.39E−18 |
| 1452072_at | Myct1 | 8.18 | 5.11 | 2.96E−09 |
| 1422629_s_at | Shroom3 | 7.69 | 5.09 | 1.13E−41 |
| 1416474_at | Nope | 8.25 | 5.07 | 3.44E−32 |
| 1437889_x_at | Bgn | 8.52 | 5.06 | 3.36E−23 |
| 1455591_at | Zfp618 | 7.54 | 5.06 | 6.43E−31 |
| 1418788_at | Tek | 8.15 | 5.04 | 3.82E−11 |
| 1448664_a_at | Speg | 9.08 | 5.04 | 3.74E−09 |
| 1419811_at | Adcy9 | 9.45 | 5.03 | 3.51E−07 |
| 1416827_at | Tbxas1 | 9.90 | 5.03 | 3.26E−08 |
| 1434073_at | Gprasp2 | 8.21 | 5.02 | 2.83E−17 |
| 1449531_at | Leprel2 | 7.62 | 5.02 | 1.13E−19 |
| 1441254_at | Pard3b | 7.54 | 5.02 | 5.12E−16 |
| 1418049_at | Ltbp3 | 8.45 | 5.01 | 1.45E−09 |
| 1431890_a_at | Mllt3 | 10.65 | 5.01 | 3.35E−07 |
| 1430826_s_at | Gcnt2 | 8.51 | 5.00 | 4.76E−09 |
| 1449283_a_at | Mapk12 | 8.22 | 4.98 | 3.68E−07 |
| 1438530_at | Tfpi | 7.96 | 4.97 | 9.81E−17 |
| 1450062_a_at | Maged1 | 8.32 | 4.96 | 1.72E−09 |
| 1427104_at | Zfp612 | 7.58 | 4.94 | 1.69E−14 |

TABLE 2-continued

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1455521_at | Klfl2 | 8.92 | 4.94 | 1.48E−07 |
| 1425506_at | Mylk | 10.04 | 4.93 | 4.81E−11 |
| 1419123_a_at | Pdgfc | 8.79 | 4.92 | 5.21E−18 |
| 1447845_s_at | Vnn1 | 7.79 | 4.92 | 5.88E−36 |
| 1424595_at | F11r | 7.41 | 4.89 | 6.51E−16 |
| 1460465_at | A930038C07Rik | 8.21 | 4.89 | 1.13E−09 |
| 1441114_at | 9330156P08Rik | 7.89 | 4.88 | 7.59E−17 |
| 1426782_at | Gpr125 | 8.52 | 4.87 | 5.45E−11 |
| 1418176_at | Vdr | 7.74 | 4.87 | 1.27E−21 |
| 1440935_at | — | 7.59 | 4.85 | 3.38E−23 |
| 1432198_at | — | 7.87 | 4.85 | 3.01E−12 |
| 1418586_at | Adcy9 | 8.80 | 4.82 | 5.40E−09 |
| 1418879_at | 9030611O19Rik | 7.72 | 4.80 | 8.71E−19 |
| 1445377_at | — | 7.23 | 4.80 | 2.98E−21 |
| 1438048_at | Myct1 | 8.06 | 4.79 | 4.83E−20 |
| 1420859_at | Pkia | 7.63 | 4.77 | 2.20E−26 |
| 1417837_at | Phlda2 | 7.07 | 4.77 | 1.17E−20 |
| 1454745_at | Arhgap29 | 8.15 | 4.77 | 9.02E−10 |
| 1456225_x_at | Trib3 | 9.12 | 4.76 | 9.83E−08 |
| 1445363_at | 2810055G20Rik | 7.73 | 4.75 | 3.14E−21 |
| 1432057_a_at | Prdm5 | 8.05 | 4.75 | 3.61E−08 |
| 1436244_a_at | Tle2 | 7.67 | 4.75 | 3.40E−22 |
| 1434188_at | Slc16a12 | 8.57 | 4.73 | 1.24E−20 |
| 1458942_at | C230037E05Rik | 7.77 | 4.71 | 7.67E−15 |
| 1444615_x_at | Runx1t1 | 8.36 | 4.71 | 4.82E−12 |
| 1454862_at | Phldb2 | 7.99 | 4.69 | 1.40E−11 |
| 1418500_at | Nap1l3 | 8.16 | 4.69 | 2.80E−14 |
| 1436426_at | Cc2d2a | 8.37 | 4.68 | 3.87E−09 |
| 1429359_s_at | Rbpms | 9.24 | 4.68 | 1.24E−08 |
| 1457806_at | B830028B13Rik | 7.74 | 4.66 | 3.17E−09 |
| 1441373_at | — | 9.63 | 4.64 | 1.95E−07 |
| 1439894_at | A730056I06Rik | 7.96 | 4.61 | 5.18E−09 |
| 1460356_at | Esam1 | 7.56 | 4.58 | 1.52E−09 |
| 1417952_at | Cyp2j6 | 8.61 | 4.58 | 1.31E−13 |
| 1443941_at | Gm447 | 7.02 | 4.56 | 1.40E−21 |
| 1418713_at | Pcbd1 | 7.83 | 4.53 | 1.49E−08 |
| 1452473_at | Prr15 | 7.58 | 4.53 | 3.82E−19 |
| 1456437_x_at | C1r /// C1rb | 9.26 | 4.52 | 4.69E−15 |
| 1450924_at | Hdgfrp3 | 8.86 | 4.51 | 2.11E−07 |
| 1427912_at | Cbr3 | 7.32 | 4.51 | 2.12E−09 |
| 1430221_at | 9130008F23Rik | 7.86 | 4.51 | 1.18E−13 |
| 1455812_x_at | Vasn | 8.04 | 4.49 | 4.18E−20 |
| 1456229_at | Hoxb3 | 9.15 | 4.48 | 2.26E−15 |
| 1448727_at | Tle6 | 7.97 | 4.47 | 2.72E−09 |
| 1416368_at | Gsta4 | 8.16 | 4.46 | 9.01E−10 |
| 1445148_at | — | 9.48 | 4.45 | 1.33E−10 |
| 1439364_a_at | Mmp2 | 7.07 | 4.44 | 6.95E−09 |
| 1437451_at | 1110006O17Rik | 7.62 | 4.44 | 1.05E−26 |
| 1454557_at | 6720454L07Rik | 7.42 | 4.43 | 6.90E−10 |
| 1420930_s_at | Ctnnal1 | 8.33 | 4.41 | 2.40E−07 |
| 1448545_at | Sdc2 | 7.01 | 4.41 | 1.70E−17 |
| 1446585_at | — | 7.10 | 4.41 | 2.22E−24 |
| 1417021_a_at | Spo11 | 7.74 | 4.40 | 1.96E−10 |
| 1416598_at | Glis2 | 7.54 | 4.40 | 1.19E−09 |
| 1446930_at | — | 8.51 | 4.39 | 8.17E−07 |
| 1431353_at | Pabpc4l | 8.04 | 4.39 | 1.58E−32 |
| 1439300_at | Chic1 | 7.97 | 4.39 | 6.44E−10 |
| 1437833_at | Ltbp3 | 7.57 | 4.38 | 5.72E−23 |
| 1429167_at | Ccdc112 | 7.42 | 4.38 | 6.76E−12 |
| 1429510_at | 2810410L24Rik | 8.04 | 4.37 | 6.12E−11 |
| 1454691_at | Nrxn1 | 8.34 | 4.37 | 2.79E−08 |
| 1449174_at | Art4 | 7.80 | 4.35 | 3.06E−08 |
| 1423352_at | Crispld1 | 7.36 | 4.32 | 5.16E−11 |

TABLE 2-continued

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1428604_at | 2610305D13Rik | 7.70 | 4.32 | 1.34E−12 |
| 1437798_at | 6720422M22Rik | 7.29 | 4.29 | 9.43E−17 |
| 1446303_at | Igf1r | 8.03 | 4.29 | 1.96E−07 |
| 1441531_at | LOC100043487 /// Plcb4 | 7.62 | 4.28 | 7.95E−16 |
| 1424634_at | Tceal1 | 7.60 | 4.22 | 1.87E−07 |
| 1457885_at | — | 7.99 | 4.21 | 6.83E−12 |
| 1416779_at | Sdpr | 7.38 | 4.21 | 3.92E−08 |
| 1435600_s_at | BC020535 | 7.84 | 4.20 | 2.79E−21 |
| 1454849_x_at | Clu | 8.42 | 4.20 | 5.48E−08 |
| 1432011_at | 2900052L18Rik | 7.64 | 4.18 | 1.24E−12 |
| 1417753_at | Pkd2 | 7.38 | 4.16 | 2.73E−07 |
| 1443682_at | AI662476 | 7.17 | 4.14 | 8.12E−13 |
| 1425315_at | Dock7 | 9.11 | 4.14 | 9.38E−08 |
| 1448926_at | Hoxa5 | 7.82 | 4.13 | 5.04E−11 |
| 1457313_at | Ocrl | 7.68 | 4.11 | 5.39E−14 |
| 1460077_at | Ttc3 | 9.45 | 4.11 | 2.55E−07 |
| 1443117_at | Eya1 | 9.75 | 4.10 | 3.31E−07 |
| 1458309_at | — | 8.10 | 4.10 | 2.02E−15 |
| 1424713_at | Calml4 | 7.33 | 4.08 | 8.70E−07 |
| 1429809_at | Tmtc2 | 7.01 | 4.03 | 2.87E−33 |
| 1449620_s_at | Adcy9 | 7.50 | 4.02 | 2.33E−13 |
| 1442740_at | Prdm5 | 7.37 | 4.02 | 4.63E−11 |
| 1453328_at | 2700008G24Rik | 7.10 | 4.02 | 5.72E−22 |
| 1427169_at | Pard3b | 7.45 | 4.01 | 4.73E−09 |
| 1444772_at | — | 7.09 | 4.00 | 4.88E−07 |
| 1438916_x_at | 6720401G13Rik | 7.14 | 4.00 | 1.42E−13 |
| 1448665_at | Dmd | 7.66 | 4.00 | 6.86E−10 |
| 1424410_at | Ttc8 | 7.56 | 3.99 | 1.28E−08 |
| 1429661_at | Rhobtb3 | 7.07 | 3.98 | 3.48E−16 |
| 1439216_at | — | 7.79 | 3.97 | 8.39E−16 |
| 1438701_at | Bicd1 | 8.07 | 3.94 | 1.66E−09 |
| 1425274_at | Asph | 7.45 | 3.91 | 2.60E−10 |
| 1426065_a_at | Trib3 | 7.04 | 3.91 | 2.52E−10 |
| 1436534_at | Trove2 | 8.46 | 3.88 | 3.40E−09 |
| 1421087_at | Per3 | 7.32 | 3.88 | 3.57E−09 |
| 1432946_at | 5230400M06Rik | 7.35 | 3.87 | 1.84E−09 |
| 1449593_at | — | 7.21 | 3.86 | 7.10E−10 |
| 1440643_at | — | 8.18 | 3.85 | 3.19E−16 |
| 1453771_at | Gulp1 | 7.06 | 3.85 | 1.39E−17 |
| 1429717_at | Ipo11 | 7.80 | 3.83 | 1.90E−12 |
| 1419286_s_at | Ift81 | 7.46 | 3.78 | 1.59E−07 |
| 1437127_at | A630033E08Rik | 8.37 | 3.77 | 7.29E−09 |
| 1431380_at | 5730409L17Rik | 7.01 | 3.74 | 3.97E−15 |
| 1428626_at | Lysmd2 | 7.33 | 3.73 | 1.68E−10 |
| 1437689_x_at | Clu | 8.75 | 3.73 | 9.66E−07 |
| 1440789_at | Neo1 | 7.71 | 3.72 | 7.99E−17 |
| 1426306_a_at | LOC100046560 /// Maged2 | 8.26 | 3.71 | 8.68E−11 |
| 1433782_at | Cldn12 | 7.08 | 3.69 | 1.03E−13 |
| 1417039_a_at | Cul7 | 8.78 | 3.64 | 1.92E−07 |
| 1446732_at | — | 7.57 | 3.64 | 3.14E−16 |
| 1445065_at | — | 7.52 | 3.64 | 3.77E−10 |
| 1460086_at | Rc3h2 | 8.11 | 3.63 | 2.08E−07 |
| 1429290_at | Cbx6 /// Npcd | 10.20 | 3.62 | 7.24E−07 |
| 1435473_at | Gm347 | 7.24 | 3.61 | 6.44E−09 |
| 1454472_at | 2900092N22Rik | 7.06 | 3.61 | 2.05E−19 |
| 1449621_s_at | Thsd1 | 7.20 | 3.56 | 4.93E−08 |
| 1427981_a_at | Csad | 10.04 | 3.54 | 1.14E−09 |
| 1440231_at | Mtap9 | 7.11 | 3.54 | 2.89E−07 |
| 1419207_at | Zfp37 | 7.19 | 3.53 | 4.12E−28 |
| 1417787_at | Dkkl1 | 7.21 | 3.53 | 5.91E−08 |
| 1442916_at | — | 7.32 | 3.52 | 8.81E−07 |

TABLE 2-continued

Annotated Genes with Highly Restricted Expression in HSCs

| Probe Set | Gene Symbol | Expression in HSCs (Log2) | Expression ratio HSC-Downstream cells (Log2) | t-test HSC:ALL |
|---|---|---|---|---|
| 1428416_at | 3110050N22Rik | 8.26 | 3.51 | 5.24E−08 |
| 1443832_s_at | Sdpr | 7.04 | 3.50 | 2.96E−07 |
| 1428446_at | Dync2li1 /// LOC100048514 | 7.62 | 3.44 | 1.50E−09 |
| 1419564_at | Zfp467 | 7.08 | 3.43 | 1.90E−13 |
| 1442791_x_at | 6720407P12Rik | 7.79 | 3.41 | 1.11E−15 |
| 1423672_at | Ttc30b | 7.88 | 3.39 | 2.63E−07 |
| 1434962_x_at | Ccl27 | 7.65 | 3.36 | 1.27E−10 |
| 1454748_at | Naprt1 | 7.37 | 3.36 | 1.66E−07 |
| 1417505_s_at | Il11ra1 /// Il11ra2 /// LOC100038993 /// RP23-388P16.3 | 8.87 | 3.35 | 9.14E−07 |
| 1440396_at | — | 7.22 | 3.26 | 4.07E−10 |
| 1439554_at | — | 7.30 | 3.23 | 5.07E−12 |
| 1459807_x_at | 4933406E20Rik | 7.11 | 3.21 | 9.16E−09 |
| 1416081_at | Smad1 | 7.04 | 3.21 | 1.28E−07 |
| 1441570_at | — | 7.62 | 3.18 | 1.94E−10 |
| 1451809_s_at | Rwdd3 | 8.42 | 3.13 | 9.22E−08 |
| 1434490_at | Scarf1 | 7.08 | 3.12 | 7.25E−16 |
| 1435704_at | C920006O11Rik | 7.32 | 3.12 | 3.26E−10 |
| 1460055_at | — | 7.71 | 3.12 | 1.79E−07 |
| 1416174_at | LOC677524 /// Rbbp9 | 9.53 | 3.10 | 5.38E−09 |
| 1436326_at | Rora | 7.21 | 3.10 | 1.23E−07 |
| 1430079_at | 5033406O09Rik | 7.15 | 3.09 | 4.28E−10 |
| 1442243_at | Per3 | 7.39 | 3.09 | 9.43E−15 |
| 1446022_at | — | 8.31 | 3.09 | 3.52E−09 |
| 1438407_at | Dsel | 7.97 | 3.09 | 8.39E−07 |
| 1422498_at | Mageh1 | 7.21 | 3.00 | 5.45E−10 |
| 1430375_a_at | Ccl27 /// LOC100039939 /// LOC100040048 /// RP23-388P16.4 | 7.87 | 3.00 | 1.71E−09 |
| 1453141_at | 0610009L18Rik | 9.24 | 2.98 | 1.82E−08 |
| 1453674_at | Gcnt2 | 7.24 | 2.97 | 1.42E−07 |
| 1443114_at | A730059M13Rik | 7.42 | 2.95 | 1.32E−08 |
| 1441635_at | — | 7.26 | 2.93 | 2.09E−07 |
| 1425114_at | Rbbp6 | 9.35 | 2.86 | 8.48E−07 |
| 1442364_at | Mapk14 | 8.69 | 2.86 | 7.48E−08 |
| 1419188_s_at | Ccl27 /// LOC100039939 /// LOC100040048 /// RP23-388P16.4 | 7.31 | 2.82 | 1.52E−14 |
| 1419054_a_at | Ptpn21 | 7.80 | 2.77 | 2.69E−09 |
| 1457529_x_at | — | 7.23 | 2.72 | 2.85E−07 |
| 1441440_at | Atg4c | 7.15 | 2.63 | 3.41E−09 |
| 1430636_at | C030010B13Rik | 7.30 | 2.61 | 1.72E−08 |
| 1429657_at | Zfand5 | 8.29 | 2.53 | 2.84E−08 |
| 1434804_at | Exoc6b | 7.28 | 2.50 | 4.65E−13 |
| 1455817_x_at | Zxdb | 8.23 | 2.30 | 1.57E−07 |

REFERENCES

Balazs, A. B., Fabian, A. J., Esmon, C. T., and Mulligan, R. C. (2006). Endothelial protein C receptor (CD201) explicitly identifies hematopoietic stem cells in murine bone marrow. Blood 107, 2317-2321.

Barker, N., van Es, J. H., Kuipers, J., Kujala, P., van den Born, M., Cozijnsen, M., Haegebarth, A., Korving, J., Begthel, H., Peters, P. J., et al. (2007). Identification of stem cells in small intestine and colon by marker gene Lgr5. Nature 449, 1003-1007.

Becker, A. J., Mc, C. E., and Till, J. E. (1963). Cytological demonstration of the clonal nature of spleen colonies derived from transplanted mouse marrow cells. Nature 197, 452-454.

Bertoncello, I., Hodgson, G. S., and Bradley, T. R. (1985). Multiparameter analysis of transplantable hemopoietic stem cells: I. The separation and enrichment of stem cells homing to marrow and spleen on the basis of rhodamine-123 fluorescence. Exp Hematol 13, 999-1006.

Bhattacharya, D., Rossi, D. J., Bryder, D., and Weissman, I. L. (2006). Purified hematopoietic stem cell engraftment of rare niches corrects severe lymphoid deficiencies without host conditioning. J Exp Med 203, 73-85.

Bryder, D., Rossi, D. J., and Weissman, I. L. (2006). Hematopoietic stem cells: the paradigmatic tissue-specific stem cell. Am J Pathol 169, 338-346.

Chambers, S. M., Shaw, C. A., Gatza, C., Fisk, C. J., Donehower, L. A., and Goodell, M. A. (2007). Aging hematopoietic stem cells decline in function and exhibit epigenetic dysregulation. PLoS Biol 5, e201.

Chen, C. Z., Li, M., de Graaf, D., Monti, S., Gottgens, B., Sanchez, M. J., Lander, E. S., Golub, T. R., Green, A. R., and Lodish, H. F. (2002). Identification of endoglin as a functional marker that defines long-term repopulating hematopoietic stem cells. Proc Natl Acad Sci USA 99, 15468-15473.

Cheng, C., Haasdijk, R., Tempel, D., van de Kamp, E. H., Herpers, R., Bos, F., Den Dekker, W. K., Blonden, L. A., de Jong, R., Burgisser, P. E., et al. (2012). Endothelial Cell-Specific FGD5 Involvement in Vascular Pruning Defines Neovessel Fate in Mice. Circulation 125, 3142-3159.

Christensen, J. L., and Weissman, I. L. (2001). Flk-2 is a marker in hematopoietic stem cell differentiation: a simple method to isolate long-term stem cells. Proc Natl Acad Sci USA 98, 14541-14546.

Colonna, M., Samaridis, J., and Angman, L. (2000). Molecular characterization of two novel C-type lectin-like receptors, one of which is selectively expressed in human dendritic cells. Eur J Immunol 30, 697-704.

Dzierzak, E., and Speck, N. A. (2008). Of lineage and legacy: the development of mammalian hematopoietic stem cells. Nat Immunol 9, 129-136.

Forsberg, E. C., Passegue, E., Prohaska, S. S., Wagers, A. J., Koeva, M., Stuart, J. M., and Weissman, I. L. (2010). Molecular signatures of quiescent, mobilized and leukemia-initiating hematopoietic stem cells. PLoS One 5, e8785.

Forsberg, E. C., Prohaska, S. S., Katzman, S., Heffner, G. C., Stuart, J. M., and Weissman, I. L. (2005). Differential expression of novel potential regulators in hematopoietic stem cells. PLoS Genet 1, e28.

Foudi, A., Hochedlinger, K., Van Buren, D., Schindler, J. W., Jaenisch, R., Carey, V., and Hock, H. (2009). Analysis of histone 2B-GFP retention reveals slowly cycling hematopoietic stem cells. Nat Biotechnol 27, 84-90.

Gazit, R., Gruda, R., Elboim, M., Arnon, T. I., Katz, G., Achdout, H., Hanna, J., Qimron, U., Landau, G., Greenbaum, E., et al. (2006). Lethal influenza infection in the absence of the natural killer cell receptor gene Ncr1. Nat Immunol 7, 517-523.

Goodell, M. A., Brose, K., Paradis, G., Conner, A. S., and Mulligan, R. C. (1996). Isolation and functional properties of murine hematopoietic stem cells that are replicating in vivo. J Exp Med 183, 1797-1806.

Goyama, S., Yamamoto, G., Shimabe, M., Sato, T., Ichikawa, M., Ogawa, S., Chiba, S., and Kurokawa, M. (2008). Evi-1 is a critical regulator for hematopoietic stem cells and transformed leukemic cells. Cell Stem Cell 3, 207-220.

Hildebrandt, M., Adjei, A., Weinshilboum, R., Johnson, J. A., Berlin, D. S., Klein, T. E., and Altman, R. B. (2009). Very important pharmacogene summary: sulfotransferase 1A1. Pharmacogenet Genomics 19, 404-406.

Hosen, N., Yamane, T., Muijtjens, M., Pham, K., Clarke, M. F., and Weissman, I. L. (2007). Bmi-1-green fluorescent protein-knock-in mice reveal the dynamic regulation of bmi-1 expression in normal and leukemic hematopoietic cells. Stem Cells 25, 1635-1644.

Ivanova, N. B., Dimos, J. T., Schaniel, C., Hackney, J. A., Moore, K. A., and Lemischka, I. R. (2002). A stem cell molecular signature. Science 298, 601-604.

Kataoka, K., Sato, T., Yoshimi, A., Goyama, S., Tsuruta, T., Kobayashi, H., Shimabe, M., Arai, S., Nakagawa, M., Imai, Y., et al. (2011). Evi1 is essential for hematopoietic stem cell self-renewal, and its expression marks hematopoietic cells with long-term multilineage repopulating activity. J Exp Med 208, 2403-2416.

Kiel, M. J., Yilmaz, O. H., Iwashita, T., Yilmaz, O. H., Terhorst, C., and Morrison, S. J. (2005). SLAM family receptors distinguish hematopoietic stem and progenitor cells and reveal endothelial niches for stem cells. Cell 121, 1109-1121.

Kubota, Y., Osawa, M., Jakt, L. M., Yoshikawa, K., and Nishikawa, S. (2009). Necdin restricts proliferation of hematopoietic stem cells during hematopoietic regeneration. Blood 114, 4383-4392.

Kurogane, Y., Miyata, M., Kubo, Y., Nagamatsu, Y., Kundu, R. K., Uemura, A., Ishida, T., Quertermous, T., Hirata, K., and Rikitake, Y. (2012). FGD5 mediates proangiogenic action of vascular endothelial growth factor in human vascular endothelial cells. Arterioscler Thromb Vasc Biol 32, 988-996.

Laugwitz, K. L., Moretti, A., Lam, J., Gruber, P., Chen, Y., Woodard, S., Lin, L. Z., Cai, C. L., Lu, M. M., Reth, M., et al. (2005). Postnatal isl1+ cardioblasts enter fully differentiated cardiomyocyte lineages. Nature 433, 647-653.

Luckey, C. J., Bhattacharya, D., Goldrath, A. W., Weissman, I. L., Benoist, C., and Mathis, D. (2006). Memory T and memory B cells share a transcriptional program of self-renewal with long-term hematopoietic stem cells. Proc Natl Acad Sci USA 103, 3304-3309.

Matsumoto, A., Takeishi, S., Kanie, T., Susaki, E., Onoyama, I., Tateishi, Y., Nakayama, K., and Nakayama, K. I. (2011). p57 is required for quiescence and maintenance of adult hematopoietic stem cells. Cell Stem Cell 9, 262-271.

Medvinsky, A., and Dzierzak, E. (1996). Definitive hematopoiesis is autonomously initiated by the AGM region. Cell 86, 897-906.

Montgomery, R. K., Carlone, D. L., Richmond, C. A., Farilla, L., Kranendonk, M. E., Henderson, D. E., Baffour-Awuah, N. Y., Ambruzs, D. M., Fogli, L. K., Algra, S., et al. (2011). Mouse telomerase reverse transcriptase (mTert) expression marks slowly cycling intestinal stem cells. Proc Natl Acad Sci USA 108, 179-184.

Morita, Y., Ema, H., Yamazaki, S., and Nakauchi, H. (2006). Non-side-population hematopoietic stem cells in mouse bone marrow. Blood 108, 2850-2856.

Muller-Sieburg, C. E., Whitlock, C. A., and Weissman, I. L. (1986). Isolation of two early B lymphocyte progenitors from mouse marrow: a committed pre-pre-B cell and a clonogenic Thy-1-lo hematopoietic stem cell. Cell 44, 653-662.

Ooi, A. G., Karsunky, H., Majeti, R., Butz, S., Vestweber, D., Ishida, T., Quertermous, T., Weissman, I. L., and Forsberg, E. C. (2009). The adhesion molecule esam1 is a novel hematopoietic stem cell marker. Stem Cells 27, 653-661.

Osawa, M., Hanada, K., Hamada, H., and Nakauchi, H. (1996). Long-term lymphohematopoietic reconstitution by a single CD34-low/negative hematopoietic stem cell. Science 273, 242-245.

Park, I. K., He, Y., Lin, F., Laerum, O. D., Tian, Q., Bumgarner, R., Klug, C. A., Li, K., Kuhr, C., Doyle, M. J., et al. (2002). Differential gene expression profiling of adult murine hematopoietic stem cells. Blood 99, 488-498.

Park, I. K., Qian, D., Kiel, M., Becker, M. W., Pihalja, M., Weissman, I. L., Morrison, S. J., and Clarke, M. F. (2003). Bmi-1 is required for maintenance of adult self-renewing haematopoietic stem cells. Nature 423, 302-305.

Paszty, C., Mohandas, N., Stevens, M. E., Loring, J. F., Liebhaber, S. A., Brion, C. M., and Rubin, E. M. (1995). Lethal alpha-thalassaemia created by gene targeting in mice and its genetic rescue. Nat Genet 11, 33-39.

Pineault, N., Helgason, C. D., Lawrence, H. J., and Humphries, R. K. (2002). Differential expression of Hox, Meis1, and Pbx1 genes in primitive cells throughout murine hematopoietic ontogeny. Exp Hematol 30, 49-57.

Raftogianis, R. B., Wood, T. C., Otterness, D. M., Van Loon, J. A., and Weinshilboum, R. M. (1997). Phenol sulfotransferase pharmacogenetics in humans: association of common SULT1A1 alleles with TS PST phenotype. Biochem Biophys Res Commun 239, 298-304.

Rossi, D. J., Bryder, D., Zahn, J. M., Ahlenius, H., Sonu, R., Wagers, A. J., and Weissman, I. L. (2005). Cell intrinsic alterations underlie hematopoietic stem cell aging. Proc Natl Acad Sci USA 102, 9194-9199.

Shojaei, F., Trowbridge, J., Gallacher, L., Yuefei, L., Goodale, D., Karanu, F., Levac, K., and Bhatia, M. (2005). Hierarchical and ontogenic positions serve to define the molecular basis of human hematopoietic stem cell behavior. Dev Cell 8, 651-663.

Siminovitch, L., McCulloch, E. A., and Till, J. E. (1963). The Distribution of Colony-Forming Cells among Spleen Colonies. J Cell Physiol 62, 327-336.

Sobanov, Y., Bernreiter, A., Derdak, S., Mechtcheriakova, D., Schweighofer, B., Duchler, M., Kalthoff, F., and Hofer, E. (2001). A novel cluster of lectin-like receptor genes expressed in monocytic, dendritic and endothelial cells maps close to the NK receptor genes in the human NK gene complex. Eur J Immunol 31, 3493-3503.

Spangrude, G. J., Heimfeld, S., and Weissman, I. L. (1988). Purification and characterization of mouse hematopoietic stem cells. Science 241, 58-62.

Suzuki, N., Ohneda, O., Minegishi, N., Nishikawa, M., Ohta, T., Takahashi, S., Engel, J. D., and Yamamoto, M. (2006). Combinatorial Gata2 and Sca1 expression defines hematopoietic stem cells in the bone marrow niche. Proc Natl Acad Sci USA 103, 2202-2207.

Tadjali, M., Zhou, S., Rehg, J., and Sorrentino, B. P. (2006). Prospective isolation of murine hematopoietic stem cells by expression of an Abcg2/GFP allele. Stem Cells 24, 1556-1563.

Taoudi, S., Gonneau, C., Moore, K., Sheridan, J. M., Blackburn, C. C., Taylor, E., and Medvinsky, A. (2008). Extensive hematopoietic stem cell generation in the AGM region via maturation of VE-cadherin+CD45+ pre-definitive HSCs. Cell Stem Cell 3, 99-108.

Thebault, P., Lhermite, N., Tilly, G., Le Texier, L., Quillard, T., Heslan, M., Anegon, I., Soulillou, J. P., Brouard, S., Charreau, B., et al. (2009). The C-type lectin-like receptor CLEC-1, expressed by myeloid cells and endothelial cells, is up-regulated by immunoregulatory mediators and moderates T cell activation. J Immunol 183, 3099-3108

Till, J. E., and Mc, C. E. (1961). A direct measurement of the radiation sensitivity of normal mouse bone marrow cells. Radiat Res 14, 213-222.

Tumbar, T., Guasch, G., Greco, V., Blanpain, C., Lowry, W. E., Rendl, M., and Fuchs, E. (2004). Defining the epithelial stem cell niche in skin. Science 303, 359-363.

Wakabayashi, Y., Watanabe, H., Inoue, J., Takeda, N., Sakata, J., Mishima, Y., Hitomi, J., Yamamoto, T., Utsuyama, M., Niwa, O., et al. (2003). Bcl11b is required for differentiation and survival of alphabeta T lymphocytes. Nat Immunol 4, 533-539.

Weissman, I. L. (2000). Stem cells: units of development, units of regeneration, and units in evolution. Cell 100, 157-168.

Wilborn, T. W., Comer, K. A., Dooley, T. P., Reardon, I. M., Heinrikson, R. L., and Falany, C. N. (1993). Sequence analysis and expression of the cDNA for the phenol-sulfating form of human liver phenol sulfotransferase. Mol Pharmacol 43, 70-77.

Wilson, A., Laurenti, E., Oser, G., van der Wath, R. C., Blanco-Bose, W., Jaworski, M., Offner, S., Dunant, C. F., Eshkind, L., Bockamp, E., et al. (2008). Hematopoietic stem cells reversibly switch from dormancy to self-renewal during homeostasis and repair. Cell 135, 1118-1129.

Wolf, N. S., Kone, A., Priestley, G. V., and Bartelmez, S. H. (1993). In vivo and in vitro characterization of long-term repopulating primitive hematopoietic cells isolated by sequential Hoechst 33342-rhodamine 123 FACS selection. Exp Hematol 21, 614-622.

Yokota, T., Oritani, K., Butz, S., Kokame, K., Kincade, P. W., Miyata, T., Vestweber, D., and Kanakura, Y. (2009). The endothelial antigen ESAM marks primitive hematopoietic progenitors throughout life in mice. Blood 113, 2914-2923.

Zhou, B., Ma, Q., Rajagopal, S., Wu, S. M., Domian, I., Rivera-Feliciano, J., Jiang, D., von Gise, A., Ikeda, S., Chien, K. R., et al. (2008). Epicardial progenitors contribute to the cardiomyocyte lineage in the developing heart. Nature 454, 109-113.

Zou, P., Yoshihara, H., Hosokawa, K., Tai, I., Shinmyozu, K., Tsukahara, F., Maru, Y., Nakayama, K., Nakayama, K. I., and Suda, T. (2011). p57(Kip2) and p27(Kip1) cooperate to maintain hematopoietic stem cell quiescence through interactions with Hsc70. Cell Stem Cell 9, 247-261.

We claim:

1. A knock-in mouse having a heterozygous knock-in at an endogenous FYVE-, RhoGE- and PH-domain containing 5 (Fgd5) genomic locus comprising an exogenous nucleic acid sequence operably linked at an endogenous Fgd5 gene promoter comprising, in a 5' to 3' direction: a 5' nucleic acid sequence of a Fgd5 gene of SEQ ID NO: 1, a hematopoietic stem cell identifier reporter nucleic acid sequence encoding a reporter molecule, and a 3' nucleic acid sequence of an Fgd5 gene of SEQ ID NO: 1, wherein the exogenous nucleic acid sequence has been introduced into the endogenous Fgd5 genomic locus by homologous recombination, wherein said exogenous nucleic acid sequence comprising the hematopoietic stem cell identifier reporter nucleic acid sequence replaces a portion of a sequence of the endogenous Fgd5 gene locus, and wherein the knock-in mouse expresses the reporter molecule in hematopoietic stem cells.

2. An isolated hematopoietic stem cell isolated from the knock-in mouse having a heterozygous knock-in at an endogenous Fgd5 genomic locus and expressing the reporter molecule of claim 1.

* * * * *

SEQUENCE LISTING

<160> NUMBER OF SEQ ID NOS: 7

<210> SEQ ID NO 1
<211> LENGTH: 88896
<212> TYPE: DNA
<213> ORGANISM: Mus musculus

<400> SEQUENCE: 1

| | | | | | | |
|---|---|---|---|---|---|---|
| ctccacagaa | agaagatact | cccgtggatg | gggctaccga | ggagccgggg | tttgaggggg | 60 |
| aagtccagga | gcatggtaca | gagcagacag | gaactgaggg | ggacctggaa | gctccagatg | 120 |
| aagaggcacc | aagtagagac | agtgaggaag | gcatggtcca | cgctctggaa | gatgaagact | 180 |
| gtgatcacga | tccagagacg | gatgggaccc | caacatcgcc | agatgaaggg | gcaccaagca | 240 |
| gagacagtga | ggaaggtgag | gaggactgtg | atcagggccc | aggtatggag | gagcatccca | 300 |
| tgagtgaaga | ggagggagaa | gaggaggagg | tgaaggagca | cgtgtacaac | agtgataaca | 360 |
| gggcaccctg | ggatggagag | gagcccttcc | ccaatgaggt | cattctcaca | catgtccgct | 420 |
| ctcagtcccc | tgaagttccc | tgttgggagc | caggccctcc | tgagactcct | ggagaggcag | 480 |
| aagaggattg | tgaagacatc | tgtaacaaca | cagaacctgg | gaaacccaat | caggacactg | 540 |
| gtcaggacac | agaggatgcc | ggcatgggat | ccctgagag | tgaggtgtcc | ccagatgtcc | 600 |
| aggagcaaga | ggcagcaacg | gacaaccctg | aggtctttga | ggaggactct | gcagatgctg | 660 |
| cagaaggtga | ggatcagata | gagcaggagg | aaccacccaa | ttgtgacgag | gaagcctata | 720 |
| atagagatgc | cgcagcagcc | accatgcagg | tgggagagga | cctcggagag | gagggagacc | 780 |
| atgtgcagga | ggaccctgct | gaggaaagct | gccagatcat | tcccttgag | agcgacagtg | 840 |
| tggaggagga | tttctcacct | acactcacag | agaatcccta | tgagattttc | caaccgaga | 900 |
| gcacttcctt | ctgcaataac | acctattccc | ttgacgagtc | agccaatggg | cacgagccag | 960 |
| tgtgcgagat | ctgtgtagag | gaggttcctg | gtgttggccc | tccacttaac | cagcatgatt | 1020 |
| ccctgccaga | tggatctgga | gaggactccc | cggtggtccc | tgatgtggtg | gtcgtgccag | 1080 |
| agaatgaggg | gcccgtggat | gatgcactca | gcagtccata | cgtgatggga | gttggcttgc | 1140 |
| tgagccttgg | agagggagcg | cagtcagaca | cccaggctgc | atcaggcact | ctgagtgggt | 1200 |
| acagtacatg | ggaggaaggg | gactctgagg | gagggcaggt | cccagtggat | aggaagaata | 1260 |
| ttgccacaag | ggcccggcct | cactctggga | aggtggctgg | tcatgttcca | gaaactgttc | 1320 |
| tagaagaaac | gggaccagaa | acctgttcat | caggcatggg | catcagagat | accagtgatg | 1380 |
| aagtgaggaa | gataggtata | ttgccagagg | gaaagcctcc | cgagtgtgtt | cgggccttgc | 1440 |
| cggccaagcc | cagagcattt | actctctacc | caaggtcctt | ctctgtagaa | ggccgggaga | 1500 |
| gtcccctgtc | catgttccgg | gagccagagg | gagccgggct | ggacagccac | cgtgtaagga | 1560 |
| ggaaagagga | caacctctct | ctgccgggcg | ccatcggctc | ctccggtagc | ttctcacagc | 1620 |
| gcagccacct | gccttccagt | ggcacctcca | caccatcctc | tgtggttgac | atcccacccc | 1680 |
| cttttgactt | ggcctgcatc | acgaagaaac | ccatcactaa | aagctcaccc | tcactcctga | 1740 |
| tagacggaga | caccctggaa | aaagcctcta | agaagaagaa | gtcctccttc | aaacgcttcc | 1800 |
| tggagctgac | gttcaggaag | aagacagaga | gcaaggtgca | cgtggacatg | aacctgtcgt | 1860 |
| cttccaggtc | ttcctctgag | tccagctacc | atggtccagc | cagggtactg | gaacttgacc | 1920 |
| gcagaagcct | cagcaactcg | ccccagctca | agtgtcgcac | tggaaagctc | cgggcctctg | 1980 |
| actcccggc | cgccctcatc | ttctacaggg | acagcaagag | gaaaggcgtc | cccttcagca | 2040 |
| ggacggtgtc | cagagtggag | tccttcgaag | accgctcccg | gccgcccttt | ctgcctctgc | 2100 |

-continued

```
ccctcaccaa gccacggtcc atctcattcc ccaatgccga cacttcggac tatgagaaca       2160
ttccagccat gaactcagac tatgagaata tccagatccc ccctcgcagg ccggtgagga       2220
ctggcacttt cacaaagctg ttcgaagaac agagccgagc cctgtccacc gcaaatgaaa       2280
atgacggcta cgtggacatg agcagcttca atgccttcga gagcaagcag cagagttcag       2340
agcaggaagc tgagaggtac gtgagtggcg ggtcctttct cacagtgtgg gcctttgtga       2400 ggcataggggg gtggaatgga tgtgcggctc tgtttctttc tagctgtgtg atttggggtg      2460
agtggctcta tctccccgaa ccactgtcac ttcacctggg aagtggggct catgtttagg       2520
aagactggag tagcttgtct gtgtgagact acagtataaa tgggacagtt ctcatgcatg       2580
tctaaaggag attgctgtca tacacacaca cacacacaca cacacacaca cacacacaca       2640
aagcaactaa gcaagaacgt tctggaatct ggccaaacga aatatctttc atcatcagaa       2700
aaatacccta attgattgat gccttcttat tgtgtacacg aagaactaga aaagacaatt       2760
tatttaaact gtccaaagag ctcacgatgc ctcgagctga atttctgaat agaagtcttg       2820
aggaggtgta tttaagttga tttttaaaaa ctggatcact ctgaaggtgg gagcagaaca       2880
ctgtggatat tgaacaatag tgggtttttc tgcttccctt ccctctggct gaaagcccct       2940
cgcttacttt acctggattg gctgttccct atgtactgta gatgcaacct agataggaca       3000
caacagcctg tctgcttgca cctcgatggg gctctcatcg gagtcacaga taattcccca       3060
aggttgcagt ttaatggagg agccccagag ttccttcttg tgtggggggac taaaccgcct      3120 tgtctgctgc ctggtgacac cgccaggcgt gtccggtgag ctgcaaggga gctagaaaga      3180
taccatgtct gcccgtggcc tggagaagac tggtaaggtg tgccagcttc atttcctgga      3240
gtatgccatg tggttcccac ctgggttcca tcttctccct acaccctggc caaggttgga      3300
ctacatccta ttttggtttg tttaccagcg tcaaagtaga caccagcctt ggagaggggc       3360
tgaatttaac ttggagagtg agaaggctag agactggagc tgactggttt atttcattaa       3420
taattatcac atggtcccaa ttagatcctg cattgtttca acctcatagc actggtgaaa       3480
acaagaccac gtttgaaaca cagcatcttc aggtgtaacg tgtggtcgcc cagcttgcta       3540 gttttttccct tgcggctggt tactcatcac ttcccaaaat tccctcccca ggttcttgga      3600
ctgcagaata ataggaagtg ttggtttgct ttgtttcccc aagtcatggt ttctctgtga       3660
aaccctggct gacttggaac tactcagtag gctgatcagc taggctttga gctcagagat       3720
ctgtctgcct ctgtctccta agatcaaagg tgtttgccct cacctcccgc tccaaagatt       3780
ttctgtgtaa ccgaggctaa atccctcatt tctccttcct gcctacccag ttcacaccac       3840
cttatcactc aaggcagata agtttgctgc tttcatcttt ggagtgacag ccttttgaag       3900
attaaaacac acttctgcgg aaccacagtt tattgttgaa gggacatttc agatgtcatt       3960
gtgtcccgca gtggaaggga aaactgaggg gcagagagga aaagtgagtt gcccagggtc      4020
tcacaggttt aggagaaacc cattctgcga ctcagacttc ctaactccta acataagaat       4080
ttgcagtggg tcgtgctaag gggcgccagg gtgagttgta caggctgtac actacaaccc       4140
cacaggtagg gccttcccct tcagtgtgt atactgtgcc caatgggatt gtgctgtaca        4200
caggcgcttg gctatatatg caaaggctat atagccttct gtactttccc cttcccggat       4260
acaaaaggag aagtccacaa caggaaataa aatatccaaa aaaaaaaaaa aatgctaatg       4320
gtactgggtc ttgacggttc actgtgtacc aggtactggg ctcagtgctt tccttgttag       4380
cctatgtctg aggtttcagg aactggcctg aggggtcctg agcccctcggc ccatctgact      4440 gacactgttc caccagggac ctgactgggt gattctcagt gccagtcagg cagagagttg       4500
```

```
agctgtcttc atttcctgct gggagataga tgaaaacgga ggagaaaatc cctgccccgg      4560
gcacagcagg cctgggcagg tgagaggccc agggtggtat ggcgttttgc ttgagtgggc      4620
gttctgagta aggcggaggg cgtatggaac agagaggcag ctgggtgcct ggggttgggg      4680
agcagatgag gcaggtagag gaaaagccaa ggcagttgtt gggagctctg agaggaggct      4740
ggactgagcc tcttggaaca catcctgacg aaggtcccag aatgggcatc gtgtttagga      4800
aatggctgaa ggccccattt gcctctgtct atggggtgg gagggagttc ttgttcaagt      4860
cagcttatct ttacctccaa aagggatgaa ggaaacggtg ttactgtgga ggttggaatg      4920
aatgtacccg agactgtaag tagaaagtac ttataaaaat taggtaaaag gaaactaaat      4980
tagcttagga gcagtctatc ttgagattgt tacttcccag gcctggtttc tgaatcaggt      5040
agaggctcac ccttgtcccc caccccaga ctctgcttac catggtcaga atggtcagag      5100
gtgtcagggt gctcagaagg tggtcagact tgtcatctag aaccatgact gctttccact      5160
gaaagtattt tcctccaaga cacgggactg tgctggctac ttggaacata gatttggatc      5220
tgaagcctgg gcatggcctg gccaggggt gatggggaac tttctgtcct cttgcaagt      5280 tgctgtcaag cagagggaca gtgttgtgag cagggacatc ataggagccc ccttcaggtc      5340
acaaagtata agtgggagtt tgtaacaaca ggctttgcca tctctgaatt tgactctccc      5400 cgccccccc accccgaaca gactttctt ccagcaggat gttgtgtagc ctcagcagtc      5460
aggagactct gtttggggac tttctctgca aggacctgtg gttcacaggc taggagctaa      5520
gctgggcttc tttggtgaca gggaactttt gagcgtggag aggaaagaac cgtgttttgt      5580
taagtgacct atctgagcac tatagttccc gggtacttcc catgctaaca gaaagccgat      5640
ctgacccagc atgcaagcat gataccttgt tctgtacgcc ccatttcagc ctgcctggtc      5700
ttcctgcctc ttgtgtgttg gtgagtctgc ttccttcagc ctcctgcctc agcacaggtt      5760
gcttctctgt atcccttgtc ctcaaagttt actgtgaaaa attctgttac taaaaagctc      5820
cacacttgac agtgagtgtc cttgtgtcca cccctaggt cctgccacac ccttcctgca      5880
gtgttggctg tctcttatcc ctctgtcagt ctgtcacaca ctgctctggg gatactgacc      5940
tagtcacaca gataccctggc agctgctgct acacgggtag acttctcagc cacatcatcc      6000
tggtattgtg gctctcctgc tgcttgtcag ccaagctcat aaccttgagt ctgtcacagt      6060
caggcaatca gcaaatatct gctgttaagt ggcgtgaatg aaggtcaaag tttatggatg      6120
taggatttga actcgattcc agagatgcta catctggagg gagaaacagg gtctctcttc      6180
tctcttctct ctctccctct cccccccccc cctctctcac atacacacac acacaaactc      6240
tctttctgcc tatgtatgcc atgatgctcc tgtctccatt gcaaggtctt agattgggga      6300
actttggagt gtattgttat cctctgctct agtgcccct ggaaggccct gagctgcagg      6360
taacaagcgg gcaatactaa tctagagccc tgtgcagccc tgcctctgat accaatgcca      6420
agaccaatgg tctagattcc atgaccacac tggagccagt gcctgttaca ttgttaccat      6480
gctatcgtat tactatgcta ccatgttacc agccagagct gggataaact catagcatgt      6540
aactagatag gaatccccgg gccccatttt ctgatgagaa gactgaggct tgctaaacta      6600
aggctgaatg ttctctgaca catggagagt aagtgaccaa accaggattg aacccaggc      6660 ctgcctgact ctccattctg ggctgtttct gtttgtactg ctgtttattt tccatagtga      6720
aggggtccca ctctgtggta ttgctaacct gacatctgct aaggtgctcc ctgaagagga      6780
aagggtgctc aggccccatc cccagtgcta gccttgctga tagtctagag gatcccagag      6840
gatatagaag aggggcgtgg tttcctatct gatggcccct ggacttttag tgcctctggc      6900
```

-continued

| | | |
|---|---|---|
| aacttatcta tagctgccag ccatgtgtta atggtgtgcc cagacatctt tccttgcttc | 6960 | |
| tctttggcct ctggtgaccg cctatgcctg agggacagcc aggagctcta gttttggggt | 7020 | |
| ctgccacctt caggggattg tcatgctcac caggggaatt ttaggagcag aatctatgta | 7080 | |
| cttgtgtctg caaagaaagt cacgggagtt ctgaggaata aggctcaagt cactctgctt | 7140 | |
| ctccttggtca cagagagctc cagtcacgct ctggtggcag gcagaacctt gctgtgctcc | 7200 | |
| gagtgcatga ggagggttgg gacaatcagg gaggggttgc cttgactggc taatggtgcc | 7260 | |
| cgtgtgagaa gcaggtagtt ctgcactaga tcctatgcta agtagcatgc aagaggggt | 7320 | |
| gggcgaggga aaaggaggaa cttgaagcac agcacagaac agtgagattt ccacgtattg | 7380 | |
| gacagagaaa gggcaagaac aatgaagacg catcccgttt gcgctcagaa gcagcctcta | 7440 | |
| ggcctctgct ctggaaaaca ctcacctcag aagtagacat ggaaaatgca tttgaggggg | 7500 | |
| ctgggtgaaa ggtgtaaaga tcaaactcag acatgtgctt tctctgatgt tcctgtaggg | 7560 | |
| caccacacag gctcagtggg gtcacccttt tgcaaacacc tgtgggaccc ttgtcccttc | 7620 | |
| agctctgtcc aggttgtggg gcaaagtctg ccctcagtgt ctgtgaacta tctggcagag | 7680 | |
| ggacaaatag aggcgatggg gttgaggtgg gagagccagg aaggtcacag tgtctcccct | 7740 | |
| ccccaaagag cagtctgtac ctggggagcc accaggtggc tcttggttga ggaacggggt | 7800 | |
| ggtaaagaat gtggggatc tgggagaaaa gtctgcccag ccatgagtct ggaggaccaa | 7860 | |
| gtatgtggct gtgaggtggg ataggggtt tcggaacagc tgaggacacc tcctggacaa | 7920 | |
| gctgtatgac cctgagcact tctgagcaca ggaaggccat agcaggtttt gtgcaggatg | 7980 | |
| ctggcacttt gctgacaggt gggacctgga ggaaagagat agggcaggca tgttagactg | 8040 | |
| gccgggctgt tactgtggtt ctgtcactag atgatgaaga taaagcttgg tttgctgagg | 8100 | |
| gagaggtggg agtgggactc tgtctccaga gcatatacag cccatccttc ttctgcagct | 8160 | |
| gtcaatgctg gaaccccgta gatggtccct gcattggtct ttctcttctc ttgtgagtct | 8220 | |
| ttgaaagtct gtccagtccc aaagaaataa ggcttgtgtt tgtttcccat aaaagacaga | 8280 | |
| gataggaaac ataagagctt acgtctttaa cctgggagtt aaatgagtga gatgaactat | 8340 | |
| aaccgtgagg taggaagagg tgagtctgca ggcaggctga ccaagaagtc cagcacagca | 8400 | |
| tccagggagg ctcctccggc tccgcccag catccttatg ctataggatt caggctactt | 8460 | |
| ccatctctcc catccacaac cagggctgca gcctctgctc ttcccagtgt ccctgtaaac | 8520 | |
| aaaggtgttt tgtagcctaa gcaagggtag gctcagtctc ctgctgatgg ccccagggtc | 8580 | |
| ctgagagcag tgtggcaggc cttcgcatct cctagcatgg tctacctcag cagtcttcca | 8640 | |
| ccatcattat gttttttgaca aatgaactca tgcggcactt tcattaaatt tcgtcggagg | 8700 | |
| gacctgtaac tgccatacag atcatcaggg tctcaagacc agcacgtgcg agcatgcggc | 8760 | |
| tgtgcggctt gttgaaattg actgatgaga atattcagtt tttaattttc tgacttaaaa | 8820 | |
| taagaccatc tgcagctgtt tctttttagca ataatttta attaaatgca ataaaaattt | 8880 | |
| acagggaacg accctaataa gaaaattgtg tcaggaacgt gcttattaga acatcgctag | 8940 | |
| cgtgatatta atccccctccc caccccaacc attctttttt tttttctttta atgtaatgaa | 9000 | |
| accctgattg ttaatcacga cgtgattttc gcttcataaa gtcaaggctt ccctgtggga | 9060 | |
| agagcagcag ccattctgtc taatagcaga caatttcgtg gtgggagtcc ttcggtagaa | 9120 | |
| tgtggagaat ggttgccgtg accagctgag ccccagagga ggagaggggc tttgttctag | 9180 | |
| tctgcatttc tgaggtcctc ctttgtccct acctgctcca tgggatgagc cactgatagc | 9240 | |
| tgtccaagac ctatccaaag agaaaagcca ctggtggctc ctattgtcgg tcagtatctt | 9300 | |

-continued

```
gctgttgctg ccattgtctg agcttctagg cagagtgggg agacggacag gggtcttacc    9360
tggctgtgac tgttctcaga agagccaggc tagaaacatg catgccatag gccagcaaga    9420
ccatcatagc ttttgagaaa gagaggagag ctgcatgcta gacagagagt agctgctgcc    9480
agggaggaag tcaggganggg cttctctgag gaggtgatgc ttgagaggaa ctgggcaatg    9540
gtcagctgtc ctccaagaag gggcatgcca ggtggaggga acagcaaaaa tggagaccct    9600
ttctcctgag gctgagaagg agggaggcta gctggaccag aatgtgagaa gcaacggggt    9660
aagtgaggct gggacagatg ggggcctggg gttttacctg ggtaagacat ttctgcagag    9720
gcatgaacac aacacacaca gaggcaggaa cataacacat ggggcttgag gctcttctgt    9780
cctttagatt tgtggtgact cctatgcagt cagggctcag tcctcagctt gctgccattg    9840
ggaagcggtg tgagccatat gtgcacaagt gtgtgcctgt gtgtgtgtgt ggtgtgcctg    9900
cctctgtgtg tgtgtgtgtg tgtgtgtgtg tgtgtgtgtg tatggtgtgc ctgcctctgt    9960
gtgtgtgtgt gtggtgtgcc tgcctctgta tatggtttgt gtgcctgcct gtgtgtgtgt   10020
gtgcctgcct gtgtgtgtgt gtgcctgcct gtgtgtgtgt gtggtgtgcc tgcctctgta   10080
tatggtgtgt gtgcctgcct ctgtgtgtgt gtgttgtgtt cctgcctctg tgtgtgtgtg   10140
tgtgtgtgtg tgtgcatgtt gtgtgttgtg tgtgcctatc tctgtgtgtg tgtggtgtgc   10200
ctgcctctgt gtgtgtgtga atgttgtgtg tgttgtatgt tcttgtctgt gtgtgtgtat   10260
gtgtggtgtg cttgcctcgg tgtgtgttat gttcctgcct atgtgtgtgt ggtgtgtgtt   10320
cctgcctcta agtgtgtgtg tattgtgtgt gcctgcctct gtgtgtgttg tgtgtgccta   10380
cctctgtgtg tgtgtgatgt gtatggattg tgtgtgtctg cttctgtgta tggtgcgtat   10440
tgtgtgtgta tgtgagtgtg tgtgtgtgtg tgtgtatgct catgtatgtg tatgtgcctg   10500
tcacgggnga ggttcacata tgccacagca tacatacaga gatcaaagtc tagccttggg   10560
tgtccatctc caccttccat cttaactgag acaggctcct tccctgttta ctgctgctgc   10620
ataggcaggc tggcctgtga gcctgcaggg attctctact gcctttcccc tcaggagcgc   10680
tgggattaaa ggtgttggca ctactgtgtc cagctttgac ataggttctg aggatccaaa   10740
cttgggttgt caggcttgtg tggtgagtga tttaaccact gaaccacctg cccacctacc   10800
ccaccccacc cccagcccca gtgatggaaa tttaagcggt gaggccaatg agaggtctcc   10860
cagcacacag gccttcctc tcgctcctct tttgttctct aaccacagct aacagcagct   10920
ttgctctatc ttgcacaagg cctgtgattg gtgcctcacc agagcaaagg ggccaatgaa   10980
gcataggcta gaccttccaa agctgagcca gcaaaatacg ttgtctttta aagttagtgc   11040
tctcgattat ctattacagt aacagaaggc tggctcacag gatccaaagc tgttcccctc   11100
atactgactc tcaggattat tttaccgggg atgtacgttc tgttgggttg gcagataatc   11160
tgaagctacc acagagtatc tgccatccag agtgggcctc tgctctatct aatgtgatct   11220
gaagtcttgg gaccaccttt gttgttttag gacagatggt ctcgggtctc tctacttctc   11280
tgcctggact ggagtgagga gtgagttgct ctgaatgcct ttgtagatgg caaggttggc   11340
tcagccactc tgtcagagga tgatgggggag ggggggggac gttgaaaaaa ctgggaggag   11400
gctcgaaaag gagatgttgc tgaactgggg ctcataccgt ctacaggaag ccgtgtgcta   11460
tgagcaggag ggagctgtgc aaggtttgga gcaagggaga gccaacatca tccttgtcca   11520
cagagaaaaa ggagactcca aagacaagtg accaaacgac tagacattga ggcgggggcag   11580
caaggccagc tgctgtatcc tctgtggttt gatggctctc caccacagat gcagttatgg   11640
cttagaaaag agtgaccggg agctctgccg agtctgaact cttcagtgta gggaactcag   11700
```

```
ggacatcggg tggctgatgg agtttgtcac ccatgaccca atagtggtag gcagcaagac    11760
aagggaagag aatgcgctca catcagctct gaccctaccg accatgggac ctgcgctccg    11820
cttgccccac ctgtcctagc ttcgtctctg ggctgccaga gtaggtgtag acgacacatg    11880
ccaagcgcat tcttgggctt ccagcagcag ctcggcctgc ctgtgctttc caagggtgtc    11940
tgctgtacgg gagccttgtg gagctcatgt tgtaccctag cactatagat gctctatgtc    12000
aatgtggcga gtcatgaatt ccgccctgag gtactgtttg gagtcagtat taatacacga    12060
gaaactgagg catgaaatgg ttaaagcaaa gcagccaagg tcagttagtt gatcaatagc    12120
agggccagga tgttcccctg cacttttcag ctacgcagca aggatcctac tcactctcta    12180
tcacccattc aatttgcaga atgtcctgtt aaggagatca gaggaagaaa ccgaataggt    12240
tctgaatagc aggggatttt gtaaggggt atgtgtctag gtttgggttc tgtcctctct    12300
ctggtttacc ccctttgcaa gcttgccaac tggaactggc atccactcgc ttgagctgca    12360
gatgctgcag gggagtgcaa gtattcagaa tgtcatcagt gttcggaata agacagctta    12420
taatgacagc actcaatttt tcctgcctga ggccaaagct aaggctcagt tgcaagcgct    12480
ttcctggcat gtgcgaggcc ctgagttcaa gtcccagcat caccatcagc cccaaaatcc    12540
aaatacagag agggaaacac tcaccgtccc agggttaaag gcacaggctg tatgctcaga    12600
gtgcctggcc atgcttagga aaagccttgg atagcctatt ccccatcccc tttgctgtgg    12660
tgaggcagga atcatgggcc ttgtgcaagg tgggacaaag ctgctgttag ctgtagttag    12720
agaacaaaag accatggctc ctctgtgttc tcaaggaaga acacgttctt cccccgagga    12780
accaaggtct ttgaaggatg ctggtggccc cggggtccca agcgccatgt cagctgctgc    12840
tgaaagtgac aaagctccct tggtcttgga ggagcctggg tctctgaccc tgatcctgtg    12900
gaggacatct tgggcagaga ttgttttcag tcatgatgtg actggtctcc atgtaaacag    12960
aacgcctatc cacatacaca gttgtctaga gccctggcta gcgcccaggg ggaatttctc    13020
caggttaagg catgaaccca agatcttgaa atgtcagact tgctttcatg atccaattcc    13080
atgattccaa ttaagcaagt tacaaaaatc aaaatcttgt gttacagtag agtcaactca    13140
aggaccgtag tcctattgtg gcaaattagg catgtccggc ggtgctgtcc tgggaagtga    13200
tgagctccct gtcatggtca ggaatcaagc acagaggaag gatctgcagg tcaggaagtc    13260
agaactgtca ctgccatcgc tggctggtgg atggggtgga ggaagtggta cctgtcctgc    13320
agcctaggag aggctgagga ggccacagga ggcccctctc gttcagtgtc cacttcacag    13380
gctcactgaa gtgccagcat ggaaagtatg ctcagaaggg actagtgggc cttcacactt    13440
catctcctgc ccgcctgcct gccttcctgc ctgccttcct tccttccttc cttccttcct    13500
tccttccttc ctacctacca acctaccctat actagggatt gaatccaggg tctggcccat    13560
gctaggaaag agctctactg gtgacctaca ttcctagttc tctcttttt tcatttaagt    13620 tttattcctt attagtgtgt atgtgtgtgt gtgtgtgtgt gtgtgtgtgt gtgtgtgtgt    13680
gtgtgtaggt gtagatgtgt gtgtaggtgt gcatgtgtgt ctatgtgtgt atctgtgtgt    13740
acatgtacgt gtgtgtgtgt gtgtgtgtgt gtgtgtgtgt gtatggtgtg tctctgcaca    13800
tgtgtgtgat gtgtgccgag gtgtgcatgt atgtctatgt gtgtgtctgt gtgtgtgtgt    13860
gtgtgtgtgt tgtgtccctg cgagtgtgta cgtagatgtg tgttgaggaa tgtgtctatg    13920
tatgttatgt gtgtgtgcag atgtgtgtcg aggtgtttgt gtgtggaggt caggagacag    13980
tttctcttct tctaccaccg gttctgaggt tgaactcagg tggtcagact cgtacagtag    14040
ctgctctccc tcgacgagcc tcccaaatcc ccgctctccc accttttatt ttcctttcag    14100
```

```
tttttgagat aagctctaag ttgcacagaa gagccttgga cttcctctga agtccagaaa    14160
ggccctgaac cttcagtcct cctgcctcag ctcatgagta gctgggacta caggtctgca    14220
ccaccaatca gcaagctcac ctgaacagca accctgcaga gtgctgcagt agcagctggg    14280
aagggcagtg gtcctgtgag cttgcaggtt gtgggaccac ctatgtgttc tttagggtaa    14340
tgcaaccagc tgagttcaga cctccttgag tcaattactt aacatctctg tgcctcagtc    14400
tcttcatctg tattttaaaa aaaaagaaaa gaaagaaaaa gaaagaaaaa gaagaaaaga    14460
aaagaaaaaa cagggaaaat agcattatct tgggagtcct ttgtggtttg aacacttgct    14520
aagcatctca agagtttgca tttcagctgc tgttggtgtt gctttggtgt ctatgggtgg    14580 cattcttttcc agacaattgg gagtccaact agtgccgttg gaaaacccaa tcacatctca    14640
gaagagcagg gtgctcctcc tttaagaagg gctacacact gggagcacat ctttatgcta    14700
tactcatcag taattccttc agtggtctgc agaatctggc ctactgcatg tgtctctatc    14760
ttgctttctg tgtgggagaa gtcgtaggtg aggtaggtgt gtatgtcagg gccaggaata    14820
taaggctcct ctcaccactg cggcaggagt gaaaatgagg gccagtagtg agctggctcg    14880
gtgggcgagg gtgctttcta cccgttccag tgacctgaat tagatcctca ggactcgggt    14940
ggtggaagga gaggaaacaa ctcccaacag ttgtcctctg acttccacac atgccctgtg    15000
atgtgtgttg ttcaataata aataaataaa caaactaaag catgaacaaa aataaagtaa    15060
gtcatgtgtg agggaacagc ccctgtttta ttttctattt caatcactgg gccttctgat    15120
agtcctataa accaagtgtt ctgagcccat tccataggtg agaaaggcaa ggttctgacc    15180
cacccatggt agaagagaca tatagtcaga ctaaatatcca cagcaccgag ccttggggtg    15240
tatgaacaga gggtgaccca gggacttccg ttcatgactg taaaatctga tcagaaaccc    15300
cgggatgctc agagagttgg aaccacaatg aagcagctca tcttcatgca ctttacagtc    15360
tgcaaagcat ttccatccta ttcgatgggc tgattccatg agtatttgct caggattcca    15420
atgaggagcc aacagggaca gacagaacac agtagagcca ggggtctgat tttctctact    15480
aggctttggg tgagacgctc tcctagaata tttccaactc ttcacccaat acagggatga    15540
tggaagcaac cagtctttgt ggggaaggta gagtgtgtgc caagggcttg ggggagggcc    15600
tggcatgtgg ttggctcttg acacaattgt gcccatgaag agggactgaa ataggaaggg    15660
ttacttaaga ctccacaggg gacaacagga aggacctgaa gctcctagag tgtcatcatt    15720
agactgagag ctcagggctg ctaaggcact gtgtgccatg gtcctaagac cagcatctga    15780
gtgagagcaa gacccagctc tgacccaggg aagggtgtat caggcctcag acacacctgg    15840
agctattctg ggtggccatg gaagaaatgg atgatgtcag tgctgggagt ctctgaccat    15900
gctccctttg ggaagcccct catagatgct ccagctggtt tccaaggagg tctctgttca    15960
aaggcaaact tccctgctgg ccacaggcca aggtcaagg ccagttcaga gctgcagagt    16020
gagtcagtag attcttggga tcaagaattc aggcaactgc tcccttttg ggatgaggag    16080 cctagtcctc ctgaaagtcc cagccattga taaaggctgt gatgaggagg agaccacagg    16140
gacactctgg gacctgtctt gcacccttgc acacaggaag gagtctgagg caggaacagg    16200
gagagagcca agctgttctg tgaatgcaga ggggaggcag atagcagggt gagacatgga    16260
gtctgacatc tggaagggg attctgtcac ttcacgggga ttctgaggga cctttctct     16320 cctcacctag gtgcccattc ctgcccacct gggtgttcat aaactctttg ccctacccac    16380
ctctcacaac ttatttctgt gtcctaggca ctgtgtgagg tgcatggtaa aagcttcaag    16440
tcagttggtg tcttccaaag gctgtgtgtg agaggcctat gttatctcgg agggacacac    16500
```

```
tctagtcccc tgccaagcac cagctcttcc ctggtggctt cagtctgcag gaatggactg   16560
ttggcattca cttagccaaa atcagccacg ttgcctgtcc tgagaagtgt ggggatccca   16620
aaggccaaag gctactcctg ggcccttctg ctaaagcagg taagggagtc acttggcaga   16680
gaaggctggc agaggcaggg tagcctgaag agcagccagg atggtgagca gcctgtgagc   16740
caagccccta gaagcaagat gcatgtgaga aaacaggttt agaacaggag tttggctctc   16800
ccaggctctc ctgctgttga gatgagaggc tagagttgct actaatctgt ctgactccag   16860
tccagtgcgt ttcactgcag gctctgccct gaggggcagg aagctgaggt gctggggctc   16920
tttatccctc ctgccagaac agatccaact cttcttttg ccctgcactt tgggcaggga   16980
aagtggccag gcatggagga aagtcttcct gttagcgttt gagctgtgct caggacactt   17040
ggagaatctg taaggtgaga aaatgtgaga gagttttgca aattctagga gctgtgtgca   17100
caagggtctc agggactaag gatgcccagc gacagatttc cccatgcagg gaggaactga   17160
gggagacaga gagccccagc tcatagttgg tctggaggag gagaggctgg ccttacccag   17220
catgtcacct gccagaccta agctccagcc ttcagcactc cctgcccctg ctgcgtagaa   17280
tggttaaatt gaccctggcc ttttcagcc tacattgaaa tcacctttga ttaactatga   17340
gcctttcacc cccaacagtt gtagaaagtg aaggggcta gcaagacaat atcctctgag   17400
cctggggcct ggcgggcctc ccagttatcc caggagaggg actgctcgcc caaggctgc   17460 ctcgtcaagc tgcatttaac ccacaatgcc ttggtgacag gcgtgtatta gccttctctg   17520
agtgggccaa ttagaggtaa tagctggggg cagggtgcta ctgaaggagc cctggcctca   17580
ggaccagcct tccctgcat ttgacaggtt ccctaggcct tagccttggt cctgcctgcc   17640
cctgtcctgc cctttctctt tgctctgaga ccagctactt ttcatgtaaa tccagcccct   17700
gcggttgaag tgaaggcaag gactttttaa aaggcatttg aagtgaccaa ttatcatcat   17760
tcataaggtg tcatttatga gccactgttt agttttagac tgagagcctt gggtctcccc   17820
ctgagaggcc ggaatttgcc ctgttttaca ttaagacact gcaactctct gctgcttgcc   17880 ttttgctgg gccctacttc ctgggttctg ttttccaatt tacacaacaa agcattcggc   17940
tgagtctcag atgccatacc ttcttcaggg agctgcagtt taccataact ttaatgcagt   18000
ggctttcaac cttcctaagg cttcagccct ttaatagagt tcctcatgtt gtggtgaccc   18060
ccaaccatag tattattctc attgctactt tataactgta attttgttac tgttataaat   18120
cgcaatgcaa atatctgtgt ttcccaatgg tcttaagtga ccctgttgaa agggtaactt   18180
gagtaggtgc ctttatctgg gcatgggtgc tgggaattac agatgtgagt caccatgtca   18240
gataagttct cagtcttaaa cacctgtatg gttggtctgg cctatccaac tctatgggtc   18300
ccagaggagc catactgcca tactgctaag gccaaagaca ccgggccaca gtgtaaaata   18360
taacagtcca aaaggtctct ccttgtgctg gtctccttgc attaaagcgc atctgaatcc   18420
tgttatttaa atcactgaga acaggtcctg gtgaggtgc gggtccaagc cacgctgggt   18480
ctcatcctgt ctcctaaaac cagtcacaga tgtccctgcc cagacaaaga gaagactgaa   18540
gacacagtgt agccagatgg tcctgggatg tcatcaggga gtccttcccc aagatcctcc   18600
ccaacctcga ctgtggggaa cacaataggc ctaacaatct tccatgcacc cagcccgctt   18660
cacctctgca gccggtgtta gctgtaagca acattgtaag cttacaggct gtggtcctga   18720
gacagtgtag caggggtgttt tgtgtcagat ggctctaatt cattgttaca cagaagaaag   18780
aactcaggca ggagggagtt ggatgcttga tctgaggagg atttgtgtct gcaccaagga   18840
ggcctggctt tccagcacct tccttcctgc tcagcgctgg actgcgaagt acagacctca   18900
```

```
gggataatct gtgttacttt ctagctggca tccagtggag ttcactgagt cttggtagga   18960
agtaaccttg tgactgtggc ccgtgagggc tcaccatgag gatcagatgg gactgtcgtg   19020
gaggggtggg tctctggcag cccagtaatg cttgctgtta gtggttgtag cctgagccct   19080
gagatgtcat ctctgggtgc tgggaggctg ctggccatga ggataggtcc tgtgacaatc   19140
tgagtatcaa gacatggagg agtgggcata gcccaaggcc atggtctcaa tggccaagtt   19200
tccccaagta ctgttgagac agtctagcca gtttggtgca gaagacattt taaatgcttc   19260
ataataggtc atgtgtgggc gggcaagatt gcccagtagg taaaggcact tgtgtgtaag   19320
cctggtgccc caagtttaat cccagatccc acaaggtagt gggagaaaat ggacttccaa   19380
gagttgtcct ctgactaccc tggagttcac aacacataca tgtgcacatg cacacacact   19440
gtacctctta ggtatatata tcttctaccc cttttattct tttaaattt ttcattcttt    19500 attatatata tatatatgag tgctctgtct ttatgcacac cagaagagga aatcagatcc   19560
cattacacca caatgtcgtg ttaatgtgag ctaccatgtg gttgctagga attgaactca   19620
ggacctctgg aagagaagtc aatgctctta accactgagc cctcttcttt tttctagaca   19680
ctgatggagg catattggat gctctttctg gagctgactc tgtcactgtt gagttcattt   19740
cttgttaggc cacatagctc tgttctgttc tttttagcga ctgcaaggat gctgagtaac   19800
tacccatgga tatctaccca ggcttacact gccctaaaac acctccatta aagttctcca   19860
gcatatttgt acacatttaa aagtatgctt gggccgggcg tggtggcgc acacctttaa    19920 tcccagcact tgggaggcag aggcaggcag atttctgagt tcgagaccag cttggtctac   19980
aaagtgagtt ccaggacagc cagagctacg tagtgaaacc gtgtctcgaa aaatacaaac   20040
aaacaaacat acaaacaaaa aacaacaata acaaaaaagt atggttgggc tggggctgat   20100
ggttactagg ggaagctgag atgggcttca caagtcctgc ctggtcacag agtgagttca   20160
aggccagtct gatctacaca gtgggacatt gcttcagaac tttacggaaa acaaacaaat   20220
aagaagccct aaaggggggc ccagatcaag caggactaga gcaagaggga gaagggaagg   20280
ggaaaaaaga cagaagccct aaaggggctg aggctgcagt ggctccgtgg aagatgcttt   20340
gcatttttga agcactgggt tccacccca aaacctaaca cacaaagtat gcttggagct    20400
gaacatgaag agcaaacaaa cctaccacgt ggataaaatc agactgtttg tagggtgtga   20460
gcatacatgg aacatttaac atggacatag ttgcttcacg ttatccagag gcttcactta   20520
tttcacttga cgcttgtcta cctgtagaat gaactcacta tgatgcctac ctatccttgc   20580
ttgtcgactt gacccatctg ggaagggga accatgttga aaaatcacct ccaacagatt    20640
ggcctgcggg catgtctgtg ggacatttga ctgattgcca attgaaggac gagggcctag   20700
accactgagc tgtatgacaa agtacactga gcctagacca ctgagctgta tgacaaagta   20760
cactgagcag aagcaggaag caagccagtt aagcagatgt gctttgtggt cctgcttcag   20820
tttctgcctc caggctcctg tcttgggttc cttccttggc ttccctcggt gatgaactgt   20880
aaaataagcc ctttcctccc caagttgttt ttgatctgag agtttcatca tagcagcagg   20940
acggagagac aggtgacagt gagctctata gatgaatcag aagtaacagt acatggcagt   21000
gacacaccac ataattctag taattgaccc cacttatcct ggtggcttct aagattctag   21060
tggaactgaa atgttctctc tctggttata taatgactgt cctaccagga cacgtcactc   21120
ctgtgtctga agcgatgctg atgcgaagag tgtatactgc tgtccagacc aaggtgcttg   21180
gagtggtaac ctcctggtta gtatgttttc tgttctataa cttgtaatgg tttgaatatg   21240
cttggctcat ggaatgtaca ctgttagaag gtgaccttgt tggagtagat gtggccttgt   21300
```

```
tggaggaagt gcatgactgt ggcggtgagc tttgaagctc tgcccagtgt gtgagattca    21360
gtcttctcct gactgccttc atatcaagat gtaggactct tggctcctac agcaccacat    21420
ctgcctggac gcggccatgc tttctgctat gatgataatg gctgaacct  ctgaacctgt    21480 aaaccagccc caattaaatg tcccttataa gagttgcctt ggttatggtg tctcttctca    21540
gcagtggaaa ccctaactaa gacaaccatt gactgttaga gtgtgacttc ttctacttat    21600
aaaaagaagt tcagtgtgtc acagtgccgt gacagacagc cgcaggcaca cactaagcac    21660
gacactgttc agaactcatg cttgtatttt ggtgacccct tgccaagctc agcttagcac    21720
ccagggtctc tcacagcctc tttcttgcgt tttcatagtg atgcgattct gctgttcttc    21780
agagtgctca agtgagcctc tgcttatcct ggatttggcc tgtctccaca agtgagatgg    21840
cggggttgag ggtgacccaa gttgacatgg tacctctcag aaggaacagt gtccagagat    21900
catctgggca gctcggatgg gacctccgat gatgggaact ttgctacact gagatcattc    21960
ataagcagaa aaacagggtg ggcagtggtg ttgcacgcct tttatcccag cactggggag    22020
gtagaggctg ggggtgggg  ttgtctctgt gtgttcaaag gcaacccagt ctacaaagca    22080
agttctagat taaacagagc tacatagtga gactctgtga acccctccca aaagaaaaag    22140
aaataaaaga aaaagacaat gacgaccaga gagttgccac tgtgaggcac taccatttgt    22200
gtgccagatg gccactctcc agtcctgggc tgcctctgtt cccacagggt tggtgtgcac    22260
ttagggatgt caggacttct gggttaaacc ctgccctgcc atggcttgtg tggaatcatg    22320
agagactgat gaatggaggt gggccatgtg aataattcat aatttagaga cacagaaagg    22380
atagaagaaa gagataagtg ggcttagtta agagctttct tagagataag atttcagaaa    22440
gatagaagga aagtcacact agaggacgcg gctagaactg tccttcccac tcgtctagaa    22500
aggatatgag ttggggagaa gatctgagag cagtcgctgt gcccaggtga gcaccacacc    22560
tgggtgttag aggtcccctg cctggtcctc cagggtgcca ggctccaggc cttgttctct    22620
gcagtcctcc ctggaaaagc atcagtgttc ctaaaagcca gatgtctgct tcaggcctct    22680
gctcggcagg gtgctcagct gagtgagcaa gggtgagtgt gcttttgttt agtgatgtct    22740
ctgctcctgg ggctgcagct ttgtggggcc ggaggaactg cagctatgcg cccgcccgag    22800
ggtaacaagc caagttgacc tccaagcagc tcacagtatt cccagctagg ctgtccagtc    22860
cacccttgta ggaaggcctc gagcctcacg atggcattcc cagccttaac tacctgctcc    22920
gtggcaggag ccagcacctc aagactagaa tggctctcct gggggacaga agcatgtgga    22980
catggccctg tcccaccaca gtggcaggag caagctcgga ggcagaggct ttgacgtaag    23040
ctgtaccagg ctgtctctca agcctgtgag gacatacatt cccttcctga cctacccttc    23100
cccagggctt cctgggagag ggcgcttcag agccacccag aaggcttcct caatcctcct    23160
cttcggcctc ttggccctgc tcctcagtct ctgtgaagca gtcagcggag atcatcttat    23220
tcccttgcac actctgagca tctatgtcaa cgtctcccta gaccacactt tgtaccaaga    23280
gtgtggattc ccttgctgtg tgtcccacac tcccaaaaat gcacagtggg cccttctcaa    23340
acacagtctg tcctttttat atagttttct gagctccccc atcctccctg gtttgtggca    23400
gtgggtatgt acattcctgt gctagcattc cctgtcagac cataaactcc tcagacagag    23460
atttgtcctc tttcctttttg actctcaggt gcattgcctg ttgaatgctg tgttggaggc    23520
aaagatgggg caggggatag gtggacagga caggacagcg tgtgtcagag cttggcccct    23580
ctatctgcaa ggccatggac tgattgctcc agcaatgccc tctctgcttt cttcccactg    23640
gggatacaga aaacaggggc actatgtatg tacgtttgaa gtatttgtta tatttatcaa    23700
```

```
atgaagttgc atgttcctaa tttaaaaatc ctgagaattg aatacttgga actccttcaa    23760
gaatgagagt ctaaattggt gcccgtcctt catgggtctc ccagctcact tgattgattt    23820
tcgttttgtt ttagtctatg gctctggatg aagggaaagg tcttcatgcc aaacctatcc    23880
cagaacttgg ccatggcaga agtcccataa atagcaagtt gggctgcagt ctgcacagca    23940
gcatggtgcc tgggtcccca cagcttggaa agcatcctcc atgtgcattc acagggtttt    24000
ccctggcaga cctgccctgc tgagccctgg cagccctgc actgtgctct ttgcttgtga    24060
gcacagaaac ctaagatacc ctctctagga aacctcctgg gggtggtgct gagttaccca    24120
ctgcaggctg tcctctgcag caggcctggc ctgcagaaca ccatccacca cgcatgcagc    24180
tctgtttgct gggaagccag gcttaattct tctgctctcc cctaaaatat catggtctga    24240
tgaacagagg agataggaac ccagaagtgt gtctgtccct acctacacgt gtgcaaaggg    24300
gcgttctcac cttcttttcca tcttcgcagc aatccctcca gacaagccaa gaaacggagg    24360
ccaagaaaaa agatctaggt tacccaggtt gcacaattca gggggtggga tttgaactca    24420
gtcttctggt ctgttcaggt atagcacccc ttaattattt aaaaatttttt taaattttat    24480
actttacatt ccaatatagc agcttcccct ccctcctctt ttcccagtcc cccctcttcc    24540
ctctcctcct tctcctcctc cagtccttct tttttcctca gaaaagggga ggggtcctc    24600
ccatggatat taattcacct tgacatgtca aattgcagta gaactagtag tgcatcttct    24660
cctgttgttg tagacaagac agtccagtag gggaaaggaa tccaagggca ggcagcagag    24720
tcagagacag ccctgctcct gctctctgga tcgccacgtg aagacccagc tgtacaacta    24780
ttaggtatgt gcagagggcg taggtccgtc ccatgcatgc tgtctgtttg gcagttcagt    24840
ctctatgagc ccctatgggc ccaggttaat tgattctgta gggttttgtg gtacccttga    24900
cctctctggc tccttcaatc ctccccctccc acctattcca caggattccc cgagctctac    24960
tttatgtttg gcagtggggt ctctgcatct gttttcatca gttactaggt gaccttaatc    25020
cttaatgtgc ctttgaaccc ttatcaaagg tactaattac caggcctcac cttgaacact    25080
gattccccag gtctgtcctg tggctcagaa gtctgcattt gtaacaggtc tccccagaat    25140
tgctgatacc tctagagaga agccccaagt tgcaggtagc ttctttaact agattcaagg    25200
acacgtcact caacccacta atcaggccca ctcaagagaa ttgggatcca attgggggta    25260
ttgaaaaaca gcctgagtaa ttgagtgaca ttcctgtatt tatgtaagtt ccccatgggg    25320
acaactagac cctatagtaa ggtgcaagct gttgtcagac aagctgaatt tatggcttac    25380
ctatagttta taggctgtgt gatttggggc tgggagcttc ccgtctctgg acatgagttt    25440
tctcgtctat gagaggaaga ctctcaggga gccagggtgg cagtgtgtat gaggaagtag    25500
ctcagtgcag ggcttgagtg gcagggagac ccagattctc ccgacgaggc tccatgtgtg    25560
ctggcctctg tctcttggag ttttgactg aggactgtgg tctggccagt tgccatagcc    25620
cgtgacccac atcttgtaac cttcttagcc taagcaagga tgtcctcctc aggtgtgaag    25680
tgacagcagg acaagtgtcc ccagtagatt tttcagcctg agtgtttcct ggggcatgat    25740
agatagatac caagaatgtg gtcctcactt cttccagaaa ggcctggagc tttcgggttt    25800
ggttttatcc ctctcctgtt ccttggagac cctgttcaga atcctgctga ttctccacac    25860
catcccttgt cccttccatt gggagactct gaaggcagaa ggaccctata gttgtgtcct    25920
gtggaggggt tgggtggcag gcaaggtttg gtccagctac actctgctgg ctttgccatt    25980
ccttctagcc tctgctccag agggttgaat ggagcggagg tagtcctgca gcaggtggtg    26040
ctgggtcccg ggctccactg gctgagtgtt tcacctccag ctggtatgtc agcattgcag    26100
```

```
ggctcttgct ttccacacac agggctgtgg cgtcatcgtg gttttattca gcagttcctc   26160
ttccacccca aaaggttcta gaagtttctt catactggga agtctaggga gaggtgagca   26220
gactggtagg aagctatgag gttctattaa ctgcagttga ggtttatcgg aacatgtggc   26280
tcaggggcta tcgttgggca aaagagaggt gcaggatggg gcagggctcg aggtggaaac   26340
tcaggaccac catcctgttg tttgttcatg ttcaggtgcc tttcggtcag agaagctctc   26400
ccaactcgta ctgtgagctt gttcacacag ctttctcttg agtctaggac tgaactggtt   26460
tccttagttg gatctgggtg cacagaacga tcttcccagt gaagaggctg tttcacatgg   26520
ggttttgggt tttccaaatc tggtggaaag atggccctag gcggcgaggc tcagggaggc   26580
atggccctgg ggatctgttt tgagctcatt gctctttctt tcatcacaag ccagaatgct   26640
ctcgatggga tgggtggttt tcccagcctt gtattgtcat ggtctgtcct gggtgtgtgg   26700
ggcaaggatg ctgccagctg gcacagttgc tgaattctca gaacccttat ttcaaagtaa   26760
ttattgacca aaaaagcaga cctagccaca cagctcataa ctacttccat atgcccagcc   26820
ttggaggccc caggaatgcc ccctaggact cctctggagt atagggagaa tggcccaaca   26880
tgccctcagc agagggtagt ctggggtgct gtccaggatc ctccagggct caggcaggga   26940
ataggagttc cccaatacag ggtgcagctt ctggccagag gtctgggtcc tggtataatt   27000
tatacaggcc tctctggctc atctctctcg ttgtcaggag tgatggtgcc tgaagtatat   27060
tccagccagg agaatcagca gaaatgtgac gtatggaagt gtttgaaagc ttcaaagtac   27120
cgtgaaattc ttagatggtt cattcagccc ttatttaggg tctaagacaa gtcaaagggg   27180
accaggctca gtaaactatc tcaggtccat atcatgtcgt tggtgacatg gcagtcagct   27240
tctgtccaac ccacagcgtc ataaggagca atgagccaag caggtgcgtg gtagccagaa   27300
ctagagccta gatgctctgg gtggccctgt tttaacaagg tgctcaggag atctcaggct   27360
ctgcagggga ggtgaggctg gcggtgggtt tgagagctct ggttatcgct acagagcaac   27420
acaaagacat gagtttcctg tcagcttctc tgctcacttc tcattagctc caagatggc   27480
aggcagggca agagctccag gttctgtttg gagaggagga aatggagaaa caactgggaa   27540
atgtagttgt ccaaggtcac tgggtaagtt acagcagaga acctcgaggt cagaagccaa   27600
ccccagatgg atcggtccct ggaagctgac ggcctggaga ccagtgtcta tgagcttgaa   27660
cttaacactt caaatccaga attctagcaa acaccatgtt ctcaactaac taactccaaa   27720
cagtgacaca gtacgcaagg caggcacgtg ctaccaccac agaggtgaga acgcttgtcc   27780
aatatcacat gcctaggaac agggtagtgt ccaggctttg gacacccata taggctattc   27840
cccctgtggt ctaagcggtc gctgtcccct gccagagctc atgggctgtt aggcagtatt   27900
ggtctggatc cctggatagg cctgggatga ggagtggcca tctagagcct cagccagcca   27960
ttgtgtgctg ggttctgtca gcggctggg tgtggcccca ggggctgcta ggccagtctc   28020
atgggaggaa gtgtcagtgt ttacaggaaa tgcaggacaa ggcctgggag atggaggagg   28080
ggtaaccagc caccctgagc actggaggtg ctcgagccca gggcggggtg cccctcttcc   28140
accccaagga cgaaggtttt tgttactctg gaaggagagt ccacttcaca agcagcctca   28200
ccctcttcc atgcctctcg cttctgaaag gacagcaccc aagttcctca gagaacattc   28260
atctttctcc ccagcagcgg actcatctgt gccctggta ctactgggcc ttgccttcct   28320
tcctttcctg ttttagaggg cagcaaggca gggccagctc tgtgtagccc cagcacctga   28380
ggggtgaggt tggcttcatg ccctagaagt tccttaagat gggtgtgaat gtggaaactt   28440
actttaaaaa caaaacaaaa caaaacaaaa aacccataaa ccctaaaaag tctaaaacag   28500
```

-continued

```
gcctggtggc ggttacacac gggcactgct aaagcctgag agtaaactcc acaatgcctt    28560
agctacttgg atgtactgaa tgcccttttg ccagagagat gaggctgggg tcagaggtgt    28620
gcttgcctgg catgcaggaa accctgggtt agactcctaa caatgcatag attgggcata    28680
gtaacaaatt cctgtaatcc tggcactaga gagacagagg cagaagaatc agaaattcaa    28740
actctctatg tagccaccct cagctacata aagagtttaa ggctagcctg gctataaga     28800
tattctctct aaaaataaga gaaaaaaacc aggcatcatg tttggggcca gacttgaact    28860
gagctacggc agctttgtct ctcacactcc atcacgcccc tctgccttcc ctaatgaacg    28920
cacatccctt tgtgccccac ctggacctcg gccagcctcc aacctgttcc ctctgtgcct    28980
cctctccagg tttccagggc cagagcgcta gaacctgatg gtgttgccat agaaacagag    29040
gttgcctttt aagggtctta gtcttgttaa taaataatt  tcagaatatg aaaggaagc     29100
ccatggacaa ttttgttaga gttaggagag aaacacaatc caggtacttt ggggaatcg     29160
cagaagctgc caaggagaga gatggagaag tcgtgtcttt cgaggtagtc atggggtaga    29220
tgtagacagt atattaagaa aagaaaaagc acgctcatga atagaagcgg gctgaggaaa    29280
gatcccccca aaacatgggc tctatggtct tttaatggcc ccccacttcc cctccagttt    29340
gtattttggt tttgcacatg ctctgttact tagatgacac cagaagggca tccagtcttg    29400
ctctgcaaac tgtttctttc acacttaatc ttaatttgtt ttttttttgag gggggattct    29460
attgttattt ttcttattct tctgtcacaa cacacgtcag gtctagaata ttacagaatc    29520
cgtttccaag ccaaagcctt tcttggctac aaaggcagag aggcctgagc tgagcacaag    29580
gtttccaccc ccaccccac  ccccacaatc accagcatct catgccagct acaatctata    29640
ctgagtgccc tccaccagca tctcatgcca gctgcaatct atactgagtg ccctccttct    29700
gggcctttag gttgccttt  ccaggactgt ccttctctgg tgactaagct atgcttctat    29760
tgggcatgct gcccgcttag tccgtcctag accaaggtat tggggaggt  ggaccagggt    29820
gtgcttccct aggctgtggc agctgtctgg gcaactgtcc actcaccagc aggccacgag    29880
tgccaggctc agattatttg cctatacatc cccggctgtg catgtaggag tgtccaggag    29940
cacaggacag cagctgagtg ttgttcgtga gatacctcgt aagcagatgc ccattgagca    30000
tctggtgagt acaggagact gtggggtttg aacatgaggc actaacagga gttcagagcc    30060
cggtgggaaa aaggctgca  gaaacctaag aatgctctgt ggagggggtg ctgtggaact    30120
caggcctgct gagaggagca gaacttggca gatcggggag ggggttggta ggtttaaaat    30180
ttatgccata ttgtgggtca ttgtgcagga aaggataaat aagtaagaac ataagctgtc    30240
ctgcaatgcc tggccccatg agctgggcag cgcttcagtt tcatcgggat aatctggtta    30300
aggagggctt cctggaggag gtggcaaacc ggtcctggta ggtgtgagga gtttcatccg    30360
caaagagttc ccagtgtttg gtccattctc agggcagaa  cgataagcct taggacgaga    30420
gtgtgtgccc tgctggagtc atcttaacct tctgggccca agtctcagca tattcaagct    30480
gtgccttcag aagtgctctg gctgagtcgc aacatattcg gggttcagtc agtgtgatgg    30540
agctatgtcc ctgctcagct gtgatgctcc agccacgtgt gactctcgtg ttcctgtgtg    30600
tcagactcat gcccaggtac ctgccctctt tgtgacaatt gcttggtgga tgctgtatac    30660
cctggcacct cccgggttgt caaaccttgc aggatgggca cctgcccaa  ggcatcagtc    30720
ttgtccaaga cagaagaggc agtaatgggc cacaggaaga gatctgtatg tatgtcctct    30780
gctccagctt aggtctgaga ggctggtagc ctggtgggca cttgcacggg tcagcacagg    30840
gctctcatgg aacagccagg gcaagtggag cctcagtttc cccagctgaa agttggcagc    30900
```

```
tagatgccag aggggaggac cctacccttc ctctgcaatg ggaggatcct gagagagaga    30960
gagagagaga gagagagaga gagagagaga gagagaggag gactcctgag gatgtctctg    31020
agcccacacc ccgtccccct cttgagatcc gctcacctct catgactctt tttcacctga    31080
aatgctttta tacagctctg gctgtatagc tgtatttaaa tatgtgcaaa tcaagtacca    31140
atgataaatc ataaggaat taattttaaa aattctttga tgtatatgta tctaattata    31200
ctatttatta aagatgagag catatgtacg tgctgaggtg ctgtacttgt ttatttttat    31260
gtaaagattt catcatggct gcctggcaca ggtcactggg cacctgggag ggctcagaat    31320
gcagtttctt cctctcgaaa gctgcagctt gctttattga cccactatgc tgtgggggag    31380
ggattggctc cacagtgacc agcagccacc cttctactgg ctcctggagg cttcagatag    31440
actgtgcaga accctgcagc cgtcgcaggc cacgatatcc tccccagctg ccagagctag    31500
aggaatcact cacacccttc ctgcgtcttt gtggttgggt tattctagaa tgatagacca    31560
gtgtgttcgt atttcctcct gctctgggcc aggccagtag ggaaagttga aaaggacagc    31620
aggacctccc agcttccaga ctgagcaccc atgggaccta gggaaacaaa tccattccag    31680
gtgttcccct gcctctgtgc ttgaactcta gataggaggg taggttcagt gataaagcag    31740
cagttcaccc gtggaggtgt agtaggctat agtgctctct tagcagaaca gcatcactcc    31800
atctgagcca tggcagaaat gatgggaccc gctgggataa tgcccagctc acgagcacct    31860
cccagagtgt acctagctct gtactgtatg tgcagtcagt ggggtcgtgc ctgggggct    31920 ggaggagtca agtcagttaa ctggaagaga acagtcacca aatacaggtt tgctgggaac    31980
ctgccctggg agacatggac atcacacacc cctggctcct ccctgggagc tggtgactgt    32040
tacagaaaca tatgcaacca tggaagaaga atataacaga acacagtatg aagaatggct    32100
tatcatctta catttgaggg aaccaagacc cagagagggg aaggagccca caggatgtca    32160
cctaccaagc tggtggcaga agaaaggcta gtagccagtc tatcggtgct aagagctctg    32220
tctgtctcat ggttcaccct ggtcttctgg tcacactgaa gcagaaaaaa attcaccaga    32280
tatttctctg aatcatctgc gcctacatat ccctgctgtc aatactcaca tgaaccccac    32340
tttacagact aggacactga ggcagggagg caggctaagt atcttttcctg gtcattggag    32400 tgctaagtgg cagaatcagg tctggtctga ggcaaacagg ttctatagca tgtatctcca    32460
cactgggcat ccagtccccc tggggaccag gatcagagtc tgctccaaga ggttctcacc    32520
tctgcaggac gggccttagc aggtattgct cagcctctga gagcactgtg gatgagcaca    32580
tctctgtggg taaattgctg tttcccactg agccagccca cttctctagg ccaggcccag    32640
gtaccaacag tgtagctgcc tgtaaggatc ggtaatggag cccccatcta ttgcctatac    32700
cggtaccctg agctgaatgt attcatcagc tttcatcact gtgacaaaat gcctgcatgc    32760
atctcttgca tagaaaaagg ctttttttagc tcaccacttt ggagctttca gtccatcatc    32820
agttggcccc attgagctgg acctgtggtg cagcatcatg atgggagcat atggctgagc    32880
caagctgcca gagatagagg gaaatgggga ggggagggga gtgccagagt cccattgtcc    32940
ccttcaagag aacattagtg taacttcatt ccacctccta ggagcaccaa cctaggaagc    33000
ttggggtctc tgggacatt cacctgatgg gagcagaggc tgctgtttgc ccaggctgaa    33060
gcccaaggca tcactagatc agcaggctca cagctctgcc ctgtagatgg ttctagactg    33120
tcacctcttt atattagtct gccacttat gagttctgca tgtctttaaa aggttttatg    33180
tcactagact tcaaacctca tgtgttatct aaaaataatc cttaaaggcc acagtaatga    33240
ttgtttccca ccaccaccac cccttggcc agaagagatg acaggattta aagaaggct    33300
```

```
aagctgagag accaaggatc agaaaattct tggaaatacc cattaaaata aaagaccaat    33360
tatgacaagt ctttgccagg atggggagga acctggacac gtgtgcagag ctggaaggga    33420
ggtaaaaccg tgagaagggt ggtctgtagt ccctaaaagt cacaacacag agcgatcatg    33480
ggcctggtag tcccacatgt acatgtgcag attagtggaa acacgagaag ctgcttaaga    33540
actggtactc cagcactccc agaagcctta gtgacaccag cacaatctag agatgggcca    33600
gatggtggtc tgtctgctca atggaatatt actttgccat gcaaagaaat gaagggtcga    33660
tgcccgctat ggcatcagtg aatcctcagc aagcctgact gagagaggga tgctgcagag    33720
aaagtcctca ttcagtgaca cctgctgaca tgaggtttag acgagaggaa gtaggctaga    33780
ggttgccagg accgcttgca cacagttaaa ggacatggag gtgataaagg tttcacctca    33840
ttagacatgg tggcaggtga atagccctct gagcgcacta aaaagcactg agtcgtgctt    33900
ggtgcagggg aaaattcatg gtccgtgagt cacatctcag aaaagctgtc ctaagtggga    33960
aacaattcct cccaccccg ggcctgtgtt ggaggagaca tcacaggtta gggagcaaga    34020
tggcttggtt ttacttatcg ggaaatggaa atccagttct ctaaaaagcc tctccttgga    34080 gcctttctg ggaaacgtta caaggctatc taccccttgg ctgacccag gcgtggaggg    34140 gcgttctccc caggaggaac ggagcagagt tcttgcagat gagagatggc ggcaggctgg    34200
ccgggccttg ggatgcctgc aggctggcct cagcccaggg gtctttgacc cagcttgttc    34260
tgtccattct ccaccccat tttacagatg ttgaaactga ggtccagtgt gcctgcccca    34320
gagttgctca tgccctggct tgatggcgag cccatcttta agtctctttc cacctcgaca    34380
tattttctct gtgctttgtc ccattcaggg aaaatgcttt gggctgggga ggcccagagt    34440
cagaagtaaa ggccaagtgt ttggaaatcc cagctttgtc ccccacccct cgttctgccc    34500
tctcctaggc tcttccagct gttgctctgg ttgtcgtcat cacatctgct agcttgccgc    34560
catctcaatt tttccagctt gcacagtgtt ccacctcagc cccctcccct cctgataggg    34620
ctggccagaa gaggtgcaca ttctggcctc agtcacacat gtcctgctcc agctggggtg    34680
gactgcgggc tcaagcttgc tagcagttcc caagagggaa tactctctga taagttatga    34740
ggccctttag actgtgtcat tagagatgga agctaacggt cagagttgga cagcggaaga    34800
ccccgtcaca gaggagacat ggcttttttac aactccaggc tgctggcaag gcctgggctc    34860
atttgtcggg tcggttaagg taacaggctc tgggcagcgt gtcatgcttt ctttaaacct    34920
gaaatggaag ttaaggtga ctcttcctct aggaaggaag gacccccttc atgtagaaaa    34980
cagccatctc taccctctcg ctttcccatg atcccacaag gcccaccggc cccagcttga    35040
tagactagaa acaagttgtg agtattggtc agctttgcac tgttgtgaca agacaccaga    35100
gagaaacacc tcaagggaga aactgttggc tgtagttcct ggcttcagat agtttcagcc    35160
tgtcatggag gggagaaaca gctagcctgt aatgtccatg aagcagagac agaattccct    35220
aggctggccg catcctccct ctttgtcccc caaggcttc agcctctggg atggtgctgc    35280
ccacattcac agtggttcta gtccttccct ggtgctctct ggaaggcttc agacacaagc    35340
agcagtgtgt agtgtgagtt ccttggcac ttccaagccc aatccagcag acagccgagg    35400
ctgctcatta ccctgagtga ctcacctaag gtctcatgga gagcaccctc ttcctgattg    35460
tgtgggttct agccctggcc acctgaccct ctcactgttt ttcccagcat cgagttacta    35520
tagagatagg accatttttta ttgcttccga gccaccagag agcagatgag gtgccagcca    35580
gtttgaggct aggcctgcag tggttttcctt attcctgtgg gctaggctga tcagtgcctc    35640
gctctgctgc tgccaggctg tggggacagc attctaacat ccagtgagtg ctctcgccac    35700
```

```
cctgctgagg gcctttgtgt ggcttcttca tcagtcctca gagcagcctg gacccctgca    35760
tcacttccca cccatcttac agatggaaat agaaaaacag ccaagaaaca gcaagttggc    35820
aggtgttggg gcactccata tcccttctca tgtgctacca tgttcctgtg ggcatgtgct    35880
tgtgtgtgtg tgtgtgtgcg tgtgtgtgtg tgtaggcctg aactcagcaa gggattcttc    35940
gtctcatttt ttcacataag gtctcactgt gtagccctag ctggcctgaa actttctatg    36000
tggacccaga tggtcttcag ctcaaagatt cacctgcctc tgcctcctga gtgctataat    36060
taaaggtaca tgtcacctcc ttggtcctgg gttttttccc ttttttctctc taccttagtt    36120 cttattcaac actggttctt tgactaggca taaaacttgt ccacttgacc aggctagctg    36180
gccagtgagc tccagggtta cctgtctttg ccgccacccc atctttccag tgttggggtt    36240
ataggcacat acctctgtgc tccacttta cctgggtgct gggaatctga gctcaggtct    36300
ttgtgcttgc atgacaggca ctttacccac tgccccagac ccccttcccc agacctgtcc    36360
actgtcttaa tcagcgtgat catgggggac aggctgagca tgggattcag tctagacaat    36420
gtcagaatgc tcacgaagag tttttagcaa aagggccaaa tgaccaaagt ggatttcaag    36480
gtctcatcag tgcgtggaaa acagacaggt ggaccgtgag aatggaatca gacgtcacag    36540
acattgaggc aggaggtggt ctgtcctacg gatgctgtga tggaggcacc agtggaactt    36600
atggaggagt ggatgtggga ggagcttgat gcccgcaaag ctggctggga gcttttccct    36660
cttctccggt ttgttctgca aaaggcctcg ccttgtcctg tactccttgc tgagggtcca    36720
gaagctcagg tgaccacttc tgccctcact attgatgacc agtggccctg tgtgtgccta    36780
acagcgtcct acagggcaaa ccatggccac ctctaagagg gagtggccca gactccctct    36840
tacctgcttg cgggataaag acaaatggtt acaggcgact ctaaaaggca gaagggctca    36900
gccacattgt tggacatgct ttcttacacc gcagactctc acagtgctac aacgacaga    36960 agggcagata cagagaggct ccagcataca acagacctgg tctggggtct tctctcctgc    37020 acctagcag gaagcttgtg gcaagaaaca ctgtctgctc tcatagttca aaagaagaaa    37080
cctacatcta acattttggg atgagaaggt ctgacctttt gagaagaagc ctctctcttg    37140
accttaggct aaattgtttt ggtcttccct cagtgtctta gcctgcctgg atctgacagg    37200
aacatggggt tgtcttaagc agcatgtgta aaggtaccag gaccgcaggg agccggactt    37260
gtctgataaa ccgaaaggga gttgctgtag ccagggtggg gagggagtgt tcactgggta    37320
ccctcccgtg tccattgggg gcttgtgaca tgagccagac aagcaactct aaccctctct    37380
cctgttctgc ctagcgccta cactgagccc tacaaggtct gtcccatctc agcggctccc    37440
agagaggacc tcacatcaga cgaagaacaa ggaagctccg aggaggagga cagtgcttca    37500
agagacccca gcctctcaca caaggtaggg caccogcagg tgaggggctg gggaaggatc    37560
tggaggcaga gatgtggagg tggagagaat gggaaagacc acaccctgcc cctgactgca    37620
gccactcctc agtcactgac tgggcagtgg cggagggagg ctctcagaag tatggttgga    37680
gacacttcct gttggaagaa gtttgggact ttccaaagtc ttcgtgggta atatggcgtg    37740
gagctgcatg ctttgtgaca agatggaccc agattctagt gtgcttaggc cttggtcatc    37800
tgtaaggtgg gaatcaggag actcagcagg ctgtggcagg agatgaggga agctgtttta    37860
gaaggggcac aaagtggctg ttgtcctggt ggagacaatc tgttcatggc gtggcacatc    37920
agtgtagatg gaagcagtat aaccttccgt ggggtgccga tcgcccctca ctatccctct    37980
tcagccttcc catgccccc aggagacgtt ccaccttgga cgtctgcagg agccatggcc    38040
gttgtctggc caccttcccc agaagccctc cccgagtctg ctcctcttc tcctcatgcc    38100
```

```
cccccccccc aatgcagttc agcctcagcc agtggccaga gaaggtggtg actgtagaag    38160
ctgggctggg acctggctct caccaagctt ctgggaagag aactgtcttt tgttttgtag    38220
ccagactttg gcttctttta aaaatacact tgggtctctg aacattattt ctccaaagtg    38280
atcaaccaaa ctgtgtagga gtcccaagga gtctatctat agtgtttcac tgccacaccc    38340
tgcctactcc tgccctgccc tgctctgccc tgcctcctcc tgcttctctc atacctcctt    38400
ctgcccctac ccagcccta ccctgtgtcc ttctgtcccc ccccgcctc cacctgcccc     38460 tgccctgcct cctcctaccc ctgtcctgcc cctgccctgc ctcctcctac ccctgccctg    38520
cctcctcctg ccctgccct gcctcctcct gccctgccc tgcctcctc tgcccctgcc      38580 ctgcctcctc ctgcccctgc cctgcctcct cctgccctg cctgcctcc tcctgcccct     38640 gccctgcctc ctcctgcccc tgcctgcct cctcctgccc ctgccctgcc tcctcctgcc    38700
cctgccctgc ctcctcctgc ccctgccctg cctcctcctg ccctgccct gcctcctcct    38760 gccctgcccc tgcctcctcc tgccctgcc ctgcctcctt ctgccctgc cctgcctcct    38820 cctgccctg ccctgcctcc tcctgcccct gccctgcctc ctcctgcccc tgcccctgcct   38880 tctcctgccc ctgccctgcc tcctcctgcc ctgccctgc ctcctcctgc ccctgccctg    38940
cctcctcccc cccccctgct cttcctcctc ctgccctact ccctgctctg ctcttttgc   39000 ttgggctgtc cagttttcc ctccatcacc ctggctctca acaacccca ctgctctcct   39060 gtccttcctg gttctcctcc tgcctctgcc ctgtctctac cctcttcctt ctgctgctga   39120
gctgcagcac agccccagag attcataacc aacattgcca actcctcctc tttacagttg    39180
aaaacacggg ctgagtgagc aagccactgg cccaggtca ccctgctggc agttgaaggg    39240
cttgggggct caaatgggtc tggctggttt gtatttgttt ttctccctcc acactttctt    39300
ctccctaaaa gaacccccgac tccttgctgg aaggaaggag aaccccacat tgctggtacc    39360
tattagagag gcttttggct ctccggagca tctctggtgt tgtgggatct ggaagcagga   39420
gaccaaaggc agggatttgg aattggtggc tgccaccagt ggcaggctct gtgctgcccc    39480
tcctccaaat gtgtcaccttt ggcccatcag cttcccaatc tctaaaatga aggtgttgg   39540 tcatgggagg gtccaacaag acagatgtga gagtgtggcc agaggctacg gcaaggacag    39600
acacagtgga gcagtgaggt cctaagaccc tgggcatcca tgtgcactca gaggtcagaa    39660
gcagggtaac ttgcaaccaa gagttggttc aaacccagcc tcttgccagc aaagtagcag    39720
acaacttctt aactgctaca tcctttggtt tctgtgaact tgaaggaata attatggcgg    39780
cagctgcaag gtgggggcgg ggccaagaga ttcagagaga tgcctgtctt gcagttagaa    39840
catacagagg tcagaggtca agagtgtgac cctgtggatc aggacagtta cgacagcgac    39900
agttgccaag gtccagtaat cctgatggt ctggctgggg tcataccaga tagagccaat    39960
ggccagacaa ggctaggcca agtcaggcca ggagtgtctt gttattctga gagcccaagg    40020
gctgagctct tgctgaagac ctcttccctc tgcagagcct gctcatctga gcatcctgag    40080 cctttttgttg ctgtgaggct tgcaagatat accagcgttg atatcacctt taaaacgaag   40140
ttttcctgga ctggggagat ggccagtgg atgatttcct gtcacactgt tccatccctg   40200
gttctcatgc tatggcatgc ttctgtaatc cgagcgccgg cactgtggca gagacaggct    40260
aattctcgaa gctcactagc ctcaccagcc caggcaaatc agcgagcttc aggttcagtg    40320
agagattttt gccccaaaa ccaaggtggg agtggtcagg gaatgtactc agggttgacc    40380 tttgcctcc cacacacaag tactcgaatg cacacaccca tatgagcaca tgtgtacaca    40440
ggaagggcaa acaattgaac aagcaaatta catttccctt gccctgtgca ttgtgcacaa    40500
```

```
catcactcca gacgggagct ggtgccctga ggtcctaaac caacccattc ccccactctc   40560
acagaactca ttcttctgga actgttcctc atccccaccc ccactcccaa ccccaccccc   40620
accacagtga tgtagatcac tgtggtttct ttattgtacc tccgaggtct tcccacgttt   40680
tccttactgc atagtattcc actattcagg tgtgctggcc acctcactgt ggaggacatt   40740
tacagtctcc gacgtgtttg ttgttcgtcg gacagcattg tggtgactag ctctcttgcc   40800
tcctcatacc caagagcaga attttcctgg actggggtgt gactcaatgg aagagggtgc   40860
ttttcttcct gtgcttgaga tcctaggttc tttcctcagc accacaagcc aaaaaaccct   40920
tccctccagg gaatctcagg agctaagaat gtgcttgatc tccacgcgtg ctcccatgtt   40980
gctcccagag gccatgctgc ccactcagac ctagcttcat attcccaaag gccccaggtc   41040
tgtggctggt gacaggcagt gaagtctcca agtgggcat cccccactc catcacagag   41100 ctggtgggt gggaagtcca aggagggctc ctttgttccc tgtcctctgt gctccctag   41160 gtcagagaat cttctggctc cacaggcaga gacccatttt cctagcctta tataggaggc   41220
aagacaggag caggcttccc agccctgacc acctctgaag agaagtgaac gtttagtagg   41280
agctcctggg gaggcccagg agggaggttt tggggtacag tggcgagctc cacccttccc   41340
agatgtgggg gggggcagg aacaggacag gaagccaagt ccagctggcc cacccccgtg   41400
tctggtctca ccctctttca ctcagacaca cagagggtgt aggttgaagg aaaggaggag   41460
agaggaagaa agagaggagg atgtaaaaat agctctgctg taaaaggcgt tcagaggcca   41520
cagactggtg cgccccgcct gcccaacaat gaatgcgctt tgcaggctaa cggggacttt   41580
tcgggcaaaa tatcagctcc cgggagacca gtgtccagcc aggagccggc ccctcctcat   41640
gcctcctccc tgcacctcct acccacaggc tgcacctagc catacttccc taagtgccag   41700
gcccttccca gccatagcct gccagcaaaa aggtctccta aggctagtcc cacaaccaca   41760
acttctgcca ggctgacctt ggctgcattc cttccacttg cgataccacc ttcacccctt   41820
ccccaagttc gtggccagtt gaaccccagt agttcccata agtccacaca gacctggagc   41880
tcagtgtgta tctgctggag acttattcct gcatattgcc ccgtttgccc cttctttgca   41940
ccctcaccca tgttcctcca ccccagcatg tttgatgagc actctgtact tgctgggtac   42000
cagctggacc gtgcgccact tagttctgta agacatgagg caagcaagct gcggtcccag   42060
aacaggggct cctggataga gatttgggga tcttggggag gagggagaag ttgggtggat   42120
tttttttcac tttctggaaa atgttatgat acaatgcaca acacatggct ttcatcgcat   42180
tagcttgcgc acgtggtgct ggggactaaa ctcagggcct tgcatgtgct gggcaagtcc   42240
ttacctctga gctgcatctc ctgggcttgg tcttctaagc atgtacagtt cagtggcatg   42300
aagcacacca ggtttgtgta gcgtccttca ccatccattt gcagaacttc tccaccattc   42360
ctaacagatg ttccatcttt gttagatacc ccttctccag cccctggtgc acactccatg   42420
gctttctgtc tctgtgggtg tgaggagtgg gtggcattgc ttcttgggac tactctcctg   42480
gttcacctca ggagtccctt aatgacattc tgttgtctca gctttcatct gtacactggg   42540
tggcttctgc cttctgactc aattgtgaat ccactgtgaa cagtgaggct gcccctcaca   42600
acggtggtat caccaagtct gtatccagaa gttgggctgc tccactgtgc aatgattctg   42660
tttttacttt tcatacagtg tgtgtgtgtg tgtgtgtgtg tgtgtgtgtg tgtgtgtgtg   42720
tgtttgtatg tgtgttcata cagtgtgtgt gtgtgtgtgg tgtggtgtgt gtgtgtgtgt   42780
gtttgtatgt gtgttcatac agtgtgtgtg tgtgtgtgtg tgtggtgtg tgtgtgtgtg   42840 tgtttgtatg tgtgttcata cagtgtgtgt gtgtggtgtg tgtgtgtgta tgtgtgttca   42900
```

```
tacagtgtgt gtgtgtgtgt gtgtgtgtgt gtgtgtgtgt ggtgtggtgt gtgtgtgtgt    42960
gtatgtgtgt tcatacagtg tgtgtgtgtg tggtgtgtgt gtgtgtgtgt gtgtgtgtgc    43020
cttcttacat tcccacctat ggtgcagaag gttccagttg ccttcctgag aagggacat    43080 cagaactcta cacatgccaa gacctctagg gagagctgtc cagagacaca aggtactagg    43140
gaaggagatg tccacggtct tcctaaagcc ctcacatgtg tcagtctcct tggcctccac    43200
gtcagcctca ccacctccct gatccaggcc ttgtctccat gtccacacaa cccccatgct    43260
cagtgccagc ctgagccctg ggggcacgg ccctgggagg tcctcctccg tagacttcat    43320
tggcactatc actgtgtctt cccctttcat ctctccagat gtcccatgtt gtcctctctg    43380
tatatggggc atttcccaag tcctggcccc ttctcagttc cttcttgcat cccgcatcct    43440
tcgcttcaca gctgcagcct tctagaccca tagattctga gacacaccgg atcgtaaagt    43500
aagctcaccg gctctctctc tctcacacac ttcagtgctt ctaatgtgaa tggtgaaggc    43560
tgatccctgc cgtgtcacat cttatcactt cgtctcagcc acataccaaa taaagtcaag    43620
cagttcccgg cctttgccca ggcacagtga ggctgcagaa ctgagtgctg cctgtcctga    43680
agccacccca ggacctttgc acttgccgtt tcctccactc tctaccctct gtgccgaacg    43740
tcacttcctg ctgttcttgc tacagcattc ctgcccattt cctgaacccg gaattgtgtc    43800
cttgtatctc tgcccacttg taggagtggc ttttgcctgt tagagcagcc ccaggaggcc    43860
tggtgcataa aaaagcagt tgttatctat ggataaacag atgagtaact gaatatattc    43920
gtttgtttcc ctgcacttga tgaaggtaca cctctgcaca tggcaggtta atagagggaa    43980
gacaccctcc atacagtggt gttgccaagg ctgggtctct tggctcccag gaacctgcaa    44040
tggctgtggt ccatgctatt gcaacaggga cattctgagt caatgtggag tcccaggagg    44100
actcattgga tccagaggta cctaaggtgc ctgggtatca catatcagtg ttgagtttag    44160
aggcagacag ggcaggtagc tggacaggag gatactgaga gtcccctacc taggggcccc    44220
agctgtttga ttgggcctca ggtcacagtc cctattattt cctccttcct ggtgttatgc    44280
agtggtctgc tgggtaccca gtgtgcaagg aaacaaccac agctcctcaa tgcctgttag    44340
acaatcagca tcccagaccc caccccaggc cccagtcaga tggcacaatg ccatgatgcc    44400
tggcatgatg tctctgaagg tcagcctcag cagcaccctc agctctgtga gatgccaatg    44460
aagatgctaa tgtggttccc aacctcagga gttcctagct tggcatgccc atcttaccaa    44520
cttgtctgtg tgatgtgtct tccagtccaa caatggctgt ctgtgaggcc ggacagcctt    44580
ggtgctgtgt gtgagccatg catatctaga gaggtatttg aggcttgggt tggggtatgc    44640
aggtggtata ggagcagagg tgggggtggg ggagctgtcc tcgtaagaga attggtcatg    44700
gttacatgaa gttaaggttt ctattgctgt gggaaaaaaa cactgaccaa aagcaacttg    44760 ggggcaaag agtttatttc agcttacagc ttacagtcca tcgtccaggg aagtcagggc    44820
aggaacccaa ggcaggagct tggaggtagg agctaataca gaggccatgg aggggtgctg    44880
cttactagct tgctccctat agcttgctca gcttgctttc ttacccaacc caggaccacc    44940
agcactgggg tggtaccacc cacagagggt tgagctctta tacattgatt taagaaaatg    45000
cacaggcttg cctactggtg gaggtttttt ttccaattga agttccctct ctctatttga    45060
ctctagcttg tgtcaagctg acacaagaac tagccagcat gcatgagaag gtgaaggatc    45120
atctacagga ggcaggagcc aacaggagaa tgtcatgcag acacctatta gcttttgaag    45180
ttatgatgaa ccttctagaa ccaaagtgag atgcagggac aagacagctg tgagatggct    45240
cctcctgctg ctagcatgga agcttgcaag ttagttatag ccactgccct aggatcccag    45300
```

-continued

```
aaggtagcac gctggaaggg gcatttagac gctctagttt tataatcatg ctaagaacat    45360
ttaatgggag gcctgccctc ttagtgtctg tctgtggtgg atgggtacag aaaacacagg    45420
agatacacac acacacacac acacacacac acacacacac acacagagag acagacagac    45480
agacagacag acagacagac acagacagac agagacagag acagacagag agacagacag    45540
agagacagaa cacacaatgg aatatggaga caatagaact caccaggtaa gggcacttgc    45600
taccaactct gacggcctga gtttgatcca catgatggaa agagaaaatt ttcatccaca    45660
agttgttccc tgacatgtgc gggcacagag agagagagag acacaaattt aacagaggaa    45720
tcgtattcag cccttaagaa ggagatcctg ccatttctag gagtgaatag catcaggda    45780 cattttgcta agtgaaggag tcggacacag tggcgattct gcagggtttc acttacacac    45840
tgcatcttgt ctaactgtgg acacgatggg tagaaggtgg tttcccagca gctgagtaaa    45900
ggagaggtag gcagctgctt ggtgaatgta ggtgtcaggg acaccaaagc cctgccctgt    45960
gtctcccaag aaggaactga aagctacctg ggctcacttc agggcctaca gcagattaga    46020
agtaacatca gcagtaaaga gatgtcacct tgggcaggga gttccaagat gccactctgt    46080
cactacaggt ccatcacata ctacagccag acccagagcc ctcccagagt tttcaggcag    46140
cttcctcccc ttccactgat cgcaggaagc catgagtttt tgctggctct tctcttccat    46200
tgtcctgcat gcatttggga attcctcttc tccatgtgac agtggggatg atcagcaagc    46260
cattttccta gtatgtctct gacttttcta gtactatgga aggctttgct gctggatctg    46320
catctcgggg ggcgggggggg gggagagaga acttggggac agagacccct ggaaccatct    46380
ggctgcctgg cagacatgac ctcagaacct ttccgcagcc ccatgacaga ccctccactc    46440
gctgaagact tgtaaagtat ctagacacgt gcccttcctg ctctgtgatt ggcttatgac    46500
aatctggtat gtgggcagcc atgtaccaga acaagttgtt gtgaggaaat tcagggcagg    46560
tgacctcttt gctgggtctt aaagtcagca tcttgggggcc cttgggattg gatattgagg    46620
ggaagcttgt attgtttttg gacagaccat cctaagggac agtcccagct gaggctgtct    46680
tacctcctgt gtcacaacac agtgccaatc aggcttgcca ttcaaaattg tgctctctag    46740
gacatgtcca tttgtgtctt atgccattcc tgtggggcag cctctgtcat agcaccgccc    46800
tcttaataac aaagggtccc aaagagtctt gttgtaacaa gccttttctc attcttgttt    46860
acacagagag cacttccatg ggctagtgct ggggtccagt tggtagagca ttttcctagc    46920
atgcttgagg ccctaagggt agcatataag ccagttgtgg tggcacacac acctgtggtc    46980
ctagccctgg ggaggtggag gcagggagat ttaatgccac cctcaagtac atcaaaccat    47040
gtttcaaaaa aaaaagaat ccatcttgta atccacttaa aaatagcaaa gttttgtggt    47100
ggtgcacacc tttaatccca gcacttggga ggcaaaggca ggtggatttc tgagtttgag    47160
gccagcctgg tctacagagt gagttccagg acagccaggg ctacacagaa aaaccttgtc    47220
tcggaaaaaa aaaaaaaaaa aaaaaaaagc aaagttcact acgtactagc ataaaaggct    47280
actatgttct gtgagtcaag gggagagaag cgtggctgga tttacatgtt taagtgccag    47340
ttgggtctga ctgagggaaa gatgagtacg ccctcctggt cccctctgtt cttactcatt    47400
gccaggatag ttccaaccag cttcagggaa gcttccagac cccacggat acttaagaaa    47460 aggaggagcc ccacccagga ctcttagagc tccctgctct gccatctggg gaaactaagg    47520
catggagaca gagacagcgc cctggactct cccttgggcc tgctgtttaa tgagattccc    47580
ttgaggaagg actggccctg agtagctgag cttaaaacca actgatttgt ctggggagag    47640
ctgaggaggg acaggactgg ctaaccctgg ggacagccct ggtgagggtc aggcagctgt    47700
```

```
caacgctcac aacctgggtc tcggcaatag cgtgtgcagg cccttgtgcc ccaaccccat   47760
gctcctggga ggagccctgt tcccagaagc atgtccctgg acactgcctt cagcctgcaa   47820
gttcacttcc tggttaagta aacatctgtt aaatgcccca gttgggcccc acccagcagc   47880
agctttggag gagaacccgg ggcaccaagc ctggcaggcc tccctagtga agacacatcc   47940
atcatcaccc tgaagctcag tggcctgcgt gtcccaccct gggtctgccc gtctgacagc   48000
agggacgtgc agagctgccc atgccaggga ccttccagaa acctgtcccc gaccctctga   48060
aatcctaaca atggtgatga cgacaatttc aaaagtctgg gaagagagca acctctccca   48120
tccatcacca cggccctgca gtgtggggtg cacaccctgt tgtccaggtg agaccatcaa   48180
ggcatgtgac caagcggtca cacattcaca gtgctgccta cagccttggg gaagaatcag   48240
gcactagcct cttcacagct ctgtggtggc tgtcctgagg atcagagagg agaaggagct   48300
gagtttaagg ggccagcctg ccagtcctg gagtgcttga cccagctagg tgccacgcag   48360
gaacacttgc cacctagaag agaataggca tgtgcagttc actgagcgca gtgcaatggg   48420
ctgacctggg atattttgac tttacaatgg gcttatcgga gcatcaaaag ctctgtgtgt   48480
gtgtgtgtgt gtgtgtgtgt gtgtgtgtgt gtgtgtgtgt gtgtgtgttc aggtttgttt   48540
ggagatgggc tctctctgtt tcccaggctg ccctaaact cctgggctca agtgatcctc   48600
ttcctccatc taggactaga gtagtacttg ccaccacatc tggcttaaca gtatcctgga   48660
cttgaagtgg gcttattaga cccagccggg gtgtcagggg agggtgtgtg ctttgccatg   48720
ctgtctcttt gttggtgctt ggacatggga gctggaccta gagtggaatc ttggctatgc   48780
aaaaagagaa aattgaagta gctagattca gggaaatagc aagtatacat aggtcagagc   48840
tatgcttagc agttcctggg taccctaccc tgggagctgt tgtgccattc agtagatgtt   48900
attgtttcct gttgacaatt ggggctcaga gaggagcaca gcacaagga ctggaagagg   48960 cagggcccaa gaattgaacc cagatcttct accacctgag cagaggctct caactaagag   49020
ttgagttatt ggcctgacaa gagactgaga tcagtttggc tcctgttctc attttataag   49080
gggacagaca gctttaggtc tcctgcctac cactgtctgt ggatgctttg ccatgtatcc   49140
cctagtctgc caaggcctgc cctgggcaga tgcatcttcc cttgtaaggg tttcccacct   49200
gctggattct gttaaagcct ctgccgtgag agcccaacac tgctcctgca gacatagatg   49260
ggatgtgagt ttggtttggt tcccttggga gggaagaggc cagcaaggc cagaggcttc   49320 ccctagtgtc tctgtactaa gagtcttctg tcttcacact ccagctggag actgcagtgt   49380
gctacagaag gaagacagag ctaggccggc ttctgccctg gtgtgacggc cacagggatt   49440
taaacttcca ggaagtcatt aggaaccggc agctggggaa aggctgtgtt tatttggcac   49500
ctaatccatg ccagacactg catggattat ctgcttttat cagcatggga cgtctgcctg   49560
gcagtgtctg gagatatttt aggtatctct ggggattggg gtgtgctgtc atcctgcaaa   49620
caggagccat gcctgctgtt gattttccta agacgcatag gaaagcacct ttggcagaaa   49680
ccaatgttgt aacccaagag cagaaaatga cttctgtcgt tctctaggtt agagctgtgg   49740
tgattaatac tgaagacttg acaggatcta gaatctccta gaaacaaact tctgagcatg   49800
gctctgaggt agtttctagg ttgggccgag ttgggaagtt gagtagggta ggtcacccta   49860
gctacatgtc tgacattttg ggatggaata agaaggagaa agtgagctga cctccagcac   49920
tcacctctct ctgttttcttg accatggata cagtgtgacc agctgccacg tctccctcgc   49980
catgatggac tgattccctg aactgggcgc caaaataaac ccttcttaag tcccttctgt   50040
caggtgttta gtgacagcag tgagaaaagt gagcactaca gatgctcata gaggctactt   50100
```

```
gagtgtgtga ccactgaaca gggtcctgaa agagtcagag agtgggatga aagatgtgg    50160 ggaaaggcat tgcgagaaag agggaagagt gtgtgctgag atcccgagtc aggaggtcat    50220
catcagaagg acaaacgtga aggattgttg atctcactc tatttcagtc gaaagcacgc    50280
aggcttgttg attctccaca gtgtgcatgg gtcagatcct tgcattgctg cgcacatttt    50340
acagagaaga aattcatgcc caaagaaaat gaatgtcttg ttcagtgatg gagagtcaga    50400
gacaggaagt agcttaattc tagagctgtg cgctgacggt acactgtgcc tgctgtaggc    50460
agccctctgg tttctcaaat agtgactcaa caggggccca atggggttag aagcacacaa    50520
ggtttaagct ctaagggcat gtttaggttg ctctgtctgc acggggaaa ttaaggtttg    50580 cttccagaaa gacacttaag aggatgccct cgtacagaga caacaggtga tcaggactgg    50640
tgggacagga tgctagagcc aaattcgtgc caccctcaca gggcatttc ctgagcactg    50700 agtcaaacac catgcagggc atttgttctg cagccttctg ggtagatact tttcatggcc    50760
acgtgcatag atgaggaaac taaggatcaa tgagtcattt gctggtggtc actctggttg    50820
tgacaaacac tcagacccac ctctgatagc aaggtcactt tcaggttgt cttctcagct    50880 accaaccctg ctcatcactg tgttttcccc cacagggtga aggacagtct agagcccttg    50940
tcatcgctca ggagctgctg tcttcagaga aagcgtgagt gccccagcag ctgcccatgg    51000
cttatacact aagccctgcc cctcctagct tggccaggat gcagttaatg cagacccatg    51060
cctctttcct tccacagata tgtgcagatg ttgcagcact taagcctggt gagttcatca    51120
ttttgattgt ctctaatgaa ttgtcccttt acagggctgg actctgagag gcagaaatca    51180
gggagcagac agggtgact acatttatag gcttagtggc tcaggctctg ggccaggctt    51240
ttcagggaag cctggccggt tgatggatgt actgggcagg atgcctccct gcctgggtgg    51300
ggtgggagct ctggcagaag gctctgggag gacgtttgag gatagatggg ggtgtcgagg    51360
gcagtttgtg tgtttgtttc tgtggtggtg gggatggaac ctatgactca cagcatgcca    51420
ggtgagtaag cattccacca ctgtgcccaa actccatgca tgtgccttat ctttgggtcc    51480
ttatgtggat cgtgatgtgc ctgcacaatg ccagttgttc agggaaccaa ggggtcttct    51540
cagtcaccct ggtctcctct ctaggagctc tccagagaca aaagcaagaa gaaatcattg    51600
agggtgcagg ggggacacca tgaatatgga gcatttgagc aggtttccgt ggggagatgg    51660
cttcggttca ggctgggtcc cagggaaggc tgcatgcagc aaagatgaca gaatggggtg    51720
ttttaggcct tgtgacagct ctcccaaatg tgtgaggagt cacagcccca ccgcagttct    51780
gccttggtcc ttgattccct ggcttcatct catgcaatgt cagagccatc tgcggccact    51840
ttaaacattt agcaggtagt gatgtataag ctcagaggac aagaacgtga ctaggcccag    51900
gtcacatagt gatggagcca aggtagaaat gggctttcct aacacgtacg ccactcttct    51960
cgtgtatgat ccagtctgca gagcaaagca ccatttccca gtgtcctgca ccaagccagg    52020
tccctgggtg agccagttaa actccacact gctgtgctat ccccatgtga gcaggaagac    52080
gtcccgtctc tgagtggaga acagaacagt cttctgattt agcatggacg ctgtttggga    52140
ttccagttct gtgtgttatt aaacctaaaa gctcccaaaa cttaagtatc ccagaccttc    52200
ccgcttcact cctaaaaggt ggctcagcaa ggcaggaag aatggagccc tgaattctgc    52260
tcccttgcct gctcctgcct ggcagcttca cacaggctgg gtactctctt ctgtccttcc    52320
agaacccggt caccaaagct tccaccctcc tgtacatcca tcagtgtcct acccagccag    52380
atgactttgg ccactcatct ccctcatccc caaggcacca catgccacaa ccacatggcc    52440
attcaccata gtccacccac tactccatta tccatcagcc atctaaccat cggtgtactg    52500
```

```
ctccatctct ctacctctgt gccagcgact caccaatcca tctttccttt catccatccg   52560
tctgtccatc caaccatact tcccttcttt ccccatccac ccactcatct cttcctttat   52620
ccatttatcc atttgtttat ccatccatcc ttccctctct tcctcattca ttgtcaatcc   52680
atctgtcaat gaatctgttg gttcattcat tctccccaag taccctcttc tcattctctc   52740
ccctccccca ttcactctga aatattatag actgtttggt tgccattgtt actgaaatag   52800
gccttggagc cccaaagatg aaaaagtccc catatttact cttgagtagg tctcagtgcg   52860
gtgtgtgtgt gtgtgtgtgt gtgtccccta cacatatgtg agtatgcttc tgtgtgtgca   52920
tgtgtgtagg cctaaagttg agtcattttc catcttttat ttattgagag aggctctctc   52980
actgaacccc atgcttacca attctagcta ttcttgctag ctgattcacc ccggggatcc   53040
cttgtcttct gtttctcaag tgctgggatt gcaggtgacc atggcagctg ctcgacttta   53100
atgtaggttc cagggatcta aattctagtc tttaggctct accataagca ttttaccat    53160 gagccatttc ctcggcctga caaatgtcat ttttgttaaa ggagaggatg gaggtgggga   53220
gatgccacac ttatgtctct cagcataaat agaatttgca cagccatgtt ttttgtgcag   53280
aatctacatg agcatgatga gagcaggctt tccagtttgc aatccaggaa ggcttatagg   53340
aaaggtgcca taaacatgga cttggaggga gagattctac caggtgcaga aggtggagtg   53400
atcagcctgg gcaggtgcat ggaacctgaa gatatatgac gtggggttga gtggtatatc   53460
gactatgcag ttaactgtgg ctgtctcaaa gaggcagaaa gtcaaaatgg gggtcaggga   53520
aggacccaaa aacaagatga gcaggttgca aggccccgac agtgctgtct tggggcttat   53580
ggttttcctc gtgtgtgagg acttggtgtt ttgaacagca ctggtctcag tcacctttgt   53640
ttctgtttac tcacttgtaa tgagatttca cctagtagaa gctgatagtt gctcccaggg   53700
gtccctcccc caaacaaagg ctctctagac tgccagtggg aaagtgtctg ctatcagatc   53760
ccctgaaaga agttctagaa cccaaaagaa ctggtgtctg gcccatgcac cacttggcac   53820
ctccttctac acttcttctg cgctccatct ttcctctgcc ttctggctgc ccctaaactg   53880
ctgtggtggg gtgtcctctt ccatcgcttg atgctcagtg tcttctcttc actcaggtct   53940
cagcccaggg gtcaccaggg aacaagcatg tccaggactc aatgatatgg agtagcatgc   54000
tactactatg ctcaaagttc ccatgccatc tttcccacag gtctcagtga agtccccatg   54060
tcatcttgtt ttcagaccct ctatcccaga gattttcaca aggcttgatg agaaactcat   54120
ctctgctcag cagcatctgg gccctaaccc agaagattca aagaccagta gtaacttgat   54180
ggttggggac tatagtctcc tgtaggtgtc ttccttgtaca tgtctggtgg cagatggtag   54240
ctactgtctg gggcctcatc tgggcctatg gccaacaaac ttacctatgc tctctcctcg   54300
tggtatccaa ataggcaagt ctggacttcc tcccagccag tggctggatg ccaagagtga   54360
ttgtcccaag agaaagccca gaggaagtgc gtgccatttt tatggccaag gcttggaagt   54420
cacgtagcgc cacttccgcc atactccact agtgggagaca gttacagagg tccacccaag   54480
ttcaagggca agggatataa tctgtaccct cagtgggagg attatcaagc acacattgca   54540
taaatatcct gtaggagata ctgttgtggt cattttggga aaacataatt caccatagac   54600 gcctttcaa aaatgatttt gtgtctctta ggaactgtgt tgatttcta gtaacaaaac   54660 ttcaaatatg gcagcttaag tcgcttagag gttatcctca tgtggaggat cttccacggc   54720
tcggaagctg cttgcatttc acaggttcct catgaacacg gatagctgct gtacccctaa   54780
cctcataccc atatcacatc cgaccccac atcatatatc tctcaggcag aaaaaaagga   54840
aaggagaaaa acaagtttca gactcccggc aggggctggt tctcttgaag atgcctaggg   54900
```

```
catcgctgga cagtttttctc ctgttgcctg tcagtgcctc gggtagccag agcaaatagg     54960
agttggtggt caaagctaag tacaactcac tggccctact tctttgtgtc catgatggag     55020
ctcagctggg aaggggacag tagatgctcc agaaaagccc tccctgttcc cagtcagcaa     55080
gggggggagg gggcctcctg ctttacacag atagaatctg tgcatagctg agaagagctt     55140
ccctcagggc agtgatttgg cagcttccgc ttcctttagc atttggcagc agtcagtgtt     55200
ggcagcagaa gcaggtggac accccgcgc gcacacacac acacacacac acacacacac     55260
acacacacac acaccaatgc tactctcctg cctcaagtca gatctctgat gtagacctag     55320
gaagtggaag tgggtgttgt ttcttaaaga aaatagaagg cttcagactg aagagattga     55380
cccagtggtt aagagcacct gttgctcttg cagaggaact tggggttcag ttctcagcac     55440
ccacattggg gttcacgact atctgtaatt ctagttcctg gggatcctat gctctcttct     55500
ggccattctg gcagtgcatg cacatgctat gcagactaca agctgcattt aaaaaaaaaa     55560
aaaaggaaga agcgaaggag ggagggaagg gtgagctcat aaaaaggcag gtgagatgaa     55620
actgtgcctc aggagagtta gaggctcaca gtcacaggca gccatgacaa gtccctgagg     55680
tgaacattca gagagatagc cgtcacctat ggtgtaatta gggacctgga ggaagagagg     55740
caggtccttc acttcttctg tccccagaat ataggagagt ttcacatcat accagggcag     55800
catcagcaga aaggaagaac cttcaatctc atagggcaag ggagttttga ctcttgtggg     55860
tttgaggtgt gtgtggtggg agataagttc caaaacccag cctgtgcact agaagccaat     55920
gaggcactga taaatttagc tgtaacgcaa ggctgacttg gatctgagca gtgggaaggg     55980
atagacttta catgcagatg ctgtgggcag ggagataact caactctgtg agaactgcaa     56040
gcttacagtt gctctctgtt cttggccctc agagagagac tgcagccact gtagcctgtt     56100
tagggacagg gagcaggaca tagctgatct gtaatcagac actgaggaat tctcagccct     56160
atggcagcag ctttggttat acctcccagg tcctggaatt ccccagctct tgtcagtggc     56220
tggtgtgata actgctggcc cagtgtatct aagactcttc accgttaagg tcatcgatac     56280
tgctgctacc atcactatcg ctggtcactc ccactgcccc ttcaaacggc tgctctgctg     56340
aaactctcac aggtgatgtg agctccaggc tctgccacca attctgtctt catctcttct     56400
gctccccttg aagcccaaag ccatgggtac cctcagatag ccatcgtttc tagggctcag     56460
cctcatgact cactcttctg tggctgtggg tgctaccgct ggctgggcac tgcctctctc     56520
tgccttacag gtggggcatc acaggagggc atttctagtg gctctccagt gacctggaca     56580
gtctgttttct atagccagag aggtgttagc atcaaccaca gcagaccttc acgtaaatgg     56640
atcactgtgc ttacacaagt cacaccagtc tcagcctcta aaccctggga aggctctcac     56700
tctctggcgt gctgggaaat ggttcagggt ctgatagcat tcatgagact ggtgattgga     56760
aacgtccttg gtaaatgtct tttttcaaag aaagatttat ttattatatt tatgtgaata     56820
cactgtagct gtttttagac acaccagaag agggcatcag attctattac agatggttgt     56880
gaggcaccat gtggttgctg ggaattgaac tcaggacctt tggaagagca atcagtgccc     56940
ttaaccactg agccatctct ccagcccccct tagtaaactt aagacacag cttaaggctg     57000
ttatggctgt ggctgcatgt acaggagctc aacttcggta gccacaatca tcttgtggct     57060
tcctcatggg ggtctctggg ctgcttggtg cttggcagac tggcaatttg attgacagtt     57120
ctctgctcaa gatagccagg acatccactg agcacaccgc ctaccaggga gtcaagtagt     57180
ccatctcatt tgtttacggg aagataaaca tcaataggac ttaaaatatg aacttgttga     57240
aagcattgtt ttagctatgt ttagtgtgct ttcaacaatg ctcacctcct gcccagcacc     57300
```

```
ccaaagacac gtgaactccc cttacctgtc tcattcccag ggtggaagct taatagacag   57360
cttctgagcc acaggctctc catagctacc tcctttcttc caaagccaca gtgatgggca   57420
gaagaccttc caagggcagg tggccagacc ttcctctcct gtactgtctc acacttctta   57480
ttgtccctgg taccttgctg gttgggcaat accccacccc aggcatttgt tggcccgttc   57540
cagtaggttt tcagaattct tcctagcgtg acccctcctt cagagcacag cactctttgg   57600
cttcctcacg tttgtggttc cccagactcc tgctgctgct ggtttcctgg ttctgttgtg   57660
ggaagatgca tttctttggt tttcttagat ggattgagac ttctgttata gcctagcaca   57720
aggccaccat gggctgggga ctgcgccatt tgtcgtttgt gttttggctc aggtgtgacc   57780
tctgttccca tctctctttg ggggctgtgt tgcttgagcc ctctgaagtt ggtgcatttt   57840
ttagtggacc tctctggctg ggcatctgtc ccatgctctc cctcatagag tgggtgtcct   57900
ctttggaagt aatgcctata aggacagcca tgaacacagg gcaggacact tctgaagtat   57960
ccagcccagc tttccaggtg taggggaagg agtctcagag gaaggtatat ctagtagcca   58020
gggaaggaaa gctcgccact gcagtgatca agatgtgcac aggccttata gccagctggg   58080
gtgagcatgt tgggacttga gagatgttcc cagccaggtg gaggatgtta tgagagggga   58140
aactgagaaa gctgaggcca gcaggaaaag gaaagataga gagccttcat gccatatgta   58200
gcttcatccc aagggagtgt ctgggaagct gttggtgact ccaggaagaa atgctgtggc   58260
atgctgaaaa ggccaccgac tgtgtgccct tagtgactag gtatgtggtg agaggctggg   58320
ctgatcccag ggagttaggg gctctagagc ggccatgcaa gcaaacattc tatgaagtta   58380
gggactccag aagaagaccc aagcacagtg aagaccggac atggctgggg aaggggacgt   58440
ggtctctcca gggaagtcat gggtaagtca gggcttgggt accctgggca ggacgtaggt   58500
tttggctgag gccacgagga gataatgtga ttcaggtttt gtgggtctcc agtggagaac   58560
actgtcccct ctcccaggtg gtgtgaaccg cagtgaagta tctgtactct cctggacagg   58620
gctgaccccc ttgggtcacc ctctcagggt gctcaaggca aactcggggt ctgcaggact   58680
ctgatgtcag gacggttatg agtttattat cagaattgtc tggcattgtc ttcccaacca   58740 cccccccatct gtgctccttc ccctccgtag gccaagtcag tgtccaaggt gacaggtatg   58800
acagggttgg tgactgctat gtgccaaccc ttcacatgtt gtctcaattg gttgcacatt   58860
atatatccat aagagatagc agagtaacag gcctagatac tgcgtctcag aagtgagtga   58920
ctttccctgg gtcacacagc tggggtgaag tagtactatg gttttctaac tatagagccc   58980
tgggaaggaa agtggtgttc ctctaacctg gaggaatgac gtcagggaaa actttctgag   59040
gagatgggtc ttaaccagca gaaagcaggg acaaacctga gggaacaact cccgagggag   59100
ggtggtgaag acattgaacc atctaggaag tctcttcatg tcatatgtca gctctcaacg   59160
ggacacagag ccctagtgac tcaggtgggc aggcataggg aagaaagtta aggaaggatg   59220
ccctagtggg gttgagtggc agtgggaaat tctgtggacc aaaggttaac ccagacaacc   59280
tccttttacc actatggcta tctcctgctt atcttgcctc cctgcctgtg gttactgtta   59340
ggacattttt gttattttta ttgtggtcat tttgagacag gctctcaatg tgttgcccaa   59400
gctgtccttg aactcatgat cccctacctc ggcctcctaa tgtgtgcttc actgtatcct   59460
gctaggaaat atgttttaat tgagcaggta aaaccttcct tctagccggg gagtgggtgg   59520
tggtgcgtgc ctgtaatcct agcacttggg aggtagaggc aggcgggttt ctgagttcga   59580
ggccagccag gtctacagag tgagttccag gacaggtagg actacacaga gaaacctgt   59640 cttgaaaaac ggaaaacaaa acaaaaaata cctccttctg tcttttgagt cttgctgtct   59700
```

```
cttctaggca tcctgagatc actgacatct tggaagtttt agggggaca cattttagct   59760
caacaaggaa ccatgattgc tctctccatg gttagcaagg gatgaagtgg gagccacggg   59820
gagacccatg gagaaggtcg gggcctgagt aggtgctatt gcctcctgtg tgttcatgcc   59880
gcccttcctc catgaccctg aatgatgagg cagtaggtga cctttggagg gtttaggaaa   59940
cagtaaaaaa agaagaaaga aagaaagaaa gaaagaaaga aagaaagaaa gaaagaaaga   60000
aagaaagaaa gaaagaaaga aagaaggtaa gtacagtatt ccaatttggc ccccatcact   60060
gaggagagtc tgaaaattgt tgcttttaa aaacattctt gtagcttgcc tatattaagt     60120
gaattaattt taacaataaa gctcatgtat gtgtgtaaga agacagatac aacttccatc   60180
attccaaaaa atgtctgtcc ctgccaatga cagaggtccc cagggtatat gcattagtgc    60240
tccttgacat ctagtttgta ttttttttt taagatttat tttatgtatg tgagtacact      60300
gtagctgtct tcagacacat cagaagagtg catcggatcc cattacagat ggttgtgagc    60360
caccatatgg ttgctgggaa ttgaactcag gacctctggg agagcagtca gtactcttaa    60420
ccactgagtc atctctccag ccctagtttg tattttctat aaatgtacat gttctgggca    60480
tttaatttaa atggaatctt aagctatagt ctctctggtt ggttttttc ccctagcat     60540
atgctgtcag ggctcctccc tctttgcacg tgttggtatt tcatccattt aaagctgagt    60600
cgtagtcctt ggtgaatgta ccccagcctg tacctttacc agaggatggg cgtttgggtt    60660
cttacttgtg tgtaatggta agctgcaggg agcatgtgtg tctacagttc tcttgggctg    60720
gctcctgggt ctcacagtga ctctgtaacc ttttgaggga ccacatggtt tttcctagag    60780
tcttatttcc attcaccctg catttaaaag ggcaatagac cgaagaaatg attccatcac    60840
ccaagtcttc aagtcctgct tcatgagtca gtgagtctgt gggagttact taaaggaata    60900
tgactgactc aggatcggct gcatcactga aaattctcac ccaagagtgg gcaatgactc    60960
ttagaagctg ctttaccaga gtctcctgct tgcagataga tttaccactg aagagtctct    61020
gctccctgtc catcatttac agcttccatg tgccttatat atttgttttg ttttgttttg   61080
ttttgtttga gacagggttt ctctatgtag ccctggctgt cctggaactc actctgtaga    61140
ccaggctggc ctcgaactca gaaattcgcc tgtctctgcc tcccaagtgc tggcagtaaa   61200
ggcgtgcacc gccacgcccg gctgtttctt gagttttaag agctgtatga ggatcccgca    61260
gaagggagtt gctcagtgca ggggatgcag gtacacaccc tcatcccata gacctccaca   61320
gtctctactc cttgtaatgc cagttactgt gagcctgtgg cagctggcct ggcaggtgtg   61380
ggctcggttt tgcatgtttc cctaaggaca cgtggtacag agcatctttc cttgagctcc   61440
ttgaccatct gtacatgatt cttggagac ttgtcattta aagataaata agtctattat    61500
caaacaggat ttacaaatat tttctctcat tctctaggtc ttcttactc cctttttcaaa    61560
ctccacccat ctgtctatcc atccatccat ccatccatcc atccatccat ccatccgtat   61620
tagatggaac ccagtatctt gatggaaccc agtatcttaa gtatgctaaa caagtgctct    61680
accactgagc tatgttccaa tcctcaactt taccctcttg atactggtta gagtgtatta    61740
aaaaagcagt ctaagagagc catgaggagc aagccactaa gcagcactcc tccatggcct    61800
ctgcttcagt tcctgcctcc aggttcctac cctaactttt ccagatgatg gactgtaagc    61860
tgtaaattga agaaaccctt ttctccccag gttgcttctg gtcatgattt ccttacaata    61920
agagaaaaca aactccgaca ggtggcaaag cgtgatcttc aaatcatgca tagcaaggga    61980
tagcagccac tagtgctaaa gtaatgtttt aattatgttc tgtgagaaaa actgtgagtt    62040
tcctctgccc tccccctccc ccatccttat ggtgctgtga gttgatgcct atgtatggtc    62100
```

```
taaggggaaa aagtgacgaa gggcatgtca ggctcctgtg agttcacttt ggtactcttg    62160
cactttgggg tcacaggcac ctgctgtggg ctttctttct ttctttcttt ctttctttct    62220
ttctttcttt ctttctttct ttctttcttt ctttcttcct ttctttctgt gtatatgtgt    62280 gttgggggg  gggcgcttct catgtagcct aaactggcct caaactctat gtagcccaag    62340
ataaccttga acttctgttc taccataatc ttctatttta aaattttaa  attatacttt    62400 cgtgtgtttt tatattgtgt ctgagtgtta tgagagtgta tgtgtgtata cacactcatg    62460
tcactgaaca catgtggaga tcagaggaca gctaatggga gtcagttttc gtcttccaat    62520
ctgtgggtct cagggattga acttgccatg cttggcaaca ggtgtcttaa cccactaagc    62580
catcccattg gtcctgctct ggcttcttac agttcttttt tgagaaacta gaaagcaagg    62640
actttgcatt ttcttagaga aggaattgat gactaactcc ctgtcttgta aaagaaaggc    62700
atcagcatgg cactgctctg tgtaaacaaa caaaaaaaaa aagacagccc tgcaccaagc    62760
aggtacaagc tggccttcct ggtccacagg tgacagtgtg gagccaatga cactggcctc    62820
agctcttgca gctgcacagg tcaaagatct ggagcctcaa gggccctcca tgcgtaacag    62880
gcctctgggg ttgcaggatt tccatggagc cgtcctgagg gccttggaga acgtagagca    62940
agagggcaga gagccactgg cccaggagga gctgcgcag  ggcctgcggg agctcccagc    63000
tatctgtgac cttcaccagg gcatcctgga gagcctggag cagaggctgg gggattggtg    63060
agcagcctgg ggtcccacac cccacttatg ccacctaggg gtgggggaa  cagacgaaaa    63120 cctccacaaa tacaaaacgc tgactccagg ggacaaacag ggagcccagc gacaggtggt    63180
aagttgtgtg tgccccaagc gaaacagcct ttagaacccc acctctcacc cttcactcat    63240
cccaaggctg acttctcact gcctgtcctc tccctaacag tggggagggc cagccgcagg    63300
tggccgacat cttcctggcc caggaacagg agttcgagca tcatgccgca cacatcctgc    63360
aatttgacag gtacctgggg ctgctcgctg agagctgcct gctctcaccc cggctagcca    63420
ccacggtccg ggagtttgag gtgagtacca ggtctttaga gactctgcca taaagatgca    63480
ctggggccca ggcaggggga catggagaga cttaaaagaa gtaaatgaga catacaggag    63540
gaatgagcta ggcagtaggt ggggagaccc agcagaaact agaatgccca cccgacagga    63600
ggggaaccca gaacagagtg acccctgctg ggcagtaggt gtggtaggcc acaagagagt    63660
cctgcaacta gttctcccat cactatcaac caagcaggga gataacccag ccagaggata    63720
accaaggaaa tggttagccc aaactggaag cctagcttct gagattgcaa aggggacctt    63780
acctctgtta ctaatgtcag acacaatagg gcctcagaga agtgacttat tgagcctgac    63840
tatgaacctg gagggatgat ccggaagggc ttcctggtgg aagacgacct gggtctgaca    63900
atgtgggaga tgaagggtgc ctgtgggcgg tggggtctct gactgcatct ctcctcccct    63960
cctcaagcag cagagttcac aaggggg tgg ccagagcatg aagcatcgta tgctgcgtgt    64020
ggtccagcgc ctcttccagt accaagtgct gctcactggt gagccatctg ggtcacaggc    64080
ggactgaggt ggggtaacgt gggacaagaa cttcccttca tgtatgtaag caggtgtagg    64140
gaaaatggca ctactcagat acccagggcc ccacagattc aactttgctt cagtggctct    64200
cccgtcccca aacctagaaa ccgagtgaca ttctcactgt gcatttccta aatcagctga    64260
cattttacag aagctgcctt cctaggtgag aataatggac gttcctcctc aggcccgtgg    64320
cacccctgtg gctttgctgc atactacctc tcgagacctg tccttcccag ctctgtgaaa    64380
ggtctccagc ctccctcccg ccttctgtcc cttcgccact ctggctgcct cttctcttta    64440
ccctatcagt gaatataact gtcttcgtca ctattctact gctgtgaagg gacaccattg    64500
```

```
ccaagacagc tcttataaga gagatttaat tagaggctgg tttacagttt ccagaggttt    64560
agtccattat catcatggca ggacgtatgg aggacatggt gctgaagtat ctcagagctg    64620
gtcgctgatc tgcaggcagg caggcaggca ggcaggcact tggcttggca tggactttttg   64680
agccatcaaa gatcacctcc aataacacac ttcctctaac aaggccacac ctcaggatcc    64740
ttctaatcct tccaaatagt gccactccct gctgaccagg catccaaaca tacaagccta    64800
tggcgagggg tgggggaggt cattctcatt caaaccgcca cagtgacctc cagggccca    64860
acctcaggcc ctcagtctct gcctcataga tccccccaca cctctgtgct gagccccact    64920
cactgtgtac agcctcccac atagaatcag tccctatcct gtttctgaga ctcccatggg    64980
tgtccttctg acccccgtg gggcagggca catgcagttt cacgggtcac aaggaaattg     65040
tgctgggttt gaggtcaaga gaatctgctt tttcaattga tgaagtagcc actgggccct    65100
gccagtgtcc cagccctggc agtggcagca aatgacagtt caaatggaga gattcaacac    65160
tatgacaagg catgggctta gcatatgcca ggccctgagt ccatctccag caccaatgat    65220
tttatatcta aatatgcaaa tatattaaaa cacatgaata tataatatct gtgttgaaaa    65280
tgctaccaaa aaacaagtta cagggttagg aagggggct gatatgtaag atacagcaga     65340
gaagacctct ccaaggaggt gagatggaac aaagatgtga gaaagaaat ggtacaaagc     65400
tctagaaaac atgatgaggt ccaagggtag gaacaagctt gggatgttca aggagcagca    65460
agactgcctg tatggccagg agcaaggcag agggttgcta gcagggttag gaccacatca    65520
ggggtcctat aatatagaca tggagcagcc tagctgagta tattctgcat atgacacctc    65580
taagttatcc cctagagact ccttcagtct cttgaaatga cctctaccat ccttagctag    65640
ggtgttggga gggggctgg ggactctgac aagcagagga agagaaggtc atggagttgg     65700
atagtccagg aaggatgctt tgtttaaaat attcactgct cccttaactg tgccatgttc    65760
ccttctgggt tggtgcctca gcccctacca gggtggaccc actatgatat agtcacactg    65820
taatataacg ctgtgtagct tgtcatatct tgtaaccagg aaacagtaga cagcaagtac    65880
tttcttgtgc ctgcacccca gaggtatagc cataacaagc acacagcaga tcatgaatag    65940
ataggggctg aatgagttag tgactggtag tggtggccag gatgctaaga gggtcctggt    66000
cttagggtgg gctaatgtgt tgaaaaagtg gatgccccag tctggtggag gtcaccgtgg    66060
agggcaggag actgtctcac tggtaaaact gacagttgtt tctccctctc cctccagatt    66120
atttaaataa cctgtgcccg gactcagcag agtacgacaa cactcagagt aagtctgggg    66180
agaccctgga gggaggtcca cctcttcttg tgtctcctgt tcaccaacac tcaaatctac    66240
accagtgtcc agtgtagacc tagagcaacc cagctgtgtg tatactgcat acgacacctc    66300
tggggtatct gccagagatt cctcaagtct cttgagatga cctttaccat ccttagctgt    66360
gggagcctgg gggtctgacc agcagaggaa gagaaggtca cacagttggg tgatctaagg    66420
atgctttgtt taagatgttc accactccct taagcacacc atgttccctt ctgggctggt    66480
gcctcagccc ctaccaggtt ggacctagtg tagcatagtc agcagccatg gaaacaaggg    66540
cagtcctgga cgagttgggg ttaggttcac aacctgttgc tatagtggga aaatctggtg    66600
tcgtctcatc ttcgtagccc accacacagg agacagagga gacacacaga gaaaaggtgg    66660
cctagtcctt ataaagctgc tatttgccct ttcctctcca ggtgctctga ctctcatctc    66720
taaagtgaca gaccgtgcca acgaaagcat ggaacagggg gtaagtccca ccattggctt    66780
cttctccagg gtggagtcta aggcctgctt cactcttctc atctgacttg tgatacccca    66840
ttgtctgtct cctggggccc tgcaaagagc cttgggttct ggccttacac tcattgtatg    66900
```

```
agcctgaggc tgagttctaa cttagtggga gaattcggca atccattagt catgtctgta    66960
actggtataa aagaaggtga tggtggtatg tatgccaagg cattgctcag cagatgtgct    67020
gtggcaggta cacagagaac ccacagggaa taggaaatgg agtctggaga cactgcttat    67080
ataagtcagg ccttgagctc agcagagcag tgaccatgat ataaataacc atggataatg    67140
gttaatggag aggaggggct gagggttcaa aggatggagt gccccaaagt taggaggagg    67200
taggatcact tgtgatgaga ggatacactg tggagggctc tgcatacttg tacatgtaga    67260
tgagaagaca aggaagaaaa ggcctgggag gaggctggga gtaggagatc tagggtacat    67320
cagctgtgtt ttgtcactta gtgtgactaa taggactaga tctggaaaca ggctagagct    67380
ggctacagtg ggaagctgga gggacggttt gaatacacgg gttagttgtc ggggctactt    67440
ctgggggttc aaactgtcac agtcatccgg tcctcttacc tccccgtgag aggtttggac    67500
ttcactcttt gtcactttgg catcctatgc atacagtgag gcttcctctg tgcagctgag    67560
atgcttagag gccaggaccc tgtctgtagc atctggtggt attctctaca tcctgcttca    67620
ggaagtcctg tctctgttgg catgaacatg tctctcctcc tcaggagagt atgaggtcca    67680
atacacagta cctataagag ggatggggca gccatacttg gctctctcaa ggtgaggcac    67740
atgctgtggt gaaagacaca ggcaagctgc tttgggtgag acaccctgt gcttgattgt    67800 cttaactgta ccttagtccc cagtgagcca cactctacct gcccattccc aactccttgg    67860
tctccggtag caatctctgc actcacctcc cgtgagacca gcttccacta cagtcggctc    67920
tggagatcag gaggtggttg tctctctgtg cccagcctta tttcacttaa catagtgatc    67980
cccagttccc tttcttgttt aaatggaggg attttgttct ttctcaggtt gaatcatact    68040
ctgttgtgtg aacggatgga cttttcttgt ctacttctct gtagacagca tttatgcttc    68100
tgttcctatg ctgttgagag cagtgctgta gcaatcatgg gaaacacgtgt ggatatctat    68160 gtgagatgcc tgctctgata aaattgctgg atcatacagt aggtttagtg gtttgcagag    68220
agggagactc catacttatt gccataaggt gtagcttgct ggggtcccag caggggtctc    68280
tgttctccac actctttccc ctcttcttca attctttctt ctgaggtagg tggtgtctcg    68340
tgggtctggt ttgtattccc cagtgatgag tgactgacgt tgaacacttt tgcatacacc    68400
tgtcagccat gtgtatgttg tctttgtaga aatgtccatc cacaactgca gccagttgtt    68460
attgctgctg ctgttgtgtt ttgttctgcc tgcctctgcc tctcaggtgc taggattaaa    68520
ggcgtgtgcc acctctccta gcccttagcc tagggtctaa ctgtacagtt gtcacacaac    68580
ctgtctccag aacgtctta tcttcccaga ctgaaactct gttctcctta aacaccagtc    68640
ccacccagcc cctggtgccc accatgctac tttctgaaca tattttattt tttagaacaa    68700
attttagatt atagaaatat ttaagaagat agtgccaaga gttcccacag gttctgttgt    68760
ttccccattt ttaatgtttt ctatgaacgt gaagccctgg ttgtgttaag agccagtgtg    68820
gaaacagcat tattacccat agtttgcata ggcccaatgc cctgttccag gatccatccc    68880
ttttggttgt tacatctttg aagggtccac gtacagccag tttctcagat gttccctgac    68940
tttgatgacc gtaaaggtct tgagggagca tggtcaggta cccagtgttg gaatctgatg    69000 ttttccccctt tatgagaccg gatttgtggg tacataggaa ggagatcaca aaggcaggat    69060
tccatcttgt catggcatgt tgtgaccctg gtcacctgac tgagtttatg tgttcctttc    69120
ccactgtctc tgattaaaaa aaaaagtcac tgtgcacagc ccacatgtaa gcagtacaga    69180
gaaacctgtt ccctcttctt ttaagctgac gacgtcctaa gtgttctgga gtcacttgta    69240
ggagatgtct ctcccacttc aatgatgggt gcagcccacc ctcaaacata aacagtccat    69300
```

```
tcatttatgt tggtaccaat ttacgtatat ttattttagc ccatgttgtt ttatttattt    69360
ctcaaataga gaagggtcaa tttctaaacc cacaatattg ggaatggaag aattccttct    69420
gcaagaatgg ttctgtctgc cctcccctt gtagggttta gtcagcctct tgttagttcc     69480
tttattcttc tgtcacttgt tcctcacctc cttaacaaga atgttaggac tttccaggct    69540
cattggtctt atttctgtcc ctgtcttagg ataaactatc tctccaaggt ccttgaatga    69600
gagagagctc agaggggaag cccagaaacc aagctctagg tccaaggcat actgtgctgt    69660
aggctctcat ttctgaaatt ctgttctcct taaacaccac tcccatcctg ctcctggtgc    69720
ccaccatgct actttctgaa cacattttat tttttagaac aaatttggaa gctcctggct    69780
gacagagtca agaaaggggt gtgtatgtgt ctactgacct atgtgtagac gtgcgcaacg    69840
ataggatgga tattcccata cctaaccaat ctgtcctctc gcgtcaccca gatggctcca    69900
gattctcagc ttaccaaaag ccctcactcc acaagaaagg acctgcctcc caccatccct    69960
ctcccaagca gttagttgtg cagtttacct tcacaattta cctttgaaaa atatttgtcc    70020
tggatattaa aaactggttt ggtccatttt ttttctctc tgagtaactt ggagacggca     70080
caccgctgtc ttctgactca cacagtctct gctaagatga tgcttatgtt tgccctctgt    70140
ggtggtttgc actctgaatg ccgtgatatc ttctctgtta atgggcacag tagctcatgc    70200
atataatctc agaagttaag aggctgagac aggatggctg caagttcaag gccagcttaa    70260
gctatataac aagagcatgt gtgtgtatgt gtgtatacgc gcatacacac acacacacgt    70320
gtgtgtgtgt gtgtgtgtgc atgcatatac ttcacatata tacaaacaca tacatattta    70380
cacggtgtga tttggggaag gatgtctgga aatccttaag gggactgggc tgtgttggac    70440
ctacctatct ccagcttctt gcttggatct gggctttggt gagcattcat ttactttgga    70500
aaagtctctt gctgtattat ctcaccgccc ctaattcccc cccccccac acacacatgc     70560 atacactcct ttctctctgt ttggggtatg tatatgtatt cacaaacatg tacatgcata    70620
tgaaggtcaa tgttggtcaa tcttttttcaa ttgctctcca cctaattttt aaattagttc   70680
tttgaggatt tcacacaatg tattctgata ctattcaacc tcttccccca ggaccaactc    70740
cctcctctcc ccaccccaat ttgtgctctt gctctccctc ctctctctcc ctctcccatc    70800
tggtccagtc agtgatggca atgcataaac tcacgagtat gtggctttct acaggaacct    70860
ggtggacata ctgggattg catccttaaa gaaaactgat ccccctcca gctcctacca      70920 actgccaaca tctccttagt taggagctgg gcctcatgct caccttcctc tctccaggct    70980
ggcttgggtt ttttcaagtc cacactgtca acaattgcag tgagttcatc tgtacagctg    71040
ccccgatgag tctggaaaac agttttcttc taggcatcca ctgcttctgg cctttacagt    71100
cttcttgctc cttccacact gatcgattcc tgagccttga gaggcaggg tgtgacacag     71160 gtgtcccaat tggggctgag cattctgcag tctcttattc tctacaccct ggccaatggt    71220
ggatgcctac tgctaacagc agcttctctg gtgaaggttg agagatgtac tgatgcactg    71280
gacatcagtt tactgtgatg tccatctggc agaataacag tggtgggttc cctgctgggg    71340
cctatgacct accttgccat gggctcttgg ccctagtgat ggtgccaggg ataggtttca    71400
ttttgtagag tgagtctcca ccttttttaa aaaagacaga gtctctctac attgctctgg    71460
ctatcctgga actcactgtg tagactaggg tagctttgaa gtcagagaga tccaccagac    71520
tctacctccc aagtactagg attaaagaca tgtgccacca cacctggtaa cccacttat     71580 tttttaagac atagtctctc actgaccctg gaactcattg atgcagctag gctgactggt    71640
catgtctcca gtgatggggt tataggtgct atgcccagct tttgcgtggg tacgggggc     71700
```

```
tgacctcaga gcttcatgta tgcattcaca gcaagcactt tagccactgg tccatctccc   71760
cagcccctct gtcttcactc tgtgtactag atagagatct gtcttcatga cctctggctc   71820
ttcctttcct caactttgtt cagttcatag ccaaacctgt gaagagtttt caagcctggt   71880
attgtaggtt gcctgttttt gttttaatt cctctgaact cctctgtgag gtcagcagcc    71940
ctgatgaagt tctgtctact aatacatggc attgaccttt gcaccagacc ctctaacata   72000
atagttgctt tggtccttgg ctcagagctc aacacctgt cactcattct gcatgtgtgg    72060
tgtactttct ctgaaaaaaa aaatgagtt gggtttatgt cttagttagg gttttactgc    72120
tgtgaacaga caccatgacc aaggcaactc ttataagaac aacatttaat tggggctggc   72180
ttaaaggttc agaggttcag tccattatca tcaagatagg agcatgacag catccaggca   72240
ggcatggtgc aggaggagct gagagttcta catcttcatc tggaggccac tagcagaata   72300
ttggcttcca agcaactagg acaagggtat taaagcccaa acccacagta acacacctaa   72360
tccaacaagg ttactcttcc taataatgcc actccctggg ccaagcatat acaaaccatc   72420
acagtttgtc ttcctggttt aatattttaa atgcttatt attttattat tctatgatta    72480
tgggtggttt gcctgcatgt aagtctgtgt gcctcatgtg tgcctggagc tgtggagac    72540 caggagaggt cattggatcc cctggagctg aagttacaca tggttatgag ctgacatgtg   72600
ggtacgggaa ctcaatccca ggtccgtggg aagagcagcc agtgtcttct gctgagccag   72660 cttttccagcc tgcccacccc acaacctaag ttggttttgg atatatgttc tcatgaattt   72720
tttctttaaa aactagattt gataacttct tacacataaa gatggatttt gatccatgtt   72780
ccctcctagt cctcccaagc atctccagtt tctctatgtc cctttctatc attatgataa   72840
ttcgccaagt ccaactagtt cttcctgctg gaatgttggc tgatgttggt gtggttttgg   72900
gcaggtctca ggcaggcgac cgaagctgct gtgggttgat gaatgcaatg gccgtgtcac   72960
gtctagaaga tggcatttca cggcactcct ctccatcatc ccgtccttgg actttgtctg   73020
tccccccatt ttatagcgta ctctgagcct taagtgtaag gggtggatat agatttccca   73080
cttaaagctg aatactcaat caccctttaa actcagcacg ttaacactta ggagtctgag   73140
cattgtagag cgaaacttct ctcaccaaga ttgaggacaa cactcattta gatgtgtaaa   73200
tatgaatatt cagaatgcac tttgacaatg tgtccattta tcaaggccac agtagtgaat   73260
ttcctcctag ggcctatcta aaaacacagg tgggcttttg actaaggtta tagtgataga   73320
cgtgacttcc ctgctgtgga aatccaatcc aaaagtggct ggttactccc ctagccttca   73380
tgccatgatt gcaccagtgt gagcatcgtg cctcaaaggt cagtattgaa gcatgcaacg   73440
tttgtatctg aataatacct ttgatggctt ttctctccca gcagcctcca tagcgctatg   73500
aaagctaacc atccaggaag aagttttcag gtccattcca gcttggtttc tttatgtctt   73560
gcaaccagag tattcctgtg actcttggtc ataccaggct ctgtgaacat aagctctgtg   73620
gaggctgaaa gggccagcat ttgcatcttg gttttggttg tactatgtgt ggtgagatgc   73680
agagagtgtg gccagttgat tcagtcctgt cataggttct gctgggtttg ggaatagtct   73740
atcctccatc tttgtcagcc tcatcttcct ccatagctta tgtgtctgtg gggccctaag   73800
tgctgagttc tctcttacat tcatttccag tctttgtttc cagaaatctc tacaggcagt   73860
agggtcctcc tctccccgtg cgtgccttct ctgaggtggg gcatgtctgg ctgcctagtg   73920
ctttgtggca gccccactct accttgggcc tgaggctggg cttggacaga tctttgccca   73980
ttctctgggc tagtcagctt ctgtgtgctg tcagggcaca gcacagagcc ctcttctcag   74040
agcctttgcc tgagggttaa gtggacttct agcctcccca gtgctgaaac cttatattca   74100
```

```
gcttgctcag tgccatttca caggactctg acccctccca tgtgccctca gcgcctgaca    74160
gacacctaga agagagcttg caggttggtt cctatccata gtgtctgtag ctttattacc    74220
ctgaattgtg ttaccagccc acacttgacc ttcacaaagt caaggacatt tcaattgcct    74280
tctttcaaaa taagtactct tttctttttc ccatgcattg tgttcatatg cttgaagatc    74340
ccagaacaaa cagctcatgg agtcagttct ccttttcctc taagcggggt ctaagagaac    74400
cttaggtcat caggcttggg agcaagtgcc atctctcggt ggccctccat tcttgtaacc    74460
tccatctgcc agcctcccct tcctcccact gtggccaagg gtgtgaccca tcccttcacc    74520
tttcatctct gggagagagc ccatgctgcc tgccgtttct tggagtttgg attttagact    74580
ggtcttttct gagctgttct cctcctctga cgaggaagcc atgtcccctt acagaggata    74640
cataatgcct ggtaggggag tggaggggta accatctcct gtccctgccc acaggaaaac    74700
ctgcagaagc tggtccacat cgagtacagt gtacgaggcc aaggggacct cctccagcca    74760
ggaagggtga gtgcagcctg ggcaaggaca agggccagct tgactctgat aagcccattg    74820
ttcagctggg ctgcccccag acggctctgg ctgcaggtgc tgtttaggag gggtggggga    74880
catggtgcac caccctggag cttgtctgca ccccgccttc cataatgccc tctcggggca    74940
gttaaagaaa cagtgccaat cagttctgct cactgtagct gccctgggt agctctccag     75000 tgagggaata aaaaaaaaat gtacccagtg tttatagttt caggttgtca ggaaagcaga    75060
gctcagagta gctctcgaaa gacaagcccc aagaaagcag cataaaaata gcattcttaa    75120
caaaacaggg gctggggtgg cactcagggg tggagcgcat gcattgcatg tgcaaggtcc    75180
tgggttctct gcccagaaag ggaggggtgg gagagagatt gattgatttg cgtgttagct    75240
tccagatgca aaacatacaa ctcagctcag aaagcagcta aaagtgtgat cattgccagt    75300
tggagtgagg gagcgagcca catcggcagg atgctgcgag tctgggattc tctgaaatct    75360
catgtggttc tgactgagag accctgagct ccgcagacct cactaagcct gtgtttgtag    75420
ccttcagaag gatgaggctg gagtgactat ccgcaggtcc agatgttcag caggcctccg    75480
aagggcacgt tctgaatgga ccctttgtag tgctgtttag ggagagagtc gtaagtggga    75540
ctcctacttg gtggctggaa cattgttgag cttgtgtgag gacatttcca gaaggccgga    75600
ttgcccagct tgagttcctg ggccaggagt ctctataagc tgtccctggg taccctggca    75660
gccatggaga ctgcttccta cagactttgt cattctacct ctgaggttag cttctctccc    75720
ccacaggagt tcctgaagga agggacactg atgagggtga gagggaaaag ccgacacccc    75780
cgccacctgt tcctggtaag cactggagat aaggcaggtc ccatcgttag cttttctagag   75840 ccagcatttg gtgacaagca gaggagccag gacagccttt aggatgtaac gctgagcctt    75900
caaaactaaa caaaacaaga tgaaacaaaa caaacaacaa aaaaaaacca cactgcttat    75960
atgttatttg aatgcttggg ggacagggag tgtagctgtt aaaatgaata gctcatatgc    76020
ctaccataat tggttcaaac cagggctttc ttctggtact ataactacac tcaggcactt    76080
tctgtggtat gtacaacagc agaggggtga ggaaaccaac ttgtctaggt tcctcagcag    76140
agggccaaga cccagagcgt agccagggtt gagcttccag tccatcactc tgtgagagtg    76200
agcatacatg acacttctga ggacacagac ccacacttgg aacattaggg aatatccaag    76260
acctttgggc tagcgacgtc aacccagggt ctcatgctat aagtagcttc tttgctccaa    76320
tctaggaccc caagacacta caccttctgt gctgcctacc tccagaacaa gtgtctcaga    76380
cagtcaggat ttaaagagga aaggcaagat ccacctccca gttctggagg taccagtcct    76440
tggtggggtg gccttgtagc tttgggccta tagccaagta gcacaacaag tgagccatcg    76500
```

```
ttcacctcat ggctaggaag caagagacag gaaggggaag gggttgggtt cccacagtct   76560
cctcaaggtc acgctgggat gacctaactt cctctcacta ggcccctaccc tctgagggtt   76620 ccatgccttc caacagtgcc atcctttgga ctgcactttc aacacagtgg ccattaggga   76680
accccccaag agccaaactg tgggcctgct gttttctggg tatctctgtt tccccattct   76740
tttgcccttc agtgttgttc ttgtgactgt cgatggggct gccttcagct gcctccccat   76800
accgccagaa ctttatatag catgacggta gcacagctat gagctctgtg cacccagcac   76860
tcactgggcc aacaccccca ggctgggaca tgagtgcaga gatcgcttac agccttgtcc   76920
tcagccttca gaatgtaatg aaagggaaat acatagacta acagccaaga gtcgggagat   76980
gaaatagagg ggagtcttgg gaataggcag tcagtggagg tggaggaggg tcacgcattg   77040
aagtgaaagc agccactgta gctatgctca aggatcggtt gggtgtccga gttccctgga   77100
gaggctgcct ctattaaacc ctgaagcaag ggaggctgtc tgctttcttt tactaccatg   77160
tgcggcgtcc cttagattga actgagtcat cagtcttggc agcaattgtt tttacccgct   77220
agagcaattg cttttaccca tctcactggc tcccacttca tttcatttct ttctttaaag   77280
gcatggtgcc acgacgtagc cctggttgtc ttgggacttg ccatgcagac ctcgctggct   77340
tctaatccac agattcacct gcctctgtct cctgcgtgct gggatttaa agacacgggc   77400 cacctcacca gccccccact tcatttctta actactttgt agagtcctat gtggcagcct   77460
caagttacat gctggtctct gttggctagt gtaaaccatt gtatgattac catttggatc   77520
aggattgaga gcgtttgcaa cacttccaga aagctccacc aacgctggca atcggtcttc   77580
cccaagtgac ccaggcacta agtggcctga ttgctgttgc tttaggttgg actttcacat   77640
aaaggcggtg ggctgcactt acagcatctg acctccccc tcacaatgcc tgtgatccta   77700
tcacgaggct acagtctggc agcctgctcg tttgggttgc tgtgtggtat ttcacagtct   77760
gactggacca cggttcttta tccatcaact gtaaaggata tttggttagt tctcccttg   77820 gggctgtgac acataatgtt ctctgacact tggtgccaga gcattggcag atgtgccaag   77880
tccttttgag cattcctgta ggagtataat tgtcatgatg aggtgtgcac cgaggactac   77940
tggctgcctg caccccagag ctcagggacc tgctacgtat agagcttgct gcagccttcg   78000
gggccaggac tggtgtgact tgtgtgcctt ctctgcagat gaatgacaca ctcctgtaca   78060
cacatcccca gaaggatggg aagtaccggc tgaagagctc gctgccagtg gccaacatga   78120
aggtagatat cgaaaaccag gtaccctggg gtaggcgtgt catcacaggg aagatgctgg   78180
ggagatggat ccagccttc ttctctctac ggaggaccaa ggcccagga tacagcgttc   78240 agtgaggact gctgcaggtt taaacatagg ggctgcccag ctacaactag ggatcaatga   78300
tatattctca gagtggataa gacatggaga ggaaagggtc accccaggag gaggacagta   78360
agtgcagaaa ccgcttggag ggagccaaca aacaggttta ggttacattg ttaaaaccct   78420
ctagaacctt tctatcatcc caaacagaaa ctgtctccat taaacactga gtcctgtttg   78480
ttctatctct ataaatgtaa ctggttgaat gacttcatgt gggtagagtt ccagcatttg   78540
gcttcttgga gctggctggc ttcacttagt gttgtgttca agatttctgt gtggaagttt   78600
ggtcagtctc cttccttttc tgggcaccca catctgcccc ctctgtctct ctacctctct   78660
gtgtatctct atctttatgc ctctctcatc tctgtctgcc tctgtgtgtg tgtttgtgtg   78720
ttcatgcacg catgtgtgtg catattctcg gttcattcac cactgaacat gtctcagctg   78780
ttgcatgtgt gatgtgtgga ctagcatggt ttatcttggt ctcaaacacg agggtgcgtg   78840
ggcacattgg ggaattcttg ggatggagaa cattctggaa tgttatttct gataccatct   78900
```

| | |
|---|---|
| gaggatggtg cctgagaagg aaatgctgag atgagaaggc aggacagctg ggaatgaaag | 78960 |
| catccatgct ggtcagaacc ctgtccagcc actaccagcc actagcagtg acaaagctg | 79020 |
| tccgtgctcc tcccctccc acctgaaca gatgctattg gtttccctgg caggtcagcc | 79080 |
| gccctgtgat ggacaaagtg ccctatgctc tgaagatcga aactcctgag tcttgtctga | 79140 |
| cactgtctgc aaggtatggg gagccatact ctagctgcag tgccctctgc tggccgccat | 79200 |
| ggcatacgac acttagatac gcaggcataa catacaaaaa aataaatatt ttaagatgaa | 79260 |
| gataaatatt ttaagatgaa gataaagtta agaattgagc aaaatacctg aagttgacct | 79320 |
| ctgacctcct cactcatatc tacgtgtacg caacacacac aaaacacaca ggcatggaca | 79380 |
| tgcatgcaca cacgtacaca cgtgcgtgca aatagaaagc aataactaaa agaaaaaaga | 79440 |
| aaagaagaac tcctgaggtt tggggcttat ctcagtgata gcgtgtctgg ctgacatact | 79500 |
| aaggccctgg ttcaggcttc agcagcacaa aaccaaacat aaatgccagc tcctatgccc | 79560 |
| agaggtctgt aggccccatg aaagtatctc attaaaaaat gttatagatg attgtctcag | 79620 |
| catgaggttc tcaggtgact catatgtgtc gtgtgctcag tgggctgtca gccttggcac | 79680 |
| tctcgacagg acaaaaggga agtgatgagt ggttgcccat ctctgaccat tccgtcgtct | 79740 |
| tttggggagg ctcttggtag gtggaaggat gctgtactta aaacaacatg agccagttgt | 79800 |
| ctgataaaca aaatctattt ctcccaggct aggagttagg aaatgcaaga ccaaggtgcc | 79860 |
| ggtcgatctg gggtctggag agagcccat gtatgtagat ggcacctgtt tgctgtaata | 79920 |
| tagaagagac aaaggggggtc ccacaaggga gagggaagac ttcctgtagg tagtgattcc | 79980 |
| tgggatagct ccaccacctc tcctctctgc ctgatgcctt gtggctcagt gtgtagcttc | 80040 |
| tggtgacaga ctacaccgat tgtctgctcc tgcctgtcct atggcctgga gtaccagctg | 80100 |
| ccattgatat atctgcccac tggagggggga ttatacattc cctttaagca gtgtcaccct | 80160 |
| ggctgcctac cttactgccg gccaaagtgg caccttctcc ctgcccaggc tgtgggatgc | 80220 |
| tccagtgcag ggcgagggcg acacctagtg ggcactaaga atatctaccc agctttctcc | 80280 |
| tgggcttgga cattggggct caactagggc ccagaggctg ctgaactcgc agcaagagag | 80340 |
| agggtgccaa gcagagccac agcaccttgg ctcaccgagt ctgtgccgac agctcctgcg | 80400 |
| cggagcggga cgagtggcac tactgtctga gcagagccct tccggaggat tacaagactc | 80460 |
| aggccctggc tgccttccac cacagtgtgg aggtgagtgg gggccactcc agggttccta | 80520 |
| gggtgggtcc tgccatatcc tcctcacaga gacaagttcc tcctgtcctc ggggccctgg | 80580 |
| caacaccctc atcggtcccg cctaccatgc ttctgttaga gcgtggcacc acagttcaac | 80640 |
| ccaggagcat gccctgcagt ctggcaagca gaccagggga cagagtagac ttgactccga | 80700 |
| attagggaga aaggggctgc acttccccaa ctgtcccttg gcctctctcc tgactgtggt | 80760 |
| tgctggctgc cgcagatccg ggaaaggctg gggatcagcc tcggtgagag gctccccacc | 80820 |
| ctggtgcctg tcactcatgc catgatgtgc atgaactgcg gctgtgactt ctccctcacc | 80880 |
| gtgaggcgcc accactgcca tgcctgcggc aaggtgagtg acagactggg gggaaggtgt | 80940 |
| gcttggggag gggatgggga catgttcctg cttgtggagc tcagggggcc agaggaagat | 81000 |
| gaattcaagg ccagcctgag aggtagagct tgttcctgtc ggtatcactg aaatccactg | 81060 |
| atcatggcag tcccaggcct ttctgccaca ccatgttaat aacacgggag aactcaccat | 81120 |
| tatggtcact ggagggggagt gttatcttat ggttatgagc acagctcttc agaaaagcag | 81180 |
| gcgcttgctc agagacattc tacagcccag gctggaagag caggggcccg tgtgacacag | 81240 |
| agcagctagg gtcctgggggc tgcctggagg aggtgagggc tgggctaaac tgagagggtg | 81300 |

-continued

```
actgacagct taaatgtgtg ttctcaacat ggcgtcagat tgtgtgccgg aactgctctc    81360
gaaacaagta cccattgaag tgcctcaaga acaggatggc caaggtctgt gatggctgct    81420
tccgggagct gaagttgagg aatgggcctg tcccaggctc catgagaggt aactttacaa    81480
ggcccttgcc ttcttcagg cctggtggct tctccccaag ttctcatgat gcctctatgg    81540
cccgggttcc tgcttgaatc tgctttctcc agaagaagag agatgaggtt ctgcataaag    81600 gcagcccct ggggaggcca aggctcaaga cctgggttcc atgggaacct gacagctgct    81660
ctgtccctat gaaggcaggg ctgctgtggc tgtccgccat ggatggttct ttggggttat    81720
tcgatatttg tctatatggt tatatgcatg tgggtgcagg taccctgaa ggccaaaata    81780 aggcagatat gttcttaact gctgagccat ctccccagct ctctgtaggg cttctatgaa    81840
tattccatga gcctgctgtc tttgaatttt tgtggcaggt ttgggaggct gcttgggagg    81900
ggcttgggag tcaggaaagg agagagagag agtcccctag aagctgaatt gaccctgag    81960 acttggtact taagtgacag gctgtgccca gaagtatcag gccagagaga cagcagatgt    82020
atcttgggcc ttcttgaagc cacacccaga ggaagcatag tcctgctggt ggatccagga    82080
caactgttca atgtcctggg aaaatgccac catgccccag agcctctgct cagcatcagc    82140
aggaaggggc atgccagcca tcctgggccc gtctcctccc acccgcaccc ccatgagcct    82200
tggagggact tgagccagca ctccagacaa ccctccccct ggcttctcac ctctgcagag    82260
cgtccagtca gcatgagctt cccactgtcc tcgtcccgct ttcctcggg cagcgccttg    82320 tcctctgtct tccagagtat tagcccctca actttcaaga agcagaaaaa agtcccttcg    82380
gctctgtccg aggtaaggtg tgcatgggag acagtgcttg ggaggttcct gtcctctgga    82440
ggcatgctca gatcctcctg tacccagcct ggccaggctc ttctgcacaa agagaactcc    82500
tccctgaaag aactcaatag tgagcccagg tagtgccatt gctaaggata tccctgtct    82560 tcagaagaca tctgtgggct gcagaggagc tccagaggca tcttgtgtcc ctccttggct    82620 ttatttttc ttttttccttc cccatactgt agaattagtg cccgcaggc ctgctcaggt    82680 gagctgcaat cacggttaat tgtcccatgt cagtatttgt gagccccacg tgttctcggg    82740
ctgcagggag ggaacagcac aggtgctgag ccccctaag gctgactgtg caagaaacct    82800
gaaaactggc tgcgcacaag tccgtcatgc agacagggcc cccaagcaat gtgtgcccat    82860
gaggagagcc ttcggagcca agaggcatgg ccagctgcat ccaagtccct gttaacaggc    82920
atcatgaagc agtgggtgtg tgaagatgcg ctagggagtg aagatcggtg gatgagtgct    82980
atctcagcca ttaacttatt ccatttgcca actgaagttc ttggaattac gactagggca    83040
tagcttaatg gaaaagcgcc tacctctgcg acgagaattc cttgaaggac ccgtcaagga    83100
gtgttcacgt gttcacaata cagagctgtg ttcactgttc ctggtttcct cctgccagct    83160
ccttggtcca gtggagaaga tgagcatccc acagctcagc accttctccc attgctgggg    83220
ctctgcctcc acagcattgc ttcccagggg aaagggagg aaacctgtgt gagcacctga    83280
gtaagctcct agaagattgc agaatcagat ccctggaggg gctccatcag ggatcccaga    83340
gcccaggcaa gagttagggg gtcctcatgg ccttgcacca ggacagaatc aaccccggct    83400
tcctttccag cctgagctgg ttgtagattc taggctccaa atcctgagtg tttgctgaga    83460
gtcccaagct gaaggggggct gcacttcagg aagtcccttg ttcctcaggg tctcagttcc    83520
catccataaa atgagaaagt cagaggaaac tatccctgaa cgtggccatg ttgctttcta    83580
gtgcactcac tgtaagtcag gcatgtctgt ctgtcaggat gtctcatgac ttgtaagata    83640
atggaggccc tcaggaggtc agtaaattgc ctggtgatgt ccatagttac tgctggagcc    83700
```

```
tggtgagaac cctgaaatcc ctccaagcca aactgggagg gcgtctcttt tgttatcttt    83760
gctttctggt gctcgtggta aaacccaggg cctcatagat gctcacacag tgtgccagaa    83820
ccccaatcag tgttagccac tgccagagcc tgtgcagcag agtgtcacct aaaagctggc    83880
agcagtatga cacagtagga ctgcgtctac tacaccagtc aggagcccct tcccccata     83940 cctgttaggt aataggtaca agattccttt taagtgcaag gtgttctaag ctaaggttaa    84000
atccatcttg ccgtctgggg tgtgtgtgtg tgtgtgtgtg atcccagtag ggacaggcct    84060
tctggaggca gctttggact tttacatcga cttcttagac actgaagcag ttttgctgac    84120
ctcaagagtc cagagatcag ctttcgaact gatggtctgc ccagcccgt tttgactgcc     84180 tgctttgctt cccttccacc aggtggccgc gtcaggagag ggctctgcca tcagcggcta    84240
cttgagccgc tgtaagagtg gcaagcggcg ctggaagaaa ctctggctcg tcatcaaggg    84300
caaagtactc tacacctact tggccagcga ggtagaatcc tttctgaggc tgttcttgca    84360
gggaggcctg cgttaagtgt gtgtgtgtga gacagtaggg gtggagggc agccagcttc     84420 agtcttcatc attacttatc acctgcaggc ataagtcagg gacaccgaaa cctcttctgg    84480
tggtaatcaa gtctttatgc tggagtgtgg gtgtgaacac tcaccgagta cttaaatgtc    84540
acaggcttga cagccaggac aaagtcacaa gagaaaactc atttctgtct ccatcttggt    84600
tgcttggggc aacaagcagc agctcagaga gaactgcccc ctgtgtgcct gtccattgct    84660
tttactaaaa taactgaggg ttccagtaag gcttctaaat acacacacat tgctgcttgc    84720
ataggacata ctggttttag cttctaagct acaagcaagg gcgggggcta cagctcagtt    84780
ggtaggatgc ttgcccagca tgcaggaagc gtggggttca gtcccagct cacatagcct     84840 cgctgtggtg gtgcaggcct gtaattctag cactgaagtg ggaggaacag aagttcaagg    84900
tcatcctcaa ctacatcatg agttcaaagc cagtctggac cacatgatct cctatctcaa    84960
aaagaaaata caaacaagag tgccctaaag cctactctgc tcccaaggta gagagatgtg    85020
ggctgtcatg gtttgatctc actggccagt cccgcggagg ctgaacgggt tggaaagtaa    85080
gatggtttct atctccaggt cccaccacct tggggcttcc atagccaaat ccactttaca    85140
gtcaagactt acaggtgccc caaccactgt tgaagaacgt gctcgttagt ctaaggctgg    85200
gccttctcag gtgacctgcc tcctctccac agacttgcag ctgtggtggt cactgtgtgt    85260
gtcatcttta ggcactggac cagcagacag agggtccctt ggttcatttg tctacagttg    85320
agcacagctc agagcagccc cctcctaaga aggcatgcct tagagctgag catggtgcta    85380
cgtgccagtg gtcctggca ctcagaaaaa tgagacaggg gaattactat gatccctagg     85440
ccagcctggg ctacaatgta aggctgtata taataataat aattaatgat aataataata    85500
ataaaagcaa ggcaggacag tggtagggca cattgtattc tgccaggtta gaggatttct    85560
agcttggcaa ggctctgtgt ctgagcagag ttgccatctg ccaggtgctt tctccagaca    85620
gtaaccttag gtagcgggtg cgtgcttgac ccccttcttc tgggttaact ctctctaagt    85680
gtgtatcatg aagtctttgc ttcttataaa catcactttc catcctataa gctttctccc    85740
taggttaaag ccttgacttt tcctctgcac actgttccca gtgtcctgtg tgtgtccatc    85800
tcatgagcac tcatgctgtc atagcctaga ctctgcagga ctcttgctaa gccccttga    85860 acaaaggctt ggcagaatgt ctgctgaatg tgctgcctga acaaactctg ggacactaaa    85920
acattgagta ctctagtctg taggaagaac tctggaaggc tgtgagttca aatcttagct    85980
cttcctccat gctaagtgtg tgctcttgga acgttgcttt tctgtgtcgat ggtagagaat    86040 ttcaaagata atggctctga acatgcccag ctctagtttg ctgtcagaac ctgttaagtc    86100
```

```
gctttccttt cctggactgg ccctggctga aagccaggtg atcagagtct tccacactca    86160
cagcactcct ccactagatg caaggatcaa ccataggggc tgatacaggt gtgggttttt    86220
aaaatctttt atttattatt tgacagtttt acatctgtat acaatgtatc ttgatcttct    86280
ccacccctta ctccaccaac acccctccca ccatcatgcc ctctcatgtg tttgtgtgtg    86340
tatgtgtata tatatgtgta tatatacata tatatacaca catgtataca tatatgcatg    86400
tgtatgtata tgtgtatgta tgaatgtata tgtatgtgtg tatgtatatg tatgtgcata    86460
tttttaacgt gtatattgtg tgtatgtatg tgtgtatatt gtgtgtatgt atgtgtgtat    86520
ttctatgcag gtgtgtgtgt atgtgtgtgt atgtgtgtat atgtatgtat gtataggtat    86580
gtgtgttttg tgtgtgtatg tgtgtatgtg tgtataggta tgtgtgtatg tatatgtatg    86640
tgtgtggttt tgtgtgtgta tgtgtatatg tgtatgtatt gtgtgtgtgt gtgtgtgtgt    86700
gtatgtgtgt atgtatgtat atgtatgtgt gtgtgtgtgt atgtgtgtgt cacccactga    86760
atccagttag tgccacctat tggatgctgc ccgaccttgc tggcttgatt ctgtccaggc    86820
acccatagct gcagtgagtt cattacaagg actatgtcac acccacattc acagcactcc    86880
tcccatcctt cagctccgtg attctttctc tcattatcct ttctgatgtt ccctgagcct    86940
tggggatgga ggggttttaa caccaggttt tccttctatc ctctgcagga caaagtggcc    87000
atggagagca tacctctgct gggttttact attgccccag aaaaggagga gggcagcagc    87060
gaagtgggcc ctgtttttca tctttatcac aagaaacccc tgttttacag cttcaaagca    87120
gaggacagca attctgctca gaggtaccag tgacagctag tcttctattt cctcggctgt    87180
cttgcagaga aatgcagtgt tgtcctgcat tgttctatgc aggcccctgg gggtccaagc    87240
acagctgtgg gcctgcatgt tctcaactgt gagacttaga cactcatgat tctgttctat    87300
gggatgacat tggttccggc aactttcaca cagtctggaa ctgtttgcta aatgtgggaa    87360
gtgtgtctgg gaagtagata caaagataca atccttggct tcaggccacc aggaatctag    87420
tccagtcaca tagatacccca gtgctgtctc tgtttcacag atggatggag gccatggaag    87480
atgccagtgt gttatagcag tcaccaggcc catggactaa caacaaactc ctacattaac    87540
tcgagaaccc ttccggaagt gactcctgct ttcagctcat ctggatgcac gtgtgggttc    87600
tgtgtggagc ttgacctcaa ggcgaaaccc caagagctat ttatagacat cttctttttct    87660 gcctccatgt ttcccaaccc caatcacaga ctgtacaccc ttatctaaaa gtgagttaaa    87720
atttagtacc ttgaagacgt ggaaaccaag tgaaaaagac acttagaaat gtgggctttt    87780
tagtagaaac tggctttttc tggttttact cctggtgact aagaccactt tcaacttttcc    87840 gcactctcca tatggtgcct caggtgatgt gggagccaga caggaagtat cagctgtgta    87900
tctaagcact ttactatcct gctgagctgc agcctccagg gctgtgtctt ccaaggaatg    87960
gctgcaaact tcggtgcaaa gtgactcctg cagccttact gtggcttgcc accctaagga    88020
gggaggggct cagcaccaca ccagggctgc cctctaaagc atcacagatc cctcaaacat    88080
ggaagacctg catctgcgtt aagtttctgt gtgcattcct gtgtccacac tgtgcaggct    88140
gaccatcctg ttgatgggag tctgtcctct ttgtaacacg tgtccttggg ctgtaccagc    88200
cacaccaagc ttacttttttg agagaggtaa aggagaaaga gagaagttgg gtcatcagaa    88260
agtggtctgc acagaaggct tggccagccc ggaggcactg agtggctgga agacactttg    88320
cacacctgag gccgacagca tcacctcccct ctgggcacct gaggcagagc catcacctgc    88380
tggccagttc tttatgccga atggatttta caaaatgcag gaggaggaac aggattcctc    88440
ttcactatcc ctacagttgg gaaaaaaaaa aaaatgcctc catttttctga aatctcttcc    88500
```

| | |
|---|---:|
| tgccttgtcc cctacaaaaa agattttttgt aaaacaaaca aacaaacaaa ccaccatctc | 88560 |
| aaggacttat ttacattaat tatgttcagg gatttctttt tctagtttga agttcttttt | 88620 |
| caatgttttt gcagtcggtg tatagttagt aattcaagtc ggatggaaga caagtgttac | 88680 |
| tgttcacttc acaatcctag gatccttcct agagtcactc acatgggacc cggacaccga | 88740 |
| gacccaggaa cctttagaga gtggagctgg actcaaggac agtaatcctc ttcctttggt | 88800 |
| ttcattttc tatgatttca attgcaggag accaactgtg gactgaaaat attaaatgga | 88860 |
| aaattccaga aataaaagtg catgaatttc cagtca | 88896 |

<210> SEQ ID NO 2
<211> LENGTH: 5636
<212> TYPE: DNA
<213> ORGANISM: Mus musculus

<400> SEQUENCE: 2

| | |
|---|---:|
| ctccacagaa agaagatact cccgtggatg gggctaccga ggagccgggg tttgaggggg | 60 |
| aagtccagga gcatggtaca gagcagacag gaactgaggg ggacctggaa gctccagatg | 120 |
| aagaggcacc aagtagagac agtgaggaag gcatggtcca cgctctggaa gatgaagact | 180 |
| gtgatcacga tccagagacg gatgggaccc caacatcgcc agatgaaggg gcaccaagca | 240 |
| gagacagtga ggaaggtgag gaggactgtg atcagggccc aggtatggag gagcatccca | 300 |
| tgagtgaaga ggagggagaa gaggaggagg tgaaggagca cgtgtacaac agtgataaca | 360 |
| gggcaccctg ggatggagag gagcccttcc ccaatgaggt cattctcaca catgtccgct | 420 |
| ctcagtcccc tgaagttccc tgttgggagc caggccctcc tgagactcct ggagaggcag | 480 |
| aagaggattg tgaagacatc tgtaacaaca cagaacctgg gaaacccaat caggacactg | 540 |
| gtcaggacac agaggatgcc ggcatgggat cccctgagag tgaggtgtcc ccagatgtcc | 600 |
| aggagcaaga ggcagcaacg gacaaccctg aggtctttga ggaggactct gcagatgctg | 660 |
| cagaaggtga ggatcagata gagcaggagg aaccacccaa ttgtgacgag gaagcctata | 720 |
| atagagatgc cgcagcagcc accatgcagg tgggagagga cctcggagag gagggagacc | 780 |
| atgtgcagga ggaccctgct gaggaaagct gccagatcat tccctttgag agcgacagtg | 840 |
| tggaggagga tttctcacct acactcacag agaatcccta tgagattttc ccaaccgaga | 900 |
| gcacttcctt ctgcaataac acctattccc ttgacgagtc agccaatggg cacgagccag | 960 |
| tgtgcgagat ctgtgtagag gaggttcctg tgttggccc tccacttaac cagcatgatt | 1020 |
| ccctgccaga tggatctgga gaggactccc cggtggtccc tgatgtggtg gtcgtgccag | 1080 |
| agaatgaggg gcccgtggat gatgcactca gcagtccata cgtgatggga gttggcttgc | 1140 |
| tgagccttgg agagggagcg cagtcagaca cccaggctgc atcaggcact ctgagtgggt | 1200 |
| acagtacatg ggaggaaggg gactctgagg gagggcaggt cccagtggat aggaagaata | 1260 |
| ttgccacaag ggcccggcct cactctggga aggtggctgg tcatgttcca gaaactgttc | 1320 |
| tagaagaaac gggaccagaa acctgttcat caggcatggg catcagagat accagtgatg | 1380 |
| aagtgaggaa gataggtata ttgccagagg gaaagcctcc cgagtgtgtt cgggccttgc | 1440 |
| cggccaagcc cagagcattt actctctacc caaggtcctt ctctgtagaa ggccgggaga | 1500 |
| gtccctgtc catgttccgg gagccagagg gagccgggct ggacagccac cgtgtaagga | 1560 |
| ggaaagagga caacctctct ctgccggggcg ccatcggctc ctccggtagc ttctcacagc | 1620 |
| gcagccacct gccttccagt ggcacctcca ccatcctcc tgtggttgac atcccacccc | 1680 |
| cttttgactt ggcctgcatc acgaagaaac ccatcactaa aagctcaccc tcactcctga | 1740 |

```
tagacggaga cacccctggaa aaagcctcta agaagaagaa gtcctccttc aaacgcttcc   1800
tggagctgac gttcaggaag aagacagaga gcaaggtgca cgtggacatg aacctgtcgt   1860
cttccaggtc ttcctctgag tccagctacc atggtccagc cagggtactg gaacttgacc   1920
gcagaagcct cagcaactcg ccccagctca agtgtcgcac tggaaagctc cgggcctctg   1980
actccccggc cgccctcatc ttctacaggg acagcaagag gaaaggcgtc cccttcagca   2040
ggacggtgtc cagagtggag tccttcgaag accgctcccg gccgcccttt ctgcctctgc   2100
ccctcaccaa gccacggtcc atctcattcc ccaatgccga cacttcggac tatgagaaca   2160
ttccagccat gaactcagac tatgagaata tccagatccc ccctcgcagg ccggtgagga   2220
ctggcacttt cacaaagctg ttcgaagaac agagccgagc cctgtccacc gcaaatgaaa   2280
atgacggcta cgtggacatg agcagcttca atgccttcga gagcaagcag cagagttcag   2340
agcaggaagc tgagagcgcc tacactgagc cctacaaggt ctgtcccatc tcagcggctc   2400
ccagagagga cctcacatca gacgaagaac aaggaagctc cgaggaggag gacagtgctt   2460
caagagaccc cagcctctca cacaagggtg aaggacagtc tagagccctt gtcatcgctc   2520
aggagctgct gtcttcagag aaagcatatg tgcagatgtt gcagcactta agcctggatt   2580
tccatggagc cgtcctgagg gccttggaga acgtagagca agagggcaga gagccactgg   2640
cccaggagga gctgcggcag ggcctgcggg agctcccagc tatctgtgac cttcaccagg   2700
gcatcctgga gagcctggag cagaggctgg gggattgtgg ggagggccag ccgcaggtgg   2760
ccgacatctt cctggcccag gaacaggagt tcgagcatca tgccgcacac atcctgcaat   2820
ttgacaggta cctggggctg ctcgctgaga gctgcctgct ctcacccggg ctagccacca   2880
cggtccggga gtttgagcag agttcacaag ggggtggcca gagcatgaag catcgtatgc   2940
tgcgtgtggt ccagcgcctc ttccagtacc aagtgctgct cactgattat ttaaataacc   3000
tgtgcccgga ctcagcagag tacgacaaca ctcagagtgc tctgactctc atctctaaag   3060
tgacagaccg tgccaacgaa agcatggaac agggggaaaa cctgcagaag ctggtccaca   3120
tcgagtacag tgtacgaggc caaggggacc tcctccagcc aggaagggag ttcctgaagg   3180
aagggacact gatgagggtg agagggaaaa gccgacaccc ccgccacctg ttcctgatga   3240
atgacacact cctgtacaca catccccaga aggatgggaa gtaccggctg aagagctcgc   3300
tgccagtggc caacatgaag gtcagccgcc ctgtgatgga caaagtgccc tatgctctga   3360
agatcgaaac tcctgagtct tgtctgacac tgtctgcaag ctcctgcgcg gagcgggacg   3420
agtggcacta ctgtctgagc agagcccttc cggaggatta caagactcag gccctggctg   3480
ccttccacca cagtgtggag atccgggaaa ggctggggat cagcctcggt gagaggctcc   3540
ccaccctggt gcctgtcact catgccatga tgtgcatgaa ctgcggctgt gacttctccc   3600
tcaccgtgag gcgccaccac tgccatgcct gcggcaagat tgtgtgccgg aactgctctc   3660
gaaacaagta cccattgaag tgcctcaaga caggatggc caaggtctgt gatggctgct   3720
tccgggagct gaagttgagg aatgggcctg tcccaggctc catgagagag cgtccagtca   3780
gcatgagctt cccactgtcc tcgtcccgct tttcctcggg cagcgccttg tcctctgtct   3840
tccagagtat tagcccctca actttcaaga agcagaaaaa agtcccttcg gctctgtccg   3900
aggtggccgc gtcaggagag ggctctgcca tcagcggcta cttgagccgc tgtaagagtg   3960
gcaagcggcg ctggaagaaa ctctggctcg tcatcaaggg caaagtactc tacacctact   4020
tggccagcga ggacaaagtg gccatggaga gcataccttct gctgggtttt actattgccc   4080
cagaaaagga ggagggcagc agcgaagtgg gccctgtttt tcatctttat cacaagaaaa   4140
```

```
ccctgtttta cagcttcaaa gcagaggaca gcaattctgc tcagagatgg atggaggcca    4200
tggaagatgc cagtgtgtta tagcagtcac caggcccatg gactaacaac aaactcctac    4260
attaactcga gaacccttcc ggaagtgact cctgctttca gctcatctgg atgcacgtgt    4320
gggttctgtg tggagcttga cctcaaggcg aaaccccaag agctatttat agacatcttc    4380
ttttctgcct ccatgtttcc caaccccaat cacagactgt acacccttat ctaaaagtga    4440
gttaaaattt agtaccttga agacgtgaaa accaagtgaa aaagacactt agaaatgtgg    4500
gctttttagt agaaactggc tttttctggt tttactcctg gtgactaaga ccactttcaa    4560
ctttccgcac tctccatatg gtgcctcagg tgatgtggga gccagacagg aagtatcagc    4620
tgtgtatcta agcactttac tatcctgctg agctgcagcc tccagggctg tgtcttccaa    4680
ggaatggctg caaacttcgg tgcaaagtga ctcctgcagc cttactgtgg cttgccaccc    4740
taaggaggga ggggctcagc accacaccag gctgccctc taaagcatca cagatccctc    4800
aaacatggaa gacctgcatc tgcgttaagt ttctgtgtgc attcctgtgt ccacactgtg    4860
caggctgacc atcctgttga tgggagtctg tcctctttgt aacacgtgtc cttgggctgt    4920
accagccaca ccaagcttac tttttgagag aggtaaagga gaaagagaga agttgggtca    4980
tcagaaagtg gtctgcacag aaggcttggc cagcccggag gcactgagtg gctggaagac    5040
actttgcaca cctgaggccg acagcatcac ctccctctgg gcacctgagg cagagccatc    5100
acctgctggc cagttcttta tgccgaatgg attttacaaa atgcaggagg aggaacagga    5160
ttcctcttca ctatccctac agttgggaaa aaaaaaaaaa tgcctccatt ttctgaaatc    5220
tcttcctgcc ttgtccccta caaaaaagat ttttgtaaaa caaacaaaca aacaaaccac    5280
catctcaagg acttatttac attaattatg ttcagggatt tctttttcta gtttgaagtt    5340
ctttttcaat gtttttgcag tcggtgtata gttagtaatt caagtcggat ggaagacaag    5400
tgttactgtt cacttcacaa tcctaggatc cttcctagag tcactcacat gggacccgga    5460
caccgagacc caggaacctt tagagagtgg agctggactc aaggacagta atcctcttcc    5520
тттggттттca tttttctatg atttcaattg caggagacca actgtggact gaaaatatta    5580
aatggaaaat tccagaaata aagtgcatg aatttccagt caaaaaaaaa aaaaaa       5636

<210> SEQ ID NO 3
<211> LENGTH: 1813
<212> TYPE: DNA
<213> ORGANISM: Mus musculus

<400> SEQUENCE: 3
taccagtggg ctcaaatgct tgatgtgtta gagcacccag tcctctgtta catcttctcc      60
tgggtcagga ccaggctggc atctggagct gctatcacac tcagacctca gcaaagatag     120
acagaagatg aggcctgtct gaaggtgtca gcttagagtt acatgtctga agtttcact     180
ttgctggagt atggatagag atgtgaccag gccctgctgg ctgctcagga gagacatggg     240
acttggacct tggagactgt gccactggtc tgcttcttgt cttaacatgt cctacgctat     300
tcttctcagg ggttcacctt ctcccagagg cctctcagtc acggcagtac ttcctggcta     360
actcctgacg cgtgtgctca ctgcacatcc cttaccttc cagtctgcgt gcctctgcat     420
ccctgagggt cacagtcttt tgtagctacc catattaata tatgccattt cctttcttcc     480
atgacatttg ggggtgctgg ctggatactc cagaaatacg cagacttcct cagtcaaagg     540
acatacagca ttgtgtgtcc ttgttgtgtc agttgtgaac agatgaagtg atggctattc     600
aaccatagca tcccatagct gcagcttgct ttctctctct ctcccccgc accccccct      660
```

```
gatgttctaa cttcacaacg gattttcctc tgggcccaat gaaagcgtct cgtctgtagt      720
gttggtctgg ctggcttggt tagggtgctc atgaacacca gctctgtgag gaccctggga      780
gcctgaccgt caagttcatc ttttctcat ggtggcagga cacacagaga tcattcaatc      840
agtagtttct ggtgaatgaa tgaaaagatc ttggcacatt gttcaaggta cacaggattt      900
tgttgagttg atcgctgtta gctggactgg aggaagctct gttccccat tcacagaatg      960
aactgttact attaggtcag agactttctg tgtttcagat aggatttcat gtgggccagg     1020
ctggccttga actcactatg ttgctgagga tgaccttgac cttgaatttt tgaaccccta     1080
gcttctactc tccagacctg gggtactagg tttatggggg ctggggatca aatttagggt     1140
tgcctgcgtg ggaggcaaat attctagcaa tgaggctata tccacatctc tgctaaagga     1200
tttcaaggat gtgggatgaa ggaagggat gaaggtccga aacaagtcac agagtgggaa     1260
ctctcctcca tctttccttc accaggctgt ttgaacaatt ttgagcataa gttaattgtg     1320
tttcttctcc ttgtctctgt ttttgcgctg cagattcacc aaagccacca cttgctccca     1380
agccaaaggt tgctaccaac ccttatgcac cggcagccaa gtttccccct tcacagaggc     1440
ctgacagctt ccccagtccc aactccatgt ccaggggccc caagcccct atcgctccta     1500
agcccagact gactggcccc agtgagtacc tgaacaacag cctcggcaaa tgcagcaatg     1560
ggaggctgct ctgtgaggac cggggcctgt acgacggaca ccactccacc ctgaattgct     1620
tggagttgga gcctgatgag cagtatatca tggttcccag ggctccacag aaagaagata     1680
ctcccgtgga tggggctacc gaggagccgg ggtttgaggg ggaagtccag gagcatggta     1740
cagagcagac aggaactgag ggggacctgg aagctccaga tgaagaggca ccaagtagag     1800
acagtgagga agc                                                         1813

<210> SEQ ID NO 4
<211> LENGTH: 2899
<212> TYPE: DNA
<213> ORGANISM: Mus musculus

<400> SEQUENCE: 4
gaagaaacgg gaccagaaac ctgttcatca ggcatgggca tcagagatac cagtgatgaa       60
gtgaggaaga taggtatatt gccagaggga aagcctcccg agtgtgttcg ggccttgccg      120
gccaagccca gagcatttac tctctaccca aggtccttct ctgtagaagg ccgggagagt      180
cccctgtcca tgttccggga gccagaggga gccgggctgg acagccaccg tgtaaggagg      240
aaagaggaca acctctctct gccgggcgcc atcggctcct ccggtagctt ctcacagcgc      300
agccacctgc cttccagtgg cacctccaca ccatcctctg tggttgacat cccacccct       360
tttgacttgg cctgcatcac gaagaaaccc atcactaaaa gctcaccctc actcctgata      420
gacggagaca ccctggaaaa agcctctaag aagaagaagt cctccttcaa acgcttcctg      480
gagctgacgt tcaggaagaa gacagagagc aaggtgcacg tggacatgaa cctgtcgtct      540
tccaggtctt cctctgagtc cagctaccat ggtccagcca gggtactgga acttgaccgc      600
agaagcctca gcaactcgcc ccagctcaag tgtcgcactg gaaagctccg ggcctctgac      660
tccccggccg ccctcatctt ctacagggac agcaagagga aggcgtccc cttcagcagg      720
acggtgtcca gagtggagtc cttcgaagac cgctcccggc cgccctttct gcctctgccc      780
ctcaccaagc cacggtccat ctcattcccc aatgccgaca cttcggacta tgagaacatt      840
ccagccatga actcagacta tgagaatatc cagatccccc ctcgcaggcc ggtgaggact      900
ggcacttca caaagctgtt cgaagaacag agccgagccc tgtccaccgc aaatgaaaat      960
```

```
gacggctacg tggacatgag cagcttcaat gccttcgaga gcaagcagca gagttcagag    1020
caggaagctg agaggtacgt gagtggcggg tcctttctca cagtgtgggc ctttgtgagg    1080
catagggggt ggaatggatg tgcggctctg tttctttcta gctgtgtgat ttggggtgag    1140
tggctctatc tccccgaacc actgtcactt cacctgggaa gtgggctca  tgtttaggaa    1200 gactggagta gcttgtctgt gtgagactac agtataaatg ggacagttct catgcatgtc    1260
taaaggagat tgctgtcata cacacacaca cacacacaca cacacacaca cacacacaaa    1320
gcaactaagc aagaacgttc tggaatctgg ccaaacgaaa tatctttcat catcagaaaa    1380 atacctaat  tgattgatgc cttcttattg tgtacacgaa gaactagaaa agacaattta    1440
tttaaactgt ccaaagagct cacgatgcct cgagctgaat ttctgaatag aagtcttgag    1500
gaggtgtatt taagttgatt tttaaaaact ggatcactct gaaggtggga gcagaacact    1560
gtggatattg aacaatagtg ggttttttctg cttcccttcc ctctggctga aagcccctcg    1620
cttactttac ctggattggc tgttccctat gtactgtaga tgcaacctag ataggacaca    1680
acagcctgtc tgcttgcacc tcgatggggc tctcatcgga gtcacagata attccccaag    1740
gttgcagttt aatggaggag ccccagagtt ccttcttgtg tgggggacta aaccgccttg    1800
tctgctgcct ggtgacaccg ccaggcgtgt ccggtgagct gcaagggagc tagaaagata    1860
ccatgtctgc ccgtggcctg gagaagactg gtaaggtgtg ccagcttcat ttcctggagt    1920
atgccatgtg gttcccacct gggttccatc ttctccctac accctggcca aggttggact    1980
acatcctatt ttggtttgtt taccagcgtc aaagtagaca ccagccttgg agaggggctg    2040
aatttaactt ggagagtgag aaggctagag actggagctg actggtttat ttcattaata    2100
attatcacat ggtcccaatt agatcctgca ttgtttcaac ctcatagcac tggtgaaaac    2160
aagaccacgt ttgaaacaca gcatcttcag gtgtaacgtg tggtcgccca gcttgctagt    2220
ttttcccttg cggctggtta ctcatcactt cccaaaattc cctccccagg ttcttggact    2280
gcagaataat aggaagtgtt ggtttgcttt gtttccccaa gtcatggttt ctctgtgaaa    2340
ccctggctga cttggaacta ctcagtaggc tgatcagcta ggctttgagc tcagagatct    2400
gtctgcctct gtctcctaag atcaaaggtg tttgccctca cctcccgctc caaagatttt    2460
ctgtgtaacc gaggctaaat ccctcatttc tcctttctgc ctacccagtt cacaccacct    2520
tatcactcaa ggcagataag tttgctgctt tcatctttgg agtgacagcc ttttgaagat    2580
taaaacacac ttctgcggaa ccacagttta ttgttgaagg acatttcag  atgtcattgt    2640 gtcccgcagt ggaagggaaa actgaggggc agagaggaaa agtgagttgc ccagggtctc    2700
acaggtttag gagaaaccca ttctgcgact cagacttcct aactcctaac ataagaattt    2760
gcagtgggtc gtgctaaggg gcgccagggt gagttgtaca ggctgtacac tacaacccca    2820
caggtagggc cttcccctct cagtgtgtat actgtgccca atgggattgt gctgtacaca    2880
ggcgcttggc tatatatgc                                                2899
```

<210> SEQ ID NO 5
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 5
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggcccgta      420
atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagta a              711

<210> SEQ ID NO 6
<211> LENGTH: 1356
<212> TYPE: PRT
<213> ORGANISM: Mus musculus

<400> SEQUENCE: 6

Met Val His Ala Leu Glu Asp Glu Asp Cys Asp His Asp Pro Glu Thr
1               5                   10                  15

Asp Gly Thr Pro Thr Ser Pro Asp Glu Gly Ala Pro Ser Arg Asp Ser
                20                  25                  30

Glu Glu Gly Glu Glu Asp Cys Asp Gln Gly Pro Gly Met Glu Glu His
            35                  40                  45

Pro Met Ser Glu Glu Gly Glu Glu Glu Val Lys Glu His Val
        50                  55                  60

Tyr Asn Ser Asp Asn Arg Ala Pro Trp Asp Gly Glu Glu Pro Phe Pro
65                  70                  75                  80

Asn Glu Val Ile Leu Thr His Val Arg Ser Gln Ser Pro Glu Val Pro
                85                  90                  95

Cys Trp Glu Pro Gly Pro Pro Glu Thr Pro Gly Glu Ala Glu Glu Asp
            100                 105                 110

Cys Glu Asp Ile Cys Asn Asn Thr Glu Pro Gly Lys Pro Asn Gln Asp
        115                 120                 125

Thr Gly Gln Asp Thr Glu Asp Ala Gly Met Gly Ser Pro Glu Ser Glu
    130                 135                 140

Val Ser Pro Asp Val Gln Glu Gln Ala Ala Thr Asp Asn Pro Glu
145                 150                 155                 160

Val Phe Glu Glu Asp Ser Ala Asp Ala Ala Glu Gly Glu Asp Gln Ile
                165                 170                 175

Glu Gln Glu Glu Pro Pro Asn Cys Asp Glu Glu Ala Tyr Asn Arg Asp
            180                 185                 190

Ala Ala Ala Ala Thr Met Gln Val Gly Glu Asp Leu Gly Glu Glu Gly
        195                 200                 205

Asp His Val Gln Glu Asp Pro Ala Glu Glu Ser Cys Gln Ile Ile Pro
    210                 215                 220

Phe Glu Ser Asp Ser Val Glu Glu Asp Phe Ser Pro Thr Leu Thr Glu
225                 230                 235                 240
```

```
Asn Pro Tyr Glu Ile Phe Pro Thr Glu Ser Thr Ser Phe Cys Asn Asn
                245                 250                 255

Thr Tyr Ser Leu Asp Glu Ser Ala Asn Gly His Glu Pro Val Cys Glu
        260                 265                 270

Ile Cys Val Glu Glu Val Pro Gly Val Gly Pro Pro Leu Asn Gln His
            275                 280                 285

Asp Ser Leu Pro Asp Gly Ser Gly Glu Asp Ser Pro Val Val Pro Asp
        290                 295                 300

Val Val Val Pro Glu Asn Glu Gly Pro Val Asp Asp Ala Leu Ser
305                 310                 315                 320

Ser Pro Tyr Val Met Gly Val Gly Leu Leu Ser Leu Gly Gly Ala
                325                 330                 335

Gln Ser Asp Thr Gln Ala Ala Ser Gly Thr Leu Ser Gly Tyr Ser Thr
            340                 345                 350

Trp Glu Glu Gly Asp Ser Glu Gly Gly Gln Val Pro Val Asp Arg Lys
        355                 360                 365

Asn Ile Ala Thr Arg Ala Arg Pro His Ser Gly Lys Val Ala Gly His
    370                 375                 380

Val Pro Glu Thr Val Leu Glu Glu Thr Gly Pro Glu Thr Cys Ser Ser
385                 390                 395                 400

Gly Met Gly Ile Arg Asp Thr Ser Asp Glu Val Arg Lys Ile Gly Ile
                405                 410                 415

Leu Pro Glu Gly Lys Pro Pro Glu Cys Val Arg Ala Leu Pro Ala Lys
            420                 425                 430

Pro Arg Ala Phe Thr Leu Tyr Pro Arg Ser Phe Ser Val Glu Gly Arg
        435                 440                 445

Glu Ser Pro Leu Ser Met Phe Arg Glu Pro Glu Gly Ala Gly Leu Asp
    450                 455                 460

Ser His Arg Val Arg Arg Lys Glu Asp Asn Leu Ser Leu Pro Gly Ala
465                 470                 475                 480

Ile Gly Ser Ser Gly Ser Phe Ser Gln Arg Ser His Leu Pro Ser Ser
                485                 490                 495

Gly Thr Ser Thr Pro Ser Ser Val Val Asp Ile Pro Pro Phe Asp
            500                 505                 510

Leu Ala Cys Ile Thr Lys Lys Pro Ile Thr Lys Ser Ser Pro Ser Leu
        515                 520                 525

Leu Ile Asp Gly Asp Thr Leu Glu Lys Ala Ser Lys Lys Lys Ser
    530                 535                 540

Ser Phe Lys Arg Phe Leu Glu Leu Thr Phe Arg Lys Lys Thr Glu Ser
545                 550                 555                 560

Lys Val His Val Asp Met Asn Leu Ser Ser Arg Ser Ser Ser Glu
                565                 570                 575

Ser Ser Tyr His Gly Pro Ala Arg Val Leu Glu Leu Asp Arg Arg Ser
            580                 585                 590

Leu Ser Asn Ser Pro Gln Leu Lys Cys Arg Thr Gly Lys Leu Arg Ala
        595                 600                 605

Ser Asp Ser Pro Ala Ala Leu Ile Phe Tyr Arg Asp Ser Lys Arg Lys
    610                 615                 620

Gly Val Pro Phe Ser Arg Thr Val Ser Arg Val Glu Ser Phe Glu Asp
625                 630                 635                 640

Arg Ser Arg Pro Pro Phe Leu Pro Leu Pro Leu Thr Lys Pro Arg Ser
                645                 650                 655
```

-continued

```
Ile Ser Phe Pro Asn Ala Asp Thr Ser Asp Tyr Glu Asn Ile Pro Ala
            660                 665                 670

Met Asn Ser Asp Tyr Glu Asn Ile Gln Ile Pro Pro Arg Arg Pro Val
            675                 680                 685

Arg Thr Gly Thr Phe Thr Lys Leu Phe Glu Glu Gln Ser Arg Ala Leu
            690                 695                 700

Ser Thr Ala Asn Glu Asn Asp Gly Tyr Val Asp Met Ser Ser Phe Asn
705                 710                 715                 720

Ala Phe Glu Ser Lys Gln Gln Ser Ser Gln Glu Ala Glu Ser Ala
            725                 730                 735

Tyr Thr Glu Pro Tyr Lys Val Cys Pro Ile Ser Ala Ala Pro Arg Glu
            740                 745                 750

Asp Leu Thr Ser Asp Glu Glu Gln Gly Ser Ser Glu Glu Asp Ser
            755                 760                 765

Ala Ser Arg Asp Pro Ser Leu His Lys Gly Glu Gly Gln Ser Arg
            770                 775                 780

Ala Leu Val Ile Ala Gln Glu Leu Leu Ser Ser Glu Lys Ala Tyr Val
785                 790                 795                 800

Gln Met Leu Gln His Leu Ser Leu Asp Phe His Gly Ala Val Leu Arg
            805                 810                 815

Ala Leu Glu Asn Val Glu Gln Glu Gly Arg Glu Pro Leu Ala Gln Glu
            820                 825                 830

Glu Leu Arg Gln Gly Leu Arg Glu Leu Pro Ala Ile Cys Asp Leu His
            835                 840                 845

Gln Gly Ile Leu Glu Ser Leu Glu Gln Arg Leu Gly Asp Cys Gly Glu
            850                 855                 860

Gly Gln Pro Gln Val Ala Asp Ile Phe Leu Ala Gln Glu Gln Glu Phe
865                 870                 875                 880

Glu His His Ala Ala His Ile Leu Gln Phe Asp Arg Tyr Leu Gly Leu
            885                 890                 895

Leu Ala Glu Ser Cys Leu Leu Ser Pro Arg Leu Ala Thr Thr Val Arg
            900                 905                 910

Glu Phe Glu Gln Ser Ser Gln Gly Gly Gly Gln Ser Met Lys His Arg
            915                 920                 925

Met Leu Arg Val Val Gln Arg Leu Phe Gln Tyr Gln Val Leu Leu Thr
            930                 935                 940

Asp Tyr Leu Asn Asn Leu Cys Pro Asp Ser Ala Glu Tyr Asp Asn Thr
945                 950                 955                 960

Gln Ser Ala Leu Thr Leu Ile Ser Lys Val Thr Asp Arg Ala Asn Glu
            965                 970                 975

Ser Met Glu Gln Gly Glu Asn Leu Gln Lys Leu Val His Ile Glu Tyr
            980                 985                 990

Ser Val Arg Gly Gln Gly Asp Leu  Leu Gln Pro Gly Arg  Glu Phe Leu
            995                 1000                1005

Lys Glu  Gly Thr Leu Met Arg  Val Arg Gly Lys Ser  Arg His Pro
       1010                1015                1020

Arg His  Leu Phe Leu Met Asn  Asp Thr Leu Leu Tyr  Thr His Pro
       1025                1030                1035

Gln Lys  Asp Gly Lys Tyr Arg  Leu Lys Ser Ser Leu  Pro Val Ala
       1040                1045                1050

Asn Met  Lys Val Ser Arg Pro  Val Met Asp Lys Val  Pro Tyr Ala
       1055                1060                1065
```

-continued

```
Leu Lys Ile Glu Thr Pro Glu Ser Cys Leu Thr Leu Ser Ala Ser
    1070                1075                1080

Ser Cys Ala Glu Arg Asp Glu Trp His Tyr Cys Leu Ser Arg Ala
    1085                1090                1095

Leu Pro Glu Asp Tyr Lys Thr Gln Ala Leu Ala Ala Phe His His
    1100                1105                1110

Ser Val Glu Ile Arg Glu Arg Leu Gly Ile Ser Leu Gly Glu Arg
    1115                1120                1125

Leu Pro Thr Leu Val Pro Val Thr His Ala Met Met Cys Met Asn
    1130                1135                1140

Cys Gly Cys Asp Phe Ser Leu Thr Val Arg Arg His His Cys His
    1145                1150                1155

Ala Cys Gly Lys Ile Val Cys Arg Asn Cys Ser Arg Asn Lys Tyr
    1160                1165                1170

Pro Leu Lys Cys Leu Lys Asn Arg Met Ala Lys Val Cys Asp Gly
    1175                1180                1185

Cys Phe Arg Glu Leu Lys Leu Arg Asn Gly Pro Val Pro Gly Ser
    1190                1195                1200

Met Arg Glu Arg Pro Val Ser Met Ser Phe Pro Leu Ser Ser Ser
    1205                1210                1215

Arg Phe Ser Ser Gly Ser Ala Leu Ser Ser Val Phe Gln Ser Ile
    1220                1225                1230

Ser Pro Ser Thr Phe Lys Lys Gln Lys Lys Val Pro Ser Ala Leu
    1235                1240                1245

Ser Glu Val Ala Ala Ser Gly Glu Gly Ser Ala Ile Ser Gly Tyr
    1250                1255                1260

Leu Ser Arg Cys Lys Ser Gly Lys Arg Arg Trp Lys Lys Leu Trp
    1265                1270                1275

Leu Val Ile Lys Gly Lys Val Leu Tyr Thr Tyr Leu Ala Ser Glu
    1280                1285                1290

Asp Lys Val Ala Met Glu Ser Ile Pro Leu Leu Gly Phe Thr Ile
    1295                1300                1305

Ala Pro Glu Lys Glu Glu Gly Ser Ser Glu Val Gly Pro Val Phe
    1310                1315                1320

His Leu Tyr His Lys Lys Thr Leu Phe Tyr Ser Phe Lys Ala Glu
    1325                1330                1335

Asp Ser Asn Ser Ala Gln Arg Trp Met Glu Ala Met Glu Asp Ala
    1340                1345                1350

Ser Val Leu
    1355

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```